(12) United States Patent
Baker et al.

(10) Patent No.: US 11,717,532 B2
(45) Date of Patent: Aug. 8, 2023

(54) METHODS AND COMPOSITIONS FOR TREATING WOUNDS UTILIZING CHITOSAN COMPOUNDS

(71) Applicant: SYNEDGEN, INC., Claremont, CA (US)

(72) Inventors: Shenda M. Baker, Upland, CA (US); William P. Wiesmann, Chevy Chase, MD (US); Ruth Baxter, Los Angeles, CA (US)

(73) Assignee: SYNEDGEN, INC., Claremont, CA (US)

( * ) Notice: Subject to any disclaimer, the term of this patent is extended or adjusted under 35 U.S.C. 154(b) by 0 days.

(21) Appl. No.: 15/923,696

(22) Filed: Mar. 16, 2018

(65) Prior Publication Data

US 2018/0200286 A1 Jul. 19, 2018

Related U.S. Application Data

(63) Continuation of application No. 15/173,218, filed on Jun. 3, 2016, now abandoned, which is a continuation of application No. 13/639,560, filed as application No. PCT/US2011/031385 on Apr. 6, 2011, now Pat. No. 9,439,925.

(60) Provisional application No. 61/451,430, filed on Mar. 10, 2011, provisional application No. 61/321,437, filed on Apr. 6, 2010.

(51) Int. Cl.
| | |
|---|---|
| *A61K 31/722* | (2006.01) |
| *A61K 47/61* | (2017.01) |
| *A61L 26/00* | (2006.01) |
| *C08L 5/08* | (2006.01) |

(52) U.S. Cl.
CPC ............ *A61K 31/722* (2013.01); *A61K 47/61* (2017.08); *A61L 26/0023* (2013.01); *A61L 26/0066* (2013.01); *C08L 5/08* (2013.01); *A61L 2300/404* (2013.01); *A61L 2300/41* (2013.01); *A61L 2300/64* (2013.01)

(58) Field of Classification Search
CPC .............. A61K 31/722; A61K 47/4823; A61L 26/0023; A61L 26/0066; A61L 2300/404; A61L 2300/06; A61L 2300/41; C08L 5/008
USPC .............................................. 514/55; 536/20
See application file for complete search history.

(56) References Cited

U.S. PATENT DOCUMENTS

| | | | |
|---|---|---|---|
| 4,409,205 A * | 10/1983 | Shively | A61K 9/0048 424/78.04 |
| 4,532,134 A | 7/1985 | Malette et al. | |
| 5,610,184 A * | 3/1997 | Shahinian, Jr. | A61K 31/24 514/540 |
| 6,114,382 A | 9/2000 | Moretti | |
| 6,323,189 B1 | 11/2001 | Hardinge-Lyme | |
| 6,962,151 B1 | 11/2005 | Knoch et al. | |
| 7,618,382 B2 | 11/2009 | Vogel et al. | |
| 8,119,780 B2 | 2/2012 | Baker et al. | |
| 8,399,635 B2 | 3/2013 | Baker et al. | |
| 8,658,775 B2 | 2/2014 | Baker et al. | |
| 8,916,542 B2 | 12/2014 | Baker et al. | |
| 9,012,429 B2 | 4/2015 | Baker et al. | |
| 9,029,351 B2 | 5/2015 | Baker et al. | |
| 9,234,050 B2 | 1/2016 | Baker et al. | |
| 9,439,925 B2 | 9/2016 | Baker et al. | |
| 9,732,164 B2 | 8/2017 | Baker et al. | |
| 10,022,393 B2 | 7/2018 | Baker et al. | |
| 10,716,803 B2 | 7/2020 | Baker et al. | |
| 2006/0029675 A1 | 2/2006 | Ginther | |
| 2006/0149171 A1 | 7/2006 | Vogel et al. | |
| 2007/0281904 A1 | 12/2007 | Baker et al. | |
| 2009/0202430 A1 | 8/2009 | Hoemann et al. | |
| 2009/0274770 A1 | 11/2009 | Gammelsaeter et al. | |
| 2010/0130443 A1 | 5/2010 | Baker et al. | |
| 2011/0206654 A1 | 8/2011 | Hodin et al. | |
| 2011/0263504 A1 | 10/2011 | Cerami et al. | |
| 2012/0295355 A1 | 11/2012 | Baker et al. | |
| 2012/0301408 A1 | 11/2012 | Baker et al. | |
| 2012/0329751 A1 | 12/2012 | Baker et al. | |
| 2013/0164311 A1 | 6/2013 | DeCarlo et al. | |
| 2013/0210761 A1 | 8/2013 | Baker et al. | |
| 2014/0080785 A1 | 3/2014 | Baker et al. | |
| 2014/0221308 A1 | 8/2014 | Baker et al. | |
| 2015/0031610 A1 | 1/2015 | Baker et al. | |
| 2015/0224044 A1 | 8/2015 | Baker et al. | |
| 2016/0022564 A1 | 1/2016 | Townsend et al. | |
| 2016/0022730 A1 | 1/2016 | Baker et al. | |

(Continued)

FOREIGN PATENT DOCUMENTS

| | | |
|---|---|---|
| CA | 2763092 A1 | 12/2010 |
| CN | 1965650 A | 5/2007 |
| JP | 2003012702 A | 1/2003 |

(Continued)

OTHER PUBLICATIONS

Lin et al. (Taiwan Nongye Huaxue Yu Shipin Kexue (2009) (abstract sent).*
And Mitsuyama et al. (Hindawi Publishing Corporation Mediators of Inflammation vol. 2006, Article ID 26875, pp. 1-7).*
Pfister et al. (Investigative Ophthalmology & Visual Science (1978), 17(10), 1019-24).*
Burns et al. (Docum. Ophthal. Proc. Series, vol. 18, 245-251; Hockwin et al. (eds.), Progress in Anterior Eye Segment Research and Practice © Dr W. Junk b.v. Publishers 1979).*

(Continued)

*Primary Examiner* — Layla D Berry
(74) *Attorney, Agent, or Firm* — Goodwin Procter LLP

(57) ABSTRACT

Described herein are methods of treating wounds, the method comprising administering to a subject an effective amount of a composition comprising a soluble or derivatized chitosan wherein the soluble or derivatized chitosan when administered contacts the wound, thereby treating the wound.

19 Claims, 16 Drawing Sheets

(56) References Cited

U.S. PATENT DOCUMENTS

| | | | |
|---|---|---|---|
| 2017/0119810 A1 | 5/2017 | Baker et al. | |
| 2017/0136056 A1 | 5/2017 | Baker et al. | |

FOREIGN PATENT DOCUMENTS

| | | | | |
|---|---|---|---|---|
| JP | 2008507380 A | 3/2008 | | |
| WO | 9945945 A1 | 9/1999 | | |
| WO | WO 00/30609 A1 * | 6/2000 | | |
| WO | WO-2004026200 A2 | 4/2004 | | |
| WO | 2004068971 A1 | 8/2004 | | |
| WO | WO-2004071186 A1 | 8/2004 | | |
| WO | WO-2006014917 A2 | 2/2006 | | |
| WO | 2007/142704 A3 | 5/2008 | | |
| WO | WO-2010021930 A1 * | 2/2010 | ........... | A61K 31/722 |
| WO | WO-2011/028967 A1 | 3/2011 | | |
| WO | 2011127144 A1 | 10/2011 | | |
| WO | 2014047506 A1 | 3/2014 | | |
| WO | 2016/040899 A1 | 3/2016 | | |
| WO | WO-2018202783 A1 | 11/2018 | | |

OTHER PUBLICATIONS

Alsarra et al. "Chitosan topical gel formulation in the management of burn wounds" International Journal of Biological Macromolecules (2009) vol. 45. pp. 16-21.
Bayat A. et al., "Skin scarring." BMJ, 2003; 326:88-92.
Doi K. et al., J Clin Invest. 2009; 119(10):2868-78.
Fang RC and Mustoe FA, "Animal models of wound healing: utility in transgenic mice." J Biomater Sci Polym Ed. 2008; 19(8):989-1005.
Grose R. and Werner S., "Wound healing studies in transgenic and knockout mice. A review." Methods Mol Med. 2003; 78:191-216.
Ito et al. "Anti-ulcer Effects of Chitin and Chitosan, Healthy Foods, in Rats", Jp. J. Pharmacol. 82, pp. 218-225 (2000).
Jawad et al. "Effect of Chitosan Sheets on Wound Healing" Basrah Journal of Veterinary Research (2007) vol. 6, pp. 81-95.
Kara CO, "Animal models of sinusitis: relevance to human disease." Curr Allergy Asthma Rep. 2004; 4(6):496-9.
Kweon et al. "Preparation of water-soluble chitosan/heparin complex and its application as wound healing accelerator" Biomaterials (2003) vol. 24, pp. 1595-1601.
Mathers et al. , Invest Opthalmol Vis Sci. 1989; 30(11 ):2403-6.
Matsubara M., Invest Ophthalmol Vis Sci. 1991; 32(13):3221-37.
Nakajima M. et al. , otolaryngology—Head and Neck Surgery, 131(2), 198-199, (2004).
Nemzek JA and Kim J, Comp Med. 2009; 59(4):321-30.
Olerud JE, "Models for diabetic wound healing and healing into percutaneous devices." J Biometer Sci Polym Ed. 2008; 19(8): 1007-20.
Roques C. et al., Lower Extremity Wounds, 2007; 6(4):249-53.
Santos Heredero FX et al., Annals of Burns and Fire Disasters, IX—n. 2 (Jun. 1996).
Schon MP, "Animal models of psoriasis: a critical appraisal." Exp Dermatol. 2008; 17(8):703-12.
Sonis ST et al., "An Animal Model for Mucositis Induced by Cancer Chemotherapy", Oral Surg Oral Med Oral Pathol, 69(4), pp. 437-443, (1990).
Stevenson JM et al., Methods Mal Med. 2003; 78:95-105.
Supplementary European Search Report from corresponding European Application EP 11766639 dated Jul. 23, 2013.
Ueno et al. "Topical formulations and wound healing applications of chitosan" Advanced Drug Delivery Reviews (2001) vol. 52, pp. 105-115.
Junping Li, et al. "Drug-Induced Ocular Disorders", Drug Safety 2008; 31 (2); p. 127-141.
Wolfgang Bernauer, Ocular surface problems following topial medication,Klin Monatsbl Augenheilkd 2002; 219: 240-242.
International Search Report and Written Opinion for corresponding International Application No. PCT/US2017/22698 dated Jun. 9, 2017.
Extended European Search Report for EP17767522 dated Aug. 26, 2019 (4 pages).
Tang, H et al, "Antibacterial action of a novel functionalized chitosan-arginine against Gram-negative bacteria" Acta Biomaterialia 2010, vol. 6, Issue 7, pp. 2562-2571.
Brook et al. "Management of Postirradiation Infection: Lessons Learned from Animal Models" Military Medicine, vol. 169, 2004, pp. 194-197.
Carden et al, Journal of Pathology, 2000, 190, 255-66.
CDC Fact Sheet on ARS. 2005.
Gorbach, Medical Microbiology, 4th Ed., 1996, pp. 1-9.
Hafer et al. "The NIAID Radiation Countermeasures Program Business Model" Biosecurity and Bioterrorism, vol. 8, No. 4, 2010, pp. 357-363.
Headley et al, Am. Fam. Physician 2003, 68, 323-28.
International Search Report and Written Opinion for PCT/US13/061027 dated Feb. 4, 2014.
Singh et al. "Medical Countermeasures for Radiation Exposure and Related Injuries: Characterization of Medicines, FDA—Approval Status and Inclusion into the Strategic National Stockpile" Health Physics, vol. 108, No. 6, 2015, pp. 607-630.
SurgWiki, Jan. 10, 2012, pp. 1-7.
The Merck Manual, 1992, pp. 1276-1277 and p. 1285.
Thuijls, et al., "Intestinal barrier loss in sepsis", Netherlands Journal of Critical Care, 15 {4): 199-203, 2011.

* cited by examiner

SGN-01: DSS-Induced Colitis Endoscopy Images Day 12

SGN-02: TNBS-Induced Colitis Endoscopy Images Day 5

METHODS AND COMPOSITIONS FOR TREATING WOUNDS UTILIZING CHITOSAN COMPOUNDS

PRIORITY CLAIM

The present application is a continuation of Ser. No. 15/173,218 filed Jun. 3, 2016, which is a continuation of U.S. Ser. No. 13/639,560, filed Dec. 14, 2012, which is a national stage application under 35 U.S.C. § 371 of International Application No. PCT/US2011/031385, filed Apr. 6, 2011, published as International Publication No. WO2011/127144 on Oct. 13, 2011, which claims the benefit of U.S. provisional application Nos. 61/321,437, filed on Apr. 6, 2010, and 61/451,430, filed on Mar. 10, 2011. The contents of the aforementioned applications are incorporated herein by reference in their entirety.

GOVERNMENT SUPPORT

This invention was made with government support under grant number W81-XWH-05-1-0504 awarded by the DoD/Army/MRMC. The government has certain rights in the invention.

FIELD OF THE INVENTION

The invention relates to soluble chitosans and derivatized chitosans and their use to treat a wound in a subject.

BACKGROUND

Wounds encountered in clinical settings can cast severe physical, emotional and financial burdens on patients. In humans and other animals, wound injury triggers a series of intricate biological events towards wound healing. Poor wound healing can increase the morbidity and mortality rate, for example, in patients undergoing cancer therapy or with chronic disease.

SUMMARY OF THE INVENTION

Compositions comprising soluble chitosans and derivatized chitosans (e.g., liquid, solid particulate and semisolid compositions) and related methods of use are described herein. In these embodiments, the derivatized chitosans are water soluble. Exemplary methods using the compositions described herein include, for example, methods of treating a wound (e.g., a chronic wound or burn) in a subject, e.g., the wound is not infected (e.g., bacterially or virally infected) or is infected (e.g., bacterially or virally infected) when treated; methods of treating mucositis or ulceration in a subject that has been treated or is being treated for cancer (e.g., with chemotherapy or radiation therapy), or has been treated or is being treated with immunosuppressive therapy; methods of treating a symptom of a chronic disease (e.g., an inflammatory disorder such as an inflammatory gastrointestinal disorder) in a subject, e.g., a symptom of a chronic disease comprising a wound and/or associated with poor or slow wound healing; methods of treating a wound in a subject, e.g., a wound resulted from an infection and the wound is not infected (e.g., bacterially or virally infected) or is still infected (e.g., bacterially or virally infected) when treated with the composition described herein; methods of treating a subject that has been exposed to a chemical, biological or radiological agent, or has suffered chemical, biological, or radiological injury; methods of treating a subject receiving a surgical procedure or having undergone a surgical procedure (e.g., an eye surgery). In some embodiments, the composition described herein can result in a synergistic effect when the composition is used to treat a wound in a subject in combination with a second agent. Wound dressings and medical devices comprising soluble chitosans and derivatized chitosans (e.g., liquid, solid particulate and semi-solid compositions) and related methods of use are also described herein.

In one aspect, the invention features a method of treating a wound, the method comprising administering to a subject an effective amount of a composition comprising a soluble or derivatized chitosan wherein the soluble or derivatized chitosan when administered contacts the wound, thereby treating the wound.

In an embodiment, the composition reduces the healing time or increases the healing rate of the wound. In some embodiments, the composition decreases the inflammation associated with wound or healing of the wound. In some embodiment, the composition decreases the magnitude or extent of scarring.

In an embodiment, the subject or wound is not infected, e.g., bacterially or virally infected, when treated with the composition. In another embodiment, the subject or wound is infected, e.g., bacterially or virally infected, when treated with the composition.

In an embodiment, the subject is a human or an animal (e.g., a farm, circus or zoo animal, or a companion pet).

In an embodiment, the subject has a chronic disease. In an embodiment, the chronic disease is selected from the group consisting of inflammatory bowel disease (IBD) (e.g., Crohn's disease), diabetes (e.g., diabetes mellitus types 1 or type 2), chronic kidney disease (CKD), chronic obstructive pulmonary disease (COPD), hypothyroidism, multiple sclerosis, rheumatoid arthritis, hepatic encephalopathy, peritonitis, periodontitis, sinusitis, rhinitis, sepsis, and systemic lupus erythematosus.

In an embodiment, the subject has been treated or is being treated with one or more of the cancer therapies, e.g., chemotherapy or radiation therapy. In an embodiment, the composition is administered to the subject before, during, or after the subject is treated with the cancer therapy. In an embodiment, the composition is administered to the subject prior to the therapy, e.g., for at least about 1 day, 2 days, 3 days, 5 days, or 1 week. In an embodiment, the composition is administered to the subject less than about 1 day, 2 days, 4 days, 1 week, 2 weeks, 3 weeks, or 4 weeks after the subject is treated with the cancer therapy.

In an embodiment, the subject has been treated or is being treated with an immunosuppressive therapy. In an embodiment, the composition is administered to the subject prior to the therapy, e.g., for at least about 1 day, 2 days, 3 days, 5 days, or 1 week. In an embodiment, the composition is administered to the subject less than about 1 day, 2 days, 4 days, 1 week, 2 weeks, 3 weeks, or 4 weeks after the subject is treated with the immunosuppressive therapy.

In an embodiment, the wound is caused by e.g., chemotherapy, radiation therapy, immunosuppressive therapy, chemical damage, biological damage, radiological damage, or immunodeficiency or compromise of immune system (e.g., primary immunodeficiency or acquired immunodeficiency (e.g., AIDS, malnutrition, aging, particular medications (e.g. chemotherapy, disease-modifying antirheumatic drugs, immunosuppressive drugs after organ transplants, glucocorticoids)).

In an embodiment, the wound is the result of an infection, e.g., bacterial or viral infection, and wherein the infection is no longer present when the wound is treated. In another embodiment, the wound is the result of an infection, e.g., bacterial or viral infection, and wherein the infection is still present when the wound is treated.

In an embodiment, the wound is an acute wound. In an embodiment, the wound is a chronic wound, e.g., a wound that does not heal in an orderly set of stages, in a predictable amount of time, or within three months. In an embodiment, the wound is a surgical wound, e.g., a wound resulted from medical grafting (e.g., skin or bone grafting) at the donor site and/or the graft site, or full thickness or partial thickness excision. In an embodiment, the wound is a burn. In an embodiment, the burn is caused by e.g., heat, electricity, chemicals, light, radiation, or friction. In an embodiment, the burn is a first, second, third, or fourth-degree burn. In an embodiment, the burn is a superficial, superficial partial-thickness, deep partial-thickness, or full-thickness burn. In an embodiment, the burn affects e.g., skin (epidermal tissue and dermis) and/or deeper tissues, e.g., muscle, bone, and blood vessels. In an embodiment, the method further comprises administering to the subject a second burn treatment, e.g., antibiotics, stopping the burning process at the source, cooling the burn wound, intravenous fluids, debridement (removing devitalized tissue and contamination), cleaning, dressing (e.g., biosynthetic dressing), pain management (e.g., analgesics (e.g., ibuprofen, acetaminophen), narcotics, local anesthetics), hyperbaric oxygenation, surgical management, control of infection, or control of hyper-metabolic response. In an embodiment, the second burn therapy comprises an antibiotic. In an embodiment, the composition overcomes (e.g., reduces, decreases, prevents) a deleterious effect of the antibiotic in burn wound healing.

In an embodiment, the wound is in the epidermis, dermis or hypodermis. In an embodiment, the wound is in the mucosal membrane.

In an embodiment, the wound is in the eye.

In an embodiment, the wound is a venous ulcer, a diabetic ulcer, a corneal ulcer (or damage to the corneal epithelium), an oral ulcer, a peptic ulcer, or a pressure ulcer.

In an embodiment, the composition is administered to the subject less than about 5 minutes, 15 minutes, 30 minutes, 1 hour, 2 hours, 4 hours, 6 hours, 12 hours, 24 hours, 2 days, 3 days, 4 days, 5 days, 6 days, 7 days, 2 weeks, 4 weeks, 2 months, 4 months, 6 months, 8 months, 10 months, or 1 year after the subject is wounded.

In an embodiment, the healing time of the wound (e.g., the length of one or more of the inflammatory, proliferative, or remodeling phase of wound healing) is reduced by at least about 10%, 20%, 30%, 40%, 50%, 60%, 70%, 80%, 90%, or 95%, compared to the healing time of the wound (e.g., the length of one or more of the inflammatory, proliferative, or remodeling phase of wound healing) that has not been contacted with the soluble or derivatized chitosan.

In an embodiment, the wound healing rate (e.g., the absolute area healed per day, the percentage of initial area healed per day, or the greatest average wound margin distance from the wound centre divided by the time to complete wound closure) is increased by at least about 1, 2, 3, 4, 5, 6, 7, 8, 9, or 10 fold, compared to the healing rate of the wound that has not been contacted with the soluble or derivatized chitosan.

In an embodiment, the method further comprises administering to the subject a second wound therapy, e.g., antibiotic or antibacterial use, debridement, irrigation, negative pressure wound therapy (vacuum-assisted closure), warming, oxygenation, moist wound healing, removing mechanical stress, and/or adding cells (e.g., keratinocytes) or other materials (e.g., artificial skin substitutes that have fibroblasts and/or keratinocytes in a matrix of collagen) to secrete or enhance levels of healing factors (e.g., vascular endothelial growth factor (VEGF), insulin-like growth factor (IGF), platelet-derived growth factor (PDGF), transforming growth factor-$\beta$ (TGF-$\beta$), and epidermal growth factor (EGF)).

In an embodiment, the second wound therapy comprises a negative pressure wound therapy (vacuum-assisted closure).

In an embodiment, the second wound therapy comprises an antibiotic. In an embodiment, the composition overcomes (e.g., reduces, decreases, prevents) a deleterious effect of the antibiotic in wound healing.

In an embodiment, the second wound therapy comprises a steroidal or non-steroidal anti-inflammatory drug (NSIAD). In an embodiment, the composition acts additively or synergysically with the steroidal or non-steroidal anti-inflammatory drug.

In an embodiment, the composition is administered topically or orally, e.g., by topical rinse, gel, spray, oral, enema, inhalation, dry powder, aerosolized liquid, aerosolized powder, or eye drop. In some embodiments, the composition is administered orally to treat a wound (e.g., damaged mucosa) in the gastrointestinal tract and/or an inflammatory gastrointestinal disorder. In some embodiments, the composition is administered topically to treat a wound and/or reduce or prevent a scar, e.g., in the eye.

In an embodiment, the composition is administered before, during or after one or more of the wound healing phase, e.g., inflammatory, proliferative, or remodeling phases.

In an embodiment, the effective amount is therapeutically effective amount.

In one embodiment, the soluble or derivatized chitosan is soluble in aqueous solution from about pH 6.8 to about pH 7.4.

In one embodiment, the soluble or derivatized chitosan is soluble in aqueous solution from about pH 3 to about pH 9.

In one embodiment, the soluble or derivatized chitosan is soluble in aqueous solution from about pH 5.0 to about pH 6.0, e.g., in wounds or duodenum.

In one embodiment, the soluble or derivatized chitosan is soluble in aqueous solution from about pH 2.0 to about pH 4.0, e.g., in stomach.

In one embodiment, the soluble or derivatized chitosan is soluble in aqueous solution from about pH 8.0 to about pH 8.5, e.g., in lower part of the gastrointestinal tract.

In one embodiment the soluble chitosan is underivatized.

In one embodiment, the derivatized chitosan comprises a chitosan of the following formula (I):

formula (I)

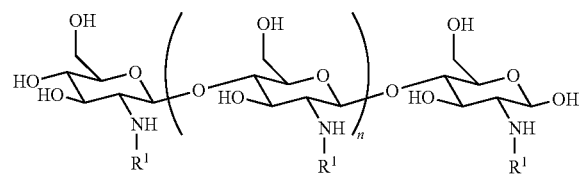

wherein:
n is an integer between 20 and 6000; and
each $R^1$ is independently selected for each occurrence from hydrogen, acetyl, and either:
a) a group of formula (II):

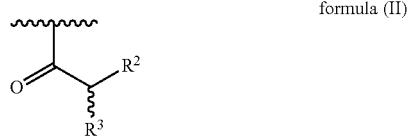

formula (II)

wherein $R^2$ is hydrogen or amino; and
$R^3$ is amino, guanidino, $C_1$-$C_6$ alkyl substituted with an amino or guanidino moiety, or a natural or unnatural amino acid side chain;
or
b) $R^1$, when taken together with the nitrogen to which it is attached, forms a guanidine moiety;
wherein at least 25% of $R^1$ substituents are H, at least 1% of $R^1$ substituents are acetyl, and at least 2% of $R^1$ substituents are a group of formula (II) or are taken together with the nitrogen to which they are attached to form a guanidine moiety.

In one embodiment the derivatized chitosan comprises of the following formula (I) wherein at least 90% by number or weight of $R^1$ moieties are as defined in formula (I) (e.g., at least about 95%, at least about 96%, at least about 97%, at least about 98%, or at least about 99%):

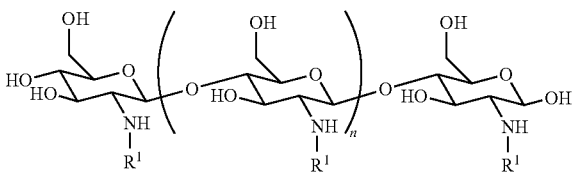

formula (I)

wherein:
n is an integer between 20 and 6000; and
each $R^1$ is independently selected for each occurrence from hydrogen, acetyl, and either:
a) a group of formula (II):

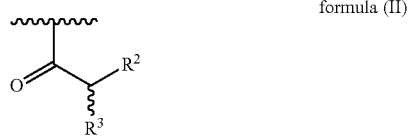

formula (II)

wherein $R^2$ is hydrogen or amino; and
$R^3$ is amino, guanidino, $C_1$-$C_6$ alkyl substituted with an amino or guanidino moiety, or a natural or unnatural amino acid side chain;
or
b) $R^1$, when taken together with the nitrogen to which it is attached, forms a guanidine moiety;
wherein at least 25% of $R^1$ substituents are H, at least 1% of $R^1$ substituents are acetyl, and at least 2% of $R^1$ substituents are a group of formula (II) or are taken together with the nitrogen to which they are attached to form a guanidine moiety.

In some embodiments, between 25-95% of $R^1$ substituents are hydrogen.

In some embodiments, between 55-90% of $R^1$ substituents are hydrogen.

In some embodiments, between 1-50% of $R^1$ substituents are acetyl.

In some embodiments, between 4-20% of $R^1$ substituents are acetyl.

In some embodiments, between 2-50% of $R^1$ substituents are a group of formula (II).

In some embodiments, between 4-30% of $R^1$ substituents are a group of formula (II).

In some embodiments, 55-90% of $R^1$ substituents are hydrogen, 4-20% of $R^1$ substituents are acetyl, 4-30% of $R^1$ substituents are a group of formula (II).

In some embodiments, $R^2$ is amino and $R^3$ is an arginine side chain.

In some embodiments, $R^1$ is selected from one of the following:

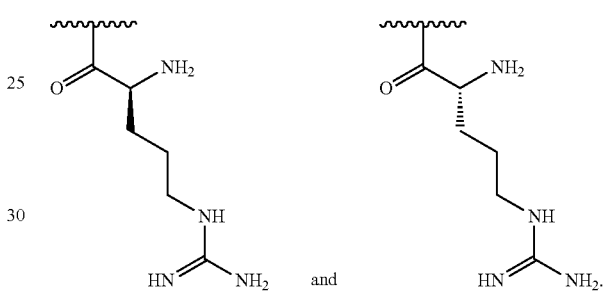

In some embodiments, $R^2$ is amino and $R^3$ is a lysine side chain.

In some embodiments, $R^1$ is selected from one of the following:

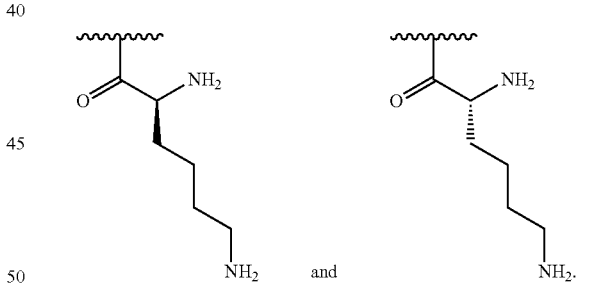

In some embodiments, $R^2$ is amino and $R^3$ is a histidine side chain.

In some embodiments, $R^1$ is selected from one of the following:

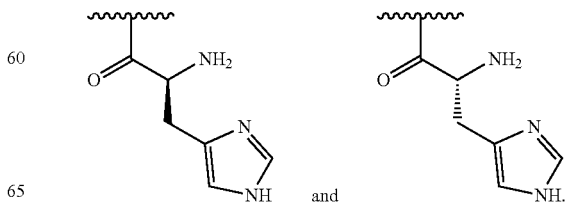

In some embodiments, at least 1% of $R^1$ substituents are selected from one of the following:

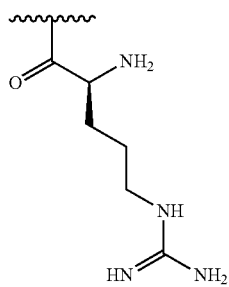 and 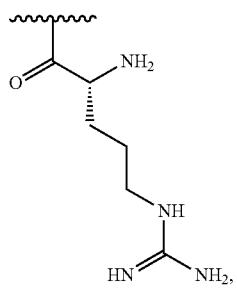

AND at least 1% of $R^1$ substituents are selected from the following:

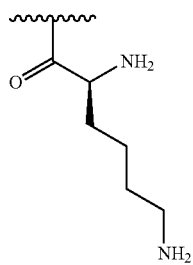 and 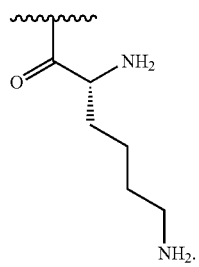

In some embodiments, $R^2$ is amino and $R^3$ is a substituted $C_1$-$C_6$ alkyl.

In some embodiments, $R^3$ is $C_1$-$C_6$ alkyl substituted with an amino group.

In some embodiments, $R^3$ is $C_1$ alkyl substituted with an amino group.

In some embodiments, $R^3$ is $C_2$ alkyl substituted with an amino group.

In some embodiments, $R^3$ is $C_3$ alkyl substituted with an amino group.

In some embodiments, $R^3$ is $C_4$ alkyl substituted with an amino group.

In some embodiments, $R^3$ is $C_5$ alkyl substituted with an amino group.

In some embodiments, $R^3$ is $C_6$ alkyl substituted with an amino group.

In some embodiments, $R^1$ is selected from one of the following:

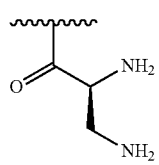 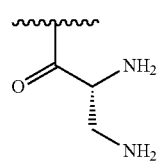 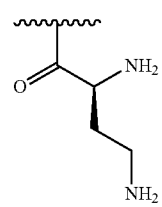

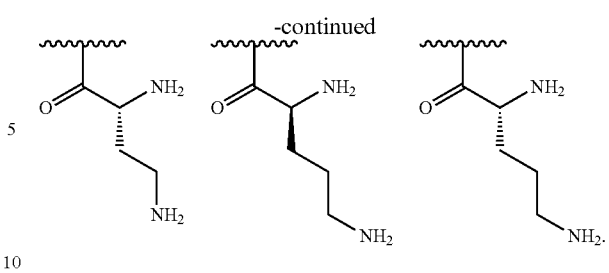

In some embodiments, $R^3$ is $C_1$-$C_6$ alkyl substituted with a guanidino group.

In some embodiments, $R^3$ is $C_1$ alkyl substituted with a guanidino group.

In some embodiments, $R^3$ is $C_2$ alkyl substituted with a guanidino group.

In some embodiments, $R^3$ is $C_3$ alkyl substituted with a guanidino group.

In some embodiments, $R^3$ is $C_4$ alkyl substituted with a guanidino group.

In some embodiments, $R^3$ is $C_5$ alkyl substituted with a guanidino group.

In some embodiments, $R^3$ is $C_6$ alkyl substituted with a guanidino group.

In some embodiments, $R^1$ is selected from one of the following:

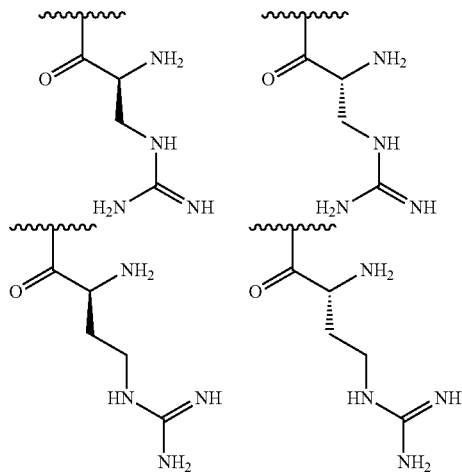

In some embodiments, wherein $R^2$ is amino that is substituted with a nitrogen protecting group prior to substitution on chitosan and removed subsequent to substitution on chitosan.

In some embodiments, the nitrogen protecting group is tert-butyloxycarbonyl (Boc).

In some embodiments, in the synthetic process a nitrogen protecting group is used, which can provide an intermediate polymer having a nitrogen protecting group such as Boc.

In some embodiments, $R^2$ is amino.

In some embodiments, $R^2$ is hydrogen and $R^3$ is amino.

In some embodiments, $R^2$ is hydrogen and $R^3$ is guanidino.

In some embodiments, $R^2$ is hydrogen and $R^3$ is a substituted $C_1$-$C_6$ alkyl.

In some embodiments, $R^3$ is $C_1$-$C_6$ alkyl substituted with an amino group.

In some embodiments, $R^3$ is $C_1$ alkyl substituted with an amino group.

In some embodiments, $R^3$ is $C_2$ alkyl substituted with an amino group.

In some embodiments, $R^3$ is $C_3$ alkyl substituted with an amino group.

In some embodiments, $R^3$ is $C_4$ alkyl substituted with an amino group.

In some embodiments, $R^3$ is $C_5$ alkyl substituted with an amino group.

In some embodiments, $R^3$ is $C_6$ alkyl substituted with an amino group.

In some embodiments, $R^1$ is selected from one of the following:

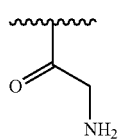 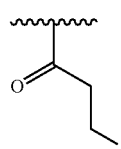 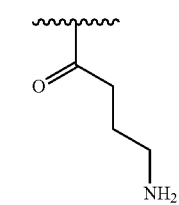

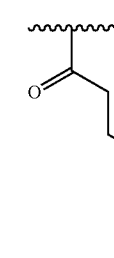 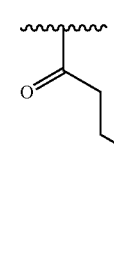

In some embodiments, $R^3$ is $C_1$-$C_6$ alkyl substituted with a guanidino group.

In some embodiments, $R^3$ is $C_1$ alkyl substituted with a guanidino group.

In some embodiments, $R^3$ is $C_2$ alkyl substituted with a guanidino group.

In some embodiments, $R^3$ is $C_3$ alkyl substituted with a guanidino group.

In some embodiments, $R^3$ is $C_4$ alkyl substituted with a guanidino group.

In some embodiments, $R^3$ is $C_5$ alkyl substituted with a guanidino group.

In some embodiments, $R^3$ is $C_6$ alkyl substituted with a guanidino group.

In some embodiments, $R^1$ is selected from one of the following:

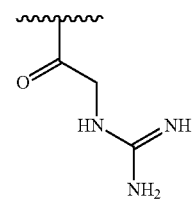 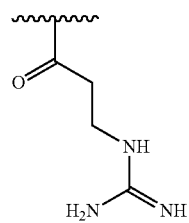

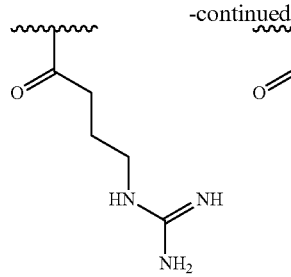 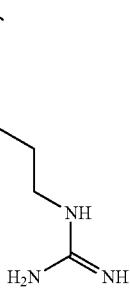

In some embodiments, at least 25% of $R^1$ substituents are H, at least 1% of $R^1$ substituents are acetyl, and at least 2% of $R^1$ substituents independently selected from any of the formulae specifically shown above.

In some embodiments, the functionalized chitosan of formula (I) may be further derivatized on the free hydroxyl moieties.

In some embodiments, the molecular weight of the functionalized chitosan is between 5,000 and 1,000,000 Da.

In some embodiments, the molecular weight of the functionalized chitosan is between 10,000 and 350,000 Da.

In some embodiments, the molecular weight of the functionalized chitosan is between 10,000 and 60,000 Da.

In some embodiments, the molecular weight of the functionalized chitosan is between 15,000 and 45,000 Da.

In some embodiments, the molecular weight of the functionalized chitosan is between 15,000 and 35,000 Da.

In some embodiments, the molecular weight of the functionalized chitosan is between 15,000 and 25,000 Da.

In some embodiments, the functionalized chitosan is soluble in aqueous solution between pH 6 and 8.

In some embodiments, the functionalized chitosan is soluble in aqueous solution between pH 6.8 and pH 7.4.

In one embodiment, the chitosan is functionalized at between 5% and 50%.

In a preferred embodiment, the chitosan is functionalized at between 20% and 30%.

In one embodiment, the degree of deacetylation (% DDA) of the derivatized chitosan is between 75% and 95%.

In one embodiment, the degree of deacetylation (% DDA) of the derivatized chitosan is between 80% and 90%.

In one embodiment, the polydispersity index (PDI) of the derivatized chitosan is between 1.0 and 2.5.

In one embodiment, the polydispersity index (PDI) of the derivatized chitosan is between 1.2 and 1.8.

In some embodiments, the functionalized chitosan is substantially free of other impurities.

In another aspect, the invention features a method of treating mucositis or ulceration, or a symptom of mucositis or ulceration, the method comprising administering to a subject an effective amount of a composition comprising a soluble or derivatized chitosan, thereby treating mucositis or ulceration, or the symptom of mucositis or ulceration.

In an embodiment, the subject has been treated or is being treated for cancer with chemotherapy (e.g., 5-fluorouracil (5-FU), irinotecan, or melphalan hydrochloride), or radiation therapy. In another embodiment, the subject has been treated or is being treated with immunosuppressive therapy. In another embodiment, the subject has been treated or is being treated with radiation therapy.

In an embodiment, the mucositis or ulceration occurs, e.g., in the gastrointestinal (GI) tract, e.g., mouth, tongue, throat, sinus, esophagus, stomach, large or small intestine.

In an embodiment, the symptom of mucositis comprises thinning of the mucosal lining, inflammation, ulceration, peripheral erythema, pain, and/or dysgeusia.

In an embodiment, mucositis or ulceration is the result of an infection, e.g., bacterial or viral infection, and wherein the infection is no longer present when mucositis is treated. In another embodiment, mucositis or ulceration is the result of an infection, e.g., bacterial or viral infection, and wherein the infection is present when mucositis is treated.

In an embodiment, the composition reduces the severity of mucositis (e.g., oral mucositis) by at least 1, 2, 3 or 4 grades, e.g., based on the World Health Organization (WHO) Oral Toxicity score, the National Cancer Institute Common Toxicity Criteria (NCI-CTC) for Oral Mucositis, or the Oral Mucositis Assessment Scale (OMAS).

In an embodiment, the composition reduces the healing time or increases the healing rate of mucositis or ulceration, for example, relative to control or standard of care. In some embodiments, the composition decreases the inflammation associated with mucositis or ulceration or healing of the mucositis or ulceration.

In an embodiment, the healing time of mucositis (e.g., the length of one or more of the initiation, message generation, signaling and amplification, ulceration, or healing phase of mucositis) or ulceration is reduced by at least about 10%, 20%, 30%, 40%, 50%, 60%, 70%, 80%, 90%, or 95%, compared to the healing time of mucositis that has not been contacted with the soluble or derivatized chitosan.

In an embodiment, the composition is administered to the subject before, during, or after the subject is treated with the cancer therapy. In an embodiment, the composition is administered to the subject prior to the therapy, e.g., for at least about 1 day, 2 days, 3 days, 5 days, or 1 week. In an embodiment, the composition is administered to the subject less than about 1 day, 2 days, 3 days, 4 days, 5 days, 6 days, 1 week, 2 weeks, 3 weeks, or 4 weeks after the subject is treated with the cancer therapy.

In an embodiment, the method further comprises administering to the subject a second mucositis therapy, e.g., antibiotics, oral hygiene, water-soluble jellies, salt mouthwash, keratinocyte growth factor (KGF), cytokines or modifier of inflammation (e.g., IL-1, IL-10, IL-11, TGF-β), amino acid supplementation (e.g., glutamine), vitamin, colony-stimulating factor (CSF), cryotherapy, laser therapy, barrier protection agent (e.g., concentrated oral gel product (e.g., GELCLAIR®), or medicinal mouthwash (e.g., CAPHOSOL®, MUGARD®).

In an embodiment, the second mucositis therapy comprises an antibiotic. In an embodiment, the composition overcomes (e.g., reduces, decreases, prevents) a deleterious effect of the antibiotic in the healing of mucositis.

In an embodiment, the second mucositis therapy comprises a steroid. In an embodiment, the composition acts additively or synergistically with the steroid to reduce inflammation and increase the healing in mucositis.

In an embodiment, the composition is administered topically or orally, e.g., by topical rinse, gel, spray, oral, enema, inhalation, dry powder, aerosolized liquid, aerosolized powder, or eye drop. In some embodiments, the composition is administered orally to treat a wound (e.g., damaged mucosa) in the gastrointestinal tract and/or an inflammatory gastrointestinal disorder. In some embodiments, the composition is administered topically to treat a wound and/or reduce or prevent a scar, e.g., in the eye.

In an embodiment, the composition is administered before, during or after one or more of the healing phase of mucositis, e.g., initiation, message generation, signaling and amplification, ulceration, or healing phase.

In an embodiment, the effective amount is therapeutically effective amount.

In one embodiment, the soluble or derivatized chitosan is soluble in aqueous solution from about pH 6.8 to about pH 7.4.

In one embodiment, the soluble or derivatized chitosan is soluble in aqueous solution from about pH 3 to about pH 9.

In one embodiment, the soluble or derivatized chitosan is soluble in aqueous solution from about pH 5.0 to about pH 6.0, e.g., in wounds or duodenum.

In one embodiment, the soluble or derivatized chitosan is soluble in aqueous solution from about pH 2.0 to about pH 4.0, e.g., in stomach.

In one embodiment, the soluble or derivatized chitosan is soluble in aqueous solution from about pH 8.0 to about pH 8.5, e.g., in lower part of the gastrointestinal tract.

In one embodiment, the soluble chitosan is underivatized.

In one embodiment, the derivatized chitosan comprises a chitosan of the following formula (I):

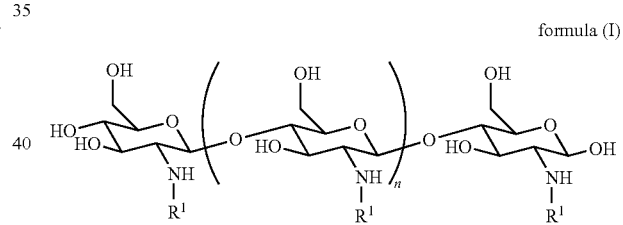

formula (I)

wherein:
n is an integer between 20 and 6000; and
each $R^1$ is independently selected for each occurrence from hydrogen, acetyl, and either:
a) a group of formula (II):

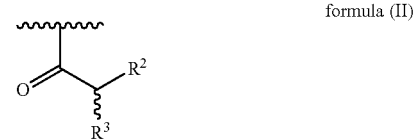

formula (II)

wherein $R^2$ is hydrogen or amino; and
$R^3$ is amino, guanidino, $C_1$-$C_6$ alkyl substituted with an amino or guanidino moiety, or a natural or unnatural amino acid side chain;
or
b) $R^1$, when taken together with the nitrogen to which it is attached, forms a guanidine moiety;
wherein at least 25% of $R^1$ substituents are H, at least 1% of $R^1$ substituents are acetyl, and at least 2% of $R^1$ substituents are a group of formula (II) or are taken together with the nitrogen to which they are attached to form a guanidine moiety.

In one embodiment, the derivatized chitosan comprises of the following formula (I) wherein at least 90% by number or weight of $R^1$ moieties are as defined in formula (I) (e.g., at least about 95%, at least about 96%, at least about 97%, at least about 98%, or at least about 99%):

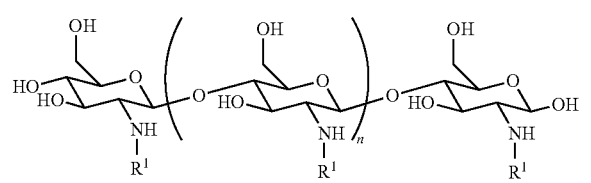

formula (I)

wherein:

n is an integer between 20 and 6000; and each $R^1$ is independently selected for each occurrence from hydrogen, acetyl, and either:

a) a group of formula (II):

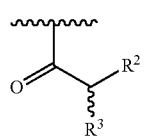

formula (II)

wherein $R^2$ is hydrogen or amino; and $R^3$ is amino, guanidino, $C_1$-$C_6$ alkyl substituted with an amino or guanidino moiety, or a natural or unnatural amino acid side chain;

or b) $R^1$, when taken together with the nitrogen to which it is attached, forms a guanidine moiety;

wherein at least 25% of $R^1$ substituents are H, at least 1% of $R^1$ substituents are acetyl, and at least 2% of $R^1$ substituents are a group of formula (II) or are taken together with the nitrogen to which they are attached to form a guanidine moiety.

In some embodiments, between 25-95% of $R^1$ substituents are hydrogen.

In some embodiments, between 55-90% of $R^1$ substituents are hydrogen.

In some embodiments, between 1-50% of $R^1$ substituents are acetyl.

In some embodiments, between 4-20% of $R^1$ substituents are acetyl.

In some embodiments, between 2-50% of $R^1$ substituents are a group of formula (II).

In some embodiments, between 4-30% of $R^1$ substituents are a group of formula (II).

In some embodiments, 55-90% of $R^1$ substituents are hydrogen, 4-20% of $R^1$ substituents are acetyl, 4-30% of $R^1$ substituents are a group of formula (II).

In some embodiments, $R^2$ is amino and $R^3$ is an arginine side chain.

In some embodiments, $R^1$ is selected from one of the following:

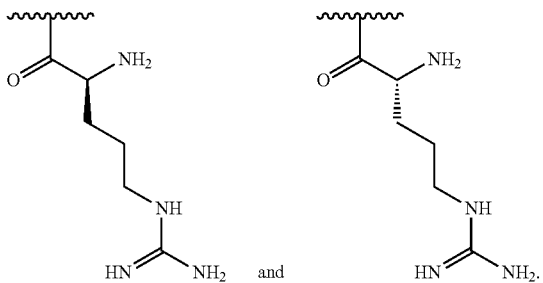 [SMILES: *C(=O)[C@@H](N)CCCNC(=N)N ; *C(=O)[C@H](N)CCCNC(=N)N]

In some embodiments, $R^2$ is amino and $R^3$ is a lysine side chain.

In some embodiments, $R^1$ is selected from one of the following:

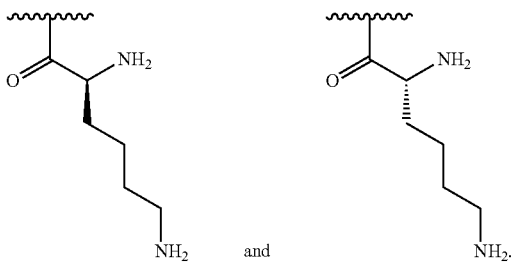 [SMILES: *C(=O)[C@@H](N)CCCCN ; *C(=O)[C@H](N)CCCCN]

In some embodiments, $R^2$ is amino and $R^3$ is a histidine side chain.

In some embodiments, $R^1$ is selected from one of the following:

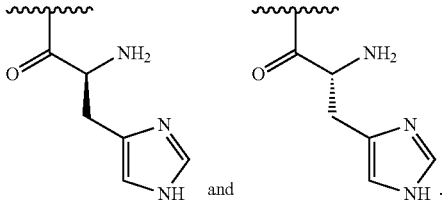 [SMILES: *C(=O)[C@@H](N)Cc1c[nH]cn1 ; *C(=O)[C@H](N)Cc1c[nH]cn1]

In some embodiments, at least 1% of $R^1$ substituents are selected from one of the following:

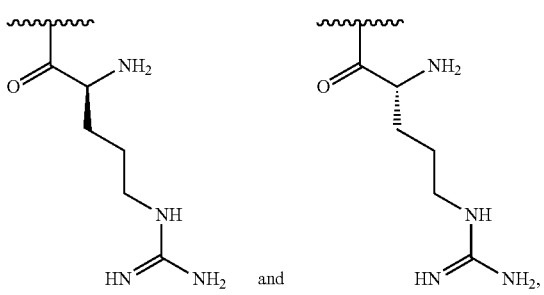 [SMILES: *C(=O)[C@@H](N)CCCNC(=N)N ; *C(=O)[C@H](N)CCCNC(=N)N]

AND at least 1% of $R^1$ substituents are selected from the following:

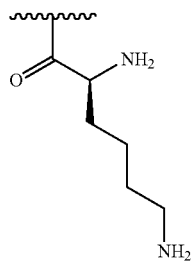 and 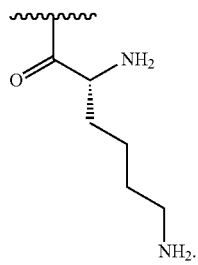

In some embodiments, $R^2$ is amino and $R^3$ is a substituted $C_1$-$C_6$ alkyl.

In some embodiments, $R^3$ is $C_1$-$C_6$ alkyl substituted with an amino group.

In some embodiments, $R^3$ is $C_1$ alkyl substituted with an amino group.

In some embodiments, $R^3$ is $C_2$ alkyl substituted with an amino group.

In some embodiments, $R^3$ is $C_3$ alkyl substituted with an amino group.

In some embodiments, $R^3$ is $C_4$ alkyl substituted with an amino group.

In some embodiments, $R^3$ is $C_5$ alkyl substituted with an amino group.

In some embodiments, $R^3$ is $C_6$ alkyl substituted with an amino group.

In some embodiments, $R^1$ is selected from one of the following:

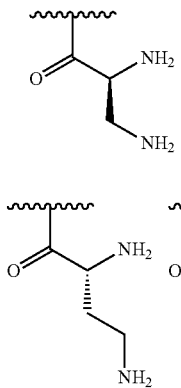 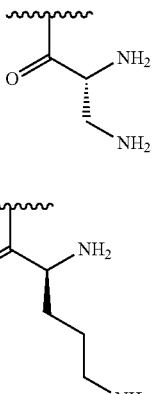 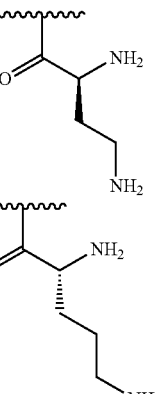

In some embodiments, $R^3$ is $C_1$-$C_6$ alkyl substituted with a guanidino group.

In some embodiments, $R^3$ is $C_1$ alkyl substituted with a guanidino group.

In some embodiments, $R^3$ is $C_2$ alkyl substituted with a guanidino group.

In some embodiments, $R^3$ is $C_3$ alkyl substituted with a guanidino group.

In some embodiments, $R^3$ is $C_4$ alkyl substituted with a guanidino group.

In some embodiments, $R^3$ is $C_5$ alkyl substituted with a guanidino group.

In some embodiments, $R^3$ is $C_6$ alkyl substituted with a guanidino group.

In some embodiments, $R^1$ is selected from one of the following:

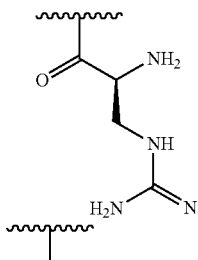 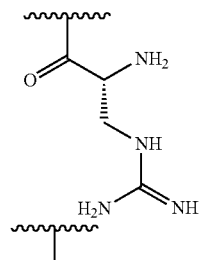

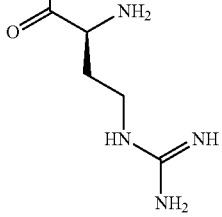 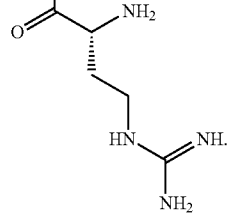

In some embodiments, wherein $R^2$ is amino that is substituted with a nitrogen protecting group prior to substitution on chitosan and removed subsequent to substitution on chitosan.

In some embodiments, the nitrogen protecting group is tert-butyloxycarbonyl (Boc).

In some embodiments, in the synthetic process a nitrogen protecting group is used, which can provide an intermediate polymer having a nitrogen protecting group such as Boc.

In some embodiments, $R^2$ is amino.

In some embodiments, $R^2$ is hydrogen and $R^3$ is amino.

In some embodiments, $R^2$ is hydrogen and $R^3$ is guanidino.

In some embodiments, $R^2$ is hydrogen and $R^3$ is a substituted $C_1$-$C_6$ alkyl.

In some embodiments, $R^3$ is $C_1$-$C_6$ alkyl substituted with an amino group.

In some embodiments, $R^3$ is $C_1$ alkyl substituted with an amino group.

In some embodiments, $R^3$ is $C_2$ alkyl substituted with an amino group.

In some embodiments, $R^3$ is $C_3$ alkyl substituted with an amino group.

In some embodiments, $R^3$ is $C_4$ alkyl substituted with an amino group.

In some embodiments, $R^3$ is $C_5$ alkyl substituted with an amino group.

In some embodiments, $R^3$ is $C_6$ alkyl substituted with an amino group.

In some embodiments, $R^1$ is selected from one of the following:

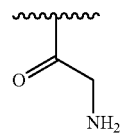 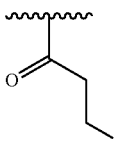 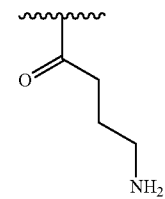

In some embodiments R³ is $C_1$-$C_6$ alkyl substituted with a guanidino group.

In some embodiments, R³ is $C_1$ alkyl substituted with a guanidino group.

In some embodiments, R³ is $C_2$ alkyl substituted with a guanidino group.

In some embodiments, R³ is $C_3$ alkyl substituted with a guanidino group.

In some embodiments, R³ is $C_4$ alkyl substituted with a guanidino group.

In some embodiments, R³ is $C_5$ alkyl substituted with a guanidino group.

In some embodiments, R³ is $C_6$ alkyl substituted with a guanidino group.

In some embodiments, R¹ is selected from one of the following:

In some embodiments, at least 25% of R¹ substituents are H, at least 1% of R¹ substituents are acetyl, and at least 2% of R¹ substituents independently selected from any of the formulae specifically shown above.

In some embodiments, the functionalized chitosan of formula (I) may be further derivatized on the free hydroxyl moieties.

In some embodiments, the molecular weight of the functionalized chitosan is between 5,000 and 1,000,000 Da.

In some embodiments, the molecular weight of the functionalized chitosan is between 10,000 and 350,000 Da.

In some embodiments, the molecular weight of the functionalized chitosan is between 10,000 and 60,000 Da.

In some embodiments, the molecular weight of the functionalized chitosan is between 15,000 and 45,000 Da.

In some embodiments, the molecular weight of the functionalized chitosan is between 15,000 and 35,000 Da.

In some embodiments, the molecular weight of the functionalized chitosan is between 15,000 and 25,000 Da.

In some embodiments, the functionalized chitosan is soluble in aqueous solution between pH 6 and 8.

In some embodiments, the functionalized chitosan is soluble in aqueous solution between pH 6.8 and pH 7.4.

In one embodiment, the chitosan is functionalized at between 5% and 50%.

In a preferred embodiment, the chitosan is functionalized at between 20% and 30%.

In one embodiment, the degree of deacetylation (% DDA) of the derivatized chitosan is between 75% and 95%.

In one embodiment, the degree of deacetylation (% DDA) of the derivatized chitosan is between 80% and 90%.

In one embodiment, the polydispersity index (PDI) of the derivatized chitosan is between 1.0 and 2.5.

In one embodiment, the polydispersity index (PDI) of the derivatized chitosan is between 1.2 and 1.8.

In some embodiments, the functionalized chitosan is substantially free of other impurities.

In yet another aspect, the invention features a method of treating a symptom of a chronic disease, the method comprising administering to a subject an effective amount of a composition comprising a soluble or derivatized chitosan, thereby treating the symptom of the chronic disease.

In an embodiment, the symptom of the chronic disease comprises at least one wound. In an embodiment, the chronic disease is associated with poor or slow wound healing.

In an embodiment, the chronic disease is selected from the group consisting of inflammatory bowel disease (IBD) (e.g., Crohn's disease), diabetes (e.g., diabetes mellitus types 1 or type 2), chronic kidney disease (CKD), chronic obstructive pulmonary disease (COPD), hypothyroidism, multiple sclerosis, rheumatoid arthritis, sinusitis, rhinitis, sepsis, peritonitis, periodontitis, hepatic encephalopathy, and systemic lupus erythematosus.

In an embodiment, the subject has a wound. In an embodiment, the wound is an acute wound. In an embodiment, the wound is a chronic wound, e.g., a wound that does not heal in an orderly set of stages, in a predictable amount of time, or within three months. In an embodiment, the wound is a surgical wound, e.g., a wound resulted from medical grafting (e.g., skin or bone grafting) at the donor site and/or the graft site, full thickness or partial thickness excision. In an embodiment, the wound is a burn wound. In an embodiment, the wound is in the epidermis, dermis or hypodermis. In an embodiment, the wound is in the mucosal membrane. In an embodiment, the wound is a venous ulcer, a diabetic ulcer, corneal ulcer (or damage to the corneal epithelium), an oral ulcer, a peptic ulcer, or a pressure ulcer.

In an embodiment, the wound is the result of an infection, e.g., bacterial or viral infection, and wherein the infection is no longer present when the wound is treated. In an embodiment, the wound is the result of an infection, e.g., bacterial or viral infection, and wherein the infection is still present when the wound is treated.

In an embodiment, the composition is administered to the subject less than about 5 minutes, 15 minutes, 30 minutes, 1 hour, 2 hours, 4 hours, 6 hours, 12 hours, 24 hours, 2 days, 3 days, 4 days, 5 days, 6 days, 7 days, 2 weeks, 4 weeks, 2 months, 4 months, 6 months, 8 months, 10 months, or 1 year after the subject is wounded.

In an embodiment, the composition reduces the healing time or increase the healing rate of the wound. In some embodiments, the composition decreases the inflammation associated with wound or healing of the wound.

In an embodiment, the healing time of the wound (e.g., the length of one or more of the inflammatory, proliferative, or remodeling phase of wound healing) is reduced by at least about 10%, 20%, 30%, 40%, 50%, 60%, 70%, 80%, 90%, or 95%, compared to the healing time of the wound (e.g., the length of one or more of the inflammatory, proliferative, or remodeling phase of wound healing) that has not been contacted with the soluble or derivatized chitosan.

In an embodiment, the wound healing rate (e.g., the absolute area healed per day, the percentage of initial area healed per day, or the greatest average wound margin distance from the wound centre divided by the time to complete wound closure) is increased by at least about 1, 2, 3, 4, 5, 6, 7, 8, 9, or 10 fold, compared to the healing rate of the wound that has not been contacted with the soluble or derivatized chitosan.

In an embodiment, the method further comprises administering to the subject a second wound therapy, e.g., antibiotic or antibacterial use, debridement, irrigation, negative pressure wound therapy (vacuum-assisted closure), warming, oxygenation, moist wound healing, removing mechanical stress, and/or adding cells (e.g., keratinocytes) or other materials (e.g., artificial skin substitutes that have fibroblasts and/or keratinocytes in a matrix of collagen) to secrete or enhance levels of healing factors (e.g., vascular endothelial growth factor (VEGF), insulin-like growth factor (IGF), platelet-derived growth factor (PDGF), transforming growth factor-β (TGF-β), and epidermal growth factor (EGF)).

In an embodiment, the second wound therapy comprises a negative pressure wound therapy (vacuum-assisted closure).

In an embodiment, the second wound therapy comprises an antibiotic. In an embodiment, the composition overcomes (e.g., reduces, decreases, prevents) a deleterious effect of the antibiotic in wound healing.

In an embodiment, the second wound therapy comprises a steroidal or non-steroidal anti-inflammatory drug (NSIAD). In an embodiment, the composition acts additively or synergysically with the steroidal or non-steroidal anti-inflammatory drug. In an embodiment, the composition is administered topically or orally, e.g., by topical rinse, gel, spray, oral, enema, inhalation, dry powder, aerosolized liquid, aerosolized powder, or eye drop. In some embodiments, the composition is administered orally to treat a wound (e.g., damaged mucosa) in the gastrointestinal tract and/or an inflammatory gastrointestinal disorder. In some embodiments, the composition is administered topically to treat a wound and/or reduce or prevent a scar, e.g., in the eye.

In an embodiment, the composition is administered before, during or after one or more of the wound healing phase, e.g., inflammatory, proliferative, or remodeling phase.

In an embodiment, the effective amount is therapeutically effective amount.

In one embodiment, the soluble or derivatized chitosan is soluble in aqueous solution from about pH 6.8 to about pH 7.4.

In one embodiment, the soluble or derivatized chitosan is soluble in aqueous solution from about pH 3 to about pH 9.

In one embodiment, the soluble or derivatized chitosan is soluble in aqueous solution from about pH 5.0 to about pH 6.0, e.g., in wounds or duodenum.

In one embodiment, the soluble or derivatized chitosan is soluble in aqueous solution from about pH 2.0 to about pH 4.0, e.g., in stomach.

In one embodiment, the soluble or derivatized chitosan is soluble in aqueous solution from about pH 8.0 to about pH 8.5, e.g., in lower part of the gastrointestinal tract.

In one embodiment, the derivatized chitosan comprises a chitosan of the following formula (I):

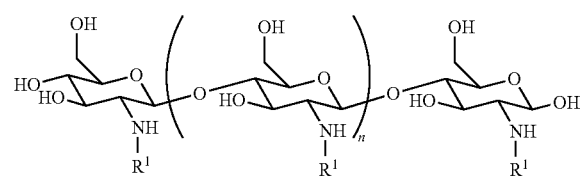

formula (I)

wherein:

n is an integer between 20 and 6000; and each $R^1$ is independently selected for each occurrence from hydrogen, acetyl, and either:

a) a group of formula (II):

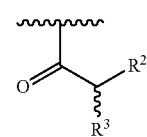

formula (II)

wherein $R^2$ is hydrogen or amino; and $R^3$ is amino, guanidino, $C_1$-$C_6$ alkyl substituted with an amino or guanidino moiety, or a natural or unnatural amino acid side chain;

or b) $R^1$, when taken together with the nitrogen to which it is attached, forms a guanidine moiety;

wherein at least 25% of $R^1$ substituents are H, at least 1% of $R^1$ substituents are acetyl, and at least 2% of $R^1$ substituents are a group of formula (II) or are taken together with the nitrogen to which they are attached to form a guanidine moiety.

In one embodiment, the derivatized chitosan comprises of the following formula (I) wherein at least 90% by number or weight of $R^1$ moieties are as defined in formula (I) (e.g., at least about 95%, at least about 96%, at least about 97%, at least about 98%, or at least about 99%):

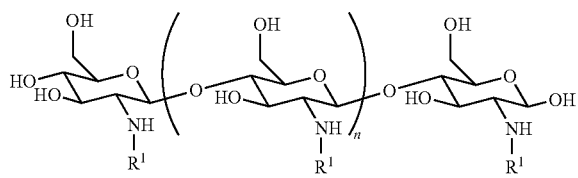

formula (I)

wherein:

n is an integer between 20 and 6000; and each $R^1$ is independently selected for each occurrence from hydrogen, acetyl, and either:

a) a group of formula (II):

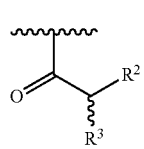

formula (II)

wherein $R^2$ is hydrogen or amino; and $R^3$ is amino, guanidino, $C_1$-$C_6$ alkyl substituted with an amino or guanidino moiety, or a natural or unnatural amino acid side chain;

or b) $R^1$, when taken together with the nitrogen to which it is attached, forms a guanidine moiety;

wherein at least 25% of $R^1$ substituents are H, at least 1% of $R^1$ substituents are acetyl, and at least 2% of $R^1$ substituents are a group of formula (II) or are taken together with the nitrogen to which they are attached to form a guanidine moiety.

In some embodiments, between 25-95% of $R^1$ substituents are hydrogen.

In some embodiments, between 55-90% of $R^1$ substituents are hydrogen.

In some embodiments, between 1-50% of $R^1$ substituents are acetyl.

In some embodiments, between 4-20% of $R^1$ substituents are acetyl.

In some embodiments, between 2-50% of $R^1$ substituents are a group of formula (II).

In some embodiments, between 4-30% of $R^1$ substituents are a group of formula (II).

In some embodiments, 55-90% of $R^1$ substituents are hydrogen, 4-20% of $R^1$ substituents are acetyl, 4-30% of $R^1$ substituents are a group of formula (II).

In some embodiments, $R^2$ is amino and $R^3$ is an arginine side chain.

In some embodiments, $R^1$ is selected from one of the following:

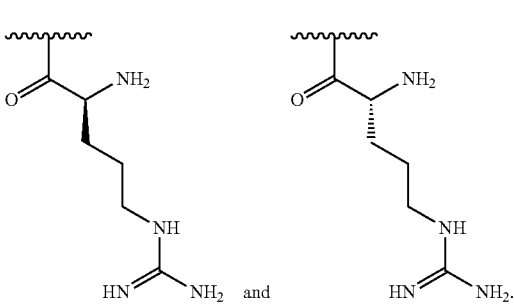 [SMILES: *C(=O)[C@@H](N)CCCNC(=N)N ; *C(=O)[C@H](N)CCCNC(=N)N]

In some embodiments, $R^2$ is amino and $R^3$ is a lysine side chain.

In some embodiments, $R^1$ is selected from one of the following:

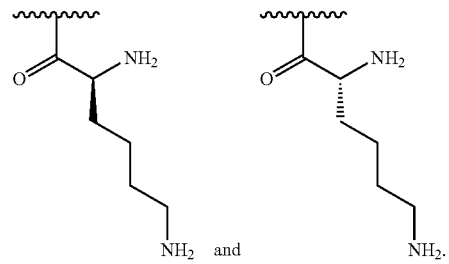 [SMILES: *C(=O)[C@@H](N)CCCCN ; *C(=O)[C@H](N)CCCCN]

In some embodiments, $R^2$ is amino and $R^3$ is a histidine side chain.

In some embodiments, $R^1$ is selected from one of the following:

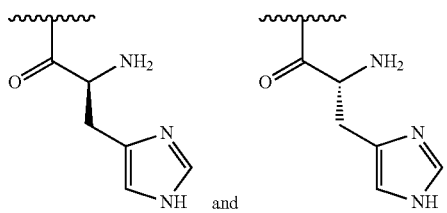

In some embodiments, at least 1% of $R^1$ substituents are selected from one of the following:

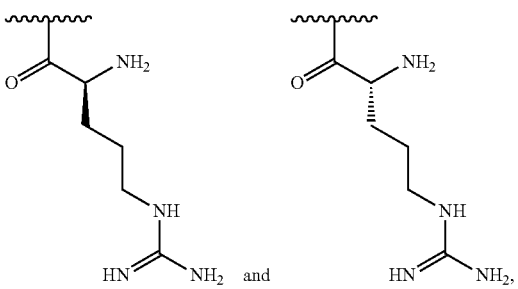 [SMILES: *C(=O)[C@@H](N)CCCNC(=N)N ; *C(=O)[C@H](N)CCCNC(=N)N]

AND at least 1% of $R^1$ substituents are selected from the following:

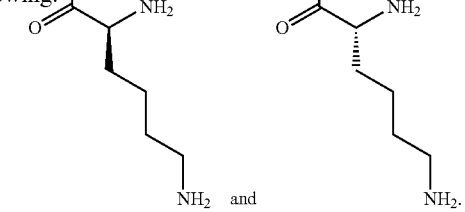

In some embodiments, $R^2$ is amino and $R^3$ is a substituted $C_1$-$C_6$ alkyl.

In some embodiments, $R^3$ is $C_1$-$C_6$ alkyl substituted with an amino group.

In some embodiments, $R^3$ is $C_1$ alkyl substituted with an amino group.

In some embodiments, $R^3$ is $C_2$ alkyl substituted with an amino group.

In some embodiments, $R^3$ is $C_3$ alkyl substituted with an amino group.

In some embodiments, $R^3$ is $C_4$ alkyl substituted with an amino group.

In some embodiments, $R^3$ is $C_5$ alkyl substituted with an amino group.

In some embodiments, $R^3$ is $C_6$ alkyl substituted with an amino group.

In some embodiments, $R^1$ is selected from one of the following:

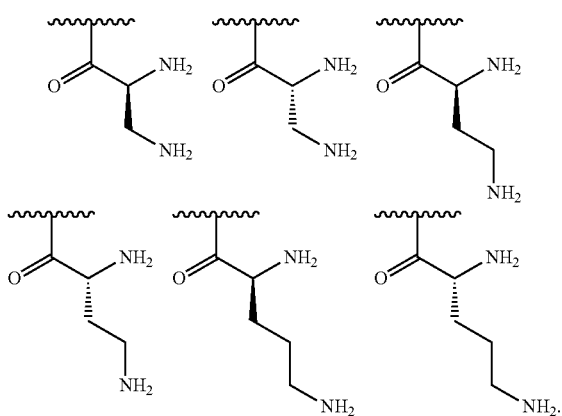

In some embodiments, R is $C_1$-$C_6$ alkyl substituted with a guanidino group.

In some embodiments, $R^3$ is $C_1$ alkyl substituted with a guanidino group.

In some embodiments, $R^3$ is $C_2$ alkyl substituted with a guanidino group.

In some embodiments, $R^3$ is $C_3$ alkyl substituted with a guanidino group.

In some embodiments, $R^3$ is $C_4$ alkyl substituted with a guanidino group.

In some embodiments, $R^3$ is $C_5$ alkyl substituted with a guanidino group.

In some embodiments, $R^3$ is $C_6$ alkyl substituted with a guanidino group.

In some embodiments, $R^1$ is selected from one of the following:

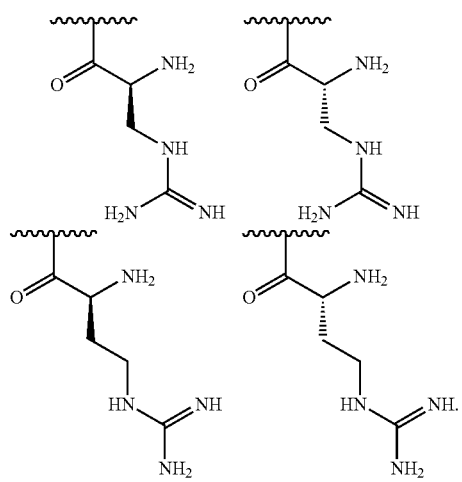

In some embodiments, wherein $R^2$ is amino that is substituted with a nitrogen protecting group prior to substitution on chitosan and removed subsequent to substitution on chitosan.

In some embodiments, the nitrogen protecting group is tert-butyloxycarbonyl (Boc).

In some embodiments, in the synthetic process a nitrogen protecting group is used, which can provide an intermediate polymer having a nitrogen protecting group such as Boc.

In some embodiments, $R^2$ is amino.

In some embodiments, $R^2$ is hydrogen and $R^3$ is amino.

In some embodiments, $R^2$ is hydrogen and $R^3$ is guanidino.

In some embodiments, $R^2$ is hydrogen and $R^3$ is a substituted $C_1$-$C_6$ alkyl.

In some embodiments, $R^3$ is $C_1$-$C_6$ alkyl substituted with an amino group.

In some embodiments, $R^3$ is $C_1$ alkyl substituted with an amino group.

In some embodiments, $R^3$ is $C_2$ alkyl substituted with an amino group.

In some embodiments, $R^3$ is $C_3$ alkyl substituted with an amino group.

In some embodiments, $R^3$ is $C_4$ alkyl substituted with an amino group.

In some embodiments, $R^3$ is $C_5$ alkyl substituted with an amino group.

In some embodiments, $R^3$ is $C_6$ alkyl substituted with an amino group.

In some embodiments, $R^1$ is selected from one of the following:

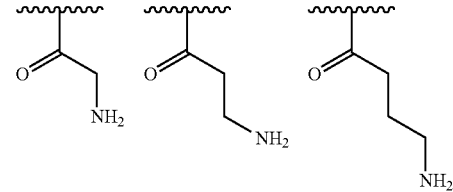

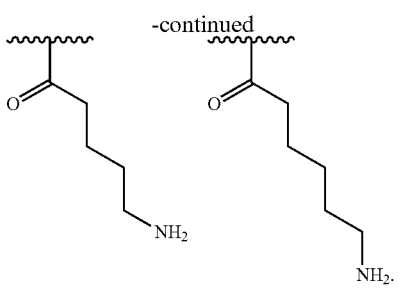

In some embodiments, $R^3$ is $C_1$-$C_6$ alkyl substituted with a guanidino group.

In some embodiments, $R^3$ is $C_1$ alkyl substituted with a guanidino group.

In some embodiments, $R^3$ is $C_2$ alkyl substituted with a guanidino group.

In some embodiments, $R^3$ is $C_3$ alkyl substituted with a guanidino group.

In some embodiments, $R^3$ is $C_4$ alkyl substituted with a guanidino group.

In some embodiments, $R^3$ is $C_5$ alkyl substituted with a guanidino group.

In some embodiments, $R^3$ is $C_6$ alkyl substituted with a guanidino group.

In some embodiments, $R^1$ is selected from one of the following:

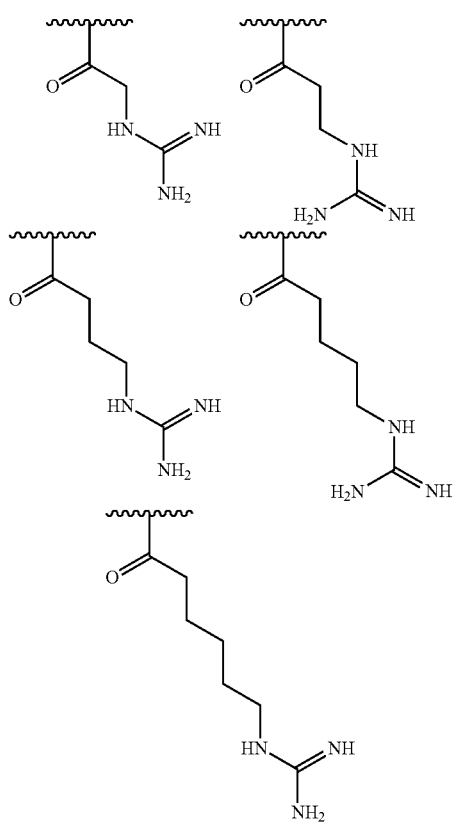

In some embodiments, at least 25% of $R^1$ substituents are H, at least 1% of $R^1$ substituents are acetyl, and at least 2% of $R^1$ substituents independently selected from any of the formulae specifically shown above.

In some embodiments, the functionalized chitosan of formula (I) may be further derivatized on the free hydroxyl moieties.

In some embodiments, the molecular weight of the functionalized chitosan is between 5,000 and 1,000,000 Da.

In some embodiments, the molecular weight of the functionalized chitosan is between 10,000 and 350,000 Da.

In some embodiments, the molecular weight of the functionalized chitosan is between 10,000 and 60,000 Da.

In some embodiments, the molecular weight of the functionalized chitosan is between 15,000 and 45,000 Da.

In some embodiments, the molecular weight of the functionalized chitosan is between 15,000 and 35,000 Da.

In some embodiments, the molecular weight of the functionalized chitosan is between 15,000 and 25,000 Da.

In some embodiments, the functionalized chitosan is soluble in aqueous solution between pH 6 and 8.

In some embodiments, the functionalized chitosan is soluble in aqueous solution between pH 6.8 and pH 7.4.

In one embodiment, the chitosan is functionalized at between 5% and 50%.

In a preferred embodiment, the chitosan is functionalized at between 20% and 30%.

In one embodiment, the degree of deacetylation (% DDA) of the derivatized chitosan is between 75% and 95%.

In one embodiment, the degree of deacetylation (% DDA) of the derivatized chitosan is between 80% and 90%.

In one embodiment, the polydispersity index (PDI) of the derivatized chitosan is between 1.0 and 2.5.

In one embodiment, the polydispersity index (PDI) of the derivatized chitosan is between 1.2 and 1.8

In some embodiments, the functionalized chitosan is substantially free of other impurities.

In one aspect, the invention features a method of treating a wound in a subject, wherein the wound is a result of an acute or chronic infection, the method comprising administering to a subject an effective amount of a composition comprising a soluble or derivatized chitosan, thereby treating the wound.

In an embodiment, the subject or the wound is no longer infected (e.g., bacterial or viral infected) when treated with the composition. In an embodiment, the subject or the wound is infected (e.g., bacterial or viral infected) when treated with the composition.

In an embodiment, the subject has a chronic disease, e.g., inflammatory bowel disease (IBD) (e.g., Crohn's disease), diabetes (e.g., diabetes mellitus types 1 or type 2), chronic kidney disease (CKD), chronic obstructive pulmonary disease (COPD), hypothyroidism, multiple sclerosis, rheumatoid arthritis, peritonitis, periodontitis, sinusitis, rhinitis, sepsis, hepatic encephalopathy, and systemic lupus erythematosus.

In an embodiment, the wound is in the epidermis, dermis or hypodermis. In an embodiment, the wound is in the mucosal membrane.

In an embodiment, the wound is a venous ulcer, a diabetic ulcer, a corneal ulcer (or damage to the corneal epithelium), an oral ulcer, a peptic ulcer, or a pressure ulcer.

In an embodiment, the composition is administered to the subject less than about 5 minutes, 15 minutes, 30 minutes, 1 hour, 2 hours, 4 hours, 6 hours, 12 hours, 24 hours, 2 days, 3 days, 4 days, 5 days, 6 days, 7 days, 2 weeks, 4 weeks, 2 months, 4 months, 6 months, 8 months, 10 months, or 1 year after the subject is wounded.

In an embodiment, the composition is administered to the subject prior to mucosal damage, e.g., for at least about 1 day, 2 days, 3 days, 5 days, or 1 week.

In an embodiment, the composition reduces the healing time or increase the healing rate of the wound. In some embodiments, the composition decreases the inflammation associated with wound or healing of the wound.

In an embodiment, the healing time of the wound (e.g., the length of one or more of the inflammatory, proliferative, or remodeling phase of wound healing) is reduced by at least about 10%, 20%, 30%, 40%, 50%, 60%, 70%, 80%, 90%, or 95%, compared to the healing time of the wound (e.g., the length of one or more of the inflammatory, proliferative, or remodeling phase of wound healing) that has not been contacted with the soluble or derivatized chitosan.

In an embodiment, the wound healing rate (e.g., the absolute area healed per day, the percentage of initial area healed per day, or the greatest average wound margin distance from the wound centre divided by the time to complete wound closure) is increased by at least about 1, 2, 3, 4, 5, 6, 7, 8, 9, or 10 fold, compared to the healing rate of the wound that has not been contacted with the soluble or derivatized chitosan.

In an embodiment, the method further comprises administering to the subject a second wound therapy, e.g., antibiotic or antibacterial use, debridement, irrigation, negative pressure wound therapy (vacuum-assisted closure), warming, oxygenation, moist wound healing, removing mechanical stress, and/or adding cells (e.g., keratinocytes) or other materials (e.g., artificial skin substitutes that have fibroblasts and/or keratinocytes in a matrix of collagen) to secrete or enhance levels of healing factors (e.g., vascular endothelial growth factor (VEGF), insulin-like growth factor (IGF), platelet-derived growth factor (PDGF), transforming growth factor-β (TGF-β), and epidermal growth factor (EGF)).

In an embodiment, the second wound therapy comprises a negative pressure wound therapy (vacuum-assisted closure).

In an embodiment, the second wound therapy comprises an antibiotic. In an embodiment, the composition overcomes (e.g., reduces, decreases, prevents) a deleterious effect of the antibiotic in wound healing.

In an embodiment, the second wound therapy comprises a steroidal or non-steroidal anti-inflammatory drug (NSIAD). In an embodiment, the composition acts additively or synergysically with the steroidal or non-steroidal anti-inflammatory drug.

In an embodiment, the composition is administered topically or orally, e.g., by topical rinse, gel, spray, oral, enema, inhalation, dry powder, aerosolized powder, aerosolized liquid, eye drop. In some embodiment, the composition is combined in a multicomponent wound dressing. In some embodiments, the composition is administered orally to treat a wound (e.g., damaged mucosa) in the gastrointestinal tract and/or an inflammatory gastrointestinal disorder. In some embodiments, the composition is administered topically to treat a wound, and/or reduce or prevent a scar, e.g., in the eye.

In an embodiment, the effective amount is therapeutically effective amount.

In one embodiment, the soluble or derivatized chitosan is soluble in aqueous solution from about pH 6.8 to about pH 7.4.

In one embodiment, the soluble or derivatized chitosan is soluble in aqueous solution from about pH 3 to about pH 9.

In one embodiment, the soluble or derivatized chitosan is soluble in aqueous solution from about pH 5.0 to about pH 6.0, e.g., in wounds or duodenum.

In one embodiment, the soluble or derivatized chitosan is soluble in aqueous solution from about pH 2.0 to about pH 4.0, e.g., in stomach.

In one embodiment, the soluble or derivatized chitosan is soluble in aqueous solution from about pH 8.0 to about pH 8.5, e.g., in lower part of the gastrointestinal tract.

In one embodiment, the soluble chitosan is underivatized.

In one embodiment, the derivatized chitosan comprises a chitosan of the following formula (I):

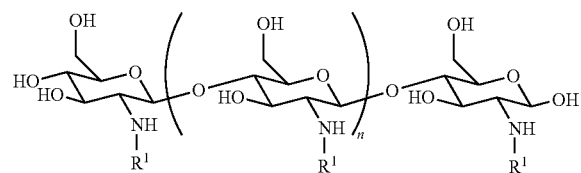

formula (I)

wherein:

n is an integer between 20 and 6000; and each $R^1$ is independently selected for each occurrence from hydrogen, acetyl, and either:

a) a group of formula (II):

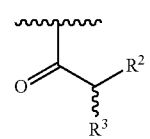

formula (II)

wherein $R^2$ is hydrogen or amino; and $R^3$ is amino, guanidino, $C_1$-$C_6$ alkyl substituted with an amino or guanidino moiety, or a natural or unnatural amino acid side chain;

or b) $R^1$, when taken together with the nitrogen to which it is attached, forms a guanidine moiety;

wherein at least 25% of $R^1$ substituents are H, at least 1% of $R^1$ substituents are acetyl, and at least 2% of $R^1$ substituents are a group of formula (II) or taken together with the nitrogen to which they are attached to form a guanidine moiety.

In one embodiment, the derivatized chitosan comprises of the following formula (I) wherein at least 90% by number or weight of $R^1$ moieties are as defined in formula (I) (e.g., at least about 95%, at least about 96%, at least about 97%, at least about 98%, or at least about 99%):

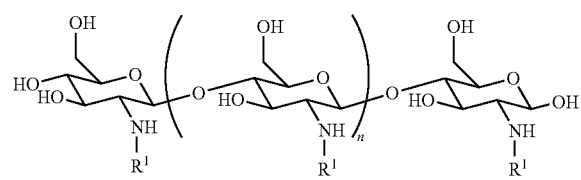

formula (I)

wherein:

n is an integer between 20 and 6000; and each $R^1$ is independently selected for each occurrence from hydrogen, acetyl, and either:

a) a group of formula (II):

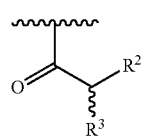

formula (II)

wherein $R^2$ is hydrogen or amino; and $R^3$ is amino, guanidino, $C_1$-$C_6$ alkyl substituted with an amino or guanidino moiety, or a natural or unnatural amino acid side chain;

or b) $R^1$, when taken together with the nitrogen to which it is attached, forms a guanidine moiety;

wherein at least 25% of $R^1$ substituents are H, at least 1% of $R^1$ substituents are acetyl, and at least 2% of $R^1$ substituents are a group of formula (II) or are taken together with the nitrogen to which they are attached to form a guanidine moiety.

In some embodiments, between 25-95% of $R^1$ substituents are hydrogen.

In some embodiments, between 55-90% of $R^1$ substituents are hydrogen.

In some embodiments, between 1-50% of $R^1$ substituents are acetyl.

In some embodiments, between 4-20% of $R^1$ substituents are acetyl.

In some embodiments, between 2-50% of $R^1$ substituents are a group of formula (II).

In some embodiments, between 4-30% of $R^1$ substituents are a group of formula (II).

In some embodiments, 55-90% of $R^1$ substituents are hydrogen, 4-20% of $R^1$ substituents are acetyl, 4-30% of $R^1$ substituents are a group of formula (II).

In some embodiments, $R^2$ is amino and $R^3$ is an arginine side chain.

In some embodiments, $R^1$ is selected from one of the following:

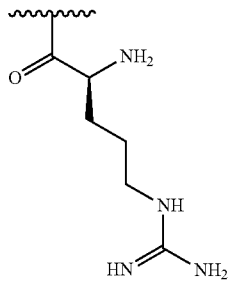 and 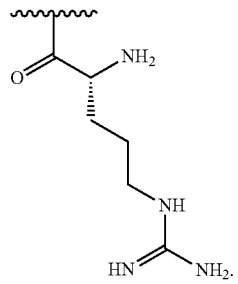

In some embodiments, $R^2$ is amino and $R^3$ is a lysine side chain.

In some embodiments, $R^1$ is selected from one of the following:

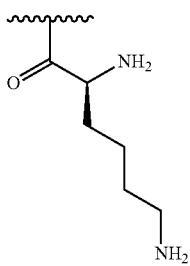 and 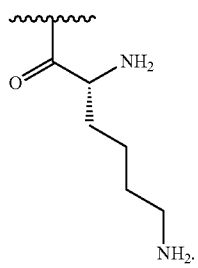

In some embodiments, $R^2$ is amino and $R^3$ is a histidine side chain.

In some embodiments, $R^1$ is selected from one of the following:

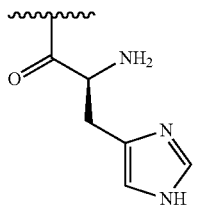 and 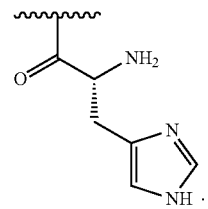

In some embodiments, at least 1% of $R^1$ substituents are selected from one of the following:

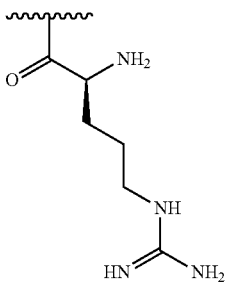 and 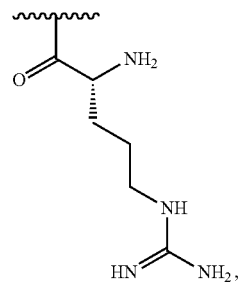

AND at least 1% of $R^1$ substituents are selected from the following:

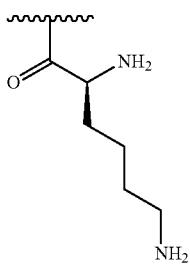 and 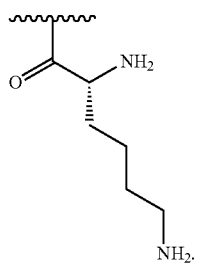

In some embodiments, $R^2$ is amino and $R^3$ is a substituted $C_1$-$C_6$ alkyl.

In some embodiments, $R^3$ is $C_1$-$C_6$ alkyl substituted with an amino group.

In some embodiments, $R^3$ is $C_1$ alkyl substituted with an amino group.

In some embodiments, $R^3$ is $C_2$ alkyl substituted with an amino group.
In some embodiments, $R^3$ is $C_3$ alkyl substituted with an amino group.
In some embodiments, $R^3$ is $C_4$ alkyl substituted with an amino group.
In some embodiments, $R^3$ is $C_5$ alkyl substituted with an amino group.
In some embodiments, $R^3$ is $C_6$ alkyl substituted with an amino group.
In some embodiments, $R^1$ is selected from one of the following:

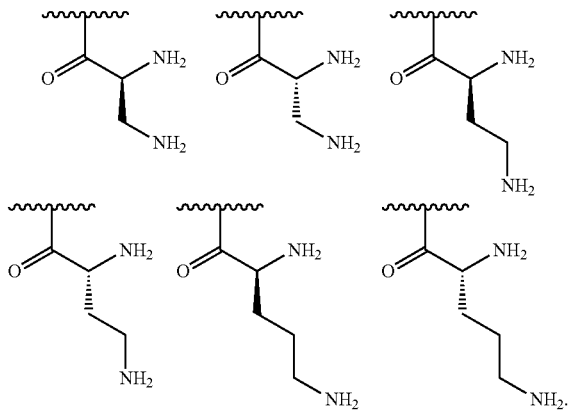

In some embodiments, $R^3$ is $C_1$-$C_6$ alkyl substituted with a guanidino group.
In some embodiments, $R^3$ is $C_1$ alkyl substituted with a guanidino group.
In some embodiments, $R^3$ is $C_2$ alkyl substituted with a guanidino group.
In some embodiments, $R^3$ is $C_3$ alkyl substituted with a guanidino group.
In some embodiments, $R^3$ is $C_4$ alkyl substituted with a guanidino group.
In some embodiments, $R^3$ is $C_5$ alkyl substituted with a guanidino group.
In some embodiments, $R^3$ is $C_6$ alkyl substituted with a guanidino group.
In some embodiments, $R^1$ is selected from one of the following:

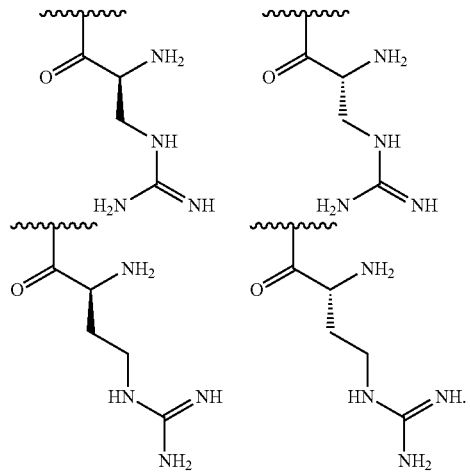

In some embodiments, wherein $R^2$ is amino that is substituted with a nitrogen protecting group prior to substitution on chitosan and removed subsequent to substitution on chitosan.
In some embodiments, the nitrogen protecting group is tert-butyloxycarbonyl (Boc).
In some embodiments, in the synthetic process a nitrogen protecting group is used, which can provide an intermediate polymer having a nitrogen protecting group such as Boc.
In some embodiments, $R^2$ is amino.
In some embodiments, $R^2$ is hydrogen and $R^3$ is amino.
In some embodiments, $R^2$ is hydrogen and $R^3$ is guanidino.
In some embodiments, $R^2$ is hydrogen and $R^3$ is a substituted $C_1$-$C_6$ alkyl.
In some embodiments, $R^3$ is $C_1$-$C_6$ alkyl substituted with an amino group.
In some embodiments, $R^3$ is $C_1$ alkyl substituted with an amino group.
In some embodiments, $R^3$ is $C_2$ alkyl substituted with an amino group.
In some embodiments, $R^3$ is $C_3$ alkyl substituted with an amino group.
In some embodiments, $R^3$ is $C_4$ alkyl substituted with an amino group.
In some embodiments, $R^3$ is $C_5$ alkyl substituted with an amino group.
In some embodiments, $R^3$ is $C_6$ alkyl substituted with an amino group.
In some embodiments, $R^1$ is selected from one of the following:

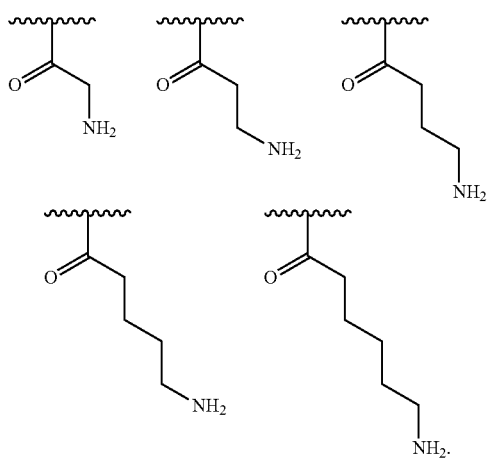

In some embodiments, $R^3$ is $C_1$-$C_6$ alkyl substituted with a guanidino group.
In some embodiments, $R^3$ is $C_1$ alkyl substituted with a guanidino group.
In some embodiments, $R^3$ is $C_2$ alkyl substituted with a guanidino group.
In some embodiments, $R^3$ is $C_3$ alkyl substituted with a guanidino group.
In some embodiments, $R^3$ is $C_4$ alkyl substituted with a guanidino group.
In some embodiments, $R^3$ is $C_5$ alkyl substituted with a guanidino group.
In some embodiments, $R^3$ is $C_6$ alkyl substituted with a guanidino group.

In some embodiments, $R^1$ is selected from one of the following:

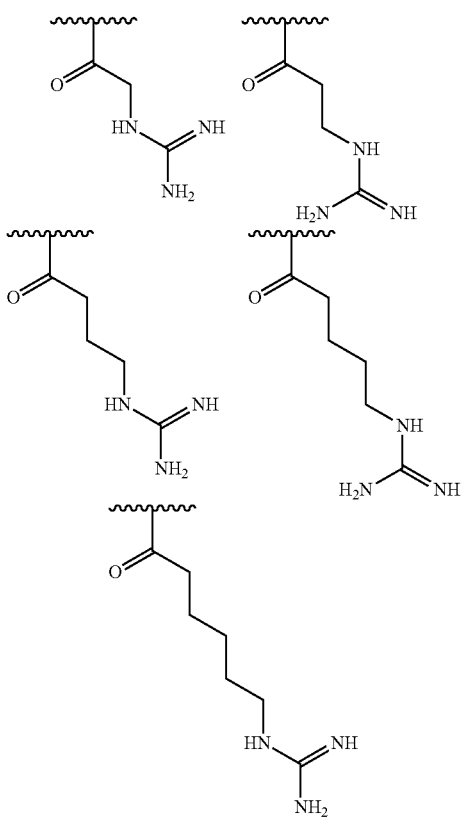

In some embodiments, at least 25% of $R^1$ substituents are H, at least 1% of $R^1$ substituents are acetyl, and at least 2% of $R^1$ substituents independently selected from any of the formulae specifically shown above.

In some embodiments, the functionalized chitosan of formula (I) may be further derivatized on the free hydroxyl moieties.

In some embodiments, the molecular weight of the functionalized chitosan is between 5,000 and 1,000,000 Da.

In some embodiments, the molecular weight of the functionalized chitosan is between 10,000 and 350,000 Da.

In some embodiments, the molecular weight of the functionalized chitosan is between 10,000 and 60,000 Da.

In some embodiments, the molecular weight of the functionalized chitosan is between 15,000 and 45,000 Da.

In some embodiments, the molecular weight of the functionalized chitosan is between 15,000 and 35,000 Da.

In some embodiments, the molecular weight of the functionalized chitosan is between 15,000 and 25,000 Da.

In some embodiments, the functionalized chitosan is soluble in aqueous solution between pH 6 and 8.

In some embodiments, the functionalized chitosan is soluble in aqueous solution between pH 6.8 and pH 7.4.

In one embodiment, the chitosan is functionalized at between 5% and 50%.

In a preferred embodiment, the chitosan is functionalized at between 20% and 30%.

In one embodiment, the degree of deacetylation (% DDA) of the derivatized chitosan is between 75% and 95%.

In one embodiment, the degree of deacetylation (% DDA) of the derivatized chitosan is between 80% and 90%.

In one embodiment, the polydispersity index (PDI) of the derivatized chitosan is between 1.0 and 2.5.

In one embodiment, the polydispersity index (PDI) of the derivatized chitosan is between 1.2 and 1.8.

In some embodiments, the functionalized chitosan is substantially free of other impurities.

In another aspect, the invention features a method of treating a wound in a subject, the method comprising administering to a subject an effective amount of a composition comprising a soluble or derivatized chitosan and a second agent, thereby treating the wound.

In an embodiment, the composition reduces the healing time or increases the healing rate of the wound. In some embodiments, the composition decreases the inflammation associated with wound or healing of the wound.

In an embodiment, the soluble or derivatized chitosan and the second agent are present at a concentration, or administered at a dose, which results in a synergistic effect, e.g., the wound healing rate is greater, e.g., at least 2, 5, 10, 20, 50 or 100 times greater, than the sum of the wound healing rates seen with either used alone.

In an embodiment, the second agent is present at a concentration, or administered at a dose, which is less than the lowest concentration or dose, that would achieve the minimum healing time or maximum healing rate of the wound in the absence of the soluble or derivatized chitosan.

In an embodiment, the second agent is present at a concentration, or administered at a dose, which is less than the lowest concentration or dose, generally used to treat the wound.

In an embodiment, the second agent is present at a concentration, or administered at a dose, which is less than 90, 80, 70, 60, 50, 40, 30, 20, 10, 5, 1, 0.1, 0.01% of the lowest concentration, or dose, that would give maximum wound healing rate in the absence of the soluble or derivatized chitosan.

In an embodiment, the second agent is present at a concentration, or administered at a dose, which is less than 90, 80, 70, 60, 50, 40, 30, 20, 10, 5, 1, 0.1, 0.01% of the lowest concentration, or dose, generally used to treat the wound.

In an embodiment, the second agent is a peptide growth factor. In another embodiment, the second agent is epidermal growth factor (EGF).

In an embodiment, the second agent comprises an antibiotic. In an embodiment, the composition overcomes (e.g., reduces, decreases, prevents) a deleterious effect of the antibiotic in wound healing.

In an embodiment, the soluble or derivatized chitosan increases a measurable effect of the second agent the by at least 2, 5, 10, 20, 50 or 100 fold, compared to the effect in the absence of the soluble or derivatized chitosan.

In an embodiment, the subject is a human, an animal (e.g., a farm, circus, or zoo animal, or a companion pet).

In an embodiment, the subject has a chronic disease. In an embodiment, the chronic disease is selected from the group consisting of inflammatory bowel disease (IBD) (e.g., Crohn's disease), diabetes (e.g., diabetes mellitus types 1 or type 2), chronic kidney disease (CKD), chronic obstructive pulmonary disease (COPD), hypothyroidism, multiple sclerosis, rheumatoid arthritis, hepatic encephalopathy, peritonitis, periodontitis, sinusitis, rhinitis, sepsis, hepatic encephalopathy, and systemic lupus erythematosus.

In an embodiment, the subject has been treated or is being treated with one or more of the cancer therapies, e.g., chemotherapy or radiation therapy. In an embodiment, the composition is administered to the subject before, during, or after the subject is treated with the cancer therapy. In an embodiment, the composition is administered to the subject prior to the therapy, e.g., for at least about 1 day, 2 days, 3 days, 5 days, or 1 week. In an embodiment, the composition is administered to the subject less than about 1 day, 2 days, 4 days, 1 week, 2 weeks, 3 weeks, or 4 weeks after the subject is treated with the cancer therapy.

In an embodiment, the subject has been treated or is being treated with immunosuppressive therapy. In an embodiment, the composition is administered to the subject prior to the therapy, e.g., for at least about 1 day, 2 days, 3 days, 5 days, or 1 week. In an embodiment, the composition is administered to the subject less than about 1 day, 2 days, 4 days, 1 week, 2 weeks, 3 weeks, or 4 weeks after the subject is treated with the immunosuppressive therapy.

In an embodiment, the wound is caused by e.g., chemotherapy, radiation therapy, immunosuppressive therapy, chemical damage, biological damage, radiological damage, or immunodeficiency or compromise of immune system (e.g., primary immunodeficiency or acquired immunodeficiency (e.g., AIDS, malnutrition, aging, particular medications (e.g. chemotherapy, disease-modifying antirheumatic drugs, immunosuppressive drugs after organ transplants, glucocorticoids)).

In an embodiment, the second agent is administered orally or topically.

In an embodiment, the wound is the result of an infection, e.g., bacterial or viral infection, and wherein the infection is no longer present when the wound is treated. In another embodiment, the wound is the result of an infection, e.g., bacterial or viral infection, and wherein the infection is present when the wound is treated.

In an embodiment, the wound is an acute wound. In an embodiment, the wound is a chronic wound, e.g., a wound that does not heal in an orderly set of stages, in a predictable amount of time, or within three months. In an embodiment, the wound is a surgical wound, e.g., a wound resulted from medical grafting (e.g., skin or bone grafting) at the donor site and/or the graft site, full thickness or partial thickness excision. In an embodiment, the wound is a burn wound.

In an embodiment, the wound is in the epidermis, dermis or hypodermis. In an embodiment, the wound is in the mucosal membrane.

In an embodiment, the wound is a venous ulcer, a diabetic ulcer, a corneal ulcer (or damage to the corneal epithelium), an oral ulcer, a peptic ulcer, or a pressure ulcer.

In an embodiment, the composition is administered to the subject less than about 5 minutes, 15 minutes, 30 minutes, 1 hour, 2 hours, 4 hours, 6 hours, 12 hours, 24 hours, 2 days, 3 days, 4 days, 5 days, 6 days, 7 days, 2 weeks, 4 weeks, 2 months, 4 months, 6 months, 8 months, 10 months, or 1 year after the subject is wounded.

In an embodiment, the healing time of the wound (e.g., the length of one or more of the inflammatory, proliferative, or remodeling phase of wound healing) is reduced by at least about 10%, 20%, 30%, 40%, 50%, 60%, 70%, 80%, 90%, or 95%, compared to the healing time of the wound (e.g., the length of one or more of the inflammatory, proliferative, or remodeling phase of wound healing) that has not been contacted with the soluble or derivatized chitosan.

In an embodiment, the wound healing rate (e.g., the absolute area healed per day, the percentage of initial area healed per day, or the greatest average wound margin distance from the wound centre divided by the time to complete wound closure) is increased by at least about 1, 2, 3, 4, 5, 6, 7, 8, 9, or 10 fold, compared to the healing rate of the wound that has not been contacted with the soluble or derivatized chitosan.

In an embodiment, the method further comprises administering to the subject a second wound therapy, e.g., antibiotic or antibacterial use, debridement, irrigation, negative pressure wound therapy (vacuum-assisted closure), warming, oxygenation, moist wound healing, removing mechanical stress, and/or adding cells (e.g., keratinocytes) or other materials (e.g., artificial skin substitutes that have fibroblasts and/or keratinocytes in a matrix of collagen) to secrete or enhance levels of healing factors (e.g., vascular endothelial growth factor (VEGF), insulin-like growth factor (IGF), platelet-derived growth factor (PDGF), transforming growth factor-β (TGF-β), and epidermal growth factor (EGF)).

In an embodiment, the second wound therapy comprises a negative pressure wound therapy (vacuum-assisted closure).

In an embodiment, the second wound therapy comprises an antibiotic. In an embodiment, the composition overcomes (e.g., reduces, decreases, prevents) a deleterious effect of the antibiotic in wound healing.

In an embodiment, the second wound therapy comprises a steroidal or non-steroidal anti-inflammatory drug (NSIAD). In an embodiment, the composition acts additively or synergysically with the steroidal or non-steroidal anti-inflammatory drug.

In an embodiment, the composition is administered topically or orally, e.g., by topical rinse, gel, spray, oral, enema, inhalation, dry powder, aerosolized liquid, eye drop. In some embodiments, the composition is administered orally to treat a wound (e.g., damaged mucosa) in the gastrointestinal tract and/or an inflammatory gastrointestinal disorder. In some embodiments, the composition is administered topically to treat a wound, and/or reduce or prevent a scar, e.g., in the eye.

In an embodiment, the composition is administered before, during or after one or more of the wound healing phase, e.g., inflammatory, proliferative, or remodeling phase.

In an embodiment, the effective amount is therapeutically effective amount.

In one embodiment, the soluble or derivatized chitosan is soluble in aqueous solution from about pH 6.8 to about pH 7.4.

In one embodiment, the soluble or derivatized chitosan is soluble in aqueous solution from about pH 3 to about pH 9.

In one embodiment, the soluble or derivatized chitosan is soluble in aqueous solution from about pH 5.0 to about pH 6.0, e.g., in wounds or duodenum.

In one embodiment, the soluble or derivatized chitosan is soluble in aqueous solution from about pH 2.0 to about pH 4.0, e.g., in stomach.

In one embodiment, the soluble or derivatized chitosan is soluble in aqueous solution from about pH 8.0 to about pH 8.5, e.g., in lower part of the gastrointestinal tract.

In one embodiment, the derivatized chitosan comprises a chitosan of the following formula (I):

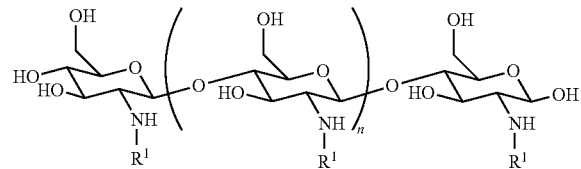

formula (I)

wherein:

n is an integer between 20 and 6000; and each $R^1$ is independently selected for each occurrence from hydrogen, acetyl, and either:

a) a group of formula (II):

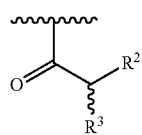

formula (II)

wherein $R^2$ is hydrogen or amino; and $R^3$ is amino, guanidino, $C_1$-$C_6$ alkyl substituted with an amino or guanidino moiety, or a natural or unnatural amino acid side chain;

or b) $R^1$, when taken together with the nitrogen to which it is attached, forms a guanidine moiety;

wherein at least 25% of $R^1$ substituents are H, at least 1% of $R^1$ substituents are acetyl, and at least 2% of $R^1$ substituents are a group of formula (II) or are taken together with the nitrogen to which they are attached to form a guanidine moiety.

In one embodiment, the derivatized chitosan comprises of the following formula (I) wherein at least 90% by number or weight of $R^1$ moieties are as defined in formula (I) (e.g., at least about 95%, at least about 96%, at least about 97%, at least about 98%, or at least about 99%):

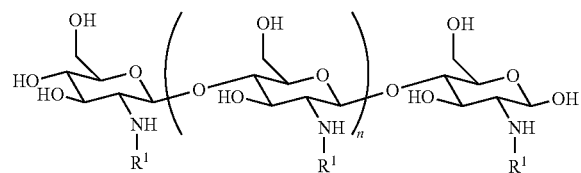

formula (I)

wherein:

n is an integer between 20 and 6000; and each $R^1$ is independently selected for each occurrence from hydrogen, acetyl, and either:

a) a group of formula (II):

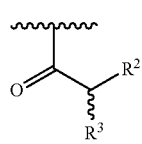

formula (II)

wherein $R^2$ is hydrogen or amino; and $R^3$ is amino, guanidino, $C_1$-$C_6$ alkyl substituted with an amino or guanidino moiety, or a natural or unnatural amino acid side chain;

or b) $R^1$, when taken together with the nitrogen to which it is attached, forms a guanidine moiety;

wherein at least 25% of $R^1$ substituents are H, at least 1% of $R^1$ substituents are acetyl, and at least 2% of $R^1$ substituents are a group of formula (II) or are taken together with the nitrogen to which they are attached to form a guanidine moiety.

In some embodiments, between 25-95% of $R^1$ substituents are hydrogen.

In some embodiments, between 55-90% of $R^1$ substituents are hydrogen.

In some embodiments, between 1-50% of $R^1$ substituents are acetyl.

In some embodiments, between 4-20% of $R^1$ substituents are acetyl.

In some embodiments, between 2-50% of $R^1$ substituents are a group of formula (II).

In some embodiments, between 4-30% of $R^1$ substituents are a group of formula (II).

In some embodiments, 55-90% of $R^1$ substituents are hydrogen, 4-20% of $R^1$ substituents are acetyl, 4-30% of $R^1$ substituents are a group of formula (II).

In some embodiments, $R^2$ is amino and $R^3$ is an arginine side chain.

In some embodiments, $R^1$ is selected from one of the following:

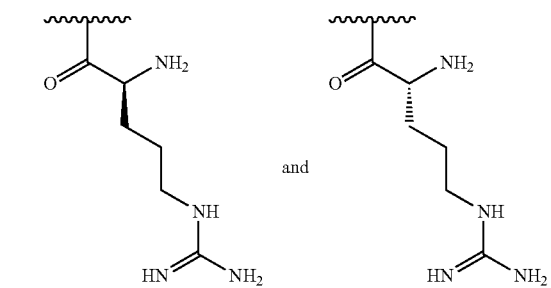

In some embodiments, $R^2$ is amino and $R^3$ is a lysine side chain.

In some embodiments, $R^1$ is selected from one of the following:

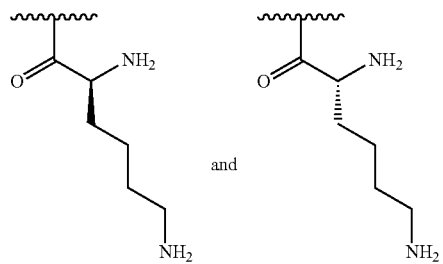

In some embodiments, $R^2$ is amino and $R^3$ is a histidine side chain.

In some embodiments, $R^1$ is selected from one of the following:

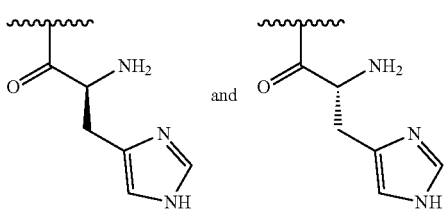

In some embodiments, at least 1% of $R^1$ substituents are selected from one of the following:

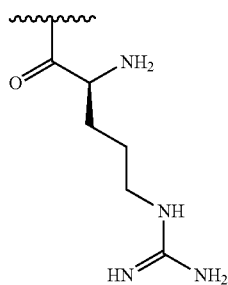 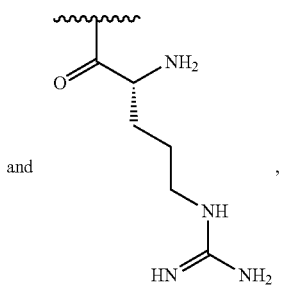

AND at least 1% of $R^1$ substituents are selected from the following:

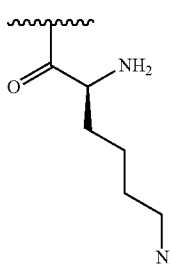 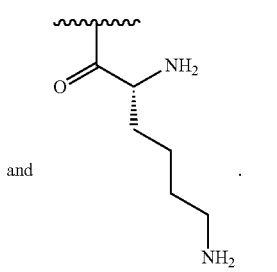

In some embodiments, $R^2$ is amino and $R^3$ is a substituted $C_1$-$C_6$ alkyl.

In some embodiments, $R^3$ is $C_1$-$C_6$ alkyl substituted with an amino group.

In some embodiments, $R^3$ is $C_1$ alkyl substituted with an amino group.

In some embodiments, $R^3$ is $C_2$ alkyl substituted with an amino group.

In some embodiments, $R^3$ is $C_3$ alkyl substituted with an amino group.

In some embodiments, $R^3$ is $C_4$ alkyl substituted with an amino group.

In some embodiments, $R^3$ is $C_5$ alkyl substituted with an amino group.

In some embodiments, $R^3$ is $C_6$ alkyl substituted with an amino group.

In some embodiments, $R^1$ is selected from one of the following:

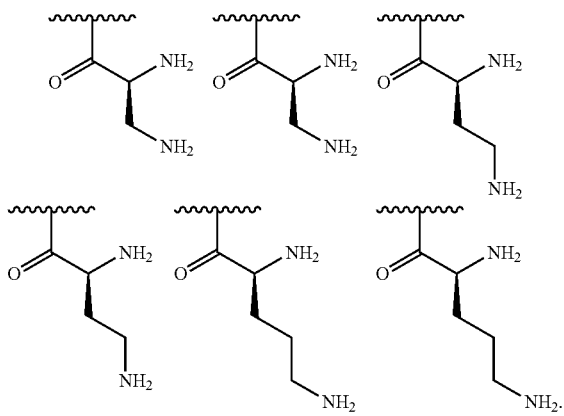

In some embodiments, R is $C_1$-$C_6$ alkyl substituted with a guanidino group.

In some embodiments, $R^3$ is $C_1$ alkyl substituted with a guanidino group.

In some embodiments, $R^3$ is $C_2$ alkyl substituted with a guanidino group.

In some embodiments, $R^3$ is $C_3$ alkyl substituted with a guanidino group.

In some embodiments, $R^3$ is $C_4$ alkyl substituted with a guanidino group.

In some embodiments, $R^3$ is $C_5$ alkyl substituted with a guanidino group.

In some embodiments, $R^3$ is $C_6$ alkyl substituted with a guanidino group.

In some embodiments, $R^1$ is selected from one of the following:

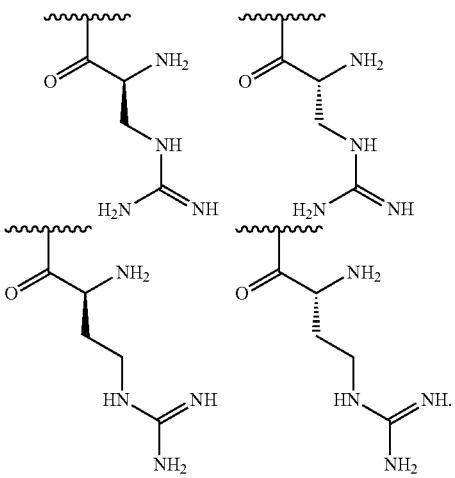

In some embodiments, wherein $R^2$ is amino that is substituted with a nitrogen protecting group prior to substitution on chitosan and removed subsequent to substitution on chitosan.

In some embodiments, the nitrogen protecting group is tert-butyloxycarbonyl (Boc).

In some embodiments, in the synthetic process a nitrogen protecting group is used, which can provide an intermediate polymer having a nitrogen protecting group such as Boc.

In some embodiments, $R^2$ is amino.

In some embodiments, $R^2$ is hydrogen and $R^3$ is amino.

In some embodiments, $R^2$ is hydrogen and $R^3$ is guanidino.

In some embodiments, $R^2$ is hydrogen and $R^3$ is a substituted $C_1$-$C_6$ alkyl.

In some embodiments, $R^3$ is $C_1$-$C_6$ alkyl substituted with an amino group.

In some embodiments, $R^3$ is $C_1$ alkyl substituted with an amino group.

In some embodiments, $R^3$ is $C_2$ alkyl substituted with an amino group.

In some embodiments, $R^3$ is $C_3$ alkyl substituted with an amino group.

In some embodiments, $R^3$ is $C_4$ alkyl substituted with an amino group.

In some embodiments, $R^3$ is $C_5$ alkyl substituted with an amino group.

In some embodiments, $R^3$ is $C_6$ alkyl substituted with an amino group.

In some embodiments, R¹ is selected from one of the following:

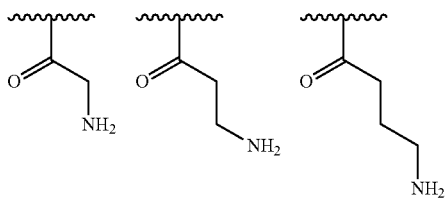

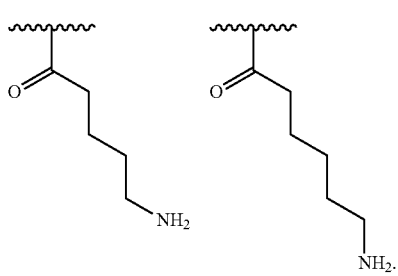

In some embodiments, R³ is C₁-C₆ alkyl substituted with a guanidino group.

In some embodiments, R³ is C₁ alkyl substituted with a guanidino group.

In some embodiments, R³ is C₂ alkyl substituted with a guanidino group.

In some embodiments, R³ is C₃ alkyl substituted with a guanidino group.

In some embodiments, R³ is C₄ alkyl substituted with a guanidino group.

In some embodiments, R³ is C₅ alkyl substituted with a guanidino group.

In some embodiments, R³ is C₆ alkyl substituted with a guanidino group.

In some embodiments, R¹ is selected from one of the following:

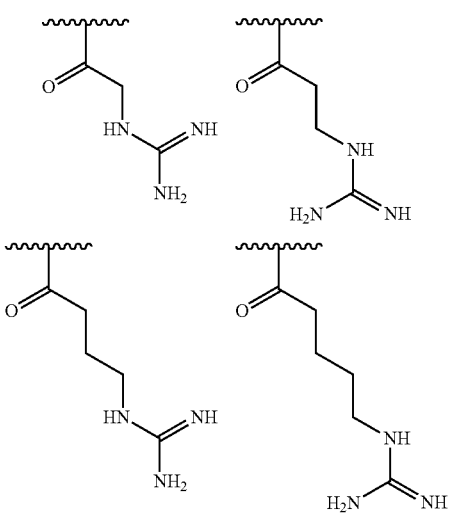

-continued

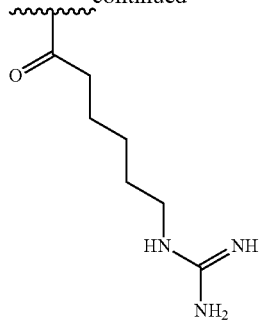

In some embodiments, at least 25% of R¹ substituents are H, at least 1% of R¹ substituents are acetyl, and at least 2% of R¹ substituents independently selected from any of the formulae specifically shown above.

In some embodiments, the functionalized chitosan of formula (I) may be further derivatized on the free hydroxyl moieties.

In some embodiments, the molecular weight of the functionalized chitosan is between 5,000 and 1,000,000 Da.

In some embodiments, the molecular weight of the functionalized chitosan is between 10,000 and 350,000 Da.

In some embodiments, the molecular weight of the functionalized chitosan is between 10,000 and 60,000 Da.

In some embodiments, the molecular weight of the functionalized chitosan is between 15,000 and 45,000 Da.

In some embodiments, the molecular weight of the functionalized chitosan is between 15,000 and 35,000 Da.

In some embodiments, the molecular weight of the functionalized chitosan is between 15,000 and 25,000 Da.

In some embodiments, the functionalized chitosan is soluble in aqueous solution between pH 6 and 8.

In some embodiments, the functionalized chitosan is soluble in aqueous solution between pH 6.8 and pH 7.4.

In one embodiment, the chitosan is functionalized at between 5% and 50%.

In a preferred embodiment, the chitosan is functionalized at between 20% and 30%.

In one embodiment, the degree of deacetylation (% DDA) of the derivatized chitosan is between 75% and 95%.

In one embodiment, the degree of deacetylation (% DDA) of the derivatized chitosan is between 80% and 90%.

In one embodiment, the polydispersity index (PDI) of the derivatized chitosan is between 1.0 and 2.5.

In one embodiment, the polydispersity index (PDI) of the derivatized chitosan is between 1.2 and 1.8.

In some embodiments, the functionalized chitosan is substantially free of other impurities.

In yet another aspect, the invention features a method of treating a subject who has been treated or is being treated for cancer with one or more cancer therapies, the method comprising administering to the subject an effective amount of a composition comprising a soluble or derivatized chitosan, thereby treating the subject.

In an embodiment, the subject has mucositis or a symptom of mucositis.

In an embodiment, the composition reduces one or more symptoms of mucositis.

In an embodiment, the cancer therapy comprises chemotherapy (e.g., 5-fluorouracil (5-FU), irinotecan, or melphalan hydrochloride) or radiation therapy.

In an embodiment, the mucositis occurs, e.g., in the gastrointestinal (GI) tract, e.g., mouth, throat, esophagus. In an embodiment, the symptom of mucositis comprises thinning of the mucosal lining, inflammation, ulceration, peripheral, erythema, pain, and/or dysgeusia.

In an embodiment, mucositis is the result of an infection, e.g., bacterial or viral infection, and wherein the infection is no longer present when the mucositis is treated.

In an embodiment, mucositis is the result of an infection, e.g., bacterial or viral infection, and wherein the infection is present when the mucositis is treated.

In an embodiment, the composition reduces the severity of mucositis (e.g., oral mucositis) by at least 1, 2, 3 or 4 grades, e.g., based on the World Health Organization (WHO) Oral Toxicity score, the National Cancer Institute Common Toxicity Criteria (NCI-CTC) for Oral Mucositis, or the Oral Mucositis Assessment Scale (OMAS).

In an embodiment, the composition reduces the healing time or increase the healing rate of mucositis. In some embodiments, the composition decreases the inflammation associated with mucositis or healing of the mucositis.

In an embodiment, the healing time of mucositis (e.g., the length of one or more of the initiation, message generation, signaling and amplification, ulceration, or healing phase of mucositis) is reduced by at least about 10%, 20%, 30%, 40%, 50%, 60%, 70%, 80%, 90%, or 95%, compared to the healing time of mucositis that has not been contacted with the soluble or derivatized chitosan.

In an embodiment, the composition is administered to the subject before, during, or after the subject is treated with the cancer therapy. In an embodiment, the composition is administered to the subject prior to the therapy, e.g., for at least about 1 day, 2 days, 3 days, 5 days, or 1 week. In an embodiment, the composition is administered to the subject less than about 1 day, 2 days, 3 days, 4 days, 5 days, 6 days, 1 week, 2 weeks, 3 weeks, or 4 weeks after the subject is treated with the cancer therapy.

In an embodiment, the composition is administered to the subject before, during, or after the subject is treated with the immunosuppressive therapy. In an embodiment, the composition is administered to the subject prior to the therapy, e.g., for at least about 1 day, 2 days, 3 days, 5 days, or 1 week. In an embodiment, the composition is administered to the subject less than about 1 day, 2 days, 3 days, 4 days, 5 days, 6 days, 1 week, 2 weeks, 3 weeks, or 4 weeks after the subject is treated with the immunosuppressive therapy.

In an embodiment, the method further comprises administering to the subject a second therapy (e.g., a second mucositis therapy), e.g., antibiotics, oral hygiene, water-soluble jellies, salt mouthwash, keratinocyte growth factor (KGF), cytokines or modifier of inflammation (e.g., IL-1, IL-10, IL-11, TGF-β), amino acid supplementation (e.g., glutamine), vitamin, colony-stimulating factor (CSF), cryotherapy, laser therapy, barrier protection agent (e.g., concentrated oral gel product (e.g., GELCLAIR®), or medicinal mouthwash (e.g., CAPHOSOL®, MUGARD®).

In an embodiment, the second therapy comprises an antibiotic. In an embodiment, the composition overcomes (e.g., reduces, decreases, prevents) a deleterious effect of the antibiotic in wound healing.

In an embodiment, the second therapy comprises a steroidal or non-steroidal anti-inflammatory drug (NSIAD). In an embodiment, the composition acts additively or synergysically with the steroidal or non-steroidal anti-inflammatory drug.

In an embodiment, the composition is administered topically or orally, e.g., by topical rinse, gel, spray, oral, enema, inhalation, dry powder, aerosolized liquid, aerosolized powder, eye drop. In some embodiments, the composition is administered orally to treat a wound (e.g., damaged mucosa) in the gastrointestinal tract and/or an inflammatory gastrointestinal disorder. In some embodiments, the composition is administered topically to treat a wound, and/or reduce or prevent a scar, e.g., in the eye.

In an embodiment, the composition is administered before, during or after one or more of the healing phase of mucositis, e.g., initiation, message generation, signaling and amplification, ulceration, or healing phase.

In an embodiment, the effective amount is therapeutically effective amount.

In one embodiment, the soluble or derivatized chitosan is soluble in aqueous solution from about pH 6.8 to about pH 7.4.

In one embodiment, the soluble or derivatized chitosan is soluble in aqueous solution from about pH 3 to about pH 9.

In one embodiment, the soluble or derivatized chitosan is soluble in aqueous solution from about pH 5.0 to about pH 6.0, e.g., in wounds or duodenum.

In one embodiment, the soluble or derivatized chitosan is soluble in aqueous solution from about pH 2.0 to about pH 4.0, e.g., in stomach.

In one embodiment, the soluble or derivatized chitosan is soluble in aqueous solution from about pH 8.0 to about pH 8.5, e.g., in lower part of the gastrointestinal tract.

In one embodiment, the derivatized chitosan comprises a chitosan of the following formula (I):

formula (I)

wherein:
n is an integer between 20 and 6000; and
each $R^1$ is independently selected for each occurrence from hydrogen, acetyl, and either:
a) a group of formula (II):

formula (II)

wherein $R^2$ is hydrogen or amino; and
$R^3$ is amino, guanidino, $C_1$-$C_6$ alkyl substituted with an amino or guanidino moiety, or a natural or unnatural amino acid side chain;
or
b) $R^1$, when taken together with the nitrogen to which it is attached, forms a guanidine moiety;
wherein at least 25% of $R^1$ substituents are H, at least 1% of $R^1$ substituents are acetyl, and at least 2% of $R^1$ substituents are a group of formula (II) or are taken together with the nitrogen to which they are attached to form a guanidine moiety.

In one embodiment, the derivatized chitosan comprises of the following formula (I) wherein at least 90% by number or weight of R¹ moieties are as defined in formula (I) (e.g., at least about 95%, at least about 96%, at least about 97%, at least about 98%, or at least about 99%):

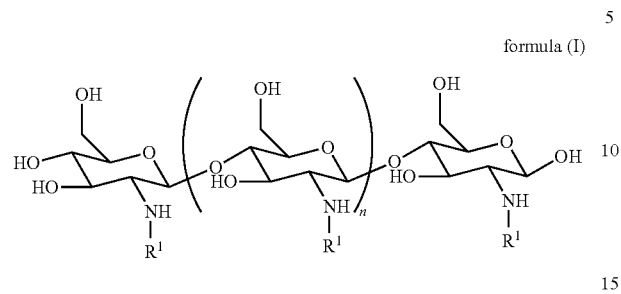

formula (I)

wherein:

n is an integer between 20 and 6000; and each R¹ is independently selected for each occurrence from hydrogen, acetyl, and either:

a) a group of formula (II):

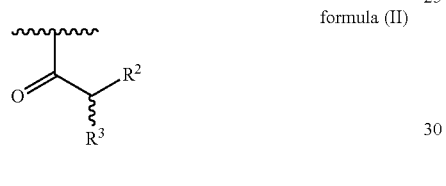

formula (II)

wherein R² is hydrogen or amino; and

R³ is amino, guanidino, $C_1$-$C_6$ alkyl substituted with an amino or guanidino moiety, or a natural or unnatural amino acid side chain;

or b) R¹, when taken together with the nitrogen to which it is attached, forms a guanidine moiety;

wherein at least 25% of R¹ substituents are H, at least 1% of R¹ substituents are acetyl, and at least 2% of R¹ substituents are a group of formula (II) or are taken together with the nitrogen to which they are attached to form a guanidine moiety.

In some embodiments, between 25-95% of R¹ substituents are hydrogen.

In some embodiments, between 55-90% of R¹ substituents are hydrogen.

In some embodiments, between 1-50% of R¹ substituents are acetyl.

In some embodiments, between 4-20% of R¹ substituents are acetyl.

In some embodiments, between 2-50% of R¹ substituents are a group of formula (II).

In some embodiments, between 4-30% of R¹ substituents are a group of formula (II).

In some embodiments, 55-90% of R¹ substituents are hydrogen, 4-20% of R¹ substituents are acetyl, 4-30% of R¹ substituents are a group of formula (II).

In some embodiments, R² is amino and R³ is an arginine side chain.

In some embodiments, R¹ is selected from one of the following:

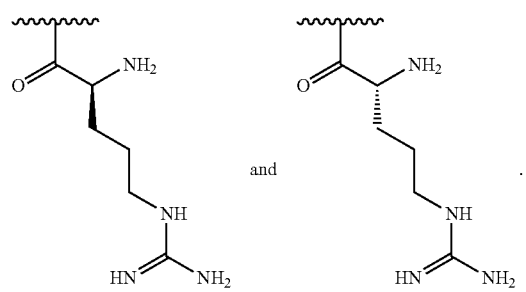 [SMILES: *C(=O)[C@@H](N)CCCNC(=N)N ; *C(=O)[C@H](N)CCCNC(=N)N]

In some embodiments, R² is amino and R³ is a lysine side chain.

In some embodiments, R¹ is selected from one of the following:

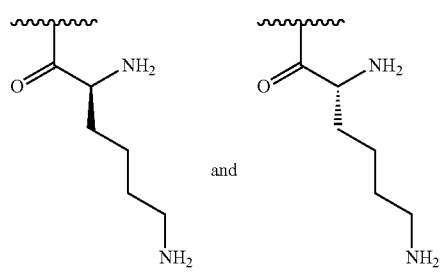

In some embodiments, R² is amino and R³ is a histidine side chain.

In some embodiments, R¹ is selected from one of the following:

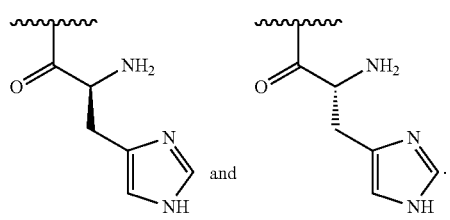 [SMILES: *C(=O)[C@@H](N)Cc1c[nH]cn1 ; *C(=O)[C@H](N)Cc1c[nH]cn1]

In some embodiments, at least 1% of R¹ substituents are selected from one of the following:

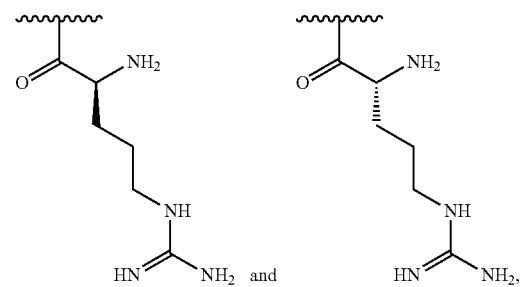 [SMILES: *C(=O)[C@@H](N)CCCNC(=N)N ; *C(=O)[C@H](N)CCCNC(=N)N]

AND at least 1% of $R^1$ substituents are selected from the following:

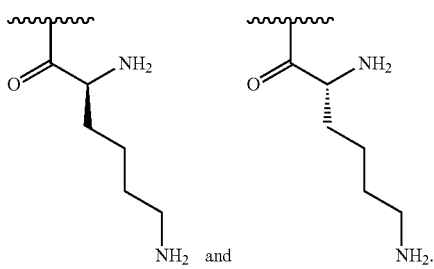 [SMILES: *C(=O)[C@@H](N)CCCCN ; *C(=O)[C@H](N)CCCCN]

In some embodiments, $R^2$ is amino and $R^3$ is a substituted $C_1$-$C_6$ alkyl.

In some embodiments, $R^3$ is $C_1$-$C_6$ alkyl substituted with an amino group.

In some embodiments, $R^3$ is $C_1$ alkyl substituted with an amino group.

In some embodiments, $R^3$ is $C_2$ alkyl substituted with an amino group.

In some embodiments, $R^3$ is $C_3$ alkyl substituted with an amino group.

In some embodiments, $R^3$ is $C_4$ alkyl substituted with an amino group.

In some embodiments, $R^3$ is $C_5$ alkyl substituted with an amino group.

In some embodiments, $R^3$ is $C_6$ alkyl substituted with an amino group.

In some embodiments, $R^1$ is selected from one of the following:

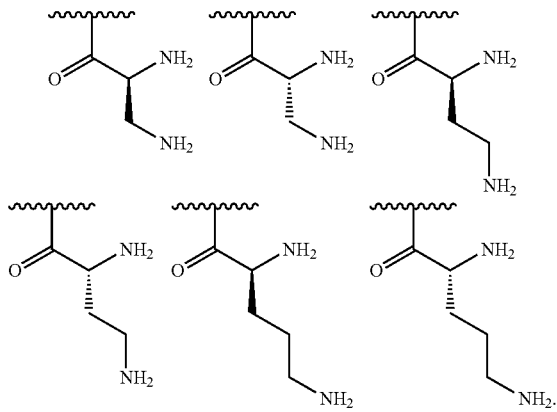

In some embodiments, $R^3$ is $C_1$-$C_6$ alkyl substituted with a guanidino group.

In some embodiments, $R^3$ is $C_1$ alkyl substituted with a guanidino group.

In some embodiments, $R^3$ is $C_2$ alkyl substituted with a guanidino group.

In some embodiments, $R^3$ is $C_3$ alkyl substituted with a guanidino group.

In some embodiments, $R^3$ is $C_4$ alkyl substituted with a guanidino group.

In some embodiments, $R^3$ is $C_5$ alkyl substituted with a guanidino group.

In some embodiments, $R^3$ is $C_6$ alkyl substituted with a guanidino group. In some embodiments, $R^1$ is selected from one of the following:

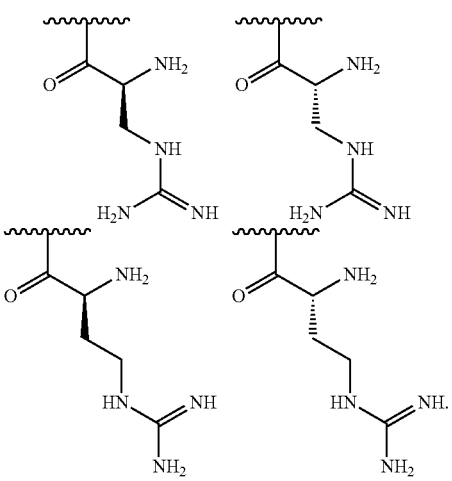

In some embodiments, wherein $R^2$ is amino that is substituted with a nitrogen protecting group prior to substitution on chitosan and removed subsequent to substitution on chitosan.

In some embodiments, the nitrogen protecting group is tert-butyloxycarbonyl (Boc).

In some embodiments, in the synthetic process a nitrogen protecting group is used, which can provide an intermediate polymer having a nitrogen protecting group such as Boc.

In some embodiments, $R^2$ is amino.

In some embodiments, $R^2$ is hydrogen and $R^3$ is amino.

In some embodiments, $R^2$ is hydrogen and $R^3$ is guanidino.

In some embodiments, $R^2$ is hydrogen and $R^3$ is a substituted $C_1$-$C_6$ alkyl.

In some embodiments, $R^3$ is $C_1$-$C_6$ alkyl substituted with an amino group.

In some embodiments, $R^3$ is $C_1$ alkyl substituted with an amino group.

In some embodiments, $R^3$ is $C_2$ alkyl substituted with an amino group.

In some embodiments, $R^3$ is $C_3$ alkyl substituted with an amino group.

In some embodiments, $R^3$ is $C_4$ alkyl substituted with an amino group.

In some embodiments, $R^3$ is $C_5$ alkyl substituted with an amino group.

In some embodiments, $R^3$ is $C_6$ alkyl substituted with an amino group.

In some embodiments, $R^1$ is selected from one of the following:

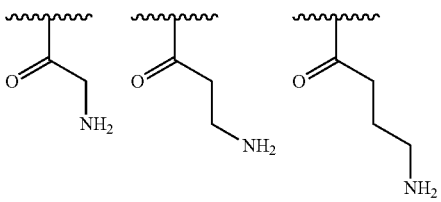

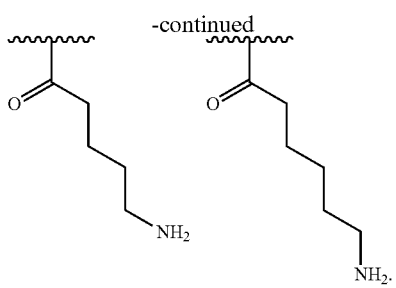

In some embodiments, $R^3$ is $C_1$-$C_6$ alkyl substituted with a guanidino group.

In some embodiments, $R^3$ is $C_1$ alkyl substituted with a guanidino group.

In some embodiments, $R^3$ is $C_2$ alkyl substituted with a guanidino group.

In some embodiments, $R^3$ is $C_3$ alkyl substituted with a guanidino group.

In some embodiments, $R^3$ is $C_4$ alkyl substituted with a guanidino group.

In some embodiments, $R^3$ is $C_5$ alkyl substituted with a guanidino group.

In some embodiments, $R^3$ is $C_6$ alkyl substituted with a guanidino group.

In some embodiments, $R^1$ is selected from one of the following:

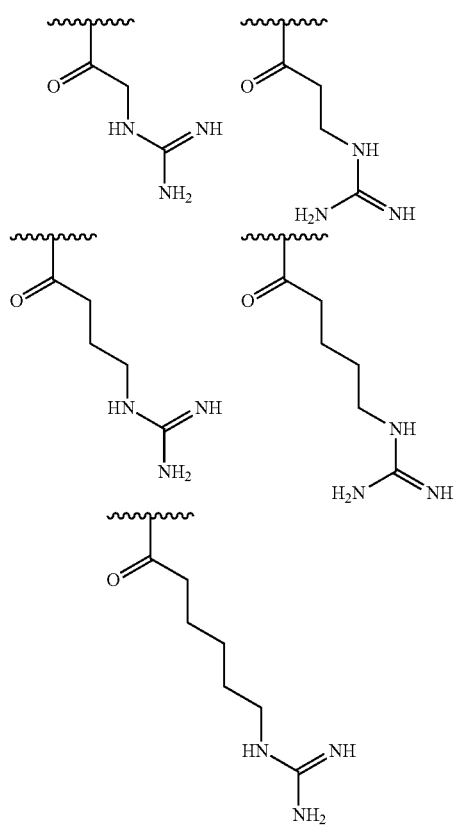

In some embodiments, at least 25% of $R^1$ substituents are H, at least 1% of $R^1$ substituents are acetyl, and at least 2% of $R^1$ substituents independently selected from any of the formulae specifically shown above.

In some embodiments, the functionalized chitosan of formula (I) may be further derivatized on the free hydroxyl moieties.

In some embodiments, the molecular weight of the functionalized chitosan is between 5,000 and 1,000,000 Da.

In some embodiments, the molecular weight of the functionalized chitosan is between 10,000 and 350,000 Da.

In some embodiments, the molecular weight of the functionalized chitosan is between 10,000 and 60,000 Da.

In some embodiments, the molecular weight of the functionalized chitosan is between 15,000 and 45,000 Da.

In some embodiments, the molecular weight of the functionalized chitosan is between 15,000 and 35,000 Da.

In some embodiments, the molecular weight of the functionalized chitosan is between 15,000 and 25,000 Da.

In some embodiments, the functionalized chitosan is soluble in aqueous solution between pH 6 and 8.

In some embodiments, the functionalized chitosan is soluble in aqueous solution between pH 6.8 and pH 7.4.

In one embodiment, the chitosan is functionalized at between 5% and 50%.

In a preferred embodiment, the chitosan is functionalized at between 20% and 30%.

In one embodiment, the degree of deacetylation (% DDA) of the derivatized chitosan is between 75% and 95%.

In one embodiment, the degree of deacetylation (% DDA) of the derivatized chitosan is between 80% and 90%.

In one embodiment, the polydispersity index (PDI) of the derivatized chitosan is between 1.0 and 2.5.

In one embodiment, the polydispersity index (PDI) of the derivatized chitosan is between 1.2 and 1.8.

In some embodiments, the functionalized chitosan is substantially free of other impurities.

In one aspect, the invention features a method of treating a subject having a chronic disease or a symptom of a chronic disease, the method comprising: administering to a subject an effective amount of a composition comprising a soluble or derivatized chitosan, thereby treating the subject.

In an embodiment, the symptom of the chronic disease comprises poor or slow poor healing. In an embodiment, the chronic disease is associated with poor or slow wound healing. In an embodiment, the chronic disease is associated with inflammation.

In an embodiment, the chronic disease is selected from the group consisting of inflammatory bowel disease (IBD) (e.g., Crohn's disease), diabetes (e.g., diabetes mellitus types 1 or type 2), chronic kidney disease (CKD), chronic obstructive pulmonary disease (COPD), hypothyroidism, multiple sclerosis, rheumatoid arthritis, hepatic encephalopathy, peritonitis, periodontitis, sinusitis, rhinitis, sepsis, and systemic lupus erythematosus.

In an embodiment, the subject has a wound. In an embodiment, the wound is an acute wound. In an embodiment, the wound is a chronic wound, e.g., a wound that does not heal in an orderly set of stages, in a predictable amount of time, or within three months. In an embodiment, the wound is a surgical wound, e.g., a wound resulted from medical grafting (e.g., skin or bone grafting) at the donor site and/or the graft site, full thickness or partial thickness excision. In an embodiment, the wound is a burn wound.

In an embodiment, the wound is in the epidermis, dermis or hypodermis. In another embodiment, the wound is in the mucosal membrane.

In an embodiment, the wound is a venous ulcer, a diabetic ulcer, a corneal ulcer (or damage to the corneal epithelium), oral ulcer, peptic ulcer, or a pressure ulcer.

In an embodiment, the wound is the result of an infection, e.g., bacterial or viral infection, and wherein the infection is no longer present when the wound is treated. In another embodiment, the wound is the result of an infection, e.g., bacterial or viral infection, and wherein the infection is still present when the wound is treated.

In an embodiment, the composition is administered to the subject less than about 5 minutes, 15 minutes, 30 minutes, 1 hour, 2 hours, 4 hours, 6 hours, 12 hours, 24 hours, 2 days, 3 days, 4 days, 5 days, 6 days, 7 days, 2 weeks, 4 weeks, 2 months, 4 months, 6 months, 8 months, 10 months, or 1 year after the subject is wounded.

In an embodiment, the composition reduces the healing time or increase the healing rate of the wound. In some embodiments, the composition decreases the inflammation associated with wound or healing of the wound.

In an embodiment, the healing time of the wound (e.g., the length of one or more of the inflammatory, proliferative, or remodeling phase of wound healing) is reduced by at least about 10%, 20%, 30%, 40%, 50%, 60%, 70%, 80%, 90%, or 95%, compared to the healing time of the wound (e.g., the length of one or more of the inflammatory, proliferative, or remodeling phase of wound healing) that has not been contacted with the soluble or derivatized chitosan.

In an embodiment, the wound healing rate (e.g., the absolute area healed per day, the percentage of initial area healed per day, or the greatest average wound margin distance from the wound centre divided by the time to complete wound closure) is increased by at least about 1, 2, 3, 4, 5, 6, 7, 8, 9, or 10 fold, compared to the healing rate of the wound that has not been contacted with the soluble or derivatized chitosan.

In an embodiment, the method further comprises administering to the subject a second wound therapy, e.g., antibiotic or antibacterial use, debridement, irrigation, negative pressure wound therapy (vacuum-assisted closure), warming, oxygenation, moist wound healing, removing mechanical stress, and/or adding cells (e.g., keratinocytes) or other materials (e.g., artificial skin substitutes that have fibroblasts and/or keratinocytes in a matrix of collagen) to secrete or enhance levels of healing factors (e.g., vascular endothelial growth factor (VEGF), insulin-like growth factor (IGF), platelet-derived growth factor (PDGF), transforming growth factor-β (TGF-β), and epidermal growth factor (EGF)).

In an embodiment, the second wound therapy comprises a negative pressure wound therapy (vacuum-assisted closure).

In an embodiment, the second wound therapy comprises an antibiotic. In an embodiment, the composition overcomes (e.g., reduces, decreases, prevents) a deleterious effect of the antibiotic in wound healing.

In an embodiment, the second wound therapy comprises a steroidal or non-steroidal anti-inflammatory drug (NSIAD). In an embodiment, the composition acts additively or synergysically with the steroidal or non-steroidal anti-inflammatory drug.

In an embodiment, the composition is administered topically or orally, e.g., by topical rinse, gel, spray, oral, enema, inhalation, dry powder, aerosolized liquid, aerosolized powder, or eye drop. In some embodiments, the composition is administered orally to treat a wound (e.g., damaged mucosa) in the gastrointestinal tract and/or an inflammatory gastrointestinal disorder. In some embodiments, the composition is administered topically to treat a wound and/or reduce or prevent a scar, e.g., in the eye.

In an embodiment, the composition is administered before, during or after one or more of the wound healing phase, e.g., inflammatory, proliferative, or remodeling phase.

In an embodiment, the effective amount is therapeutically effective amount.

In one embodiment, the soluble or derivatized chitosan is soluble in aqueous solution from about pH 6.8 to about pH 7.4.

In one embodiment, the soluble or derivatized chitosan is soluble in aqueous solution from about pH 3 to about pH 9.

In one embodiment, the soluble or derivatized chitosan is soluble in aqueous solution from about pH 5.0 to about pH 6.0, e.g., in wounds or duodenum.

In one embodiment, the soluble or derivatized chitosan is soluble in aqueous solution from about pH 2.0 to about pH 4.0, e.g., in stomach.

In one embodiment, the soluble or derivatized chitosan is soluble in aqueous solution from about pH 8.0 to about pH 8.5, e.g., in lower part of the gastrointestinal tract.

In one embodiment, the derivatized chitosan comprises a chitosan of the following formula (I):

formula (I)

wherein:

n is an integer between 20 and 6000; and each $R^1$ is independently selected for each occurrence from hydrogen, acetyl, and either:

a) a group of formula (II):

formula (II)

wherein $R^2$ is hydrogen or amino; and $R^3$ is amino, guanidino, $C_1$-$C_6$ alkyl substituted with an amino or guanidino moiety, or a natural or unnatural amino acid side chain;

or b) $R^1$, when taken together with the nitrogen to which it is attached, forms a guanidine moiety;

wherein at least 25% of $R^1$ substituents are H, at least 1% of $R^1$ substituents are acetyl, and at least 2% of $R^1$ substituents are a group of formula (II) or are taken together with the nitrogen to which they are attached to form a guanidine moiety.

In one embodiment, the derivatized chitosan comprises of the following formula (I) wherein at least 90% by number or weight of $R^1$ moieties are as defined in formula (I) (e.g., at least about 95%, at least about 96%, at least about 97%, at least about 98%, or at least about 99%):

53 formula (I)

[Structure of trisaccharide with OH, HO groups and NH-R¹ substituents]

wherein:

n is an integer between 20 and 6000; and each $R^1$ is independently selected for each occurrence from hydrogen, acetyl, and either:

a) a group of formula (II):

formula (II)

[Structure showing carbonyl with R² and R³ substituents]

wherein $R^2$ is hydrogen or amino; and $R^3$ is amino, guanidino, $C_1$-$C_6$ alkyl substituted with an amino or guanidino moiety, or a natural or unnatural amino acid side chain;

or b) $R^1$, when taken together with the nitrogen to which it is attached, forms a guanidine moiety;

wherein at least 25% of $R^1$ substituents are H, at least 1% of $R^1$ substituents are acetyl, and at least 2% of $R^1$ substituents are a group of formula (II) or are taken together with the nitrogen to which they are attached to form a guanidine moiety.

In some embodiments, between 25-95% of $R^1$ substituents are hydrogen.

In some embodiments, between 55-90% of $R^1$ substituents are hydrogen.

In some embodiments, between 1-50% of $R^1$ substituents are acetyl.

In some embodiments, between 4-20% of $R^1$ substituents are acetyl.

In some embodiments, between 2-50% of $R^1$ substituents are a group of formula (II).

In some embodiments, between 4-30% of $R^1$ substituents are a group of formula (II).

In some embodiments, 55-90% of $R^1$ substituents are hydrogen, 4-20% of $R^1$ substituents are acetyl, 4-30% of $R^1$ substituents are a group of formula (II).

In some embodiments, $R^2$ is amino and $R^3$ is an arginine side chain.

54

In some embodiments, $R^1$ is selected from one of the following:

[Two arginine-like structures with NH₂, NH, guanidino groups] and [analogous structure]

In some embodiments, $R^2$ is amino and $R^3$ is a lysine side chain.

In some embodiments, $R^1$ is selected from one of the following:

[Two lysine-like structures with NH₂ groups] and [analogous structure]

In some embodiments, $R^2$ is amino and $R^3$ is a histidine side chain.

In some embodiments, $R^1$ is selected from one of the following:

[Two histidine-like structures with imidazole rings] and [analogous structure]

In some embodiments, at least 1% of $R^1$ substituents are selected from one of the following:

[Two arginine-like structures] and [analogous structure],

AND at least 1% of $R^1$ substituents are selected from the following:

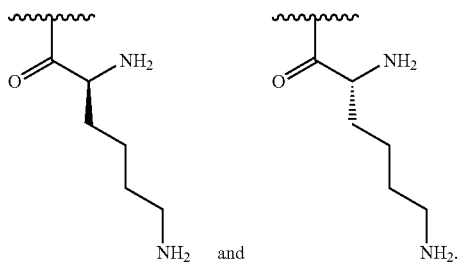 [SMILES: *C(=O)[C@@H](N)CCCCN ; *C(=O)[C@H](N)CCCCN]

In some embodiments, $R^2$ is amino and $R^3$ is a substituted $C_1$-$C_6$ alkyl.

In some embodiments, $R^3$ is $C_1$-$C_6$ alkyl substituted with an amino group.

In some embodiments, $R^3$ is $C_1$ alkyl substituted with an amino group.

In some embodiments, $R^3$ is $C_2$ alkyl substituted with an amino group.

In some embodiments, $R^3$ is $C_3$ alkyl substituted with an amino group.

In some embodiments, $R^3$ is $C_4$ alkyl substituted with an amino group.

In some embodiments, $R^3$ is $C_5$ alkyl substituted with an amino group.

In some embodiments, $R^3$ is $C_6$ alkyl substituted with an amino group.

In some embodiments, $R^1$ is selected from one of the following:

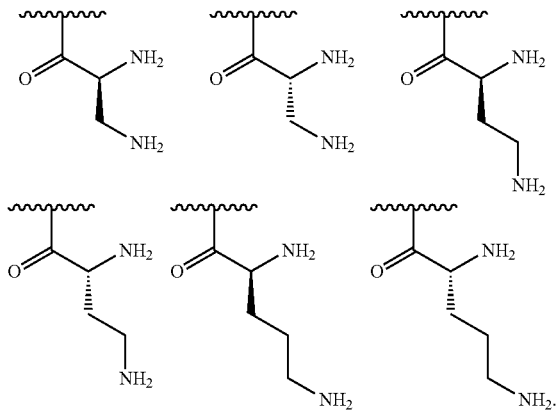

In some embodiments, $R^3$ is $C_1$-$C_6$ alkyl substituted with a guanidino group.

In some embodiments, $R^3$ is $C_1$ alkyl substituted with a guanidino group.

In some embodiments, $R^3$ is $C_2$ alkyl substituted with a guanidino group.

In some embodiments, $R^3$ is $C_3$ alkyl substituted with a guanidino group.

In some embodiments, $R^3$ is $C_4$ alkyl substituted with a guanidino group.

In some embodiments, $R^3$ is $C_5$ alkyl substituted with a guanidino group.

In some embodiments, $R^3$ is $C_6$ alkyl substituted with a guanidino group.

In some embodiments, $R^1$ is selected from one of the following:

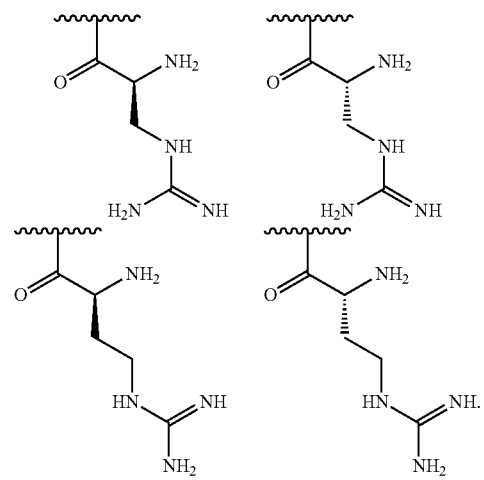

In some embodiments, wherein $R^2$ is amino that is substituted with a nitrogen protecting group prior to substitution on chitosan and removed subsequent to substitution on chitosan.

In some embodiments, the nitrogen protecting group is tert-butyloxycarbonyl (Boc).

In some embodiments, in the synthetic process a nitrogen protecting group is used, which can provide an intermediate polymer having a nitrogen protecting group such as Boc.

In some embodiments, $R^2$ is amino.

In some embodiments, $R^2$ is hydrogen and $R^3$ is amino.

In some embodiments, $R^2$ is hydrogen and $R^3$ is guanidino.

In some embodiments, $R^2$ is hydrogen and $R^3$ is a substituted $C_1$-$C_6$ alkyl.

In some embodiments, $R^3$ is $C_1$-$C_6$ alkyl substituted with an amino group.

In some embodiments, $R^3$ is $C_1$ alkyl substituted with an amino group.

In some embodiments, $R^3$ is $C_2$ alkyl substituted with an amino group.

In some embodiments, $R^3$ is $C_3$ alkyl substituted with an amino group.

In some embodiments, $R^3$ is $C_4$ alkyl substituted with an amino group.

In some embodiments, $R^3$ is $C_5$ alkyl substituted with an amino group.

In some embodiments, $R^3$ is $C_6$ alkyl substituted with an amino group.

In some embodiments, $R^1$ is selected from one of the following:

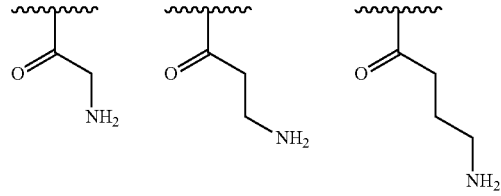

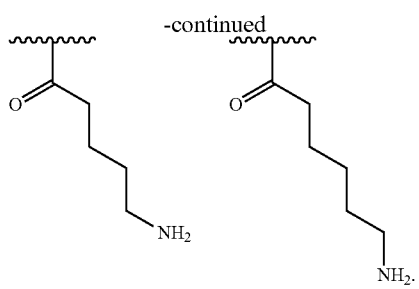

In some embodiments, $R^3$ is $C_1$-$C_6$ alkyl substituted with a guanidino group.

In some embodiments, $R^3$ is $C_1$ alkyl substituted with a guanidino group.

In some embodiments, $R^3$ is $C_2$ alkyl substituted with a guanidino group.

In some embodiments, $R^3$ is $C_3$ alkyl substituted with a guanidino group.

In some embodiments, $R^3$ is $C_4$ alkyl substituted with a guanidino group.

In some embodiments, $R^3$ is $C_5$ alkyl substituted with a guanidino group.

In some embodiments, $R^3$ is $C_6$ alkyl substituted with a guanidino group.

In some embodiments, $R^1$ is selected from one of the following:

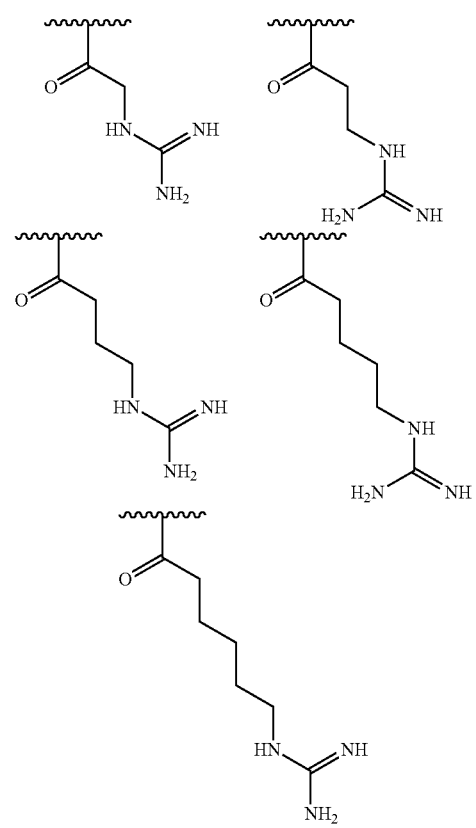

In some embodiments, at least 25% of $R^1$ substituents are H, at least 1% of $R^1$ substituents are acetyl, and at least 2% of $R^1$ substituents independently selected from any of the formulae specifically shown above.

In some embodiments, the functionalized chitosan of formula (I) may be further derivatized on the free hydroxyl moieties.

In some embodiments, the molecular weight of the functionalized chitosan is between 5,000 and 1,000,000 Da.

In some embodiments, the molecular weight of the functionalized chitosan is between 10,000 and 350,000 Da.

In some embodiments, the molecular weight of the functionalized chitosan is between 10,000 and 60,000 Da.

In some embodiments, the molecular weight of the functionalized chitosan is between 15,000 and 45,000 Da.

In some embodiments, the molecular weight of the functionalized chitosan is between 15,000 and 35,000 Da.

In some embodiments, the molecular weight of the functionalized chitosan is between 15,000 and 25,000 Da.

In some embodiments, the functionalized chitosan is soluble in aqueous solution between pH 6 and 8.

In some embodiments, the functionalized chitosan is soluble in aqueous solution between pH 6.8 and pH 7.4.

In one embodiment, the chitosan is functionalized at between 5% and 50%.

In a preferred embodiment, the chitosan is functionalized at between 20% and 30%.

In one embodiment, the degree of deacetylation (% DDA) of the derivatized chitosan is between 75% and 95%.

In one embodiment, the degree of deacetylation (% DDA) of the derivatized chitosan is between 80% and 90%.

In one embodiment, the polydispersity index (PDI) of the derivatized chitosan is between 1.0 and 2.5.

In one embodiment, the polydispersity index (PDI) of the derivatized chitosan is between 1.2 and 1.8.

In some embodiments, the functionalized chitosan is substantially free of other impurities.

In another aspect, the invention features a method of treating a subject who has suffered chemical, biological, or radiological injury, or has been affected or is being affected by one or more warfare agents (e.g., chemical warfare agent, biological warfare agent, or radiation), the method comprising administering to a subject an effective amount of a composition comprising a soluble or derivatized chitosan, thereby treating the subject.

In an embodiment, the chemical warfare agent comprises a blister or vesicant agent, including, but not limited to, chlorine, chloropicrin, chlorine, chloropicrin phosgene, lewisite, or mustard gas.

In an embodiment, the composition is administered to the subject less than about 5 minutes, 15 minutes, 30 minutes, 1 hour, 2 hours, 4 hours, 6 hours, 12 hours, 24 hours, 2 days, 3 days, 4 days, 5 days, 6 days, 7 days, 2 weeks, 4 weeks, 2 months, 4 months, 6 months, 8 months, 10 months, or 1 year after the subject has been affected by the warfare agent.

In an embodiment, the composition is administered prophylactically, prior to injury, e.g., for at least 1 day, 2 days, 3 days, 5 days, or 1 week.

In an embodiment, the subject has a wound. In some embodiments, the composition reduces the healing time or increase the healing rate of the wound. In some embodiments, the composition decreases the inflammation associated with wound or healing of the wound.

In an embodiment, the healing time of the wound (e.g., the length of one or more of the inflammatory, proliferative, or remodeling phase of wound healing) is reduced by at least about 10%, 20%, 30%, 40%, 50%, 60%, 70%, 80%, 90%, or 95%, compared to the healing time of the wound (e.g., the length of one or more of the inflammatory, proliferative, or remodeling phase of wound healing) that has not been contacted with the soluble or derivatized chitosan.

In an embodiment, the wound healing rate (e.g., the absolute area healed per day, the percentage of initial area healed per day, or the greatest average wound margin distance from the wound centre divided by the time to complete wound closure) is increased by at least about 1, 2, 3, 4, 5, 6, 7, 8, 9, or 10 fold, compared to the healing rate of the wound that has not been contacted with the soluble or derivatized chitosan. In one embodiment, the soluble or derivatized chitosan is soluble in aqueous solution from about pH 6.8 to about pH 7.4.

In one embodiment, the soluble or derivatized chitosan is soluble in aqueous solution from about pH 3 to about pH 9.

In one embodiment, the soluble or derivatized chitosan is soluble in aqueous solution from about pH 5.0 to about pH 6.0, e.g., in wounds or duodenum.

In one embodiment, the soluble or derivatized chitosan is soluble in aqueous solution from about pH 2.0 to about pH 4.0, e.g., in stomach.

In one embodiment, the soluble or derivatized chitosan is soluble in aqueous solution from about pH 8.0 to about pH 8.5, e.g., in lower part of the gastrointestinal tract.

In one embodiment, the derivatized chitosan comprises a chitosan of the following formula (I):

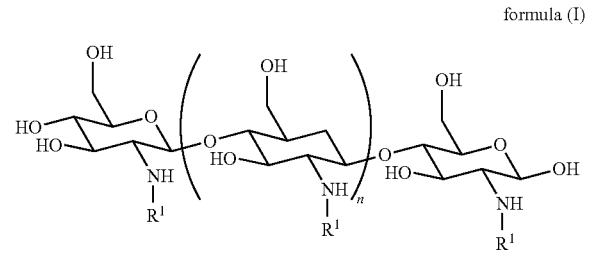

formula (I)

wherein:

n is an integer between 20 and 6000; and each $R^1$ is independently selected for each occurrence from hydrogen, acetyl, and either:

a) a group of formula (II):

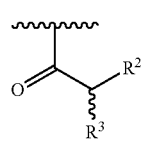

formula (II)

wherein $R^2$ is hydrogen or amino; and $R^3$ is amino, guanidino, $C_1$-$C_6$ alkyl substituted with an amino or guanidino moiety, or a natural or unnatural amino acid side chain;

or b) $R^1$, when taken together with the nitrogen to which it is attached, forms a guanidine moiety;

wherein at least 25% of $R^1$ substituents are H, at least 1% of $R^1$ substituents are acetyl, and at least 2% of $R^1$ substituents are a group of formula (II) or are taken together with the nitrogen to which they are attached to form a guanidine moiety.

In one embodiment, the derivatized chitosan comprises of the following formula (I) wherein at least 90% by number or weight of $R^1$ moieties are as defined in formula (I) (e.g., at least about 95%, at least about 96%, at least about 97%, at least about 98%, or at least about 99%):

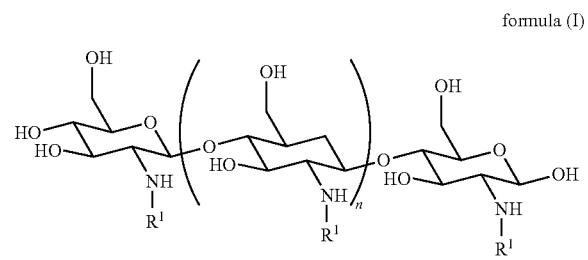

formula (I)

wherein:

n is an integer between 20 and 6000; and each $R^1$ is independently selected for each occurrence from hydrogen, acetyl, and either:

a) a group of formula (II):

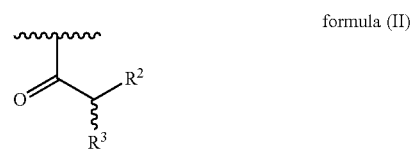

formula (II)

wherein $R^2$ is hydrogen or amino; and $R^3$ is amino, guanidino, $C_1$-$C_6$ alkyl substituted with an amino or guanidino moiety, or a natural or unnatural amino acid side chain;

or b) $R^1$, when taken together with the nitrogen to which it is attached, forms a guanidine moiety;

wherein at least 25% of $R^1$ substituents are H, at least 1% of $R^1$ substituents are acetyl, and at least 2% of $R^1$ substituents are a group of formula (II) or taken together with the nitrogen to which they are attached to form a guanidine moiety.

In some embodiments, between 25-95% of $R^1$ substituents are hydrogen.

In some embodiments, between 55-90% of $R^1$ substituents are hydrogen.

In some embodiments, between 1-50% of $R^1$ substituents are acetyl.

In some embodiments, between 4-20% of $R^1$ substituents are acetyl.

In some embodiments, between 2-50% of $R^1$ substituents are a group of formula (II).

In some embodiments, between 4-30% of $R^1$ substituents are a group of formula (II).

In some embodiments, 55-90% of $R^1$ substituents are hydrogen, 4-20% of $R^1$ substituents are acetyl, 4-30% of $R^1$ substituents are a group of formula (II).

In some embodiments, $R^2$ is amino and $R^3$ is an arginine side chain.

In some embodiments, $R^1$ is selected from one of the following:

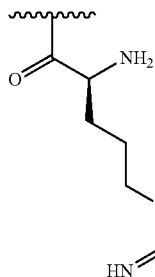 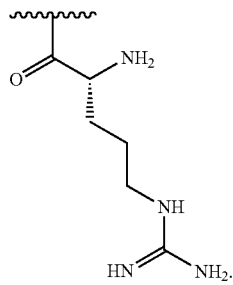

In some embodiments, $R^2$ is amino and $R^3$ is a lysine side chain.

In some embodiments, $R^1$ is selected from one of the following:

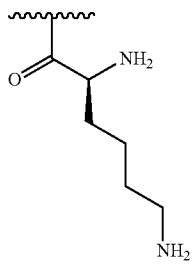 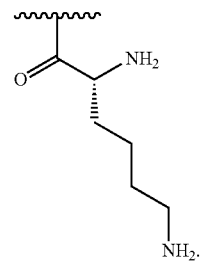

In some embodiments, $R^2$ is amino and $R^3$ is a histidine side chain.

In some embodiments, $R^1$ is selected from one of the following:

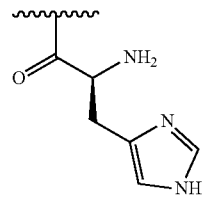 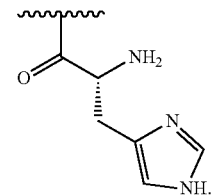

In some embodiments, at least 1% of $R^1$ substituents are selected from one of the following:

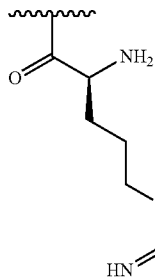 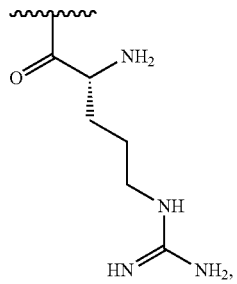

AND at least 1% of $R^1$ substituents are selected from the following:

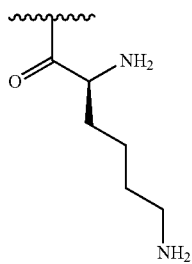 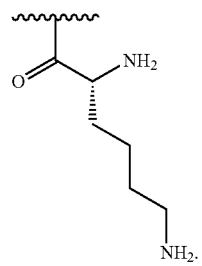

In some embodiments, $R^2$ is amino and $R^3$ is a substituted $C_1$-$C_6$ alkyl.

In some embodiments, $R^3$ is $C_1$-$C_6$ alkyl substituted with an amino group.

In some embodiments, $R^3$ is $C_1$ alkyl substituted with an amino group.

In some embodiments, $R^3$ is $C_2$ alkyl substituted with an amino group.

In some embodiments, $R^3$ is $C_3$ alkyl substituted with an amino group.

In some embodiments, $R^3$ is $C_4$ alkyl substituted with an amino group.

In some embodiments, $R^3$ is $C_5$ alkyl substituted with an amino group.

In some embodiments, $R^3$ is $C_6$ alkyl substituted with an amino group.

In some embodiments, $R^1$ is selected from one of the following:

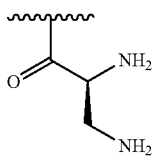 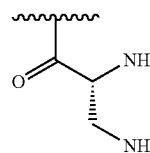 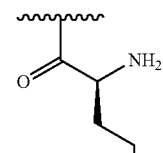

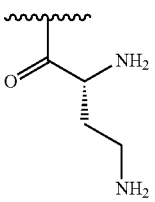 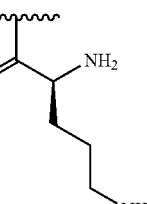 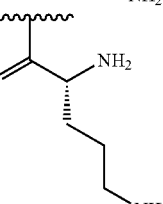

In some embodiments, $R^3$ is $C_1$-$C_6$ alkyl substituted with a guanidino group.

In some embodiments, $R^3$ is $C_1$ alkyl substituted with a guanidino group.

In some embodiments, $R^3$ is $C_2$ alkyl substituted with a guanidino group.

In some embodiments, $R^3$ is $C_3$ alkyl substituted with a guanidino group.

In some embodiments, $R^3$ is $C_4$ alkyl substituted with a guanidino group.

In some embodiments, $R^3$ is $C_5$ alkyl substituted with a guanidino group.

In some embodiments, $R^3$ is $C_6$ alkyl substituted with a guanidino group.

In some embodiments, $R^1$ is selected from one of the following:

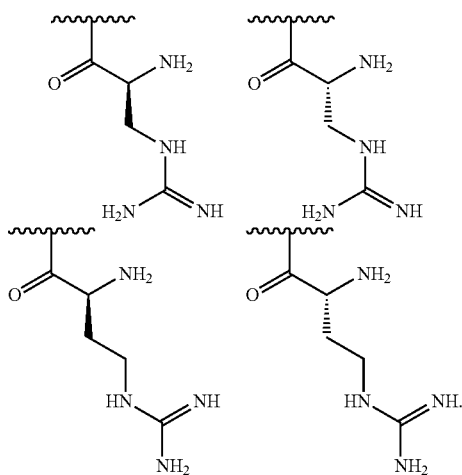

In some embodiments, wherein $R^2$ is amino that is substituted with a nitrogen protecting group prior to substitution on chitosan and removed subsequent to substitution on chitosan.

In some embodiments, the nitrogen protecting group is tert-butyloxycarbonyl (Boc).

In some embodiments, in the synthetic process a nitrogen protecting group is used, which can provide an intermediate polymer having a nitrogen protecting group such as Boc.

In some embodiments, $R^2$ is amino.

In some embodiments, $R^2$ is hydrogen and $R^3$ is amino.

In some embodiments, $R^2$ is hydrogen and $R^3$ is guanidino.

In some embodiments, $R^2$ is hydrogen and $R^3$ is a substituted $C_1$-$C_6$ alkyl.

In some embodiments, $R^3$ is $C_1$-$C_6$ alkyl substituted with an amino group.

In some embodiments, $R^3$ is $C_1$ alkyl substituted with an amino group.

In some embodiments, $R^3$ is $C_2$ alkyl substituted with an amino group.

In some embodiments, $R^3$ is $C_3$ alkyl substituted with an amino group.

In some embodiments, $R^3$ is $C_4$ alkyl substituted with an amino group.

In some embodiments, $R^3$ is $C_5$ alkyl substituted with an amino group.

In some embodiments, $R^3$ is $C_6$ alkyl substituted with an amino group.

In some embodiments, $R^1$ is selected from one of the following:

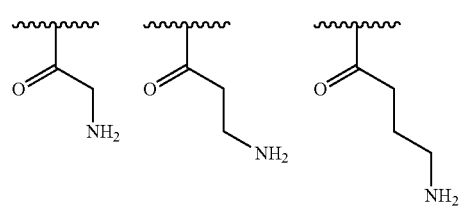

-continued

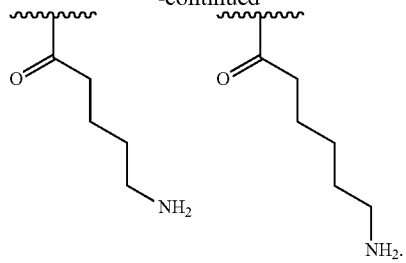

In some embodiments, $R^3$ is $C_1$-$C_6$ alkyl substituted with a guanidino group.

In some embodiments, $R^3$ is $C_1$ alkyl substituted with a guanidino group.

In some embodiments, $R^3$ is $C_2$ alkyl substituted with a guanidino group.

In some embodiments, $R^3$ is $C_3$ alkyl substituted with a guanidino group.

In some embodiments, $R^3$ is $C_4$ alkyl substituted with a guanidino group.

In some embodiments, $R^3$ is $C_5$ alkyl substituted with a guanidino group.

In some embodiments, $R^3$ is $C_6$ alkyl substituted with a guanidino group.

In some embodiments, $R^1$ is selected from one of the following:

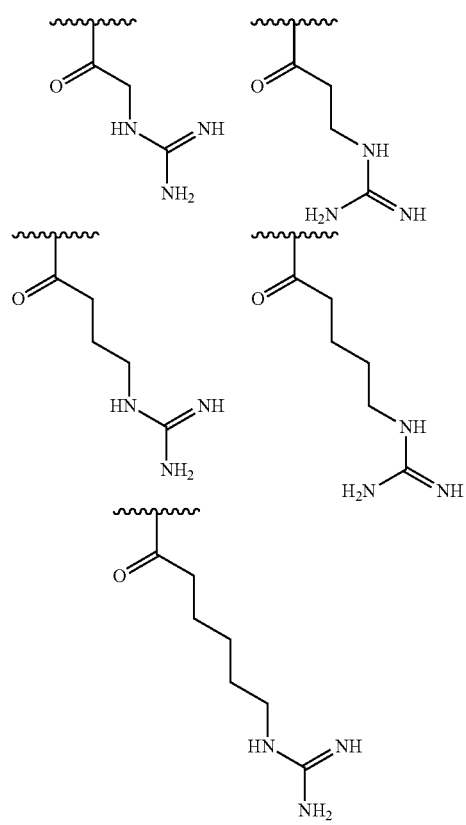

In some embodiments, at least 25% of R substituents are H, at least 1% of R substituents are acetyl, and at least 2% of $R^1$ substituents independently selected from any of the formulae specifically shown above.

In some embodiments, the functionalized chitosan of formula (I) may be further derivatized on the free hydroxyl moieties.

In some embodiments, the molecular weight of the functionalized chitosan is between 5,000 and 1,000,000 Da.

In some embodiments, the molecular weight of the functionalized chitosan is between 10,000 and 350,000 Da.

In some embodiments, the molecular weight of the functionalized chitosan is between 10,000 and 60,000 Da.

In some embodiments, the molecular weight of the functionalized chitosan is between 15,000 and 45,000 Da.

In some embodiments, the molecular weight of the functionalized chitosan is between 15,000 and 35,000 Da.

In some embodiments, the molecular weight of the functionalized chitosan is between 15,000 and 25,000 Da.

In some embodiments, the functionalized chitosan is soluble in aqueous solution between pH 6 and 8.

In some embodiments, the functionalized chitosan is soluble in aqueous solution between pH 6.8 and pH 7.4.

In one embodiment, the chitosan is functionalized at between 5% and 50%.

In a preferred embodiment, the chitosan is functionalized at between 20% and 30%.

In one embodiment, the degree of deacetylation (% DDA) of the derivatized chitosan is between 75% and 95%.

In one embodiment, the degree of deacetylation (% DDA) of the derivatized chitosan is between 80% and 90%.

In one embodiment, the polydispersity index (PDI) of the derivatized chitosan is between 1.0 and 2.5.

In one embodiment, the polydispersity index (PDI) of the derivatized chitosan is between 1.2 and 1.8.

In some embodiments, the functionalized chitosan is substantially free of other impurities.

In yet another aspect, the invention features a method of treating a wound in a subject, the method comprising applying a wound dressing comprising an effective amount of a composition comprising a soluble or derivatized chitosan to the wound, thereby treating the wound.

In an embodiment, the composition reduces the healing time or increases the healing rate of the wound. In some embodiments, the composition decreases the inflammation associated with wound or healing of the wound.

In an embodiment, the subject is a human, an animal (e.g., a farm, circus, zoo animal, or a companion pet).

In an embodiment, the subject has a chronic disease.

In an embodiment, the chronic disease is selected from the group consisting of inflammatory bowel disease (IBD) (e.g., Crohn's disease), diabetes (e.g., diabetes mellitus types 1 or type 2), chronic kidney disease (CKD), chronic obstructive pulmonary disease (COPD), hypothyroidism, multiple sclerosis, rheumatoid arthritis, hepatic encephalopathy, peritonitis, periodontitis, sinusitis, rhinitis, sepsis, and systemic lupus erythematosus.

In an embodiment, the subject has been treated or is being treated with one or more of the cancer therapies, e.g., chemotherapy or radiation therapy. In an embodiment, the composition is administered to the subject before, during, or after the subject is treated with the cancer therapy. In an embodiment, the composition is administered to the subject prior to the therapy, e.g., for at least about 1 day, 2 days, 3 days, 5 days, or 1 week. In an embodiment, the composition is administered to the subject less than about 1 day, 2 days, 4 days, 1 week, 2 weeks, 3 weeks, or 4 weeks after the subject is treated with the cancer therapy.

In an embodiment, the subject has been treated or is being treated with immunosuppressive therapy. In an embodiment, the composition is administered to the subject prior to the therapy, e.g., for at least about 1 day, 2 days, 3 days, 5 days, or 1 week. In an embodiment, the wound is caused by e.g., chemotherapy, radiation therapy, immunosuppressive therapy, chemical damage, biological damage, radiological damage, or immunodeficiency or compromise of immune system (e.g., primary immunodeficiency or acquired immunodeficiency (e.g., AIDS, malnutrition, aging, particular medications (e.g. chemotherapy, disease-modifying anti-rheumatic drugs, immunosuppressive drugs after organ transplants, glucocorticoids)).

In an embodiment, the wound is the result of an infection, e.g., bacterial or viral infection, and wherein the infection is no longer present when the wound is treated.

In an embodiment, the wound is the result of an infection, e.g., bacterial or viral infection, and wherein the infection is still present when the wound is treated.

In an embodiment, the wound is an acute wound. In an embodiment, the wound is a chronic wound, e.g., a wound that does not heal in an orderly set of stages, in a predictable amount of time, or within three months. In an embodiment, the wound is a surgical wound, e.g., a wound resulted from medical grafting (e.g., skin or bone grafting) at the donor site and/or the graft site, full thickness or partial thickness excision. In an embodiment, the wound is a burn wound.

In an embodiment, the wound is in the epidermis, dermis or hypodermis. In an embodiment, the wound is in the mucosal membrane.

In an embodiment, the wound is a venous ulcer, a diabetic ulcer, a corneal ulcer (or damage to the corneal epithelium), oral ulcer, peptic ulcer, or a pressure ulcer.

In an embodiment, the composition is administered to the subject less than about 5 minutes, 15 minutes, 30 minutes, 1 hour, 2 hours, 4 hours, 6 hours, 12 hours, 24 hours, 2 days, 3 days, 4 days, 5 days, 6 days, 7 days, 2 weeks, 4 weeks, 2 months, 4 months, 6 months, 8 months, 10 months, or 1 year after the subject is wounded.

In an embodiment, the healing time of the wound (e.g., the length of one or more of the inflammatory, proliferative, or remodeling phase of wound healing) is reduced by at least about 10%, 20%, 30%, 40%, 50%, 60%, 70%, 80%, 90%, or 95%, compared to the healing time of the wound (e.g., the length of one or more of the inflammatory, proliferative, or remodeling phase of wound healing) that has not been contacted with the soluble or derivatized chitosan.

In an embodiment, the wound healing rate (e.g., the absolute area healed per day, the percentage of initial area healed per day, or the greatest average wound margin distance from the wound centre divided by the time to complete wound closure) is increased by at least about 1, 2, 3, 4, 5, 6, 7, 8, 9, or 10 fold, compared to the healing rate of the wound that has not been contacted with the soluble or derivatized chitosan.

In an embodiment, the method further comprises administering to the subject a second wound therapy, e.g., antibiotic or antibacterial use, debridement, irrigation, negative pressure wound therapy (vacuum-assisted closure), warming, oxygenation, moist wound healing, removing mechanical stress, and/or adding cells (e.g., keratinocytes) or other materials (e.g., artificial skin substitutes that have fibroblasts and/or keratinocytes in a matrix of collagen) to secrete or enhance levels of healing factors (e.g., vascular endothelial growth factor (VEGF), insulin-like growth factor (IGF), platelet-derived growth factor (PDGF), transforming growth factor-$\beta$ (TGF-$\beta$), and epidermal growth factor (EGF)).

In an embodiment, the second wound therapy comprises a negative pressure wound therapy (vacuum-assisted closure).

In an embodiment, the second wound therapy comprises an antibiotic. In an embodiment, the composition overcomes (e.g., reduces, decreases, or prevents) a deleterious effect of the antibiotic in wound healing.

In an embodiment, the second wound therapy comprises a steroidal or non-steroidal anti-inflammatory drug (NSIAD). In an embodiment, the composition acts additively or synergysically with the steroidal or non-steroidal anti-inflammatory drug.

In an embodiment, the composition is administered topically or orally, e.g., by topical rinse, gel, spray, oral, enema, inhalation, dry powder, aerosolized liquid, eye drop.

In an embodiment, the effective amount is therapeutically effective amount.

In one embodiment, the soluble or derivatized chitosan is soluble in aqueous solution from about pH 6.8 to about pH 7.4.

In one embodiment, the soluble or derivatized chitosan is soluble in aqueous solution from about pH 3 to about pH 9.

In one embodiment, the soluble or derivatized chitosan is soluble in aqueous solution from about pH 5.0 to about pH 6.0, e.g., in wounds or duodenum.

In one embodiment, the soluble or derivatized chitosan is soluble in aqueous solution from about pH 2.0 to about pH 4.0, e.g., in stomach.

In one embodiment, the soluble or derivatized chitosan is soluble in aqueous solution from about pH 8.0 to about pH 8.5, e.g., in lower part of the gastrointestinal tract.

In one embodiment, the derivatized chitosan comprises a chitosan of the following formula (I):

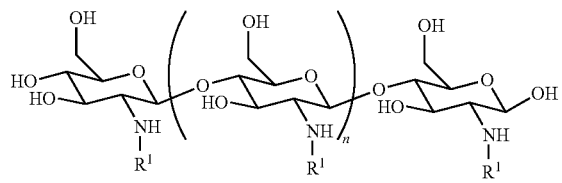

formula (I)

wherein:

n is an integer between 20 and 6000; and each $R^1$ is independently selected for each occurrence from hydrogen, acetyl, and either:

a) a group of formula (II):

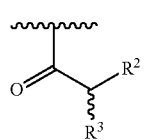

formula (II)

wherein $R^2$ is hydrogen or amino; and $R^3$ is amino, guanidino, $C_1$-$C_6$ alkyl substituted with an amino or guanidino moiety, or a natural or unnatural amino acid side chain;

or b) $R^1$, when taken together with the nitrogen to which it is attached, forms a guanidine moiety;
wherein at least 25% of $R^1$ substituents are H, at least 1% of $R^1$ substituents are acetyl, and at least 2% of $R^1$ substituents are a group of formula (II) or are taken together with the nitrogen to which they are attached to form a guanidine moiety.

In one embodiment, the derivatized chitosan comprises of the following formula (I) wherein at least 90% by number or weight of $R^1$ moieties are as defined in formula (I) (e.g., at least about 95%, at least about 96%, at least about 97%, at least about 98%, or at least about 99%):

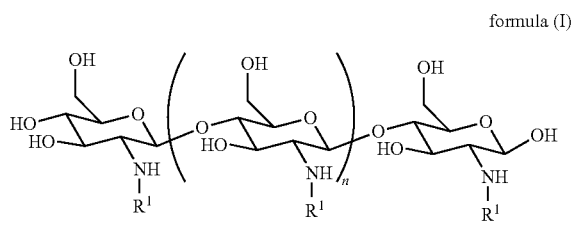

formula (I)

wherein:

n is an integer between 20 and 6000; and each $R^1$ is independently selected for each occurrence from hydrogen, acetyl, and either:

a) a group of formula (II):

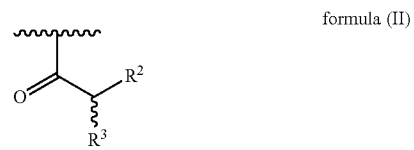

formula (II)

wherein $R^2$ is hydrogen or amino; and $R^3$ is amino, guanidino, $C_1$-$C_6$ alkyl substituted with an amino or guanidino moiety, or a natural or unnatural amino acid side chain;

or b) $R^1$, when taken together with the nitrogen to which it is attached, forms a guanidine moiety;

wherein at least 25% of $R^1$ substituents are H, at least 1% of $R^1$ substituents are acetyl, and at least 2% of $R^1$ substituents are a group of formula (II) or are taken together with the nitrogen to which they are attached to form a guanidine moiety.

In some embodiments, between 25-95% of $R^1$ substituents are hydrogen.

In some embodiments, between 55-90% of $R^1$ substituents are hydrogen.

In some embodiments, between 1-50% of $R^1$ substituents are acetyl.

In some embodiments, between 4-20% of $R^1$ substituents are acetyl.

In some embodiments, between 2-50% of $R^1$ substituents are a group of formula (II).

In some embodiments, between 4-30% of $R^1$ substituents are a group of formula (II).

In some embodiments, 55-90% of $R^1$ substituents are hydrogen, 4-20% of $R^1$ substituents are acetyl, 4-30% of $R^1$ substituents are a group of formula (II).

In some embodiments, $R^2$ is amino and $R^3$ is an arginine side chain.

In some embodiments, $R^1$ is selected from one of the following:

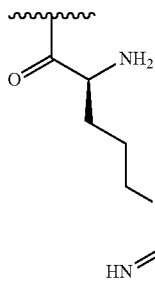 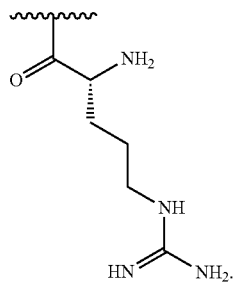

In some embodiments, $R^2$ is amino and $R^3$ is a lysine side chain.

In some embodiments, $R^1$ is selected from one of the following:

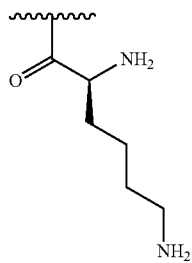 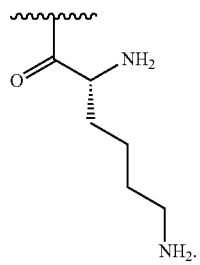

In some embodiments, $R^2$ is amino and $R^3$ is a histidine side chain.

In some embodiments, $R^1$ is selected from one of the following:

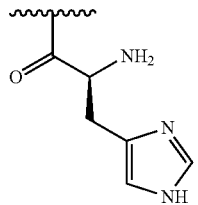 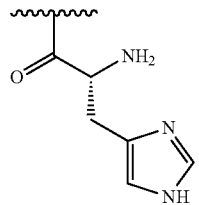

In some embodiments, at least 1% of $R^1$ substituents are selected from one of the following:

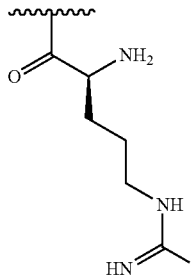 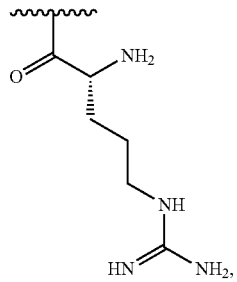

AND at least 1% of $R^1$ substituents are selected from the following:

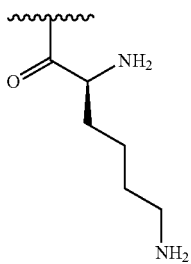 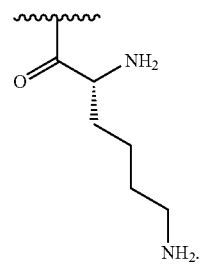

In some embodiments, $R^2$ is amino and $R^3$ is a substituted $C_1$-$C_6$ alkyl.

In some embodiments, $R^3$ is $C_1$-$C_6$ alkyl substituted with an amino group.

In some embodiments, $R^3$ is $C_1$ alkyl substituted with an amino group.

In some embodiments, $R^3$ is $C_2$ alkyl substituted with an amino group.

In some embodiments, $R^3$ is $C_3$ alkyl substituted with an amino group.

In some embodiments, $R^3$ is $C_4$ alkyl substituted with an amino group.

In some embodiments, $R^3$ is $C_5$ alkyl substituted with an amino group.

In some embodiments, $R^3$ is $C_6$ alkyl substituted with an amino group.

In some embodiments, $R^1$ is selected from one of the following:

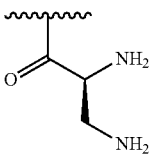 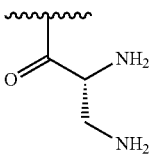 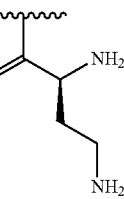

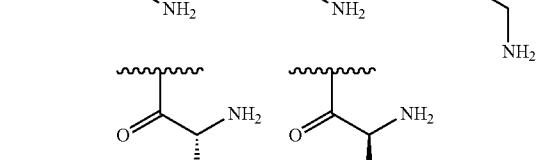

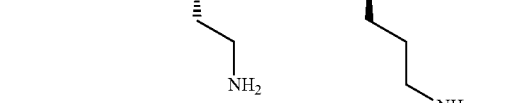

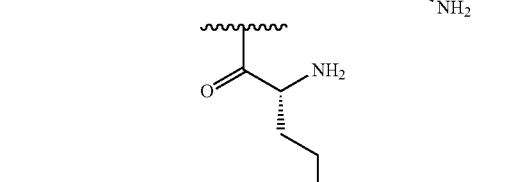

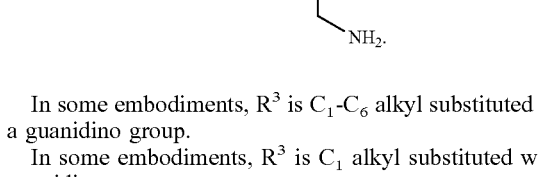

In some embodiments, $R^3$ is $C_1$-$C_6$ alkyl substituted with a guanidino group.

In some embodiments, $R^3$ is $C_1$ alkyl substituted with a guanidino group.

In some embodiments, $R^3$ is $C_2$ alkyl substituted with a guanidino group.

In some embodiments, $R^3$ is $C_3$ alkyl substituted with a guanidino group.

In some embodiments, $R^3$ is $C_4$ alkyl substituted with a guanidino group.

In some embodiments, $R^3$ is $C_5$ alkyl substituted with a guanidino group.

In some embodiments, $R^3$ is $C_6$ alkyl substituted with a guanidino group.

In some embodiments, $R^1$ is selected from one of the following:

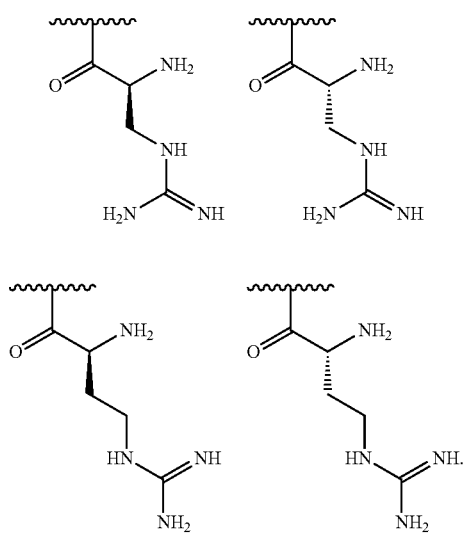

In some embodiments, wherein $R^2$ is amino that is substituted with a nitrogen protecting group prior to substitution on chitosan and removed subsequent to substitution on chitosan.

In some embodiments, the nitrogen protecting group is tert-butyloxycarbonyl (Boc).

In some embodiments, in the synthetic process a nitrogen protecting group is used, which can provide an intermediate polymer having a nitrogen protecting group such as Boc.

In some embodiments, $R^2$ is amino.

In some embodiments, $R^2$ is hydrogen and $R^3$ is amino.

In some embodiments, $R^2$ is hydrogen and $R^3$ is guanidino.

In some embodiments, $R^2$ is hydrogen and $R^3$ is a substituted $C_1$-$C_6$ alkyl.

In some embodiments, $R^3$ is $C_1$-$C_6$ alkyl substituted with an amino group.

In some embodiments, $R^3$ is $C_1$ alkyl substituted with an amino group.

In some embodiments, $R^3$ is $C_2$ alkyl substituted with an amino group.

In some embodiments, $R^3$ is $C_3$ alkyl substituted with an amino group.

In some embodiments, $R^3$ is $C_4$ alkyl substituted with an amino group.

In some embodiments, $R^3$ is $C_5$ alkyl substituted with an amino group.

In some embodiments, $R^3$ is $C_6$ alkyl substituted with an amino group.

In some embodiments, $R^1$ is selected from one of the following:

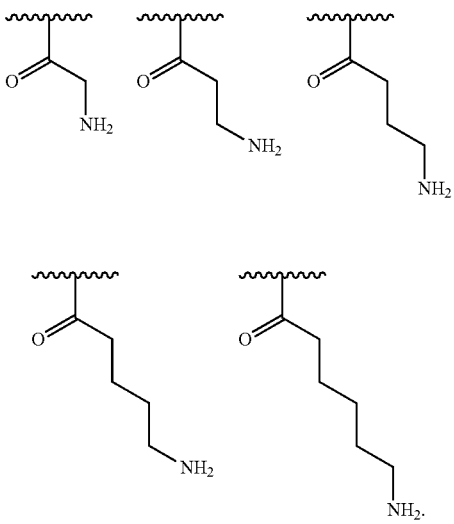

In some embodiments, $R^3$ is $C_1$-$C_6$ alkyl substituted with a guanidino group.

In some embodiments, $R^3$ is $C_1$ alkyl substituted with a guanidino group.

In some embodiments, $R^3$ is $C_2$ alkyl substituted with a guanidino group.

In some embodiments, $R^3$ is $C_3$ alkyl substituted with a guanidino group.

In some embodiments, $R^3$ is $C_4$ alkyl substituted with a guanidino group.

In some embodiments, $R^3$ is $C_5$ alkyl substituted with a guanidino group.

In some embodiments, $R^3$ is $C_6$ alkyl substituted with a guanidino group.

In some embodiments, $R^1$ is selected from one of the following:

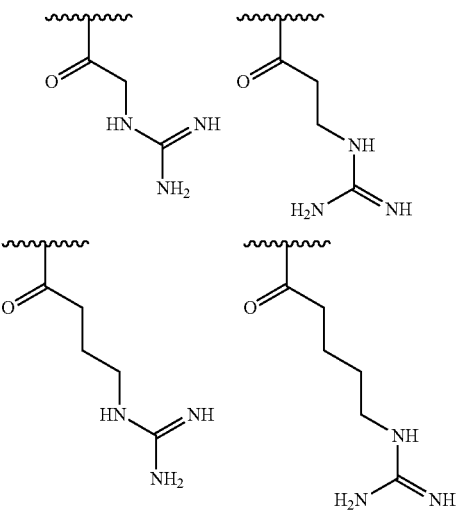

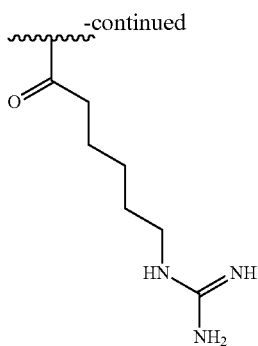

In some embodiments, at least 25% of $R^1$ substituents are H, at least 1% of $R^1$ substituents are acetyl, and at least 2% of $R^1$ substituents independently selected from any of the formulae specifically shown above.

In some embodiments, the functionalized chitosan of formula (I) may be further derivatized on the free hydroxyl moieties.

In some embodiments, the molecular weight of the functionalized chitosan is between 5,000 and 1,000,000 Da.

In some embodiments, the molecular weight of the functionalized chitosan is between 10,000 and 350,000 Da.

In some embodiments, the molecular weight of the functionalized chitosan is between 10,000 and 60,000 Da.

In some embodiments, the molecular weight of the functionalized chitosan is between 15,000 and 45,000 Da.

In some embodiments, the molecular weight of the functionalized chitosan is between 15,000 and 35,000 Da.

In some embodiments, the molecular weight of the functionalized chitosan is between 15,000 and 25,000 Da.

In some embodiments, the functionalized chitosan is soluble in aqueous solution between pH 6 and 8.

In some embodiments, the functionalized chitosan is soluble in aqueous solution between pH 6.8 and pH 7.4.

In one embodiment, the chitosan is functionalized at between 5% and 50%.

In a preferred embodiment, the chitosan is functionalized at between 20% and 30%.

In one embodiment, the degree of deacetylation (% DDA) of the derivatized chitosan is between 75% and 95%.

In one embodiment, the degree of deacetylation (% DDA) of the derivatized chitosan is between 80% and 90%.

In one embodiment, the polydispersity index (PDI) of the derivatized chitosan is between 1.0 and 2.5.

In one embodiment, the polydispersity index (PDI) of the derivatized chitosan is between 1.2 and 1.8.

In some embodiments, the functionalized chitosan is substantially free of other impurities.

In one aspect, the invention features a method of treating a subject receiving a surgical procedure or having undergone a surgical procedure, the method comprising: administering to a subject an effective amount of a composition comprising a soluble or derivatized chitosan, thereby treating the subject.

In an embodiment, the surgical procedure is selected from the group consisting of general surgery (e.g., cardiothoracic surgery, vascular surgery, plastic surgery, paediatric surgery, colorectal surgery, transplant surgery, surgical oncology, trauma surgery, endocrine surgery, breast surgery, skin surgery), otolaryngology—head and neck surgery, gynecology surgery, oral and maxillofacial surgery, orthopaedic surgery, neurosurgery, ophthalmology surgery (eye surgery), podiatric surgery, reconstructive surgery, and urology surgery.

In an embodiment, the surgical procedure of the eye is selected from the group consisting of laser eye surgery, refractive surgery, cataract surgery, glaucoma surgery, canaloplasty, corneal surgery, vitreo-retinal surgery, eye muscle surgery, and oculoplastic surgery.

In an embodiment, the subject has a wound resulting from the surgical procedure.

In an embodiment, the composition reduces scarring (e.g., size, severity) or prevents the formation of a scar, compared to the scar or formation for the scar in the subject that has not been treated with the composition. In an embodiment, the composition reduces loss of vision due to scarring.

In an embodiment, the wound is not the result of an infection. In an embodiment, the wound is the result of an infection, e.g., bacterial or viral infection, and wherein the infection is no longer present when the wound is treated. In another embodiment, the wound is the result of an infection, e.g., bacterial or viral infection, and wherein the infection is still present when the wound is treated.

In an embodiment, the composition is administered to the subject less than about 5 minutes, 15 minutes, 30 minutes, 1 hour, 2 hours, 4 hours, 6 hours, 12 hours, 24 hours, 2 days, 3 days, 4 days, 5 days, 6 days, 7 days, 2 weeks, 4 weeks, 2 months, 4 months, 6 months, 8 months, 10 months, or 1 year after the subject is wounded.

In an embodiment, the composition is administered prophylactically, prior to the surgical procedure, e.g., for at least 1 day, 2 days, 3 days, 5 days, or 1 week.

In an embodiment, the composition reduces the healing time or increase the healing rate of the wound. In some embodiments, the composition decreases the inflammation associated with wound or healing of the wound.

In an embodiment, the healing time of the wound (e.g., the length of one or more of the inflammatory, proliferative, or remodeling phase of wound healing) is reduced by at least about 10%, 20%, 30%, 40%, 50%, 60%, 70%, 80%, 90%, or 95%, compared to the healing time of the wound (e.g., the length of one or more of the inflammatory, proliferative, or remodeling phase of wound healing) that has not been contacted with the soluble or derivatized chitosan.

In an embodiment, the wound healing rate (e.g., the absolute area healed per day, the percentage of initial area healed per day, or the greatest average wound margin distance from the wound centre divided by the time to complete wound closure) is increased by at least about 1, 2, 3, 4, 5, 6, 7, 8, 9, or 10 fold, compared to the healing rate of the wound that has not been contacted with the soluble or derivatized chitosan.

In an embodiment, the method further comprises administering to the subject a second wound therapy described herein, and/or a second scar management agent described herein.

In an embodiment, the second wound therapy comprises an antibiotic. In an embodiment, the composition overcomes (e.g., reduces, decreases, and/or prevents) a deleterious effect of the antibiotic in wound healing.

In an embodiment, the second wound therapy comprises a steroidal or non-steroidal anti-inflammatory drug (NSIAD). In an embodiment, the composition acts additively or synergysically with the steroidal or non-steroidal anti-inflammatory drug.

In an embodiment, the composition is administered topically, e.g., by topical rinse, gel, and eye drop.

In an embodiment, the composition is administered before, during or after the surgical procedure.

In an embodiment, the composition is administered before, during or after one or more of the wound healing phase, e.g., inflammatory, proliferative, or remodeling phase.

In an embodiment, the effective amount is therapeutically effective amount.

In one embodiment, the soluble or derivatized chitosan is soluble in aqueous solution from about pH 6.8 to about pH 7.4.

In one embodiment, the soluble or derivatized chitosan is soluble in aqueous solution from about pH 3 to about pH 9.

In one embodiment, the derivatized chitosan comprises a chitosan of the following formula (I):

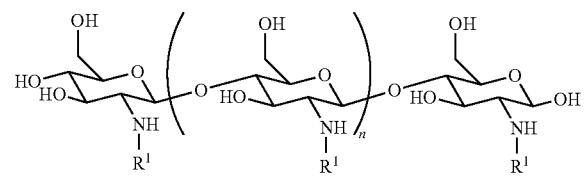

formula (I)

wherein:

n is an integer between 20 and 6000; and each $R^1$ is independently selected for each occurrence from hydrogen, acetyl, and either:

a) a group of formula (II):

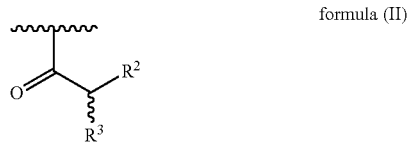

formula (II)

wherein $R^2$ is hydrogen or amino; and $R^3$ is amino, guanidino, $C_1$-$C_6$ alkyl substituted with an amino or guanidino moiety, or a natural or unnatural amino acid side chain;

or b) $R^1$, when taken together with the nitrogen to which it is attached, forms a guanidine moiety;

wherein at least 25% of $R^1$ substituents are H, at least 1% of $R^1$ substituents are acetyl, and at least 2% of $R^1$ substituents are a group of formula (II) or are taken together with the nitrogen to which they are attached to form a guanidine moiety.

In one embodiment, the derivatized chitosan comprises of the following formula (I) wherein at least 90% by number or weight of $R^1$ moieties are as defined in formula (I) (e.g., at least about 95%, at least about 96%, at least about 97%, at least about 98%, or at least about 99%):

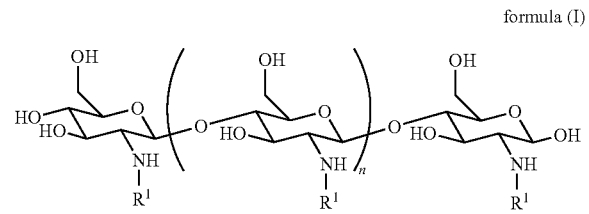

formula (I)

wherein:

n is an integer between 20 and 6000; and each $R^1$ is independently selected for each occurrence from hydrogen, acetyl, and either:

a) a group of formula (II):

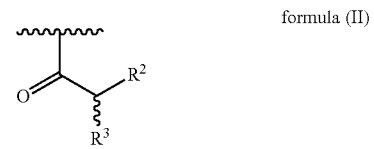

formula (II)

wherein $R^2$ is hydrogen or amino; and $R^3$ is amino, guanidino, $C_1$-$C_6$ alkyl substituted with an amino or guanidino moiety, or a natural or unnatural amino acid side chain;

or b) $R^1$, when taken together with the nitrogen to which it is attached, forms a guanidine moiety;

wherein at least 25% of $R^1$ substituents are H, at least 1% of $R^1$ substituents are acetyl, and at least 2% of $R^1$ substituents are a group of formula (II) or are taken together with the nitrogen to which they are attached to form a guanidine moiety.

In some embodiments, between 25-95% of $R^1$ substituents are hydrogen.

In some embodiments, between 55-90% of $R^1$ substituents are hydrogen.

In some embodiments, between 1-50% of $R^1$ substituents are acetyl.

In some embodiments, between 4-20% of $R^1$ substituents are acetyl.

In some embodiments, between 2-50% of $R^1$ substituents are a group of formula (II).

In some embodiments, between 4-30% of $R^1$ substituents are a group of formula (II).

In some embodiments, 55-90% of $R^1$ substituents are hydrogen, 4-20% of $R^1$ substituents are acetyl, 4-30% of $R^1$ substituents are a group of formula (II).

In some embodiments, $R^2$ is amino and $R^3$ is an arginine side chain.

In some embodiments, $R^1$ is selected from one of the following:

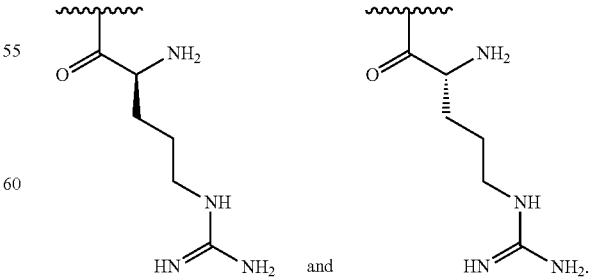

In some embodiments, $R^2$ is amino and $R^3$ is a lysine side chain.

In some embodiments, $R^1$ is selected from one of the following:

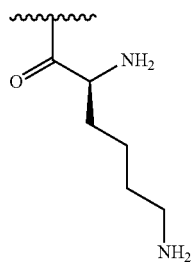 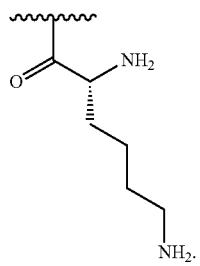
and

In some embodiments, $R^2$ is amino and $R^3$ is a histidine side chain.

In some embodiments, $R^1$ is selected from one of the following:

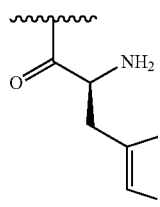 and 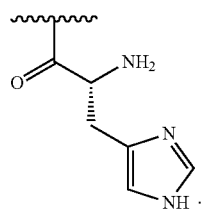

In some embodiments, at least 1% of $R^1$ substituents are selected from one of the following:

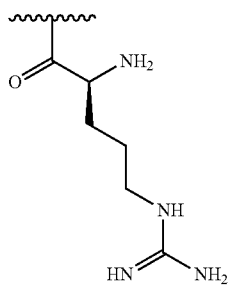 and 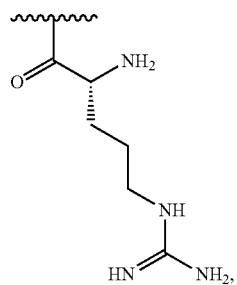

AND at least 1% of $R^1$ substituents are selected from the following:

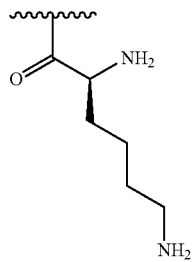 and 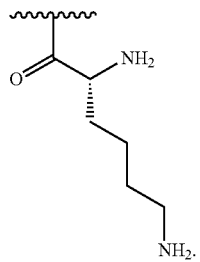

In some embodiments, $R^2$ is amino and $R^3$ is a substituted $C_1$-$C_6$ alkyl.

In some embodiments, $R^3$ is $C_1$-$C_6$ alkyl substituted with an amino group.

In some embodiments, $R^3$ is $C_1$ alkyl substituted with an amino group.

In some embodiments, $R^3$ is $C_2$ alkyl substituted with an amino group.

In some embodiments, $R^3$ is $C_3$ alkyl substituted with an amino group.

In some embodiments, $R^3$ is $C_4$ alkyl substituted with an amino group.

In some embodiments, $R^3$ is $C_5$ alkyl substituted with an amino group.

In some embodiments, $R^3$ is $C_6$ alkyl substituted with an amino group.

In some embodiments, $R^1$ is selected from one of the following:

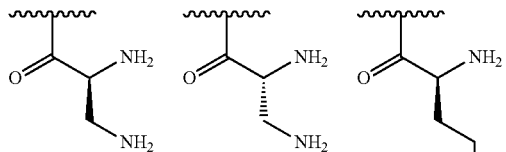

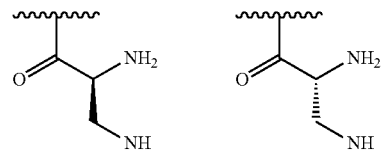

In some embodiments, $R^3$ is $C_1$-$C_6$ alkyl substituted with a guanidino group.

In some embodiments, $R^3$ is $C_1$ alkyl substituted with a guanidino group.

In some embodiments, $R^3$ is $C_2$ alkyl substituted with a guanidino group.

In some embodiments, $R^3$ is $C_3$ alkyl substituted with a guanidino group.

In some embodiments, $R^3$ is $C_4$ alkyl substituted with a guanidino group.

In some embodiments, $R^3$ is $C_5$ alkyl substituted with a guanidino group.

In some embodiments, $R^3$ is $C_6$ alkyl substituted with a guanidino group.

In some embodiments, $R^1$ is selected from one of the following:

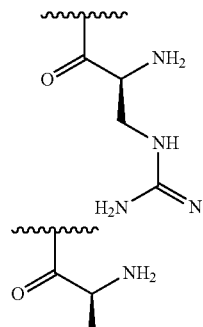 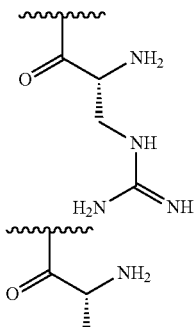

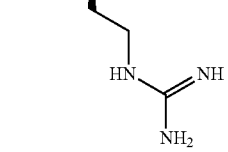 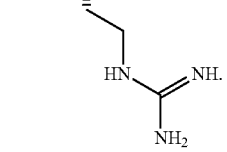

In some embodiments, wherein $R^2$ is amino that is substituted with a nitrogen protecting group prior to substitution on chitosan and removed subsequent to substitution on chitosan.

In some embodiments, the nitrogen protecting group is tert-butyloxycarbonyl (Boc).

In some embodiments, in the synthetic process a nitrogen protecting group is used, which can provide an intermediate polymer having a nitrogen protecting group such as Boc.

In some embodiments, $R^2$ is amino.

In some embodiments, $R^2$ is hydrogen and $R^3$ is amino.

In some embodiments, $R^2$ is hydrogen and $R^3$ is guanidino.

In some embodiments, $R^2$ is hydrogen and $R^3$ is a substituted $C_1$-$C_6$ alkyl.

In some embodiments, $R^3$ is $C_1$-$C_6$ alkyl substituted with an amino group.

In some embodiments, $R^3$ is $C_1$ alkyl substituted with an amino group.

In some embodiments, $R^3$ is $C_2$ alkyl substituted with an amino group.

In some embodiments, $R^3$ is $C_3$ alkyl substituted with an amino group.

In some embodiments, $R^3$ is $C_4$ alkyl substituted with an amino group.

In some embodiments, $R^3$ is $C_5$ alkyl substituted with an amino group.

In some embodiments, $R^3$ is $C_6$ alkyl substituted with an amino group.

In some embodiments, $R^1$ is selected from one of the following:

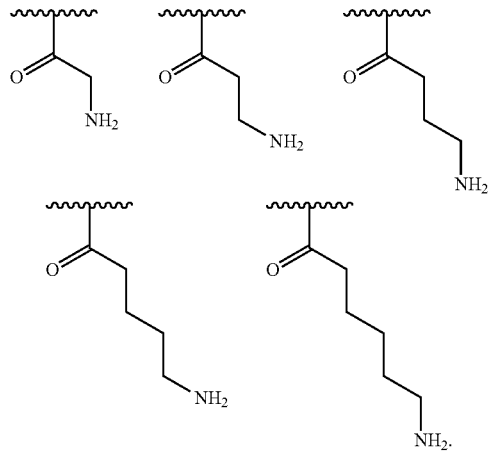

In some embodiments, $R^3$ is $C_1$-$C_6$ alkyl substituted with a guanidino group.

In some embodiments, $R^3$ is $C_1$ alkyl substituted with a guanidino group.

In some embodiments, $R^3$ is $C_2$ alkyl substituted with a guanidino group.

In some embodiments, $R^3$ is $C_3$ alkyl substituted with a guanidino group.

In some embodiments, $R^3$ is $C_4$ alkyl substituted with a guanidino group.

In some embodiments, $R^3$ is $C_5$ alkyl substituted with a guanidino group.

In some embodiments, $R^3$ is $C_6$ alkyl substituted with a guanidino group.

In some embodiments, $R^1$ is selected from one of the following:

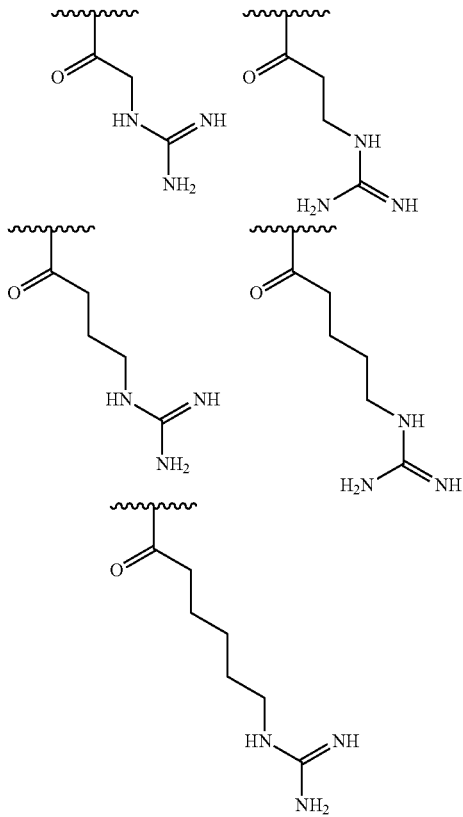

In some embodiments, at least 25% of $R^1$ substituents are H, at least 1% of $R^1$ substituents are acetyl, and at least 2% of $R^1$ substituents independently selected from any of the formulae specifically shown above.

In some embodiments, the functionalized chitosan of formula (I) may be further derivatized on the free hydroxyl moieties.

In some embodiments, the molecular weight of the functionalized chitosan is between 5,000 and 1,000,000 Da.

In some embodiments, the molecular weight of the functionalized chitosan is between 10,000 and 350,000 Da.

In some embodiments, the molecular weight of the functionalized chitosan is between 10,000 and 60,000 Da.

In some embodiments, the molecular weight of the functionalized chitosan is between 15,000 and 45,000 Da.

In some embodiments, the molecular weight of the functionalized chitosan is between 15,000 and 35,000 Da.

In some embodiments, the molecular weight of the functionalized chitosan is between 15,000 and 25,000 Da.

In some embodiments, the functionalized chitosan is soluble in aqueous solution between pH 6 and 8.

In some embodiments, the functionalized chitosan is soluble in aqueous solution between pH 6.8 and pH 7.4.

In one embodiment, the chitosan is functionalized at between 5% and 50%.

In a preferred embodiment, the chitosan is functionalized at between 20% and 30%.

In one embodiment, the degree of deacetylation (% DDA) of the derivatized chitosan is between 75% and 95%.

In one embodiment, the degree of deacetylation (% DDA) of the derivatized chitosan is between 80% and 90%.

In one embodiment, the polydispersity index (PDI) of the derivatized chitosan is between 1.0 and 2.5.

In one embodiment, the polydispersity index (PDI) of the derivatized chitosan is between 1.2 and 1.8.

In some embodiments, the functionalized chitosan is substantially free of other impurities.

In one aspect, the invention features a method of treating inflammation (e.g., reducing inflammation) in a subject, the method comprising administering to a subject an effective amount of a composition comprising a soluble or derivatized chitosan, wherein the inflammation is not associated with a bacterial infection (e.g., wherein the subject does not have a bacterial infection), thereby treating the subject.

In some embodiments, the composition reduces the level of inflammation and/or reduce the duration of inflammation, e.g., by at least 10%, 20%, 30%, 40%, 50%, 60%, 70%, 80%, or 90%, compared to the level of inflammation or the duration of inflammation in the subject that has not been treated with the composition.

In some embodiments, the composition up-regulates one or more anti-inflammatory cytokines (e.g., IL-10), and/or down-regulates one or more pro-inflammatory cytokines (e.g., TNF-α and/or IL-8).

In some embodiments, the method further comprises administering to a subject a second anti-inflammatory agent.

In some embodiments, the second anti-inflammatory agent is selected from the group consisting of a steroid (e.g., glucocorticoids (e.g., prednisolone)), a non-steroidal anti-inflammatory drug (e.g., salicylates (e.g., aspirin (acetylsalicylic acid), diflunisal, salsalate); a propionic acid derivative (e.g., ibuprofen, naproxen, fenoprofen, ketoprofen, flurbiprofen, oxaprozin, loxoprofen), an acetic acid derivative (indomethacin, sulindac, etodolac, ketorolac, diclofenac, nabumetone); an enolic acid (oxicam) derivative (e.g., piroxicam, meloxicam, tenoxicam, droxicam, lornoxicam, isoxicam); a fenamic acid derivative (fenamate) (e.g., mefenamic acid, meclofenamic acid, flufenamic acid, tolfenamic acid), a selective COX-2 inhibitor (coxib) (e.g., celecoxib, rofecoxib, valdecoxib, parecoxib, lumiracoxibm etoricoxib, firocoxib); sulphonanilide (nimesulide); a 5-LOX/COX inhibitor (licofelone); and an Immune Selective Anti-Inflammatory Derivative (ImSAID).

In an embodiment, the subject has a wound. In an embodiment, the wound is an acute wound. In an embodiment, the wound is a chronic wound, e.g., a wound that does not heal in an orderly set of stages, in a predictable amount of time, or within three months. In an embodiment, the wound is a surgical wound, e.g., a wound resulted from medical grafting (e.g., skin or bone grafting) at the donor site and/or the graft site, full thickness or partial thickness excision. In an embodiment, the wound is a burn wound. In an embodiment, the wound is in the epidermis, dermis or hypodermis. In an embodiment, the wound is in the mucosal membrane. In an embodiment, the wound is a venous ulcer, a diabetic ulcer, corneal ulcer (or damage to the corneal epithelium), an oral ulcer, a peptic ulcer, or a pressure ulcer.

In an embodiment, the composition is administered to the subject less than about 5 minutes, 15 minutes, 30 minutes, 1 hour, 2 hours, 4 hours, 6 hours, 12 hours, 24 hours, 2 days, 3 days, 4 days, 5 days, 6 days, 7 days, 2 weeks, 4 weeks, 2 months, 4 months, 6 months, 8 months, 10 months, or 1 year after the subject is wounded.

In an embodiment, the composition is administered to the subject prior to wound injury, e.g., for at least 1 day, 2 days, 3 days, 5 days, or 1 week In an embodiment, the composition reduces the healing time or increase the healing rate of the wound. In some embodiments, the composition decreases the inflammation associated with wound or healing of the wound.

In an embodiment, the healing time of the wound (e.g., the length of one or more of the inflammatory, proliferative, or remodeling phase of wound healing) is reduced by at least about 10%, 20%, 30%, 40%, 50%, 60%, 70%, 80%, 90%, or 95%, compared to the healing time of the wound (e.g., the length of one or more of the inflammatory, proliferative, or remodeling phase of wound healing) that has not been contacted with the soluble or derivatized chitosan.

In an embodiment, the wound healing rate (e.g., the absolute area healed per day, the percentage of initial area healed per day, or the greatest average wound margin distance from the wound centre divided by the time to complete wound closure) is increased by at least about 1, 2, 3, 4, 5, 6, 7, 8, 9, or 10 fold, compared to the healing rate of the wound that has not been contacted with the soluble or derivatized chitosan.

In an embodiment, the method further comprises administering to the subject a wound therapy, e.g., antibiotic or antibacterial use, debridement, irrigation, negative pressure wound therapy (vacuum-assisted closure), warming, oxygenation, moist wound healing, removing mechanical stress, and/or adding cells (e.g., keratinocytes) or other materials (e.g., artificial skin substitutes that have fibroblasts and/or keratinocytes in a matrix of collagen) to secrete or enhance levels of healing factors (e.g., vascular endothelial growth factor (VEGF), insulin-like growth factor (IGF), platelet-derived growth factor (PDGF), transforming growth factor-β (TGF-β), and epidermal growth factor (EGF)).

In an embodiment, the wound therapy comprises a negative pressure wound therapy (vacuum-assisted closure).

In an embodiment, the wound therapy comprises a steroidal or non-steroidal anti-inflammatory drug (NSIAD). In an embodiment, the composition acts additively or synergysically with the steroidal or non-steroidal anti-inflammatory drug.

In an embodiment, the composition is administered topically or orally, e.g., by topical rinse, gel, spray, oral, enema, inhalation, dry powder, aerosolized liquid, eye drop. In some embodiments, the composition is administered orally to treat an inflammatory gastrointestinal disorder.

In an embodiment, the composition is administered before, during or after one or more of the wound healing phase, e.g., inflammatory, proliferative, or remodeling phase.

In an embodiment, the effective amount is therapeutically effective amount.

In one embodiment, the soluble or derivatized chitosan is soluble in aqueous solution from about pH 6.8 to about pH 7.4.

In one embodiment, the soluble or derivatized chitosan is soluble in aqueous solution from about pH 3 to about pH 9.

In one embodiment, the soluble or derivatized chitosan is soluble in aqueous solution from about pH 5.0 to about pH 6.0, e.g., in wounds or duodenum.

In one embodiment, the soluble or derivatized chitosan is soluble in aqueous solution from about pH 2.0 to about pH 4.0, e.g., in stomach.

In one embodiment, the soluble or derivatized chitosan is soluble in aqueous solution from about pH 8.0 to about pH 8.5, e.g., in lower part of the gastrointestinal tract.

In one embodiment, the derivatized chitosan comprises a chitosan of the following formula (I):

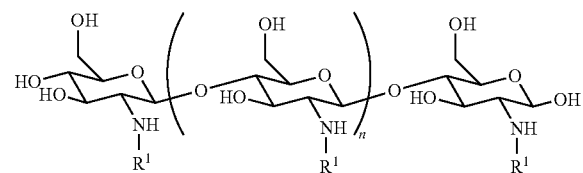

formula (I)

wherein:

n is an integer between 20 and 6000; and each $R^1$ is independently selected for each occurrence from hydrogen, acetyl, and either:

a) a group of formula (II):

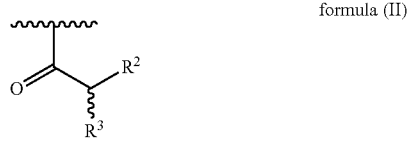

formula (II)

wherein $R^2$ is hydrogen or amino; and $R^3$ is amino, guanidino, $C_1$-$C_6$ alkyl substituted with an amino or guanidino moiety, or a natural or unnatural amino acid side chain;

or b) $R^1$, when taken together with the nitrogen to which it is attached, forms a guanidine moiety;

wherein at least 25% of $R^1$ substituents are H, at least 1% of $R^1$ substituents are acetyl, and at least 2% of $R^1$ substituents are a group of formula (II) or are taken together with the nitrogen to which they are attached to form a guanidine moiety.

In one embodiment, the derivatized chitosan comprises of the following formula (I) wherein at least 90% by number or weight of $R^1$ moieties are as defined in formula (I) (e.g., at least about 95%, at least about 96%, at least about 97%, at least about 98%, or at least about 99%):

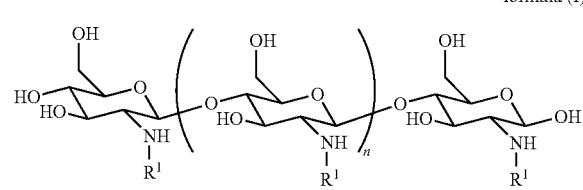

formula (I)

wherein:

n is an integer between 20 and 6000; and each $R^1$ is independently selected for each occurrence from hydrogen, acetyl, and either:

a) a group of formula (II):

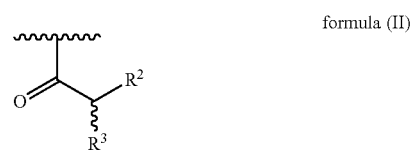

formula (II)

wherein $R^2$ is hydrogen or amino; and $R^3$ is amino, guanidino, $C_1$-$C_6$ alkyl substituted with an amino or guanidino moiety, or a natural or unnatural amino acid side chain;

or b) $R^1$, when taken together with the nitrogen to which it is attached, forms a guanidine moiety;

wherein at least 25% of $R^1$ substituents are H, at least 1% of $R^1$ substituents are acetyl, and at least 2% of $R^1$ substituents are a group of formula (II) or are taken together with the nitrogen to which they are attached to form a guanidine moiety.

In some embodiments, between 25-95% of $R^1$ substituents are hydrogen.

In some embodiments, between 55-90% of $R^1$ substituents are hydrogen.

In some embodiments, between 1-50% of $R^1$ substituents are acetyl.

In some embodiments, between 4-20% of $R^1$ substituents are acetyl.

In some embodiments, between 2-50% of $R^1$ substituents are a group of formula (II).

In some embodiments, between 4-30% of $R^1$ substituents are a group of formula (II).

In some embodiments, 55-90% of $R^1$ substituents are hydrogen, 4-20% of $R^1$ substituents are acetyl, 4-30% of $R^1$ substituents are a group of formula (II).

In some embodiments, $R^2$ is amino and $R^3$ is an arginine side chain.

In some embodiments, $R^1$ is selected from one of the following:

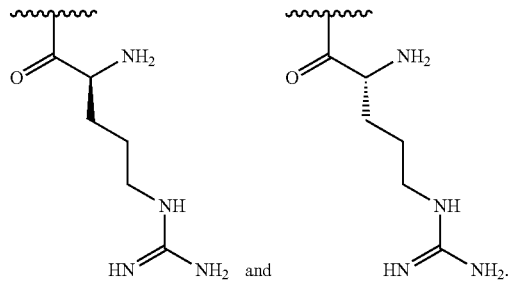 [SMILES: *C(=O)[C@@H](N)CCCNC(=N)N ; *C(=O)[C@H](N)CCCNC(=N)N]

In some embodiments, $R^2$ is amino and $R^3$ is a lysine side chain.

In some embodiments, $R^1$ is selected from one of the following:

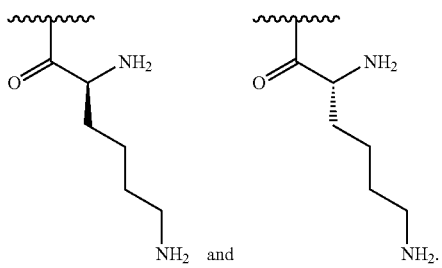 [SMILES: *C(=O)[C@@H](N)CCCCN ; *C(=O)[C@H](N)CCCCN]

In some embodiments, $R^2$ is amino and $R^3$ is a histidine side chain.

In some embodiments, $R^1$ is selected from one of the following:

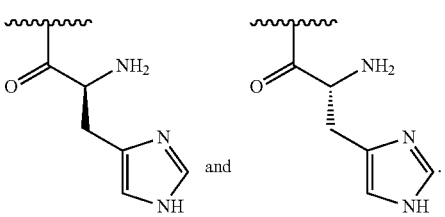 [SMILES: *C(=O)[C@@H](N)Cc1c[nH]cn1 ; *C(=O)[C@H](N)Cc1c[nH]cn1]

In some embodiments, at least 1% of $R^1$ substituents are selected from one of the following:

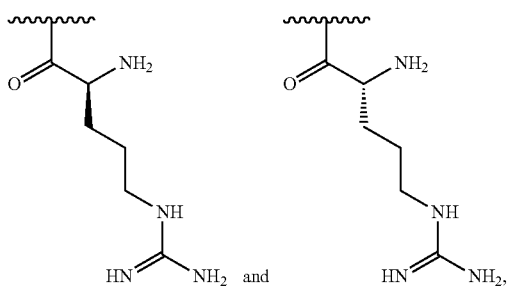 [SMILES: *C(=O)[C@@H](N)CCCNC(=N)N ; *C(=O)[C@H](N)CCCNC(=N)N]

AND at least 1% of $R^1$ substituents are selected from the following:

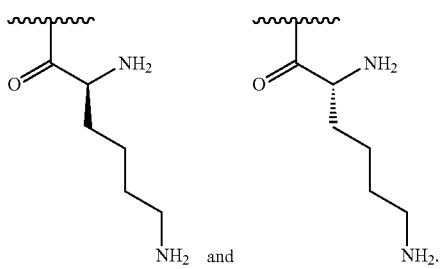 [SMILES: *C(=O)[C@@H](N)CCCCN ; *C(=O)[C@H](N)CCCCN]

In some embodiments, $R^2$ is amino and $R^3$ is a substituted $C_1$-$C_6$ alkyl.

In some embodiments, $R^3$ is $C_1$-$C_6$ alkyl substituted with an amino group.

In some embodiments, $R^3$ is $C_1$ alkyl substituted with an amino group.

In some embodiments, $R^3$ is $C_2$ alkyl substituted with an amino group.

In some embodiments, $R^3$ is $C_3$ alkyl substituted with an amino group.

In some embodiments, $R^3$ is $C_4$ alkyl substituted with an amino group.

In some embodiments, $R^3$ is $C_5$ alkyl substituted with an amino group.

In some embodiments, $R^3$ is $C_6$ alkyl substituted with an amino group.

In some embodiments, $R^1$ is selected from one of the following:

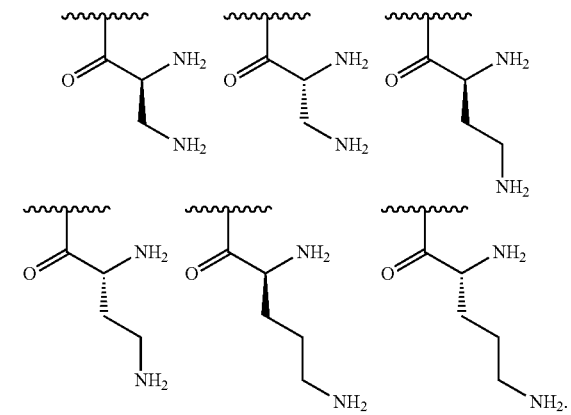

In some embodiments, $R^3$ is $C_1$-$C_6$ alkyl substituted with a guanidino group.

In some embodiments, $R^3$ is $C_1$ alkyl substituted with a guanidino group.

In some embodiments, $R^3$ is $C_2$ alkyl substituted with a guanidino group.

In some embodiments, $R^3$ is $C_3$ alkyl substituted with a guanidino group.

In some embodiments, $R^3$ is $C_4$ alkyl substituted with a guanidino group.

In some embodiments, $R^3$ is $C_5$ alkyl substituted with a guanidino group.

In some embodiments, $R^3$ is $C_6$ alkyl substituted with a guanidino group.

In some embodiments, $R^1$ is selected from one of the following:

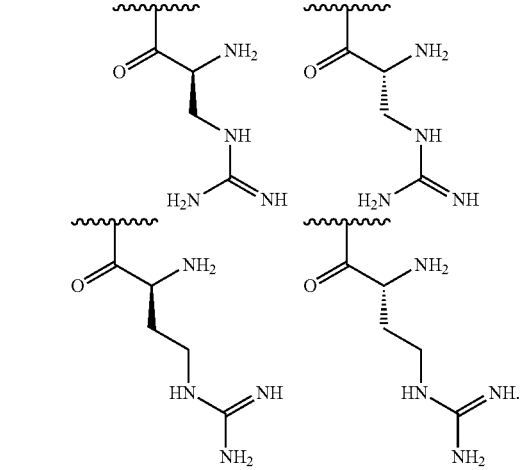

In some embodiments, wherein $R^2$ is amino that is substituted with a nitrogen protecting group prior to substitution on chitosan and removed subsequent to substitution on chitosan.

In some embodiments, the nitrogen protecting group is tert-butyloxycarbonyl (Boc).

In some embodiments, in the synthetic process a nitrogen protecting group is used, which can provide an intermediate polymer having a nitrogen protecting group such as Boc.

In some embodiments, $R^2$ is amino.

In some embodiments, $R^2$ is hydrogen and $R^3$ is amino.

In some embodiments, $R^2$ is hydrogen and $R^3$ is guanidino.

In some embodiments, $R^2$ is hydrogen and $R^3$ is a substituted $C_1$-$C_6$ alkyl.

In some embodiments, $R^3$ is $C_1$-$C_6$ alkyl substituted with an amino group.

In some embodiments, $R^3$ is $C_1$ alkyl substituted with an amino group.

In some embodiments, $R^3$ is $C_2$ alkyl substituted with an amino group.

In some embodiments, $R^3$ is $C_3$ alkyl substituted with an amino group.

In some embodiments, $R^3$ is $C_4$ alkyl substituted with an amino group.

In some embodiments, $R^3$ is $C_5$ alkyl substituted with an amino group.

In some embodiments, $R^3$ is $C_6$ alkyl substituted with an amino group.

In some embodiments, $R^1$ is selected from one of the following:

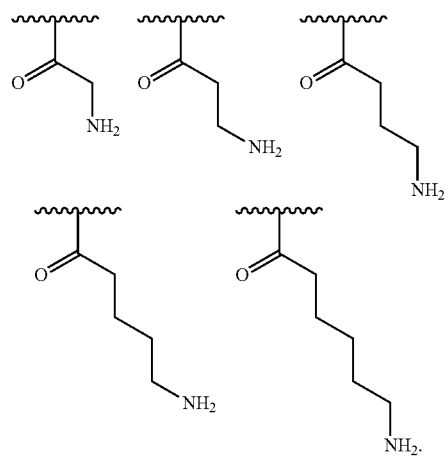

In some embodiments, $R^3$ is $C_1$-$C_6$ alkyl substituted with a guanidino group.

In some embodiments, $R^3$ is $C_1$ alkyl substituted with a guanidino group.

In some embodiments, $R^3$ is $C_2$ alkyl substituted with a guanidino group.

In some embodiments, $R^3$ is $C_3$ alkyl substituted with a guanidino group.

In some embodiments, $R^3$ is $C_4$ alkyl substituted with a guanidino group.

In some embodiments, $R^3$ is $C_5$ alkyl substituted with a guanidino group.

In some embodiments, $R^3$ is $C_6$ alkyl substituted with a guanidino group.

In some embodiments, $R^1$ is selected from one of the following:

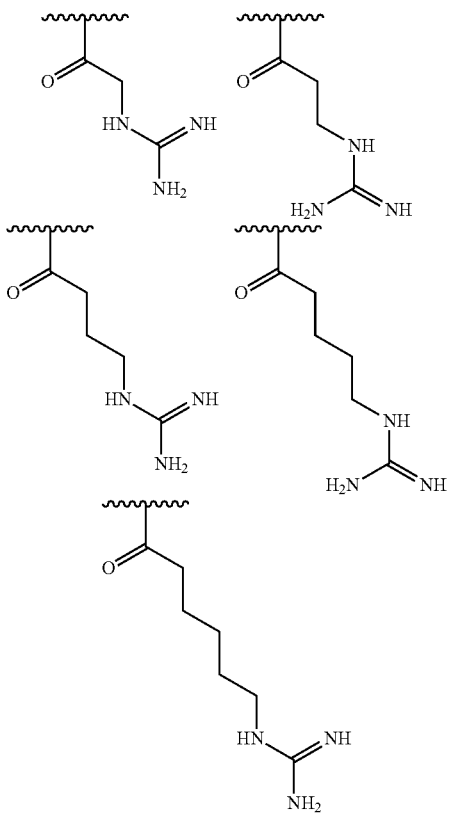

In some embodiments, at least 25% of $R^1$ substituents are H, at least 1% of $R^1$ substituents are acetyl, and at least 2% of $R^1$ substituents independently selected from any of the formulae specifically shown above.

In some embodiments, the functionalized chitosan of formula (I) may be further derivatized on the free hydroxyl moieties.

In some embodiments, the molecular weight of the functionalized chitosan is between 5,000 and 1,000,000 Da.

In some embodiments, the molecular weight of the functionalized chitosan is between 10,000 and 350,000 Da.

In some embodiments, the molecular weight of the functionalized chitosan is between 10,000 and 60,000 Da.

In some embodiments, the molecular weight of the functionalized chitosan is between 15,000 and 45,000 Da.

In some embodiments, the molecular weight of the functionalized chitosan is between 15,000 and 35,000 Da.

In some embodiments, the molecular weight of the functionalized chitosan is between 15,000 and 25,000 Da.

In some embodiments, the functionalized chitosan is soluble in aqueous solution between pH 6 and 8.

In some embodiments, the functionalized chitosan is soluble in aqueous solution between pH 6.8 and pH 7.4.

In one embodiment, the chitosan is functionalized at between 5% and 50%.

In a preferred embodiment, the chitosan is functionalized at between 20% and 30%.

In one embodiment, the degree of deacetylation (% DDA) of the derivatized chitosan is between 75% and 95%.

In one embodiment, the degree of deacetylation (% DDA) of the derivatized chitosan is between 80% and 90%.

In one embodiment, the polydispersity index (PDI) of the derivatized chitosan is between 1.0 and 2.5.

In one embodiment, the polydispersity index (PDI) of the derivatized chitosan is between 1.2 and 1.8.

In some embodiments, the functionalized chitosan is substantially free of other impurities.

In one aspect, the invention features a method of treating a wound in a subject, the method comprising: applying a negative pressure to the wound (e.g., by a vacuum); and contacting the wound with an effective amount of a composition comprising a soluble or derivatized chitosan, thereby treating the wound.

In an embodiment, the composition reduces the healing time or increases the healing rate of the wound. In some embodiments, the composition decreases the inflammation associated with wound or healing of the wound.

In an embodiment, the subject is a human, an animal (e.g., a farm, circus, or zoo animal, or a companion pet).

In an embodiment, the subject has a chronic disease. In an embodiment, the chronic disease is selected from the group consisting of inflammatory bowel disease (IBD) (e.g., Crohn's disease), diabetes (e.g., diabetes mellitus types 1 or type 2), chronic kidney disease (CKD), chronic obstructive pulmonary disease (COPD), hypothyroidism, multiple sclerosis, rheumatoid arthritis, hepatic encephalopathy, peritonitis, periodontitis, sinusitis, rhinitis, sepsis, and systemic lupus erythematosus.

In an embodiment, the subject has been treated or is being treated with one or more of the cancer therapies, e.g., chemotherapy or radiation therapy. In an embodiment, the composition is administered to the subject before, during, or after the subject is treated with the cancer therapy. In an embodiment, the composition is administered to the subject prior to the therapy, e.g., for at least about 1 day, 2 days, 3 days, 5 days, or 1 week. In an embodiment, the composition is administered to the subject less than about 1 day, 2 days, 4 days, 1 week, 2 weeks, 3 weeks, or 4 weeks after the subject is treated with the cancer therapy.

In an embodiment, the subject has been treated or is being treated with immunosuppressive therapy. In an embodiment, the composition is administered to the subject prior to the therapy, e.g., for at least about 1 day, 2 days, 3 days, 5 days, or 1 week. In an embodiment, the composition is administered to the subject less than about 1 day, 2 days, 4 days, 1 week, 2 weeks, 3 weeks, or 4 weeks after the subject is treated with the immunosuppressive therapy.

In an embodiment, the wound is caused by e.g., chemotherapy, radiation therapy, immunosuppressive therapy, chemical damage, biological damage, radiological damage, or immunodeficiency or compromise of immune system (e.g., primary immunodeficiency or acquired immunodeficiency (e.g., AIDS, malnutrition, aging, particular medications (e.g. chemotherapy, disease-modifying antirheumatic drugs, immunosuppressive drugs after organ transplants, glucocorticoids)).

In an embodiment, the wound is the result of an infection, e.g., bacterial or viral infection, and wherein the infection is no longer present when the wound is treated.

In an embodiment, the wound is the result of an infection, e.g., bacterial or viral infection, and wherein the infection is still present when the wound is treated.

In an embodiment, the wound is an acute wound. In an embodiment, the wound is a chronic wound, e.g., a wound that does not heal in an orderly set of stages, in a predictable amount of time, or within three months. In an embodiment, the wound is a surgical wound, e.g., a wound resulted from medical grafting (e.g., skin or bone grafting) at the donor site and/or the graft site, full thickness or partial thickness excision. In an embodiment, the wound is a burn wound.

In an embodiment, the wound is in the epidermis, dermis or hypodermis. In an embodiment, the wound is in the mucosal membrane.

In an embodiment, the wound is a venous ulcer, a diabetic ulcer, a corneal ulcer (or damage to the corneal epithelium), an oral ulcer, a peptic ulcer, or a pressure ulcer.

In an embodiment, the composition is administered to the subject less than about 5 minutes, 15 minutes, 30 minutes, 1 hour, 2 hours, 4 hours, 6 hours, 12 hours, 24 hours, 2 days, 3 days, 4 days, 5 days, 6 days, 7 days, 2 weeks, 4 weeks, 2 months, 4 months, 6 months, 8 months, 10 months, or 1 year after the subject is wounded. In an embodiment, the composition is administered prophylactically, prior to injury, e.g., for at least 1 day, 2 days, 3 days, 5 days, or 1 week.

In an embodiment, the healing time of the wound (e.g., the length of one or more of the inflammatory, proliferative, or remodeling phase of wound healing) is reduced by at least about 10%, 20%, 30%, 40%, 50%, 60%, 70%, 80%, 90%, or 95%, compared to the healing time of the wound (e.g., the length of one or more of the inflammatory, proliferative, or remodeling phase of wound healing) that has not been contacted with the soluble or derivatized chitosan.

In an embodiment, the wound healing rate (e.g., the absolute area healed per day, the percentage of initial area healed per day, or the greatest average wound margin distance from the wound centre divided by the time to complete wound closure) is increased by at least about 1, 2, 3, 4, 5, 6, 7, 8, 9, or 10 fold, compared to the healing rate of the wound that has not been contacted with the soluble or derivatized chitosan.

In an embodiment, the method further comprises administering to the subject a second wound therapy, e.g., antibiotic or antibacterial use, debridement, irrigation, negative pressure wound therapy (vacuum-assisted closure), warming, oxygenation, moist wound healing, removing mechanical stress, and/or adding cells (e.g., keratinocytes) or other materials (e.g., artificial skin substitutes that have fibroblasts and/or keratinocytes in a matrix of collagen) to secrete or enhance levels of healing factors (e.g., vascular endothelial growth factor (VEGF), insulin-like growth factor (IGF), platelet-derived growth factor (PDGF), transforming growth factor-$\beta$ (TGF-$\beta$), and epidermal growth factor (EGF)).

In an embodiment, the second wound therapy comprises a negative pressure wound therapy (vacuum-assisted closure).

In an embodiment, the second wound therapy comprises an antibiotic. In an embodiment, the composition overcomes (e.g., reduces, decreases, prevents) a deleterious effect of the antibiotic in wound healing.

In an embodiment, the second wound therapy comprises a steroidal or non-steroidal anti-inflammatory drug (NSIAD). In an embodiment, the composition acts additively or synergysically with the steroidal or non-steroidal anti-inflammatory drug.

In an embodiment, the composition is administered topically or orally, e.g., by topical rinse, gel, spray, oral, enema, inhalation, dry powder, aerosolized liquid, aerosolized powder, or eye drop. In some embodiments, the composition is administered orally to treat a wound (e.g., damaged mucosa) in the gastrointestinal tract and/or an inflammatory gastrointestinal disorder. In some embodiments, the composition is administered topically to treat a wound and/or reduce or prevent a scar, e.g., in the eye.

In an embodiment, the effective amount is therapeutically effective amount.

In one embodiment, the soluble or derivatized chitosan is soluble in aqueous solution from about pH 6.8 to about pH 7.4.

In one embodiment, the soluble or derivatized chitosan is soluble in aqueous solution from about pH 3 to about pH 9.

In one embodiment, the soluble or derivatized chitosan is soluble in aqueous solution from about pH 5.0 to about pH 6.0, e.g., in wounds or duodenum.

In one embodiment, the soluble or derivatized chitosan is soluble in aqueous solution from about pH 2.0 to about pH 4.0, e.g., in stomach.

In one embodiment, the soluble or derivatized chitosan is soluble in aqueous solution from about pH 8.0 to about pH 8.5, e.g., in lower part of the gastrointestinal tract.

In one embodiment, the derivatized chitosan comprises a chitosan of the following formula (I):

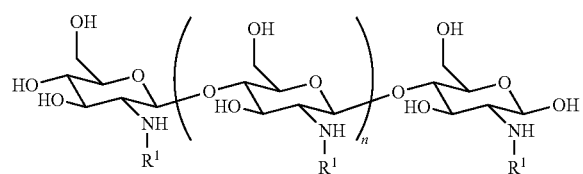

formula (I)

wherein:

n is an integer between 20 and 6000; and each $R^1$ is independently selected for each occurrence from hydrogen, acetyl, and either:

a) a group of formula (II):

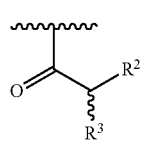

formula (II)

wherein $R^2$ is hydrogen or amino; and $R^3$ is amino, guanidino, $C_1$-$C_6$ alkyl substituted with an amino or guanidino moiety, or a natural or unnatural amino acid side chain;

or b) $R^1$, when taken together with the nitrogen to which it is attached, forms a guanidine moiety;

wherein at least 25% of $R^1$ substituents are H, at least 1% of $R^1$ substituents are acetyl, and at least 2% of $R^1$ substituents are a group of formula (II) or are taken together with the nitrogen to which they are attached to form a guanidine moiety.

In one embodiment, the derivatized chitosan comprises of the following formula (I) wherein at least 90% by number or weight of $R^1$ moieties are as defined in formula (I) (e.g., at least about 95%, at least about 96%, at least about 97%, at least about 98%, or at least about 99%):

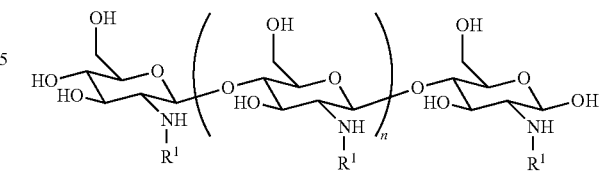

formula (I)

wherein:

n is an integer between 20 and 6000; and each $R^1$ is independently selected for each occurrence from hydrogen, acetyl, and either:

a) a group of formula (II):

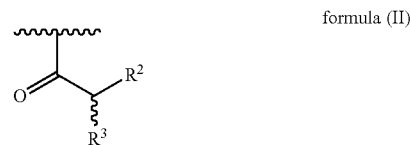

formula (II)

wherein $R^2$ is hydrogen or amino; and $R^3$ is amino, guanidino, $C_1$-$C_6$ alkyl substituted with an amino or guanidino moiety, or a natural or unnatural amino acid side chain;

or b) $R^1$, when taken together with the nitrogen to which it is attached, forms a guanidine moiety;

wherein at least 25% of $R^1$ substituents are H, at least 1% of $R^1$ substituents are acetyl, and at least 2% of $R^1$ substituents are a group of formula (II) or are taken together with the nitrogen to which they are attached to form a guanidine moiety.

In some embodiments, between 25-95% of $R^1$ substituents are hydrogen.

In some embodiments, between 55-90% of $R^1$ substituents are hydrogen.

In some embodiments, between 1-50% of $R^1$ substituents are acetyl.

In some embodiments, between 4-20% of $R^1$ substituents are acetyl.

In some embodiments, between 2-50% of $R^1$ substituents are a group of formula (II).

In some embodiments, between 4-30% of $R^1$ substituents are a group of formula (II).

In some embodiments, 55-90% of $R^1$ substituents are hydrogen, 4-20% of $R^1$ substituents are acetyl, 4-30% of $R^1$ substituents are a group of formula (II).

In some embodiments, $R^2$ is amino and $R^3$ is an arginine side chain.

In some embodiments, $R^1$ is selected from one of the following:

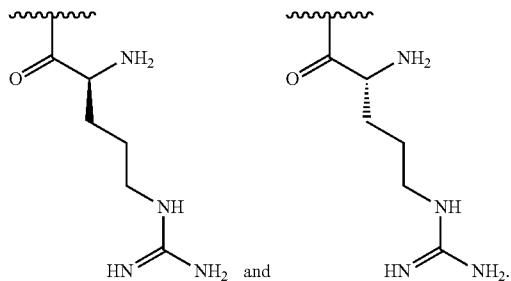 [SMILES: *C(=O)[C@@H](N)CCCNC(=N)N ; *C(=O)[C@H](N)CCCNC(=N)N]

In some embodiments, $R^2$ is amino and $R^3$ is a lysine side chain.

In some embodiments, $R^1$ is selected from one of the following:

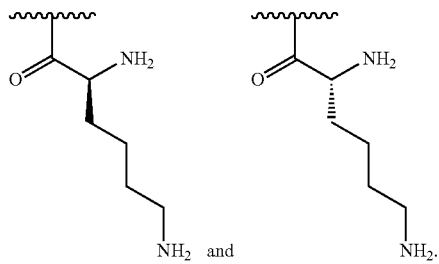 [SMILES: *C(=O)[C@@H](N)CCCCN ; *C(=O)[C@H](N)CCCCN]

In some embodiments, $R^2$ is amino and $R^3$ is a histidine side chain.

In some embodiments, $R^1$ is selected from one of the following:

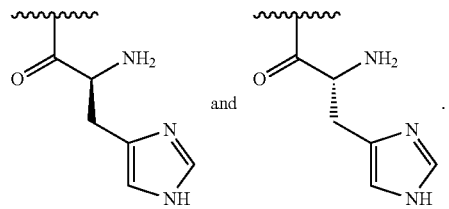 [SMILES: *C(=O)[C@@H](N)Cc1c[nH]cn1 ; *C(=O)[C@H](N)Cc1c[nH]cn1]

In some embodiments, at least 1% of $R^1$ substituents are selected from one of the following:

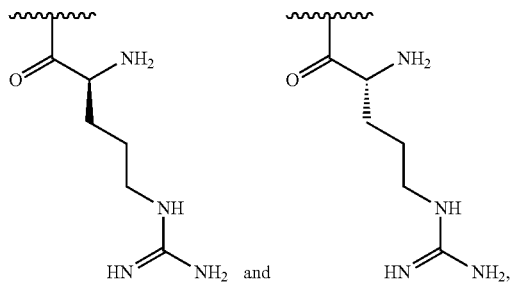 [SMILES: *C(=O)[C@@H](N)CCCNC(=N)N ; *C(=O)[C@H](N)CCCNC(=N)N]

AND at least 1% of $R^1$ substituents are selected from the following:

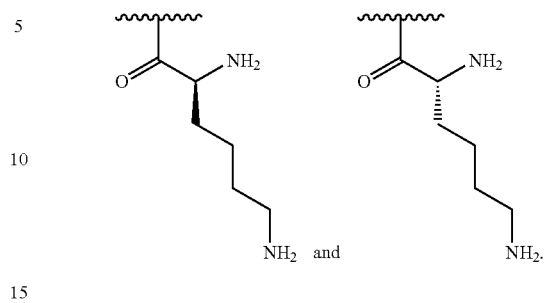

In some embodiments, $R^2$ is amino and $R^3$ is a substituted $C_1$-$C_6$ alkyl.

In some embodiments, $R^3$ is $C_1$-$C_6$ alkyl substituted with an amino group.

In some embodiments, $R^3$ is $C_1$ alkyl substituted with an amino group.

In some embodiments, $R^3$ is $C_2$ alkyl substituted with an amino group.

In some embodiments, $R^3$ is $C_3$ alkyl substituted with an amino group.

In some embodiments, $R^3$ is $C_4$ alkyl substituted with an amino group.

In some embodiments, $R^3$ is $C_5$ alkyl substituted with an amino group.

In some embodiments, $R^3$ is $C_6$ alkyl substituted with an amino group.

In some embodiments, $R^1$ is selected from one of the following:

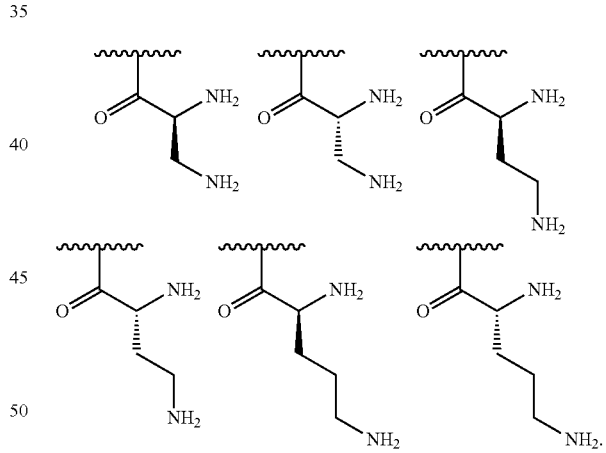

In some embodiments, $R^3$ is $C_1$-$C_6$ alkyl substituted with a guanidino group.

In some embodiments, $R^3$ is $C_1$ alkyl substituted with a guanidino group.

In some embodiments, $R^3$ is $C_2$ alkyl substituted with a guanidino group.

In some embodiments, $R^3$ is $C_3$ alkyl substituted with a guanidino group.

In some embodiments, $R^3$ is $C_4$ alkyl substituted with a guanidino group.

In some embodiments, $R^3$ is $C_5$ alkyl substituted with a guanidino group.

In some embodiments, $R^3$ is $C_6$ alkyl substituted with a guanidino group.

In some embodiments, $R^1$ is selected from one of the following:

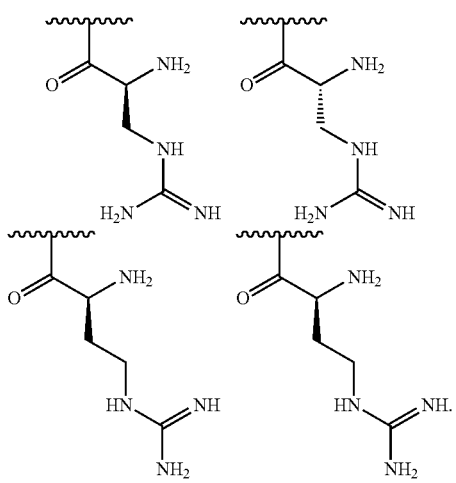

In some embodiments, wherein $R^2$ is amino that is substituted with a nitrogen protecting group prior to substitution on chitosan and removed subsequent to substitution on chitosan.

In some embodiments, the nitrogen protecting group is tert-butyloxycarbonyl (Boc).

In some embodiments, in the synthetic process a nitrogen protecting group is used, which can provide an intermediate polymer having a nitrogen protecting group such as Boc.

In some embodiments, $R^2$ is amino.

In some embodiments, $R^2$ is hydrogen and $R^3$ is amino.

In some embodiments, $R^2$ is hydrogen and $R^3$ is guanidino.

In some embodiments, $R^2$ is hydrogen and $R^3$ is a substituted $C_1$-$C_6$ alkyl.

In some embodiments, $R^3$ is $C_1$-$C_6$ alkyl substituted with an amino group.

In some embodiments, $R^3$ is $C_1$ alkyl substituted with an amino group.

In some embodiments, $R^3$ is $C_2$ alkyl substituted with an amino group.

In some embodiments, $R^3$ is $C_3$ alkyl substituted with an amino group.

In some embodiments, $R^3$ is $C_4$ alkyl substituted with an amino group.

In some embodiments, $R^3$ is $C_5$ alkyl substituted with an amino group.

In some embodiments, $R^3$ is $C_6$ alkyl substituted with an amino group.

In some embodiments, $R^1$ is selected from one of the following:

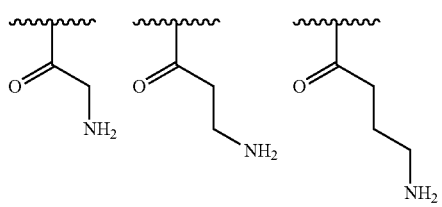

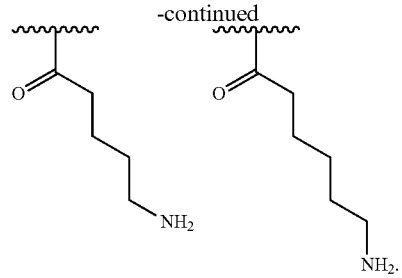

In some embodiments, $R^3$ is $C_1$-$C_6$ alkyl substituted with a guanidino group.

In some embodiments, $R^3$ is $C_1$ alkyl substituted with a guanidino group.

In some embodiments, $R^3$ is $C_2$ alkyl substituted with a guanidino group.

In some embodiments, $R^3$ is $C_3$ alkyl substituted with a guanidino group.

In some embodiments, $R^3$ is $C_4$ alkyl substituted with a guanidino group.

In some embodiments, $R^3$ is $C_5$ alkyl substituted with a guanidino group.

In some embodiments, $R^3$ is $C_6$ alkyl substituted with a guanidino group.

In some embodiments, $R^1$ is selected from one of the following:

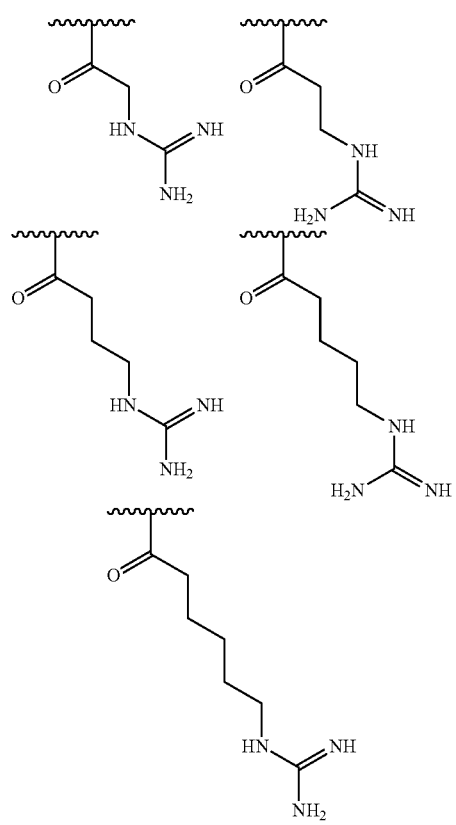

In some embodiments, at least 25% of $R^1$ substituents are H, at least 1% of $R^1$ substituents are acetyl, and at least 2% of $R^1$ substituents independently selected from any of the formulae specifically shown above.

In some embodiments, the functionalized chitosan of formula (I) may be further derivatized on the free hydroxyl moieties.

In some embodiments, the molecular weight of the functionalized chitosan is between 5,000 and 1,000,000 Da.

In some embodiments, the molecular weight of the functionalized chitosan is between 10,000 and 350,000 Da.

In some embodiments, the molecular weight of the functionalized chitosan is between 10,000 and 60,000 Da.

In some embodiments, the molecular weight of the functionalized chitosan is between 15,000 and 45,000 Da.

In some embodiments, the molecular weight of the functionalized chitosan is between 15,000 and 35,000 Da.

In some embodiments, the molecular weight of the functionalized chitosan is between 15,000 and 25,000 Da.

In some embodiments, the functionalized chitosan is soluble in aqueous solution between pH 6 and 8.

In some embodiments, the functionalized chitosan is soluble in aqueous solution between pH 6.8 and pH 7.4.

In one embodiment, the chitosan is functionalized at between 5% and 50%.

In a preferred embodiment, the chitosan is functionalized at between 20% and 30%.

In one embodiment, the degree of deacetylation (% DDA) of the derivatized chitosan is between 75% and 95%.

In one embodiment, the degree of deacetylation (% DDA) of the derivatized chitosan is between 80% and 90%.

In one embodiment, the polydispersity index (PDI) of the derivatized chitosan is between 1.0 and 2.5.

In one embodiment, the polydispersity index (PDI) of the derivatized chitosan is between 1.2 and 1.8.

In some embodiments, the functionalized chitosan is substantially free of other impurities.

In one aspect, the invention features a wound dressing, comprising a gel or an absorbable pad that holds an effective amount of a soluble or derivatized chitosan on the surface of the wound or provides continuous delivery of an effective amount of a soluble or derivatized chtiosan to the wound.

In an embodiment, the composition reduces the healing time or increase the healing rate of the wound. In some embodiments, the composition decreases the inflammation associated with wound or healing of the wound.

In an embodiment, the wound is not infected, e.g., bacterially or virally infected, when treated. In another embodiment, the wound is infected, e.g., bacterially or virally infected, when treated.

In an embodiment, the wound is caused by e.g., chemotherapy, radiation therapy, immunosuppressive therapy, chemical damage, biological damage, radiological damage, or immunodeficiency or compromise of immune system (e.g., primary immunodeficiency or acquired immunodeficiency (e.g., AIDS, malnutrition, aging, particular medications (e.g. chemotherapy, disease-modifying antirheumatic drugs, immunosuppressive drugs after organ transplants, glucocorticoids)).

In an embodiment, the wound is the result of an infection, e.g., bacterial or viral infection, and wherein the infection is no longer present when the wound is treated. In another embodiment, the wound is the result of an infection, e.g., bacterial or viral infection, and wherein the infection is still present when the wound is treated.

In an embodiment, the wound is an acute wound. In an embodiment, the wound is a chronic wound, e.g., a wound that does not heal in an orderly set of stages, in a predictable amount of time, or within three months. In an embodiment, the wound is a surgical wound, e.g., a wound resulted from medical grafting (e.g., skin or bone grafting) at the donor site and/or the graft site, or full thickness or partial thickness excision. In an embodiment, the wound is a burn. In an embodiment, the burn is caused by e.g., heat, electricity, chemicals, light, radiation, or friction. In an embodiment, the burn is a first, second, third, or fourth degree burn. In an embodiment, the burn is a superficial, superficial partial-thickness, deep partial-thickness, or full-thickness burn. In an embodiment, the burn affects e.g., skin (epidermal tissue and dermis) and/or deeper tissues, e.g., muscle, bone, and blood vessels. In an embodiment, the dressing further comprises a second burn treatment, e.g., antibiotics, pain management (e.g., analgesics (e.g., ibuprofen, acetaminophen), narcotics, local anesthetics). In an embodiment, the second burn therapy comprises an antibiotic. In an embodiment, the composition overcomes (e.g., reduces, decreases, and/or prevents) a deleterious effect of the antibiotic in burn wound healing.

In an embodiment, the wound is in the epidermis, dermis or hypodermis. In an embodiment, the wound is in the mucosal membrane.

In an embodiment, the wound is a venous ulcer, a diabetic ulcer, a corneal ulcer (or damage to the corneal epithelium), an oral ulcer, a peptic ulcer, or a pressure ulcer.

In an embodiment, the dressing further comprises a second wound therapy, e.g., antibiotic or antibacterial use. In an embodiment, the second wound therapy comprises an antibiotic. In an embodiment, the composition overcomes (e.g., reduces, decreases, and/or prevents) a deleterious effect of the antibiotic in wound healing. In an embodiment, the second wound therapy comprises a steroidal or non-steroidal anti-inflammatory drug (NSIAD). In an embodiment, the composition acts additively or synergysically with the steroidal or non-steroidal anti-inflammatory drug.

In an embodiment, the effective amount is therapeutically effective amount.

In one embodiment, the soluble or derivatized chitosan is soluble in aqueous solution from about pH 6.8 to about pH 7.4.

In one embodiment, the soluble or derivatized chitosan is soluble in aqueous solution from about pH 3 to about pH 9.

In one embodiment, the soluble or derivatized chitosan is soluble in aqueous solution from about pH 5.0 to about pH 6.0, e.g., in wounds or duodenum.

In one embodiment, the soluble or derivatized chitosan is soluble in aqueous solution from about pH 2.0 to about pH 4.0, e.g., in stomach.

In one embodiment, the soluble or derivatized chitosan is soluble in aqueous solution from about pH 8.0 to about pH 8.5, e.g., in lower part of the gastrointestinal tract.

In one embodiment, the derivatized chitosan comprises a chitosan of the following formula (I):

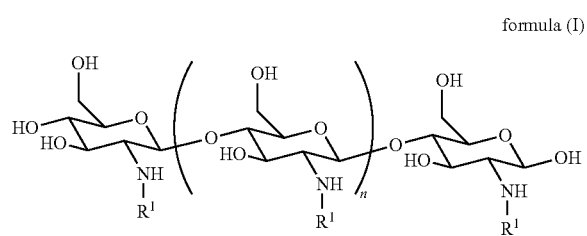

formula (I)

wherein:

n is an integer between 20 and 6000; and each $R^1$ is independently selected for each occurrence from hydrogen, acetyl, and either:

a) a group of formula (II):

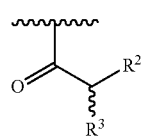

formula (II)

wherein $R^2$ is hydrogen or amino; and $R^3$ is amino, guanidino, $C_1$-$C_6$ alkyl substituted with an amino or guanidino moiety, or a natural or unnatural amino acid side chain;

or b) $R^1$, when taken together with the nitrogen to which it is attached, forms a guanidine moiety;

wherein at least 25% of $R^1$ substituents are H, at least 1% of $R^1$ substituents are acetyl, and at least 2% of $R^1$ substituents are a group of formula (II) or are taken together with the nitrogen to which they are attached to form a guanidine moiety.

In one embodiment, the derivatized chitosan comprises of the following formula (I) wherein at least 90% by number or weight of $R^1$ moieties are as defined in formula (I) (e.g., at least about 95%, at least about 96%, at least about 97%, at least about 98%, or at least about 99%):

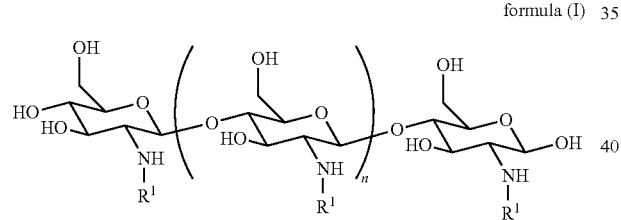

formula (I)

wherein:

n is an integer between 20 and 6000; and each $R^1$ is independently selected for each occurrence from hydrogen, acetyl, and either:

a) a group of formula (II):

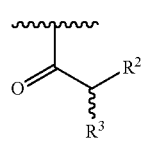

formula (II)

wherein $R^2$ is hydrogen or amino; and $R^3$ is amino, guanidino, $C_1$-$C_6$ alkyl substituted with an amino or guanidino moiety, or a natural or unnatural amino acid side chain;

or b) $R^1$, when taken together with the nitrogen to which it is attached, forms a guanidine moiety;

wherein at least 25% of $R^1$ substituents are H, at least 1% of $R^1$ substituents are acetyl, and at least 2% of $R^1$ substituents are a group of formula (II) or are taken together with the nitrogen to which they are attached to form a guanidine moiety.

In some embodiments, between 25-95% of $R^1$ substituents are hydrogen.

In some embodiments, between 55-90% of $R^1$ substituents are hydrogen.

In some embodiments, between 1-50% of $R^1$ substituents are acetyl.

In some embodiments, between 4-20% of $R^1$ substituents are acetyl.

In some embodiments, between 2-50% of $R^1$ substituents are a group of formula (II).

In some embodiments, between 4-30% of $R^1$ substituents are a group of formula (II).

In some embodiments, 55-90% of $R^1$ substituents are hydrogen, 4-20% of $R^1$ substituents are acetyl, 4-30% of $R^1$ substituents are a group of formula (II).

In some embodiments, $R^2$ is amino and $R^3$ is an arginine side chain.

In some embodiments, $R^1$ is selected from one of the following:

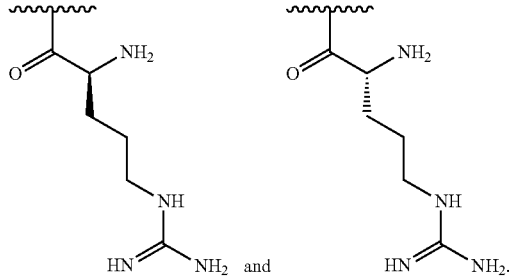 [SMILES: *C(=O)[C@@H](N)CCCNC(=N)N ; *C(=O)[C@H](N)CCCNC(=N)N]

In some embodiments, $R^2$ is amino and $R^3$ is a lysine side chain.

In some embodiments, $R^1$ is selected from one of the following:

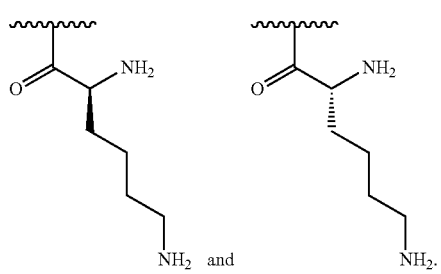 [SMILES: *C(=O)[C@@H](N)CCCCN ; *C(=O)[C@H](N)CCCCN]

In some embodiments, $R^2$ is amino and $R^3$ is a histidine side chain.

In some embodiments, $R^1$ is selected from one of the following:

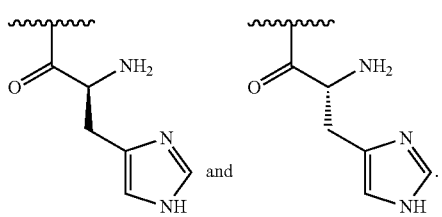 [SMILES: *C(=O)[C@@H](N)Cc1c[nH]cn1 ; *C(=O)[C@H](N)Cc1c[nH]cn1]

In some embodiments, at least 1% of $R^1$ substituents are selected from one of the following:

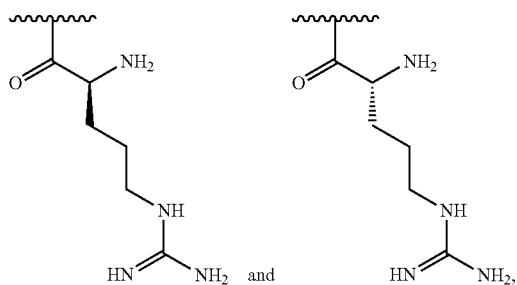 [SMILES: *C(=O)[C@@H](N)CCCNC(=N)N ; *C(=O)[C@H](N)CCCNC(=N)N]

AND at least 1% of $R^1$ substituents are selected from the following:

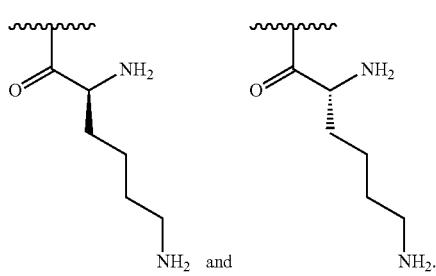 [SMILES: *C(=O)[C@@H](N)CCCCN ; *C(=O)[C@H](N)CCCCN]

In some embodiments, $R^2$ is amino and $R^3$ is a substituted $C_1$-$C_6$ alkyl.

In some embodiments, $R^3$ is $C_1$-$C_6$ alkyl substituted with an amino group.

In some embodiments, $R^3$ is $C_1$ alkyl substituted with an amino group.

In some embodiments, $R^3$ is $C_2$ alkyl substituted with an amino group.

In some embodiments, $R^3$ is $C_3$ alkyl substituted with an amino group.

In some embodiments, $R^3$ is $C_4$ alkyl substituted with an amino group.

In some embodiments, $R^3$ is $C_5$ alkyl substituted with an amino group.

In some embodiments, $R^3$ is $C_6$ alkyl substituted with an amino group.

In some embodiments, $R^1$ is selected from one of the following:

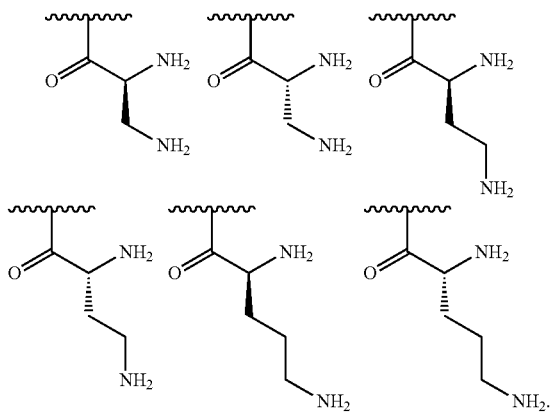

In some embodiments, $R^3$ is $C_1$-$C_6$ alkyl substituted with a guanidino group.

In some embodiments, $R^3$ is $C_1$ alkyl substituted with a guanidino group.

In some embodiments, $R^3$ is $C_2$ alkyl substituted with a guanidino group.

In some embodiments, $R^3$ is $C_3$ alkyl substituted with a guanidino group.

In some embodiments, $R^3$ is $C_4$ alkyl substituted with a guanidino group.

In some embodiments, $R^3$ is $C_5$ alkyl substituted with a guanidino group.

In some embodiments, $R^3$ is $C_6$ alkyl substituted with a guanidino group.

In some embodiments, $R^1$ is selected from one of the following:

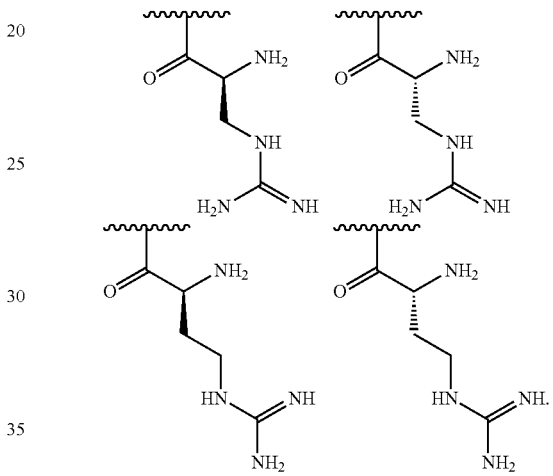

In some embodiments, wherein $R^2$ is amino that is substituted with a nitrogen protecting group prior to substitution on chitosan and removed subsequent to substitution on chitosan.

In some embodiments, the nitrogen protecting group is tert-butyloxycarbonyl (Boc).

In some embodiments, in the synthetic process a nitrogen protecting group is used, which can provide an intermediate polymer having a nitrogen protecting group such as Boc.

In some embodiments, $R^2$ is amino.

In some embodiments, $R^2$ is hydrogen and $R^3$ is amino.

In some embodiments, $R^2$ is hydrogen and $R^3$ is guanidino.

In some embodiments, $R^2$ is hydrogen and $R^3$ is a substituted $C_1$-$C_6$ alkyl.

In some embodiments, $R^3$ is $C_1$-$C_6$ alkyl substituted with an amino group.

In some embodiments, $R^3$ is $C_1$ alkyl substituted with an amino group.

In some embodiments, $R^3$ is $C_2$ alkyl substituted with an amino group.

In some embodiments, $R^3$ is $C_3$ alkyl substituted with an amino group.

In some embodiments, $R^3$ is $C_4$ alkyl substituted with an amino group.

In some embodiments, $R^3$ is $C_5$ alkyl substituted with an amino group.

In some embodiments, $R^3$ is $C_6$ alkyl substituted with an amino group.

In some embodiments, $R^1$ is selected from one of the following:

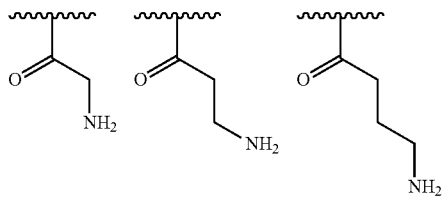

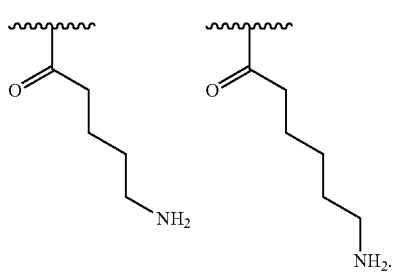

In some embodiments, $R^3$ is $C_1$-$C_6$ alkyl substituted with a guanidino group.

In some embodiments, $R^3$ is $C_1$ alkyl substituted with a guanidino group.

In some embodiments, $R^3$ is $C_2$ alkyl substituted with a guanidino group.

In some embodiments, $R^3$ is $C_3$ alkyl substituted with a guanidino group.

In some embodiments, $R^3$ is $C_4$ alkyl substituted with a guanidino group.

In some embodiments, $R^3$ is $C_5$ alkyl substituted with a guanidino group.

In some embodiments, $R^3$ is $C_6$ alkyl substituted with a guanidino group.

In some embodiments, $R^1$ is selected from one of the following:

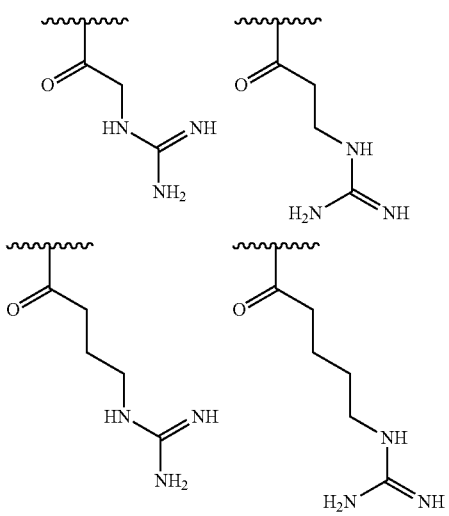

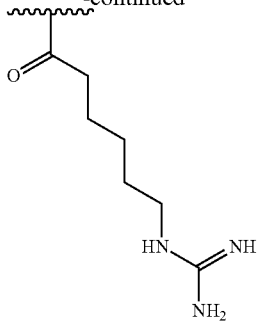

-continued

In some embodiments, at least 25% of $R^1$ substituents are H, at least 1% of $R^1$ substituents are acetyl, and at least 2% of $R^1$ substituents independently selected from any of the formulae specifically shown above.

In some embodiments, the functionalized chitosan of formula (I) may be further derivatized on the free hydroxyl moieties.

In some embodiments, the molecular weight of the functionalized chitosan is between 5,000 and 1,000,000 Da.

In some embodiments, the molecular weight of the functionalized chitosan is between 10,000 and 350,000 Da.

In some embodiments, the molecular weight of the functionalized chitosan is between 10,000 and 60,000 Da.

In some embodiments, the molecular weight of the functionalized chitosan is between 15,000 and 45,000 Da.

In some embodiments, the molecular weight of the functionalized chitosan is between 15,000 and 35,000 Da.

In some embodiments, the molecular weight of the functionalized chitosan is between 15,000 and 25,000 Da.

In some embodiments, the functionalized chitosan is soluble in aqueous solution between pH 6 and 8.

In some embodiments, the functionalized chitosan is soluble in aqueous solution between pH 6.8 and pH 7.4.

In one embodiment, the chitosan is functionalized at between 5% and 50%.

In a preferred embodiment, the chitosan is functionalized at between 20% and 30%.

In one embodiment, the degree of deacetylation (% DDA) of the derivatized chitosan is between 75% and 95%.

In one embodiment, the degree of deacetylation (% DDA) of the derivatized chitosan is between 80% and 90%.

In one embodiment, the polydispersity index (PDI) of the derivatized chitosan is between 1.0 and 2.5.

In one embodiment, the polydispersity index (PDI) of the derivatized chitosan is between 1.2 and 1.8.

In some embodiments, the functionalized chitosan is substantially free of other impurities.

In one aspect, the invention features a wound dressing, comprising: a biocompatible pad shaped to conform to a wound site; an air-tight seal removably adhered to the pad; a negative pressure source in fluid communication with the pad; and a composition comprising a soluble or derivatized chitosan.

In an embodiment, the wound dressing is adapted to be positioned adjacent to the wound. In an embodiment, the wound dressing is a foam dressing or a gauze dressing. In an embodiment, the wound dressing further comprises a flexible tube communicating between said pad and said negative pressure source. In an embodiment, the wound dressing further comprises a removable canister in fluid communication between said pad and said negative pressure source.

In an embodiment, the composition reduces the healing time or increase the healing rate of a wound. In some embodiments, the composition decreases the inflammation associated with wound or healing of the wound.

In one embodiment, the soluble or derivatized chitosan is soluble in aqueous solution from about pH 6.8 to about pH 7.4.

In one embodiment, the soluble or derivatized chitosan is soluble in aqueous solution from about pH 3 to about pH 9.

In one embodiment, the soluble or derivatized chitosan is soluble in aqueous solution from about pH 5.0 to about pH 6.0, e.g., in wounds or duodenum.

In one embodiment, the soluble or derivatized chitosan is soluble in aqueous solution from about pH 2.0 to about pH 4.0, e.g., in stomach.

In one embodiment, the soluble or derivatized chitosan is soluble in aqueous solution from about pH 8.0 to about pH 8.5, e.g., in lower part of the gastrointestinal tract.

In one embodiment, the derivatized chitosan comprises a chitosan of the following formula (I):

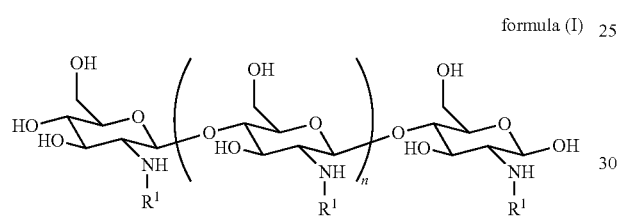

formula (I)

wherein:

n is an integer between 20 and 6000; and each $R^1$ is independently selected for each occurrence from hydrogen, acetyl, and either:

a) a group of formula (II):

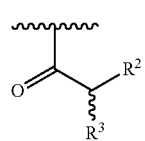

formula (II)

wherein $R^2$ is hydrogen or amino; and $R^3$ is amino, guanidino, $C_1$-$C_6$ alkyl substituted with an amino or guanidino moiety, or a natural or unnatural amino acid side chain;

or b) $R^1$, when taken together with the nitrogen to which it is attached, forms a guanidine moiety;

wherein at least 25% of $R^1$ substituents are H, at least 1% of $R^1$ substituents are acetyl, and at least 2% of $R^1$ substituents are a group of formula (II) or are taken together with the nitrogen to which they are attached to form a guanidine moiety.

In one embodiment, the derivatized chitosan comprises of the following formula (I) wherein at least 90% by number or weight of $R^1$ moieties are as defined in formula (I) (e.g., at least about 95%, at least about 96%, at least about 97%, at least about 98%, or at least about 99%):

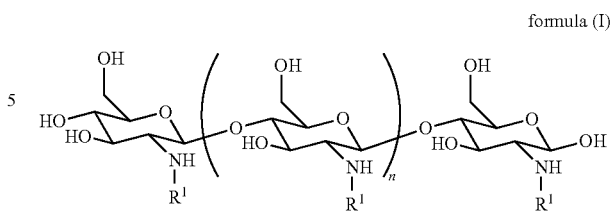

formula (I)

wherein:

n is an integer between 20 and 6000; and each $R^1$ is independently selected for each occurrence from hydrogen, acetyl, and either:

a) a group of formula (II):

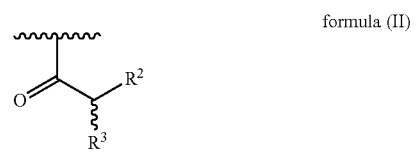

formula (II)

wherein $R^2$ is hydrogen or amino; and $R^3$ is amino, guanidino, $C_1$-$C_6$ alkyl substituted with an amino or guanidino moiety, or a natural or unnatural amino acid side chain;

or b) $R^1$, when taken together with the nitrogen to which it is attached, forms a guanidine moiety;

wherein at least 25% of $R^1$ substituents are H, at least 1% of $R^1$ substituents are acetyl, and at least 2% of $R^1$ substituents are a group of formula (II) or taken together with the nitrogen to which they are attached to form a guanidine moiety.

In some embodiments, between 25-95% of $R^1$ substituents are hydrogen.

In some embodiments, between 55-90% of $R^1$ substituents are hydrogen.

In some embodiments, between 1-50% of $R^1$ substituents are acetyl.

In some embodiments, between 4-20% of $R^1$ substituents are acetyl.

In some embodiments, between 2-50% of $R^1$ substituents are a group of formula (II).

In some embodiments, between 4-30% of $R^1$ substituents are a group of formula (II).

In some embodiments, 55-90% of $R^1$ substituents are hydrogen, 4-20% of $R^1$ substituents are acetyl, 4-30% of $R^1$ substituents are a group of formula (II).

In some embodiments, $R^2$ is amino and $R^3$ is an arginine side chain.

In some embodiments, $R^1$ is selected from one of the following:

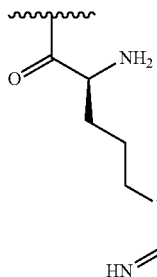 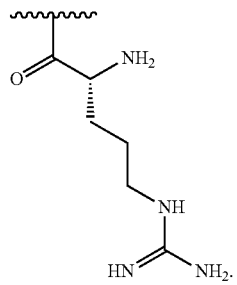

In some embodiments, $R^2$ is amino and $R^3$ is a lysine side chain.

In some embodiments, $R^1$ is selected from one of the following:

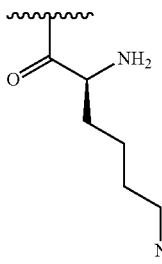 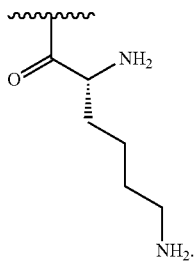

In some embodiments, $R^2$ is amino and $R^3$ is a histidine side chain.

In some embodiments, $R^1$ is selected from one of the following:

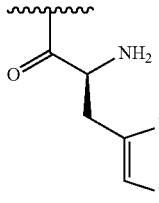 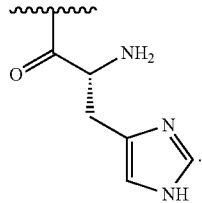

In some embodiments, at least 1% of $R^1$ substituents are selected from one of the following:

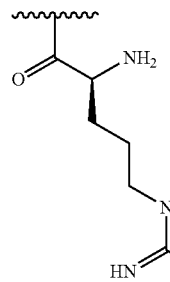 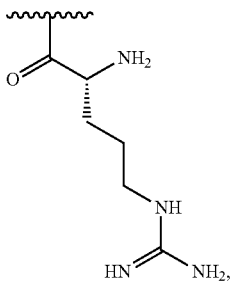

AND at least 1% of $R^1$ substituents are selected from the following:

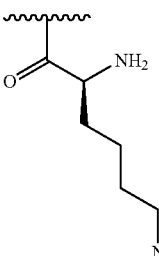 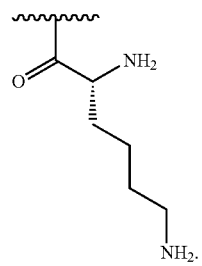

In some embodiments, $R^2$ is amino and $R^3$ is a substituted $C_1$-$C_6$ alkyl.

In some embodiments, $R^3$ is $C_1$-$C_6$ alkyl substituted with an amino group.

In some embodiments, $R^3$ is $C_1$ alkyl substituted with an amino group.

In some embodiments, $R^3$ is $C_2$ alkyl substituted with an amino group.

In some embodiments, $R^3$ is $C_3$ alkyl substituted with an amino group.

In some embodiments, $R^3$ is $C_4$ alkyl substituted with an amino group.

In some embodiments, $R^3$ is $C_5$ alkyl substituted with an amino group.

In some embodiments, $R^3$ is $C_6$ alkyl substituted with an amino group.

In some embodiments, $R^3$ is selected from one of the following:

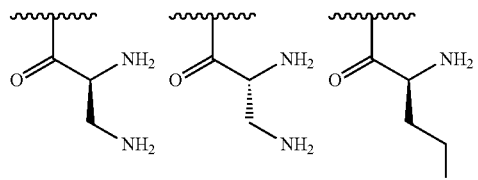

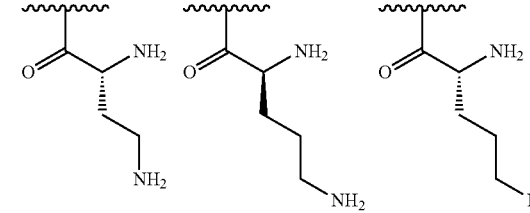

In some embodiments, $R^3$ is $C_1$-$C_6$ alkyl substituted with a guanidino group.

In some embodiments, $R^3$ is $C_1$ alkyl substituted with a guanidino group.

In some embodiments, $R^3$ is $C_2$ alkyl substituted with a guanidino group.

In some embodiments, $R^3$ is $C_3$ alkyl substituted with a guanidino group.

In some embodiments, $R^3$ is $C_4$ alkyl substituted with a guanidino group.

In some embodiments, $R^3$ is $C_5$ alkyl substituted with a guanidino group.

In some embodiments, $R^3$ is $C_6$ alkyl substituted with a guanidino group.

In some embodiments, $R^1$ is selected from one of the following:

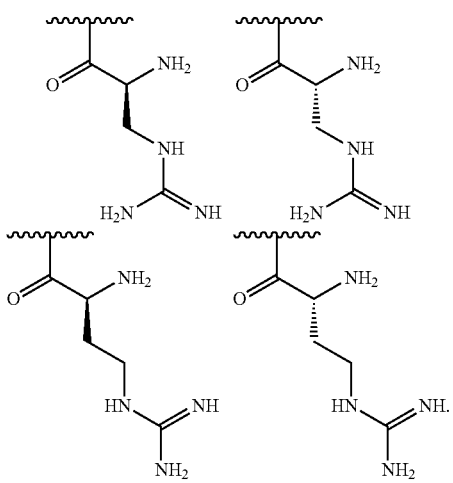

In some embodiments, wherein $R^2$ is amino that is substituted with a nitrogen protecting group prior to substitution on chitosan and removed subsequent to substitution on chitosan.

In some embodiments, the nitrogen protecting group is tert-butyloxycarbonyl (Boc).

In some embodiments, in the synthetic process a nitrogen protecting group is used, which can provide an intermediate polymer having a nitrogen protecting group such as Boc.

In some embodiments, $R^2$ is amino.

In some embodiments, $R^2$ is hydrogen and $R^3$ is amino.

In some embodiments, $R^2$ is hydrogen and $R^3$ is guanidino.

In some embodiments, $R^2$ is hydrogen and $R^3$ is a substituted $C_1$-$C_6$ alkyl.

In some embodiments, $R^3$ is $C_1$-$C_6$ alkyl substituted with an amino group.

In some embodiments, $R^3$ is $C_1$ alkyl substituted with an amino group.

In some embodiments, $R^3$ is $C_2$ alkyl substituted with an amino group.

In some embodiments, $R^3$ is $C_3$ alkyl substituted with an amino group.

In some embodiments, $R^3$ is $C_4$ alkyl substituted with an amino group.

In some embodiments, $R^3$ is $C_5$ alkyl substituted with an amino group.

In some embodiments, $R^3$ is $C_6$ alkyl substituted with an amino group.

In some embodiments, $R^1$ is selected from one of the following:

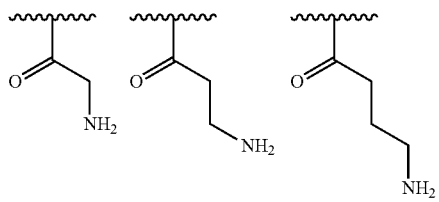

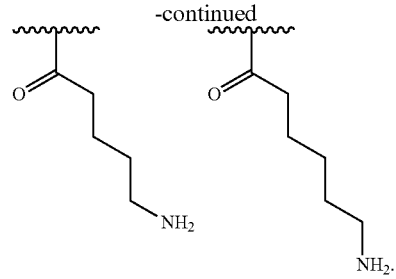

In some embodiments, $R^3$ is $C_1$-$C_6$ alkyl substituted with a guanidino group.

In some embodiments, $R^3$ is $C_1$ alkyl substituted with a guanidino group.

In some embodiments, $R^3$ is $C_2$ alkyl substituted with a guanidino group.

In some embodiments, $R^3$ is $C_3$ alkyl substituted with a guanidino group.

In some embodiments, $R^3$ is $C_4$ alkyl substituted with a guanidino group.

In some embodiments, $R^3$ is $C_5$ alkyl substituted with a guanidino group.

In some embodiments, $R^3$ is $C_6$ alkyl substituted with a guanidino group.

In some embodiments, $R^1$ is selected from one of the following:

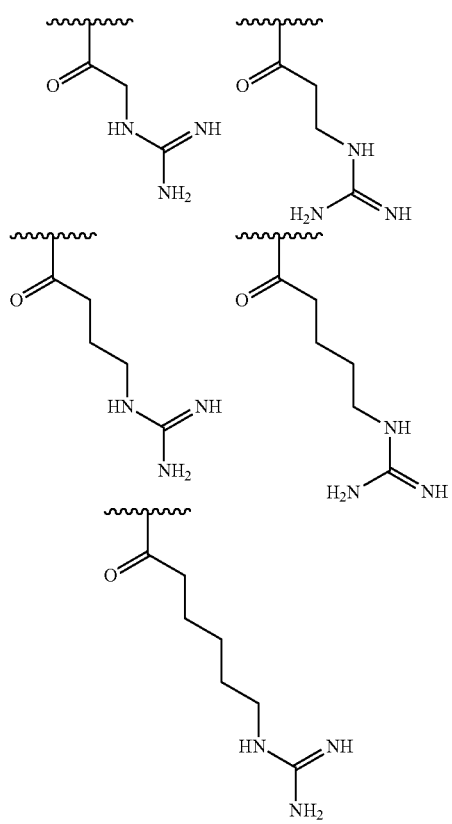

In some embodiments, at least 25% of $R^1$ substituents are H, at least 1% of $R^1$ substituents are acetyl, and at least 2% of $R^1$ substituents independently selected from any of the formulae specifically shown above.

In some embodiments, the functionalized chitosan of formula (I) may be further derivatized on the free hydroxyl moieties.

In some embodiments, the molecular weight of the functionalized chitosan is between 5,000 and 1,000,000 Da.

In some embodiments, the molecular weight of the functionalized chitosan is between 10,000 and 350,000 Da.

In some embodiments, the molecular weight of the functionalized chitosan is between 10,000 and 60,000 Da.

In some embodiments, the molecular weight of the functionalized chitosan is between 15,000 and 45,000 Da.

In some embodiments, the molecular weight of the functionalized chitosan is between 15,000 and 35,000 Da.

In some embodiments, the molecular weight of the functionalized chitosan is between 15,000 and 25,000 Da.

In some embodiments, the functionalized chitosan is soluble in aqueous solution between pH 6 and 8.

In some embodiments, the functionalized chitosan is soluble in aqueous solution between pH 6.8 and pH 7.4.

In one embodiment, the chitosan is functionalized at between 5% and 50%.

In a preferred embodiment, the chitosan is functionalized at between 20% and 30%.

In one embodiment, the degree of deacetylation (% DDA) of the derivatized chitosan is between 75% and 95%.

In one embodiment, the degree of deacetylation (% DDA) of the derivatized chitosan is between 80% and 90%.

In one embodiment, the polydispersity index (PDI) of the derivatized chitosan is between 1.0 and 2.5.

In one embodiment, the polydispersity index (PDI) of the derivatized chitosan is between 1.2 and 1.8.

In some embodiments, the functionalized chitosan is substantially free of other impurities.

In one aspect, the invention features a medical device comprising: a vacuum assisted closure unit comprising a vacuum pump fluidly connected to a dressing through an intake vent, wherein the dressing comprises a composition comprising a soluble or derivatized chitosan.

In an embodiment, the dressing is adapted to be positioned adjacent to the wound. In an embodiment, the dressing is a foam dressing or a gauze dressing. In an embodiment, the medical device further comprises a flexible tube communicating between said pad and said negative pressure source. In an embodiment, the medical device further comprises a removable canister in fluid communication between said pad and said negative pressure source.

In an embodiment, the composition reduces the healing time or increase the healing rate of a wound. In some embodiments, the composition decreases the inflammation associated with wound or healing of the wound.

In one embodiment, the soluble or derivatized chitosan is soluble in aqueous solution from about pH 6.8 to about pH 7.4.

In one embodiment, the soluble or derivatized chitosan is soluble in aqueous solution from about pH 3 to about pH 9.

In one embodiment, the soluble or derivatized chitosan is soluble in aqueous solution from about pH 5.0 to about pH 6.0, e.g., in wounds or duodenum.

In one embodiment, the soluble or derivatized chitosan is soluble in aqueous solution from about pH 2.0 to about pH 4.0, e.g., in stomach.

In one embodiment, the soluble or derivatized chitosan is soluble in aqueous solution from about pH 8.0 to about pH 8.5, e.g., in lower part of the gastrointestinal tract.

In one embodiment, the derivatized chitosan comprises a chitosan of the following formula (I):

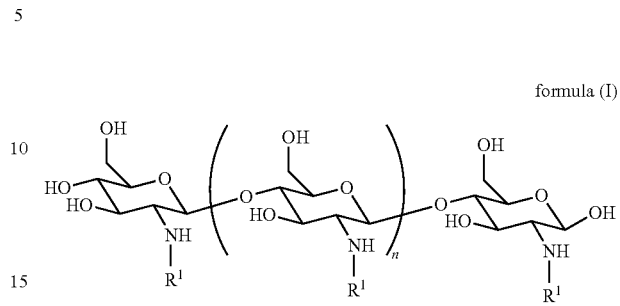

formula (I)

wherein:

n is an integer between 20 and 6000; and each $R^1$ is independently selected for each occurrence from hydrogen, acetyl, and either:

a) a group of formula (II):

formula (II)

wherein $R^2$ is hydrogen or amino; and $R^3$ is amino, guanidino, $C_1$-$C_6$ alkyl substituted with an amino or guanidino moiety, or a natural or unnatural amino acid side chain;

or b) $R^1$, when taken together with the nitrogen to which it is attached, forms a guanidine moiety;

wherein at least 25% of $R^1$ substituents are H, at least 1% of $R^1$ substituents are acetyl, and at least 2% of $R^1$ substituents are a group of formula (II) or are taken together with the nitrogen to which they are attached to form a guanidine moiety.

In one embodiment, the derivatized chitosan comprises of the following formula (I) wherein at least 90% by number or weight of $R^1$ moieties are as defined in formula (I) (e.g., at least about 95%, at least about 96%, at least about 97%, at least about 98%, or at least about 99%):

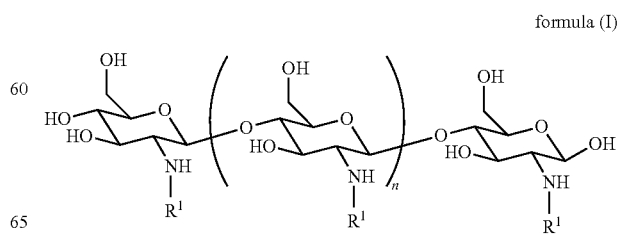

formula (I)

wherein:

n is an integer between 20 and 6000; and each $R^1$ is independently selected for each occurrence from hydrogen, acetyl, and either:

a) a group of formula (II):

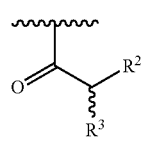

formula (II)

wherein $R^2$ is hydrogen or amino; and $R^3$ is amino, guanidino, $C_1$-$C_6$ alkyl substituted with an amino or guanidino moiety, or a natural or unnatural amino acid side chain;

or b) $R^1$, when taken together with the nitrogen to which it is attached, forms a guanidine moiety;

wherein at least 25% of $R^1$ substituents are H, at least 1% of $R^1$ substituents are acetyl, and at least 2% of $R^1$ substituents are a group of formula (II) or are taken together with the nitrogen to which they are attached to form a guanidine moiety.

In some embodiments, between 25-95% of $R^1$ substituents are hydrogen.

In some embodiments, between 55-90% of $R^1$ substituents are hydrogen.

In some embodiments, between 1-50% of $R^1$ substituents are acetyl.

In some embodiments, between 4-20% of $R^1$ substituents are acetyl.

In some embodiments, between 2-50% of $R^1$ substituents are a group of formula (II).

In some embodiments, between 4-30% of $R^1$ substituents are a group of formula (II).

In some embodiments, 55-90% of $R^1$ substituents are hydrogen, 4-20% of $R^1$ substituents are acetyl, 4-30% of $R^1$ substituents are a group of formula (II).

In some embodiments, $R^2$ is amino and $R^3$ is an arginine side chain.

In some embodiments, $R^1$ is selected from one of the following:

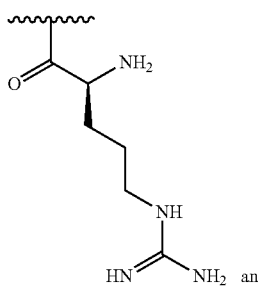 and 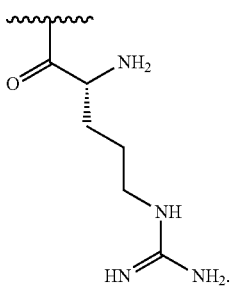

In some embodiments, $R^2$ is amino and $R^3$ is a lysine side chain.

In some embodiments, $R^1$ is selected from one of the following:

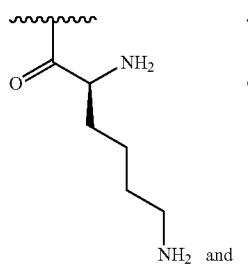 and 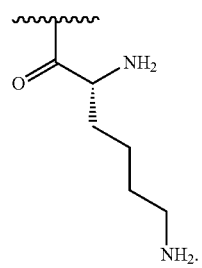

In some embodiments, $R^2$ is amino and $R^3$ is a histidine side chain.

In some embodiments, $R^1$ is selected from one of the following:

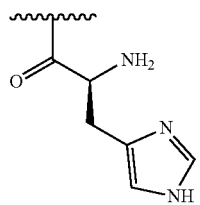 and 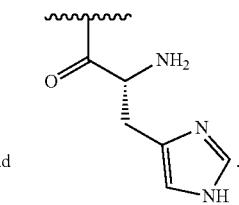

In some embodiments, at least 1% of $R^1$ substituents are selected from one of the following:

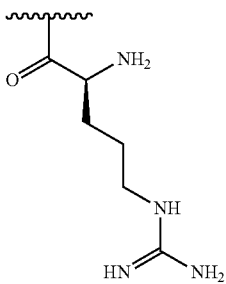 and 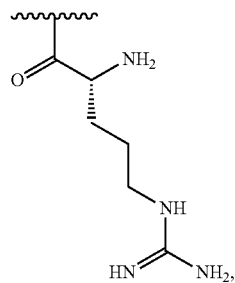

AND at least 1% of $R^1$ substituents are selected from the following:

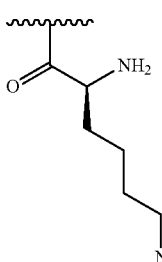 and 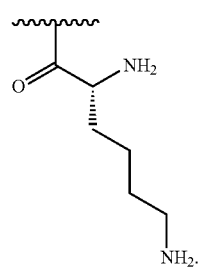

In some embodiments, $R^2$ is amino and $R^3$ is a substituted $C_1$-$C_6$ alkyl.

In some embodiments, $R^3$ is $C_1$-$C_6$ alkyl substituted with an amino group.

In some embodiments, $R^3$ is $C_1$ alkyl substituted with an amino group.

In some embodiments, $R^3$ is $C_2$ alkyl substituted with an amino group.

In some embodiments, $R^3$ is $C_3$ alkyl substituted with an amino group.

In some embodiments, $R^3$ is $C_4$ alkyl substituted with an amino group.

In some embodiments, $R^3$ is $C_5$ alkyl substituted with an amino group.

In some embodiments, $R^3$ is $C_6$ alkyl substituted with an amino group.

In some embodiments, $R^1$ is selected from one of the following:

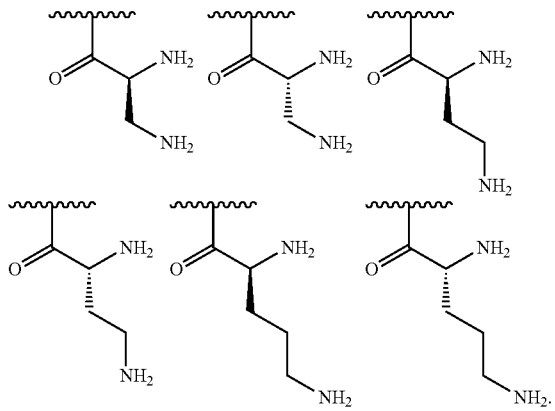

In some embodiments, $R^3$ is $C_1$-$C_6$ alkyl substituted with a guanidino group.

In some embodiments, $R^3$ is $C_1$ alkyl substituted with a guanidino group.

In some embodiments, $R^3$ is $C_2$ alkyl substituted with a guanidino group.

In some embodiments, $R^3$ is $C_3$ alkyl substituted with a guanidino group.

In some embodiments, $R^3$ is $C_4$ alkyl substituted with a guanidino group.

In some embodiments, $R^3$ is $C_5$ alkyl substituted with a guanidino group.

In some embodiments, $R^3$ is $C_6$ alkyl substituted with a guanidino group.

In some embodiments, $R^1$ is selected from one of the following:

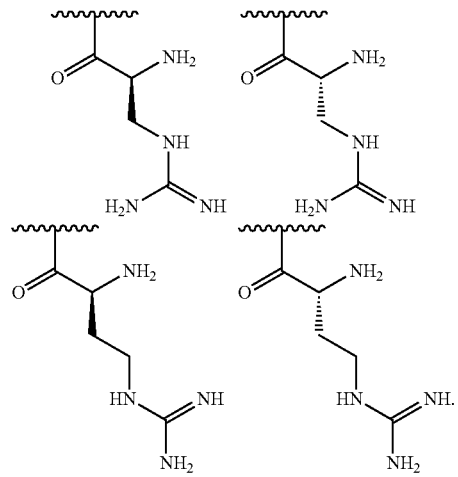

In some embodiments, wherein $R^2$ is amino that is substituted with a nitrogen protecting group prior to substitution on chitosan and removed subsequent to substitution on chitosan.

In some embodiments, the nitrogen protecting group is tert-butyloxycarbonyl (Boc).

In some embodiments, in the synthetic process a nitrogen protecting group is used, which can provide an intermediate polymer having a nitrogen protecting group such as Boc.

In some embodiments, $R^2$ is amino.

In some embodiments, $R^2$ is hydrogen and $R^3$ is amino.

In some embodiments, $R^2$ is hydrogen and $R^3$ is guanidino.

In some embodiments, $R^2$ is hydrogen and $R^3$ is a substituted $C_1$-$C_6$ alkyl.

In some embodiments, $R^3$ is $C_1$-$C_6$ alkyl substituted with an amino group.

In some embodiments, $R^3$ is $C_1$ alkyl substituted with an amino group.

In some embodiments, $R^3$ is $C_2$ alkyl substituted with an amino group.

In some embodiments, $R^3$ is $C_3$ alkyl substituted with an amino group.

In some embodiments, $R^3$ is $C_4$ alkyl substituted with an amino group.

In some embodiments, $R^3$ is $C_5$ alkyl substituted with an amino group.

In some embodiments, $R^3$ is $C_6$ alkyl substituted with an amino group.

In some embodiments, $R^1$ is selected from one of the following:

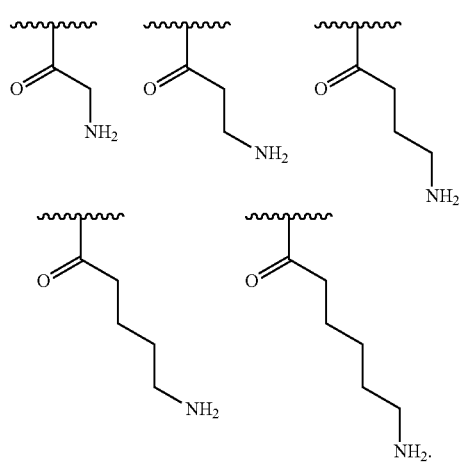

In some embodiments, $R^3$ is $C_1$-$C_6$ alkyl substituted with a guanidino group.

In some embodiments, $R^3$ is $C_1$ alkyl substituted with a guanidino group.

In some embodiments, $R^3$ is $C_2$ alkyl substituted with a guanidino group.

In some embodiments, $R^3$ is $C_3$ alkyl substituted with a guanidino group.

In some embodiments, $R^3$ is $C_4$ alkyl substituted with a guanidino group.

In some embodiments, $R^3$ is $C_5$ alkyl substituted with a guanidino group.

In some embodiments, $R^3$ is $C_6$ alkyl substituted with a guanidino group.

In some embodiments, $R^1$ is selected from one of the following:

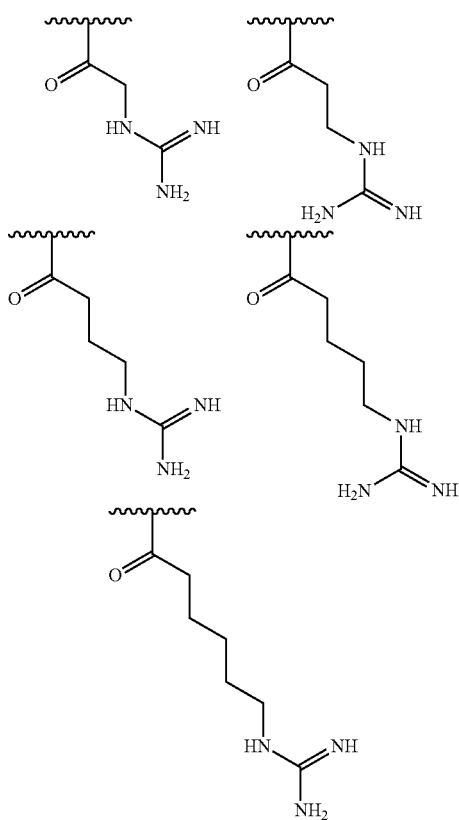

In some embodiments, at least 25% of $R^1$ substituents are H, at least 1% of $R^1$ substituents are acetyl, and at least 2% of $R^1$ substituents independently selected from any of the formulae specifically shown above.

In some embodiments, the functionalized chitosan of formula (I) may be further derivatized on the free hydroxyl moieties.

In some embodiments, the molecular weight of the functionalized chitosan is between 5,000 and 1,000,000 Da.

In some embodiments, the molecular weight of the functionalized chitosan is between 10,000 and 350,000 Da.

In some embodiments, the molecular weight of the functionalized chitosan is between 10,000 and 60,000 Da.

In some embodiments, the molecular weight of the functionalized chitosan is between 15,000 and 45,000 Da.

In some embodiments, the molecular weight of the functionalized chitosan is between 15,000 and 35,000 Da.

In some embodiments, the molecular weight of the functionalized chitosan is between 15,000 and 25,000 Da.

In some embodiments, the functionalized chitosan is soluble in aqueous solution between pH 6 and 8.

In some embodiments, the functionalized chitosan is soluble in aqueous solution between pH 6.8 and pH 7.4.

In one embodiment, the chitosan is functionalized at between 5% and 50%.

In a preferred embodiment, the chitosan is functionalized at between 20% and 30%.

In one embodiment, the degree of deacetylation (% DDA) of the derivatized chitosan is between 75% and 95%.

In one embodiment, the degree of deacetylation (% DDA) of the derivatized chitosan is between 80% and 90%.

In one embodiment, the polydispersity index (PDI) of the derivatized chitosan is between 1.0 and 2.5.

In one embodiment, the polydispersity index (PDI) of the derivatized chitosan is between 1.2 and 1.8.

In some embodiments, the functionalized chitosan is substantially free of other impurities.

DETAILED DESCRIPTION

Treatment

Figure 1:
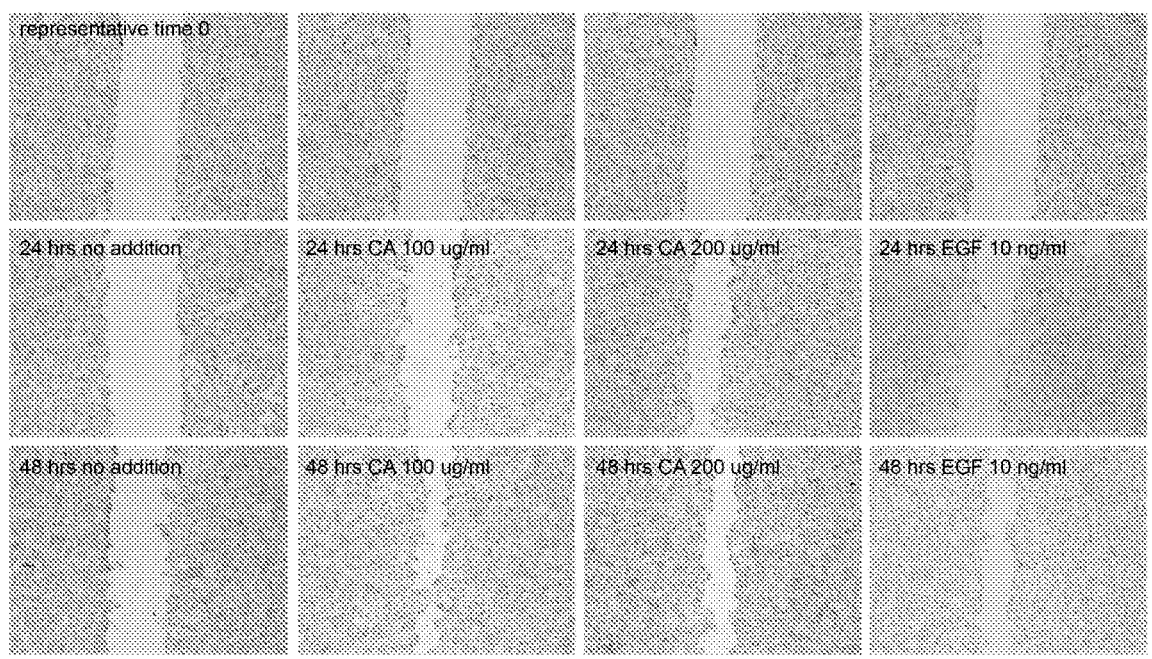
FIG. 1 depicts the effect of chitosan-arginine on in vitro scratch wound healing.

The compositions and compounds described herein (e.g., a soluble chitosan or a derivatized chitosan) can be administered to a tissue, e.g. in vitro or ex vivo, or to a subject, e.g., in vivo, to treat and/or prevent a variety of wounds or disorders, including those described herein below.

As used herein, the term "treat" or "treatment" is defined as the application or administration of a composition or compound (e.g., a compound described herein (e.g., a soluble or derivatized chitosan) to a subject, e.g., a patient, or application or administration of the composition or compound to an isolated tissue, from a subject, e.g., a patient, who has a wound or disorder (e.g., a wound or disorder as described herein), a symptom of a disorder, or a predisposition toward a disorder, with the purpose to cure, heal, alleviate, relieve, alter, remedy, ameliorate, improve or affect the wound or disorder, one or more symptoms of the disorder or the predisposition toward the disorder (e.g., to prevent at least one symptom of the disorder or to delay onset of at least one symptom of the disorder), and/or a side or adverse effect of a therapy, e.g., a cancer therapy.

As used herein, the term "prevent" or "prevention" is defined as the application or administration of a composition or compound (e.g., a compound described herein (e.g., a soluble or derivatized chitosan)) to a subject, e.g., a subject who is at risk for a disorder (e.g., a disorder described herein), or has a disposition toward a disorder, or application or administration of the compound to an isolated tissue from a subject, e.g., a subject who is at risk for a disorder (e.g., a disorder as described herein), or has a predisposition toward a disorder, with the purpose to avoid or preclude the disorder, or affect the predisposition toward the disorder (e.g., to prevent at least one symptom of the disorder or to delay onset of at least one symptom of the disorder).

As used herein, an amount of a composition or compound effective to treat a disorder, or a "therapeutically effective amount" refers to an amount of the composition or compound which is effective, upon single or multiple dose administration to a subject, in treating a tissue, or in curing, alleviating, relieving or improving a subject with a disorder beyond that expected in the absence of such treatment.

As used herein, an amount of a composition or compound effective to prevent a disorder, or "a prophylactically effective amount" of the composition or compound refers to an amount effective, upon single- or multiple-dose administration to the subject, in preventing or delaying the occurrence of the onset or recurrence of a disorder or a symptom of the disorder.

As used herein, "administered in combination" or a combined administration of two agents means that two or more agents (e.g., compounds described herein) are administered to a subject at the same time or within an interval such that there is overlap of an effect of each agent on the patient. Preferably they are administered within 60, 30, 15, 10, 5, or 1 minute of one another. Preferably the administrations of the agents are spaced sufficiently close together such that a combinatorial (e.g., a synergistic) effect is achieved. The combinations can have synergistic effect when used to treat a subject having a bacterial infection. The agents can be administered simultaneously, for example in a combined unit dose (providing simultaneous delivery of both agents). Alternatively, the agents can be administered at a specified time interval, for example, an interval of minutes, hours, days or weeks. Generally, the agents are concurrently bioavailable, e.g., detectable, in the subject. Alternately, the soluble chitosan or chitosan derivative can be administered topically, intranasally, via pulmondary aerosol or orally, and the second agent can be administered systemically.

In a preferred embodiment, the agents are administered essentially simultaneously, for example two unit dosages administered at the same time, or a combined unit dosage of the two agents. In another preferred embodiment, the agents are delivered in separate unit dosages. The agents can be administered in any order, or as one or more preparations that includes two or more agents. Alternately, the second agent can be administered systemically and can be available systemically during the administration of the first agent. In a preferred embodiment, at least one administration of one of the agents, e.g., the first agent, is made within minutes, one, two, three, or four hours, or even within one or two days of the other agent, e.g., the second agent. In some cases, combinations can achieve synergistic results, e.g., greater than additive results, e.g., at least 1.25, 1.5, 2, 4, 10, 20, 40, or 100 times greater than additive.

Subject

The subject can be a human or a non-human animal. Suitable human subjects includes, e.g., a human patient having a wound or a disorder, e.g., a wound or disorder described herein or a normal subject. The term "non-human animals" of the invention includes all vertebrates, e.g., non-mammals (such as chickens, amphibians, reptiles) and mammals, such as non-human primates, e.g., elephant, sheep, dog, cat, cow, pig, etc. Suitable animal subjects include: but are not limited to, wild animals, farm animals, zoo animals, circus animals, companion (pet) animals, domesticated and/or agriculturally useful animals. Suitable animal subjects include primates, rodents, and birds. Examples of said animals include, but not limited to, elephants, guinea pigs, hamsters, gerbils, rat, mice, rabbits, dogs, cats, horses, pigs, sheep, cows, goats, deer, rhesus monkeys, monkeys, tamarinds, apes, baboons, gorillas, chimpanzees, orangutans, gibbons, fowl, e.g., pheasant, quail (or other gamebirds), a waterfowl, ostriches, chickens, turkeys, ducks, and geese or free flying bird.

In some embodiments, the subject has a wound (e.g., a wound in the absence of infection). In some embodiments, the subject has been treated or is being treated for cancer, e.g., with chemotherapy or radiation therapy, or has been treated or is being treated with immunosuppressive therapy, and is suffering from mucositis or ulceration. In some embodiments, the subject has a chronic disease (e.g., the symptom of a chronic disease comprises a wound, or a chronic disease associated with poor or slow wound healing). In some embodiments, the subject has been exposed to a chemical, biological or radiological agent, or has suffered chemical, biological, or radiological injury.

Wound

As used herein, a wound refers to a type of injury which damages a part or tissue of the body, for example, skin (e.g., epidermis, dermis, and hypodermis) and/or underlying tissue, mucous membrane (e.g., oral mucous membrane), or other epithelia (e.g., corneal epithelium).

Wounds can be classified as open wounds and closed wounds.

An open wound refers to a type of injury in which a tissue, e.g., skin or mucous membrane, is torn, cut or punctured. Open wounds can be further classified according to the object that caused the wound. The types of open wound include, e.g., incisions or incised wounds, caused by a clean, sharp-edged object such as a knife, a razor or a glass splinter; lacerations, which are irregular tear-like wounds caused by some blunt trauma; abrasions (grazes), which are superficial wounds in which the topmost layer of the skin (the epidermis) is scraped off, often caused by a sliding fall onto a rough surface; puncture wounds, caused by an object puncturing the skin or mucous membrane, such as a nail or needle; penetration wounds, caused by an object such as a knife entering and coming out from the skin or mucous membrane; gunshot wounds (e.g., one at the site of entry and one at the site of exit), caused by a bullet or similar projectile driving into or through the body.

A closed wound refers to a type of injury without broken of the tissue (e.g., skin or mucous membrane), e.g., caused by a blunt force trauma. The types of closed wounds include, e.g., contusions or bruises, caused by a blunt force trauma that damages tissue under the skin or mucous membrane; hematomas or blood tumor, caused by damage to a blood vessel that in turn causes blood to collect under the skin or mucous membrane; crush injury, caused by a great or extreme amount of force applied over a long period of time; acute or traumatic wounds, which are the result of injuries that disrupt the tissue; and chronic wounds (e.g., pressure, venous, oral, peptic, or diabetic ulcers), caused by a relatively slow process that leads to tissue damage, often when an insufficiency in the circulation or other systemic support of the tissue causes it to fail and disintegrate. Infection can then take hold of the wound site and becomes a chronic abscess. Once the infection hits a critical point, it can spread locally or become systemic (sepsis).

Wound healing, or wound repair, refers to an intricate process in which the tissue, e.g., skin or mucous membrane, repairs itself after injury. In normal skin, the epidermis and dermis exist in a steady-state equilibrium, forming a protective barrier against the external environment. Once the protective barrier is broken, the physiologic process of wound healing is immediately set in motion.

Growth factors that can be involved in wound healing include, e.g., epidermal growth factor (EGF), transforming growth factor-α (TGF-α), hepatocyte growth factor (HGF), vascular endothelial growth factor (VEGF), platelet derived growth factor (PDGF), fibroblast growth factor 1 and 2 (FGF-1 and FGF-2), transforming growth factor-3 (TGF-β), and keratinocyte growth factor (KGF). These growth factors can play a role in wound healing, e.g., cell proliferation (e.g., proliferation of keratinocytes, fibroblasts, hepatocytes, epithelial cells, endothelial cells, and smooth muscle cells), cell migration (e.g., migration of keratinocytes), hepatocyte motility, granulation tissue formation, expression of antimicrobial peptides, vascular permeability, chemotaxis (e.g., chemotaxis of granulocyte, macrophage, fibroblast, and smooth muscle), cell activation (e.g., activation of granulocytes, macrophages, and fibroblasts), matrix metalloproteinase production, fibronectin production, hyaluronan production, angiogenesis; wound remodeling, integrin expression regulation; wound contraction; tissue inhibitors of metalloproteinases (TIMP) synthesis, fibroplasia, matrix metalloproteinase production inhibition, and keratinocyte differentiation.

The classic model of wound healing can be divided into three or four sequential, yet overlapping phases, e.g., hemostasis, inflammatory, proliferative, and remodeling phases. The composition described herein can be administered before, during, or after one or more phases of the wound healing, e.g., the hemostasis, inflammatory, proliferative, and/or remodeling phases.

In the hemostasis phase, within minutes post-injury, platelets (thrombocytes) aggregate at the injury site to form a fibrin clot, which acts to control active bleeding (hemostasis).

In the inflammatory phase, clotting continues to take place in order to stop blood loss, and various factors are released to attract cells that phagocytise debris, bacteria and damaged tissue and release factors that initiate the proliferative phase of wound healing. The clot is eventually lysed and replaced with granulation tissue and then later with collagen. Platelets release a number of factors, e.g., extracellular matrix (ECM) proteins, cytokines (e.g., growth factors), proinflammatory factors (e.g., serotonin, bradykinin, prostaglandins, prostacyclins, thromboxane, and histamine).

These factors stimulate the rate of cell division, increase cell proliferation and migration, and cause blood vessels to become dilated and porous. The types of leukocytes that arrive at the wound site include, e.g., polymorphonuclear neutrophils (PMNs), helper T cells, monocytes, and macrophages. These leukocytes function together, e.g., to phagocytise debris and bacteria, kill bacteria (e.g., by releasing free radicals), secrete proteases that break down damaged tissue, enhance vasodilation and vessel permeability, secrete a number of factors including growth factors and cytokines, induce and speed angiogenesis, stimulate cells that reepithelialize the wound, create granulation tissue, and lay down a new extracellular matrix.

Inflammation can lead to tissue damage if it lasts too long. Thus the reduction of inflammation can be a goal in therapeutic settings, for example, the presence of dirt or other objects can extend the inflammatory phase for too long, leading to a chronic wound.

In some embodiments, the compositions described herein can reduce the level of inflammation, e.g., during the inflammatory phase, and/or reduce the duration of the inflammatory phase, e.g., by at least 10%, 20%, 30%, 40%, 50%, 60%, 70%, 80%, or 90%, compared to the level of inflammation or duration of the inflammatory phase in the wound that has not been treated with the compositions described herein. The level of inflammation can be assessed by medical tests, e.g., the erythrocyte sedimentation rate (ESR) and C-reactive protein (CRP) blood tests. The compositions described herein can also up-regulate one or more anti-inflammatory cytokines (e.g., IL-10), and/or down-regulate one or more pro-inflammatory cytokines (e.g., TNF-α and IL-8).

The compositions described herein can be used in combination with one or more anti-inflammatory agents. Exemplary anti-inflammatory agents include, steroids (e.g., glucocorticoids (e.g., prednisolone)), non-steroidal anti-inflammatory drugs (e.g., salicylates (e.g., aspirin (acetylsalicylic acid), diflunisal, salsalate); propionic acid derivatives (e.g., ibuprofen, naproxen, fenoprofen, ketoprofen, flurbiprofen, oxaprozin, loxoprofen), acetic acid derivatives (indomethacin, sulindac, etodolac, ketorolac, diclofenac, nabumetone); enolic acid (oxicam) derivatives (e.g., piroxicam, meloxicam, tenoxicam, droxicam, lornoxicam, isoxicam); fenamic acid derivatives (fenamates) (e.g., mefenamic acid, meclofenamic acid, flufenamic acid, tolfenamic acid), selective COX-2 inhibitors (coxibs) (e.g., celecoxib, rofecoxib, valdecoxib, parecoxib, lumiracoxibm etoricoxib, firocoxib); sulphonanilides (nimesulide); and others (e.g., 5-LOX/COX inhibitor (licofelone)), and Immune Selective Anti-Inflammatory Derivatives (ImSAIDs).

The proliferative phase can be characterized by, e.g., angiogenesis, collagen deposition, granulation tissue formation, epithelialization, and wound contraction.

In the maturation and remodeling phase, collagen is remodeled and realigned along tension lines and cells that are no longer needed are removed by apoptosis. This process is susceptible to interruption or failure leading to the formation of chronic non-healing wounds. Factors which may contribute to this include, e.g., chronic diseases (e.g, diabetes), venous or arterial disease, old age, and infection. There are three general techniques of wound treatment; primary intention, in which all tissues, including the skin, are closed with suture material after completion of the operation; secondary intention, in which the wound is left open and closes naturally; and third intention, in which the wound is left open for a number of days and then closed if it is found to be clean. Examples of primary intention include, e.g., well repaired lacerations, well reduced bone fractures, and healing after flap surgery. Examples of secondary intention include, e.g., gingivectomy, gingivoplasty, tooth extraction sockets, and poorly reduced fractures. Examples of tertiary intention include, e.g., healing of wounds by use of tissue grafts.

Guidance for the determination of the dosage that delivers a therapeutically effective amount of the composition described herein to treat a wound may be obtained from animal models of wound healing, e.g. as described in Olerud J E, *J Biomater Sci Polym Ed.* 2008; 19(8):1007-20; Fang R C and Mustoe F A, *J Biomater Sci Polym Ed.* 2008; 19(8):989-1005; Grose R and Werner S, *Methods Mol Med.* 2003; 78:191-216.

Scaring

Scars (also called cicatrices) are areas of fibrous tissue (fibrosis) that replace normal skin or other tissue after injury. A scar can result from the biologic process of wound repair in the skin and other tissues of the body.

The compositions described herein can be used to treat a scar, reduce scarring (e.g., size, severity), or prevent the formation of a scar. For example, the composition described herein can be used to treat a subject before, during, or after a surgical procedure, e.g., to prevent the formation of a scar or reduce scaring.

Exemplary surgical procedures include, general surgery (e.g., cardiothoracic surgery, vascular surgery, plastic surgery, paediatric surgery, colorectal surgery, transplant surgery, surgical oncology, trauma surgery, endocrine surgery, breast surgery, skin surgery), otolaryngology—head and neck surgery, gynecology surgery, oral and maxillofacial surgery, orthopaedic surgery, neurosurgery, ophthalmology surgery (eye surgery), podiatric surgery, reconstructive surgery, or urology surgery. For example, the surgical procedures of the eye can include, but not limited to, laser eye surgery, refractive surgery, cataract surgery, glaucoma surgery, canaloplasty, corneal surgery, vitreo-retinal surgery, eye muscle surgery, and oculoplastic surgery.

The disclosure provides methods of treating (e.g., ameliorating, stabilizing, or eliminating) a scar (e.g., a scar in the eye, e.g., after an eye surgery) by administering a composition described herein to a subject having or suspected of having a scar.

Additionally provided are methods of treating (e.g., ameliorating, stabilizing, or eliminating) a scar (e.g., a scar in the eye, e.g., after an eye surgery) by administering a composition described herein in combination with a second therapy, e.g., an ACE inhibitor (e.g., enalapril), a steroid, a semiocclusive ointment or pressure dressing (e.g, Kelocote®), DMSO (dimethyl sulfoxide), MSM (methylsulfonylmethane), Transforming Growth Factor Beta 3 (TGF-β3), Ribosomal s6 kinase (RSK), and osteopontin.

The disclosure also provides methods of preventing a scar (e.g., a scar in the eye, e.g., after an eye surgery) by administering a composition described herein to a subject at risk of developing a scar (e.g., a subject having a surgery (e.g., an eye surgery) or a genetic predisposition thereto).

Scales useful for assessing scarring include, e.g., Vancouver Scar Scale (VSS) (Baryza M. J. et al., *J Burn Care Rehabil* 1995; 16:535-538; Roques C. et al., *Lower Extremity Wounds,* 2007; 6(4): 249-53), Visual Analogue Scale (VAS) (Beausang E. et al., *Plast Reconstr Surg,* 1998; 102: 1954-61; Roques C. et al., *Lower Extremity Wounds,* 2007; 6(4): 249-53), Modified Vancuover Scar Scale (MVSS) (Forbes-Duchart L et al., *J Burn Care Res,* 2007; 28: 460-67), Validation of Patient and Observer Scar Assessment Scale (POSAS) (Draaijers L. J. et al., *Plast Reconstr Surg,* 2004; 113: 1960-5; Roques C. et al., *Lower Extremity Wounds,* 2007; 6(4): 249-53), Patient and Observer Scar Assessment Scale (POSAS) (Van der Kar A L et al., *Plast Reconstr Surg,* 2005; 116: 514-22), Manchester Scale (Bayat A. et al., BMJ, 2003; 326:88-92; Roques C. et al., *Lower Extremity Wounds,* 2007; 6(4): 249-53).

Chronic Diseases

As used herein, a chronic disease refers to a disease in which the symptom of the disease includes at least one wound. The chronic diseases described herein can be the result of infection, e.g., bacterial infection, and the infection might no longer be present when the chronic disease or wound is treated. The symptoms of chronic diseases can sometimes be less severe than those of the acute phase of the same disease, but persist over a long period. Chronic diseases may be progressive, result in complete or partial disability, or even lead to death.

Examples of chronic diseases that can be associated with poor or slow wound healing include inflammatory bowel disease (IBD) (e.g., Crohn's disease), diabetes (e.g., diabetes mellitus types 1 or type 2), chronic kidney disease (CKD), chronic obstructive pulmonary disease (COPD), hypothyroidism, multiple sclerosis, rheumatoid arthritis, hepatic encephalopathy, peritonitis, periodontitis, sinusitis, rhinitis, sepsis, and systemic lupus erythematosus.

Chronic diseases that are not inflammatory but can produce inflammatory conditions include, e.g., cystic fibrosis and diabetes.

Inflammatory Bowel Disease (IBD).

IBD is a group of inflammatory conditions of the large intestine and, in some cases, the small intestine. The main forms of IBD are Crohn's disease and ulcerative colitis (UC). Crohn's disease can affect any part of the gastrointestinal tract, from mouth to anus (skip lesions), although a majority of the cases start in the terminal ileum. Ulcerative colitis is restricted to the colon and the rectum. Microscopically, ulcerative colitis is restricted to the mucosa (epithelial lining of the gut), while Crohn's disease affects the whole bowel wall. Other forms of IBD include, e.g., collagenous colitis, lymphocytic colitis, ischaemic colitis, diversion colitis, Behqet's syndrome, infective colitis, and indeterminate colitis.

Symptoms of IBD include, e.g., abdominal pain, vomiting, diarrhea, hematochezia, weight loss, weight gain and various associated complaints or diseases (e.g., arthritis, pyoderma gangrenosum, primary sclerosing cholangitis). Diagnosis is generally by colonoscopy with biopsy of pathological lesions. In some instances, a definitive diagnosis of neither Crohn's disease nor ulcerative colitis can be made because of idiosyncrases in the presentation. In this case, a diagnosis of indeterminate colitis may be made.

Treatment for IBD, depending on the level of severity, can include, e.g., immunosuppression to control the symptoms (e.g., azathioprine, methotrexate, or 6-mercaptopurine), mesalamine, steroids (e.g., prednisone), biologicals (e.g., infliximab), surgery (e.g., bowel resection, strictureplasty, or a temporary or permanent colostomy or ileostomy).

The disclosure provides methods of treating (e.g., ameliorating, stabilizing, or eliminating one or more symptoms of) IBD by administering a composition described herein to a subject having or suspected of having IBD. In some embodiments, the compositions described herein reduce the endoscopy colitis severity score, e.g., by at least 10, 20, 30, 40, 50, 60, 70, 80, or 90%, compared to the endoscopy colitis severity score of the subject that has not been treated with the compositions described herein.

In some embodiments, the compositions described herein are at least 10, 20, 30, 40, 50, 60, 70, 80, or 90% more effective, than a standard therapy for IBD (e.g., prednisolone), e.g., according to the endoscopy colitis severity score. Methods for measuring the endoscopy colitis severity score are described in the art, e.g., in Daperno M. et al., *Gastrointest Endosc.* 2004; 60(4):505-12.

Additionally provided are methods of treating IBD by administering a composition described herein in combination with a second therapy, e.g., an immunosuppressive (e.g., azathioprine, methotrexate, 6-mercaptopurine), a mesalamine, a steroid, and/or a biologic (e.g., infliximab).

The disclosure also provides methods of preventing IBD or a symptom thereof by administering a composition described herein to a subject at risk of developing IBD (e.g., a subject having a family member with IBD or a genetic predisposition thereto).

Guidance for the determination of the dosage that delivers a therapeutically effective amount of a composition described herein may be obtained from animal models of IBD, see, e.g., those described in U.S. Pat. No. 6,114,382, WO 2004/071186, and references cited therein.

Mucositis

As used herein, mucositis refers to the inflammation and ulceration of the mucous membranes, e.g., lining the digestive tract, e.g., as a side or adverse effect of chemotherapy and radiotherapy treatment for cancer. Mucositis can be the result of infection, e.g., bacterial infection, and the infection might no longer be present when mucositis is treated. Mucositis can occur anywhere along the gastrointestinal (GI) tract, but oral mucositis refers to the particular inflammation and ulceration that occurs in the mouth. Oral mucositis can be a common and often debilitating complication of cancer treatment.

Cancer patients, e.g., that have been treated or is being treated with chemotherapy or radiation therpy, or patients that have been treated or is being treated with immunosuppressive therapy, are more subject to wound. Cancer therapies, such as chemotherapy or radiation therpy, and immunosuppressive therapy, can kill rapid growing/dividing cells involved in wound healing. Therefore, these cancer patients often have poor or slow wound healing or need assistance in wound healing.

The pathophysiology of mucositis can be divided into its five stages; including an initiation phase, a message generation phase, a signaling and amplification phase, an ulceration phase, and a healing phase. Different cytokines are responsible for the various stages. The initiation phase is caused by the production of free radicals caused by the chemo- or radio-therapy, which damages cell DNA. This causes the production of cell transcription factors such as NFκB, which upregulates inflammatory cytokines, marking the beginning of the ulceration phase. Main inflammatory cytokines involved are IL-1 and TNF-α. During the healing phase, epithelial cells are attracted to the site of the ulcer and begin the re-epithelialization of the ulcers.

Cancer patients undergoing chemotherapy can become symptomatic four to five days after beginning treatment, reaching a peak at around day 10, and then slowly improving over the course of a few weeks. Mucositis associated with radiotherapy can appear at the end of the second week of treatment and may last or increase for six to eight weeks. As a result of cell death in reaction to chemo- or radio-therapy, the mucosal lining of the mouth becomes thin, may slough off and then become red, inflamed and ulcerated. The ulcers may become covered by a yellowish white fibrin clot (pseudomembrane). Peripheral erythema can occur. Ulcers may range from about 0.5 cm to greater than 4 cm. Oral mucositis can be painful. The degree of pain can be related to the extent of the tissue damage. Pain is often described as a burning sensation accompanied by reddening. Due to pain, the patient may experience trouble speaking, eating, or even opening the mouth. Dysgeusia, or an alteration in taste perception, is common, especially for those who are receiving concomitant radiation therapy to the neck and mouth area.

Diagnosis is based on the symptoms the patient is experiencing and the appearance of the tissues of the mouth, e.g., red burn-like sores or ulcers, following chemotherapy, bone marrow transplants or radiotherapy. The severity of oral mucositis can be evaluated using several different assessment tools, e.g., the World Health Organization (WHO) Oral Toxicity score, the National Cancer Institute Common Toxicity Criteria (NCI-CTC) for Oral Mucositis, and the Oral Mucositis Assessment Scale (OMAS). The NCI system has separate scores for appearance (erythema and ulceration) and function (pain and ability to eat solids, liquids, or nothing by mouth). The WHO score combines both elements into a single score that grades the severity of the condition from 0 (no oral mucositis) to 4 (swallowing not possible such that patient needs supplementary nutrition). The OMAS provides an objective assessment of oral mucositis based on assessment of the appearance and extent of redness and ulceration in various areas of the mouth.

Treatments of mucositis include, e.g., oral hygiene, water-soluble jellies, salt mouthwash, medicinal mouthwashes (e.g., chlorhexidine gluconate, lidocaine, CAPHOSOL®, MUGARD®), human KGF (keratinocyte growth factor, palifermin), use of cytokines and other modifiers of inflammation (e.g., IL-1, IL-10, IL-11, TGF-1), amino acid supplementation (e.g., glutamine), vitamins, colony-stimulating factors, cryotherapy, laser therapy, and barrier protection agents such as concentrated oral gel products (e.g., GEL-CLAIR®).

Guidance for the determination of the dosage that delivers a therapeutically effective amount of the composition described herein to treat mucositis may be obtained from animal models of mucositis, e.g. as described in Sonis S T et al., *Oral Surg Oral Med Oral Pathol.* 1990 April; 69(4): 437-43; and Nakajima M. et al., *Otolaryngology—Head and Neck Surgery,* 2004; 131 (2):198-199.

Burn

A burn refers to a type of skin injury caused by heat, electricity, chemicals, light, radiation, or friction. Burns can affect the skin (epidermal tissue and dermis) and/or deeper tissues, such as muscle, bone, and blood vessels. Burn injuries can be complicated by shock, infection, multiple organ dysfunction syndrome, electrolyte imbalance and respiratory distress.

Burns can be classified as first-, second-, third-, or fourth-degree. First-degree burns can involve only the epidermis and be limited to redness (erythema), a white plaque and minor pain at the site of injury. For example, most sunburns are included as first-degree burns. Second-degree burns manifest as erythema with superficial blistering of the skin, and can involve more or less pain depending on the level of nerve involvement. Second-degree burns involve the superficial (papillary) dermis and may also involve the deep (reticular) dermis layer. Third-degree burns occur when the epidermis is lost with damage to the subcutaneous tissue. Burn victims will exhibit charring and severe damage of the epidermis, and sometimes hard eschar will be present. Third-degree burns result in scarring and victims will also exhibit the loss of hair shafts and keratin. Fourth-degree burns can damage muscle, tendon, and ligament tissue, thus result in charring and catastrophic damage of the hypodermis. In some instances the hypodermis tissue may be partially or completely burned away as well as this may result in a condition called compartment syndrome.

The burn depths are described as superficial, superficial partial-thickness, deep partial-thickness, or full-thickness.

Burns can also be assessed in terms of total body surface area (TBSA), which is the percentage affected by partial thickness or full thickness burns (erythema/superficial thickness burns are not counted). The rule of nines can be used as a quick and useful way to estimate the affected TBSA. More accurate estimation can be made using Lund & Browder charts which take into account the different proportions of body parts in adults and children.

Burns can be caused by a number of substances and external sources such as exposure to chemicals (e.g., strong acids or bases, caustic chemical compounds), friction, electricity (e.g., workplace injuries, being defibrillated or cardioverted without a conductive gel, lightening), radiation (e.g., protracted exposure to UV light, tanning booth, radiation therapy, sunlamps, X-rays) and heat (e.g., scalding).

The treatments of burns include, e.g., stopping the burning process at the source, cooling the burn wound, intravenous fluids, debridement (removing devitalized tissue and contamination), cleaning, dressing (e.g., biosynthetic dressing), pain management (e.g., analgesics (e.g., ibuprofen, acetaminophen), narcotics, local anesthetics), hyperbaric oxygenation, surgical management, control of infection, control of hyper-metabolic response.

Guidance for the determination of the dosage that delivers a therapeutically effective amount of the composition described herein to treat burns may be obtained from animal models of burns, e.g. as described in Santos Heredero F X et al., *Annals of Burns and Fire Disasters,* IX—n. 2 (June 1996); and Stevenson J M et al., *Methods Mol Med.* 2003; 78:95-105.

Corneal Ulcer

Methods and composition described herein can be used to treat corneal ulcers or damages to corneal epithelia. As used herein, a corneal ulcer, or ulcerative keratitis, or eyesore refers to an inflammatory and/or infective condition of the cornea involving disruption of its epithelial layer with possible involvement of the corneal stroma.

The cornea is a transparent structure that is part of the outer layer of the eye. There are five layers in the human cornea, from outer to inner: epithelium, bowman's layer, stroma, descemet's membrane, and endothelium.

An ulcer of the cornea can heal by two methods: migration of surrounding epithelial cells followed by mitosis (dividing) of the cells, and introduction of blood vessels from the conjunctiva. Superficial small ulcers can heal rapidly by the first method. However, larger or deeper ulcers may require the presence of blood vessels to supply inflammatory cells. White blood cells and fibroblasts produce granulation tissue and then scar tissue, effectively healing the cornea.

Corneal ulcers can be caused by e.g., trauma, chemical injury, contact lenses and infections, entropion, distichiae, corneal dystrophy, and keratoconjunctivitis sicca (dry eye). Micro-organisms, e.g., bacteria (e.g., *Staphylococcus aureus, Streptococcus viridans, Escherichia coli,* Enterococci, *Pseudomonas, Nocardia*), fungi (e.g., *Aspergillus* sp., *Fusarium* sp., *Candida* sp., as also *Rhizopus, Mucor*), viruses (e.g., Herpes simplex, Herpes Zoster and Adenoviruses), protozoa, and *chlamydia* can cause infective corneal ulcer.

Superficial ulcers involve a loss of part of the epithelium. Deep ulcers extend into or through the stroma and can result in severe scarring and corneal perforation.

Descemetoceles occur when the ulcer extends through the stroma.

The location of the ulcer depends on the cause. Central ulcers can be caused by trauma, dry eye, or exposure from facial nerve paralysis or exophthalmos.

Entropion, severe dry eye and distichiasis (inturning of eye lashes) may cause ulceration of the peripheral cornea. Immune-mediated eye disease (e.g., rheumatoid arthritis, rosacea, systemic sclerosis) can cause ulcers at the border of the cornea and sclera.

Symptoms of corneal ulcers include, e.g., severe pain (e.g., due to nerve exposure), tearing, squinting, and vision loss of the eye, anterior uveitis, such as miosis (small pupil), aqueous flare (protein in the aqueous humour), and redness of the eye.

Treatments of corneal ulcer include, e.g., antibiotics, anti-fungal agents, antivirals (e.g., topical acyclovir ointment), supportive therapy (e.g., pain medications (e.g., topical cycloplegics like atropine or homatropine), conjunctival grafts or conjunctival flaps, soft contact lenses, corneal transplant, proper nutrition (e.g., protein intake, Vitamin A, Vitamin C), and topical corticosteroids.

Refractory corneal ulcers are superficial ulcers that heal poorly and tend to recur. Refractory corneal ulcers can often be seen in patient with chronic diseases, e.g., diabetes. Treatments of refractory corneal ulcer include, e.g, topical antibiotics, cycloplegic eye drops, pain medications, surgical intervention. Refractory corneal ulcers can take a long time to heal, sometimes months.

Melting ulcers are a type of corneal ulcer involving progressive loss of stroma in a dissolving fashion. It can be caused by *Pseudomonas* infection. Treatments of melting ulcers include, e.g., antibiotics and collagenase inhibitors such as acetylcysteine, and surgery in the form of corneal transplantation (penetrating keratoplasty).

Guidance for the determination of the dosage that delivers a therapeutically effective amount of the composition described herein to treat corneal ulcer may be obtained from animal models of corneal ulcer, e.g. as described in Matsubara M. *Invest Ophthalmol Vis Sci.* 1991; 32(13):3221-37.

Sinusitis and Rhinitis

Methods and composition described herein can be used to treat sinusitis and rhinitis (e.g., chronic sinusitis and chronic rhinitis).

Sinusitis is inflammation of the paranasal sinuses, which may be due to, e.g., bacteria or viral infection, allergy, chronic disease (e.g., cystic fibrosis), sinus surgery, or autoimmune issues. Sinusitis can be acute (going on less than four weeks), subacute (4-8 weeks), or chronic (going on for 8 weeks or more). Sinusitis can also be classified by the sinus cavity which it affects, e.g., maxillary, frontal, ethmoid, and sphenoid. Sinusitis can occur as part of a spectrum of diseases that affect the respiratory tract and can be linked to asthma.

Acute sinusitis is usually precipitated by an earlier upper respiratory tract infection, generally of bacterial or viral origin. If the infection is of bacterial origin, the common causative agents can be, e.g., *Streptococcus pneumoniae, Haemophilus influenzae,* and *Moraxella catarrhalis.* Other sinusitis-causing bacterial pathogens include, e.g., *Staphylococcus aureus* (e.g., methicilin resistant *S. aureus*) and other streptococci species, anaerobic bacteria, and gram negative bacteria. In some instances, viral sinusitis can result in subsequent or secondary bacterial sinusitis. Acute sinusitis can also result from fungal invasion, for example, in patients with diabetes or other immune deficiencies (e.g., AIDS or transplant patients on immunosuppressive anti-rejection medications). Chemical irritation (e.g., cigarette smoke and chorine fumes) and tooth infection can also trigger sinusitis. Symptoms of acute sinusitis include, e.g, headache/facial pain or pressure of a dull, constant, or aching sort over the affected sinuses, thick nasal discharge that is usually green in colour and may contain pus (purulent) and/or blood, infection of the eye socket, and inner ear problems.

Chronic sinusitis can be caused by various diseases that share chronic inflammation of the sinuses as a common symptom. Symptoms of chronic sinusitis may include, e.g., one or more of the following: nasal congestion, facial pain, headache, night-time coughing, an increase in previously minor or controlled asthma symptoms, general malaise, thick green or yellow discharge, feeling of facial "fullness" or "tightness" that may worsen when bending over, dizziness, aching teeth, and/or halitosis. Chronic sinusitis can lead to anosmia (a reduced sense of smell). Acute or chronic maxillary sinusitis can also be associated with a dental infection. Chronic sinusitis cases are subdivided into cases with polyps (chronic hyperplastic sinusiti) and cases without polyps. The causes of chronic hyperplastic sinusitis include allergy, environmental factors (e.g., dust or pollution), bacterial infection, or fungus (e.g., allergic, infective, or reactive), vasomotor rhinitis, abnormally narrow sinus passages (e.g., having a deviated septum).

Rhinitis refers to irritation and inflammation of some internal areas of the nose. The inflammation can result in the generating of excessive amounts of mucus, commonly producing symptoms such as runny nose, nasal congestion, sneezing, post-nasal drip, cough, and a low-grade fever. Rhinitis can be caused by chronic or acute inflammation of the mucous membrane of the nose due to, e.g., bacteria or viral infection, allergy, chronic disease (e.g., cystic fibrosis), sinus surgery, or autoimmune issues.

Rhinitis can be categorized into three types: (i) infective rhinitis (e.g., acute and chronic bacterial infections); (ii) nonallergic (vasomotor) rhinitis (e.g., autonomic, hormonal, drug-induced, atrophic, and gustatory rhinitis, and rhinitis medicamentosa); (iii) allergic rhinitis (e.g., triggered by pollen, mold, animal dander, dust and other similar inhaled allergens). Rhinitis can also be categorized as acute and chronic rhinitis. Chronic rhinitis is usually an extension of rhinitis caused by inflammation or an infection. It also may occur with diseases, e.g., syphilis, tuberculosis, rhinoscleroma, rhinosporidiosis, leishmaniasis, blastomycosis, histoplasmosis, and leprosy.

Treatments of sinusitis and rhinitis include, e.g. conservative treatment (e.g., nasal irrigation, decongestant nasal sprays containing oxymetazoline), antibiotics (e.g., amoxicillin (e.g., combined with clavulanate), fluoroquinolone, clarithromycin, tetracycline, doxycycline, and penicillins), corticosteroids (e.g., intranasal corticosteroids), antihistamines, surgery (e.g., functional endoscopic sinus surgery (FESS), balloon sinuplasty, and Caldwell-Luc radical antrostomy), and antifungals.

Guidance for the determination of the dosage that delivers a therapeutically effective amount of the composition described herein to treat sinusitis or rhinitis may be obtained from animal models of sinusitis or rhinitis, e.g. as described in Kara C O, *Curr Allergy Asthma Rep.* 2004; 4(6):496-9; and Chiu A G et al., *Am J Rhinol.* 2007; 21(1):5-9.

Inflammatory Diseases

Methods and composition described herein can be used to treat inflammatory diseases. Exemplary inflammatory diseases include, but not limited to, oral lichen planus, eczema, psoriasis, pulmonary inflammation, dermal irritation and inflammation, and complications of systemic inflammation.

Oral Lichen Planus.

Methods and composition described herein can be used to treat oral lichen planus. Oral lichen planus is an inflammatory condition that affects mucous membranes inside the mouth. Oral lichen planus may appear as white, lacy patches; red, swollen tissues; or open sores. These lesions may cause burning, pain or other discomfort. The lesions can be the result of inflammation controlled by T lymphocytes. Factors that may act as triggers of oral lichen planus include, e.g., hepatitis C infection and other types of liver disease, hepatitis B vaccine, certain types of flu vaccines, allergens, nonsteroidal anti-inflammatory drugs (e.g., ibuprofen and naproxen), and certain medications for heart disease, high blood pressure or arthritis. Treatments for oral lichen planus include, e.g, corticosteroids (e.g., topical corticosteroids, oral corticosteroids and corticosteroid injection), retinoids, and nonsterioidal ointments.

Eczema.

Methods and composition described herein can be used to treat eczema. Eczema (atopic dermatitis) is an chronic itchy inflammation of the skin, which may be accompanied by asthma or hay fever. Eczema may result from a malfunction in the body's immune system. Symptoms of eczema include, e.g., red to brownish-gray colored patches, itching, small raised bumps, thickened and cracked skin, and raw and sensitive skin from scratching. Eczema may affect any area, but it typically appears on the arms and behind the knees. It tends to flare periodically and then subside. Treatments for eczema include, e.g., corticosteroid creams or ointments, antibiotics, oral antihistamines, oral corticosteroids, immunomodulators (e.g., tacrolimus and pimecrolimus), and light therapy (phototherapy).

Psoriasis.

Methods and composition described herein can be used to treat psoriasis. Psoriasis is a chronic skin disease that affects the life cycle of skin cells. Psoriasis can result from abnormal immune system and its interaction with the environment in people who have the genetic susceptibility. Symptoms of psoriasis include, e.g., red patches of skin covered with silvery scales, small scaling spots, dry and cracked skin that may bleed, itching, burning, soreness, thickened or ridged nails, and swollen and stiff joints. Treatments for psoriasis include, e.g., topical treatment (e.g., topical corticosteroids, vitamin D analogues, anthralin, topical retinoids, calcineurin inhibitors (e.g., tacrolimus and pimecrolimus), salicylic acid, coal tar, moisturizers), light therapy (phototherapy), and oral or injected medication (e.g., retinoids, methotrexate, cyclosporine, hydroxyurea, immunomodulator drugs (biologics) (e.g., alefacept, etanercept, infliximab and ustekinumab), and thioguanine).

Pulmonary Inflammation.

Methods and composition described herein can be used to treat pulmonary inflammation (e.g., from infection, smoking, and chemical inhalation). Pulmonary inflammation can be associated with various disorders and/or conditions, e.g., histoplasmosis, bronchitis, chest pain, acute respiratory distress syndrome (ARDS), pneumonitis, chronic obstructive pulmonary disease (COPD), asthma (e.g., occupational asthma), aspergillosis, Churg-Strauss syndrome, and pneumonia. Treatments for pulmonary inflammation include, e.g., anti-inflammatory medications (e.g., steroids, non-steroidal anti-inflammatory drugs, and Immune Selective Anti-Inflammatory Derivatives (ImSAIDs)).

Dermal Irritation and Inflammation.

Methods and composition described herein can be used to treat dermal irritation and inflammation. Dermal irritation and inflammation can be associate with various diseases and/or conditions, e.g., microbial infection (e.g., bacterial, fungal, or viral infection), allgery, chronic disease (e.g., diabetes), and wound). Treatments for dermal irritation and inflammation include, e.g., topical or oral anti-inflammatory medications (e.g., steroids, non-steroidal anti-inflammatory drugs, and Immune Selective Anti-Inflammatory Derivatives (ImSAIDs)).

Complications of Systemic Inflammation.

Methods and composition described herein can be used to treat complications of systemic inflammation.

Systemic inflammation is an inflammatory state affecting the whole body, which can be a response of the immune system to infection. It can be related to sepsis. Chronic systemic inflammation is the result of release of pro-inflammatory cytokines from immune-related cells and the chronic activation of the innate immune system.

Systemic inflammation can be complicated by failure of one or more organs or organ systems, e.g., acute lung injury, acute kidney injury, shock, and multiple organ dysfunction syndrome. The treatment for systemic inflammation is directed towards the underlying problem or inciting cause and may include, e.g., adequate fluid replacement for hypovolemia, IVF/NPO for pancreatitis, epinephrine/steroids/benadryl for anaphylaxis, selenium, glutamine, aeicosapentaenoic acid, and vitamin E.

Guidance for the determination of the dosage that delivers a therapeutically effective amount of the composition described herein to treat an inflammatory disease (e.g., an inflammatory disease described herein) may be obtained from animal models of the inflammatory disease, e.g. as described in Nemzek J A and Kim *J, Comp Med.* 2009; 59(4):321-30; Schon M P, *Exp Dermatol.* 2008; 17(8):703-12; and Doi K. et al., *J Clin Invest.* 2009; 119(10):2868-78.

Chemical Warfare Agents and Injury

Methods of treating a subject who has been exposed to a chemical warfare agent or has suffered a chemical warfare injury are described herein. Chemical agents that can cause chemical injury in a subject and/or be used as a chemical warfare agent include, e.g., harassing agents (e.g., tear agents or lachrymatory agents (e.g., a-chlorotoluene, benzyl bromide, bromoacetone (BA), bromobenzylcyanide (CA), bromomethyl ethyl ketone, capsaicin (OC), chloracetophenone (MACE; CN), chloromethyl chloroformate, dibenzoxazepine (CR), ethyl iodoacetate, ortho-chlorobenzylidene malononitrile (super tear gas; CS), trichloromethyl chloroformate, and xylyl bromide), vomiting agents (e.g., adamsite (DM), diphenylchloroarsine (DA), diphenylcyanoarsine (DC))), incapacitating agents (e.g., psychological agents (e.g., 3-quinuclidinyl benzilate (BZ), phencyclidine (SN), lysergic acid diethylamide (K)), KOLOKOL-1 (tranquilizer)), lethal agents (e.g., blister agents (e.g., vesicants (e.g., nitrogen mustards (e.g., bis(2-chloroethyl)ethylamine (HN1), bis(2-chloroethyl)methylamine (HN2), tris(2-chloroethyl)amine (HN3)), sulfur mustards (e.g., 1,2-bis(2-chloroethylthio) ethane (Sesquimustard; Q), 1,3-bis(2-chloroethylthio)-n-propane, 1,4-bis(2-chloroethylthio)-n-butane, 1,5-bis(2-chloroethylthio)-n-pentane, 2-chloroethylchloromethylsulfide, bis(2-chloroethyl) sulfide (mustard gas; HD), bis(2-chloroethylthio) methane, bis(2-chloroethylthiomethyl) ether, bis(2-chloroethylthioethyl) ether (O mustard; T)), arsenicals (e.g., ethyldichloroarsine (ED), methyldichloroarsine (MD), phenyldichloroarsine (PD), 2-chlorovinyldichloroarsine (Lewisite; L))), urticants (e.g., phosgene oxime (CX))), blood agents (e.g., cyanogen chloride (CK), hydrogen cyanide (AC), arsine (SA)), choking agents or pulmonary agents (e.g., chlorine (CL), chloropicrin (PS), diphosgene (DP), phosgene (CG)), nerve agents (e.g., G series (e.g., tabun (GA), sarin (GB), soman (GD), cyclosarin (GF)), GV series (e.g., novichok agents, GV (nerve agent)), V series (e.g., VE, VG, VM, VX)).

Soluble Chitosans and Chitosan Derivatives

Methods, compounds and compositions for treating, e.g., a wound, mucositis (e.g., in a subject that has been treated or is being treated with a cancer therapy (e.g., chemotherapy or radiation therapy) or immunosuppressive therapy), a symptom of a chronic disease (e.g., comprising a wound and/or associated with poor or slow wound healing), or chemical injury, are described herein.

The compositions described herein include a soluble chitosan or a functionalized chitosan derivative.

Chitosan is an insoluble polymer derived from chitin, which is a polymer of N-acetylglucosamine that is the main component of the exoskeletons of crustaceans (e.g. shrimp, crab, lobster). Chitosan is formed from chitin by deacetylation, and as such is not a single polymeric molecule, but a class of molecules having various molecular weights and various degrees of deacetylation. The percent deacetylation in commercial chitosans is typically between 50-100%. The chitosan derivatives described herein are generated by functionalizing the resulting free amino groups with positively charged or neutral moieties, as described herein. The degrees of deacetylation and functionalization impart a specific charge density to the functionalized chitosan derivative. The resulting charge density affects solubility, and the strength of interaction with bacterial cell walls and membranes. The molecular weight is also an important factor in the tenacity of bacterial wall interaction and thus bactericidal activity. Thus, in accordance with the present invention, the degree of deacetylation, the functionalization and the molecular weight must be optimized for optimal efficacy. The derivatized chitosans described herein have a number of properties which are advantageous including solubility at physiologic pH and antimicrobial activity when in solution or dry at any pH less than about 9.

A soluble chitosan as described herein, refers to a water soluble chitosan that is not derivatized on the hydroxyl or amine moieties. A soluble chitosan is comprised of glucosamine and acetylglucosamine monomers. Generally a water soluble chitosan has a molecular weight of less than or equal to about 10 kDa and a degree of deactylation equal or greater than 80%. The soluble chitosans described herein are soluble at neutral and physiological pH. Water soluble is defined as being fully dissolvable in water at pH 7.

The chitosan derivatives described herein are generated by functionalizing the resulting free amino groups with positively charged or neutral moieties, as described herein.

Chitosans with any degree of deacetylation (DDA) greater than 50% are used in the present invention, with functionalization between 2% and 50% of the available amines. The degree of deacetylation determines the relative content of free amino groups to total monomers in the chitosan polymer. Methods that can be used for determination of the degree of deacetylation of chitosan include, e.g, ninhydrin test, linear potentiometric titration, near-infrared spectroscopy, nuclear magnetic resonance spectroscopy, hydrogen bromide titrimetry, infrared spectroscopy, and first derivative UV-spectrophotometry. Preferably, the degree of deacetylation of a soluble chitosan or a derivatized chitosan described herein is determined by quantitave infrared spectroscopy. Percent functionalization is determined as the % of derivatized amines relative to the total number of available amino moieties prior to reaction on the chitosan polymer. Preferably, the percent functionalization of a derivatized chitosan described herein is determined by H-NMR or quantitative elemental analysis. The degrees of deacetylation and functionalization impart a specific charge density to the functionalized chitosan derivative. The resulting charge density affects solubility, and strength of interaction with mammalian cell walls and mucosal membranes. The molecular weight is important in controlling the magnitude and extent of surface interaction. Thus, in accordance with the present invention, these properties must be optimized for optimal efficacy. Exemplary chitosan derivatives are described in Baker et al; Ser. No. 11/657,382 filed on Jan. 24, 2007, which is incorporated herein by reference.

The chitosan derivatives described herein have a range of polydispersity index (PDI) between about 1.0 to about 2.5. As used herein, the polydispersity index (PDI), is a measure of the distribution of molecular weights in a given polymer sample. The PDI calculated is the weight averaged molecular weight divided by the number averaged molecular weight. This calculation indicates the distribution of individual molecular weights in a batch of polymers. The PDI has a value always greater than 1, but as the polymer chains approach uniform chain length, the PDI approaches unity (1). The PDI of a polymer derived from a natural source depends on the natural source (e.g. chitin or chitosan from crab vs. shrimp vs. fungi) and can be affected by a variety of reaction, production, processing, handling, storage and purifying conditions. Methods to determine the polydispersity include, e.g., gel permeation chromatography (also known as size exclusion chromatography); light scattering measurements; and direct calculation from MALDI or from electrospray mass spectrometry. Preferably, the PDI of a soluble chitosan or a derivatized chitosan described herein is determined by HPLC and multi angle light scattering methods.

The chitosan derivatives described herein have a variety of selected molecular weights that are soluble at neutral and physiological pH, and include for the purposes of this invention molecular weights ranging from 5-1,000 kDa. Embodiments described herein are feature medium range molecular weight of derivatized chitosans (25 kDa, e.g., from about 15 to about 300 kDa) which can have clumping, diffusible and biofilm disruption properties.

The functionalized chitosan derivatives described herein include the following:
 (A) Chitosan-arginine compounds;
 (B) Chitosan-natural amino acid derivative compounds;
 (C) Chitosan-unnatural amino acid compounds;
 (D) Chitosan-acid amine compounds; and
 (E) Chitosan-guanidine compounds.
 (F) Neutral chitosan derivative compounds.
 (A) Chitosan-Arginine Compounds
In some embodiments, the present invention is directed to chitosan-arginine compounds, where the arginine is bound through a peptide (amide) bond via its carbonyl to the primary amine on the glucosamines of chitosan:

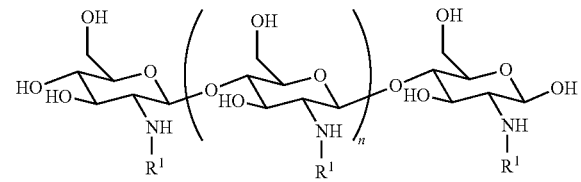

wherein each $R^1$ is independently selected from hydrogen, acetyl, and a group of the following formula:

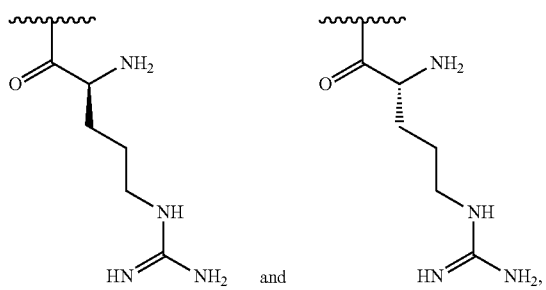 [SMILES: *C(=O)[C@@H](N)CCCNC(=N)N ; *C(=O)[C@H](N)CCCNC(=N)N]

or a racemic mixture thereof,
wherein at least 25% of $R^1$ substituents are H, at least 1% are acetyl, and at least 2% are a group of the formula shown above.

(B) Chitosan-Natural Amino Acid Derivative Compounds
In some embodiments, the present invention is directed to chitosan-natural amino acid derivative compounds, wherein the natural amino acid may be histidine or lysine. The amino is bound through a peptide (amide) bond via its carbonyl to the primary amine on the glucosamines of chitosan:

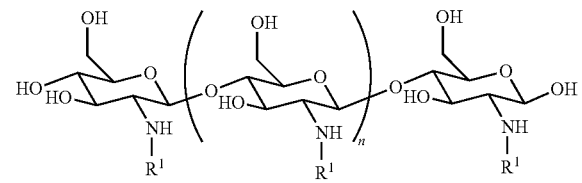

wherein each $R^1$ is independently selected from hydrogen, acetyl, and a group of the following formula:

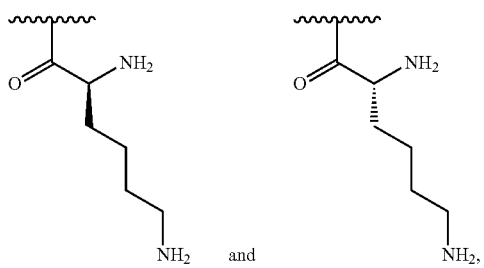 [SMILES: *C(=O)[C@@H](N)CCCCN ; *C(=O)[C@H](N)CCCCN]

or a racemic mixture thereof, wherein at least 25% of $R^1$ substituents are H, at least 1% are acetyl, and at least 2% are a group of the formula shown above; OR a group of the following formula:

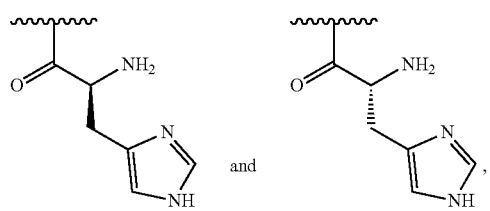 [SMILES: *C(=O)[C@@H](N)Cc1c[nH]cn1 ; *C(=O)[C@H](N)Cc1c[nH]cn1]

or a racemic mixture thereof, wherein at least 25% of $R^1$ substituents are H, at least 1% are acetyl, and at least 2% are a group of the formula shown above.

(C) Chitosan-Unnatural Amino Acid Compounds

In some embodiments, the present invention is directed to chitosan-unnatural amino acid compounds, where the unnatural amino acid is bound through a peptide (amide) bond via its carbonyl to the primary amine on the glucosamines of chitosan:

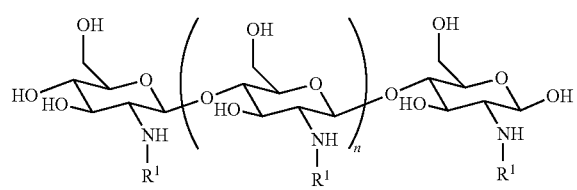

wherein each $R^1$ is independently selected from hydrogen, acetyl, and a group of the following formula:

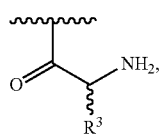

wherein $R^3$ is an unnatural amino acid side chain, and wherein at least 25% of $R^1$ substituents are H, at least 1% are acetyl, and at least 2% are a group of the formula shown above.

Unnatural amino acids are those with side chains not normally found in biological systems, such as ornithine (2,5-diaminopentanoic acid). Any unnatural amino acid may be used in accordance with the invention. In some embodiments, the unnatural amino acids coupled to chitosan have the following formulae:

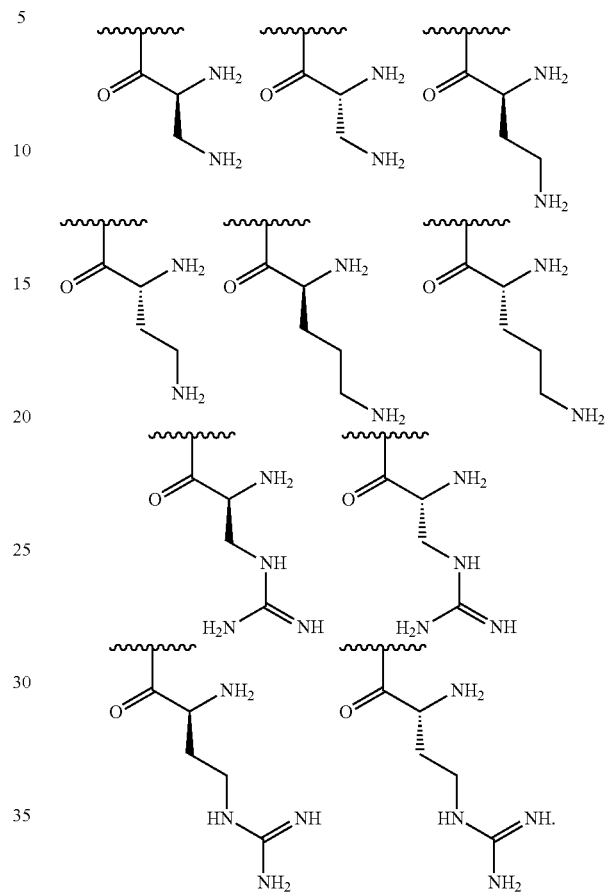

(D) Chitosan-Acid Amine Compounds

In some embodiments, the present invention is directed to chitosan-acid amine compounds, or their guanidylated counterparts. The acid amine is bound through a peptide (amide) bond via its carbonyl to the primary amine on the glucosamines of chitosan:

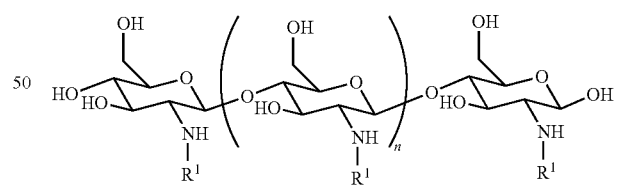

wherein each $R^1$ is independently selected from hydrogen, acetyl, and a group of the following formula:

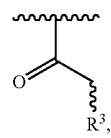

wherein $R^3$ is selected from amino, guanidino, and $C_1$-$C_6$ alkyl substituted with an amino or a guanidino group, wherein at least 25% of $R^1$ substituents are H, at least 1% are acetyl, and at least 2% are a group of the formula shown above In some embodiments, $R^1$ is selected from one of the following:

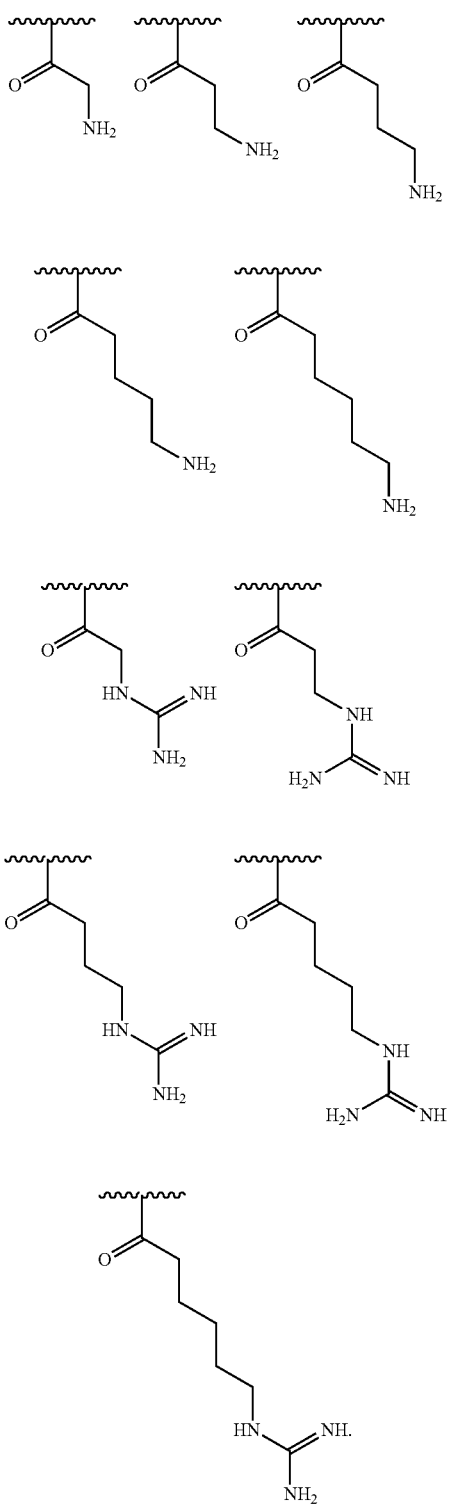

(F) Chitosan-Guanidine Compounds

In some embodiments, the present invention is directed to chitosan-guanidine compounds.

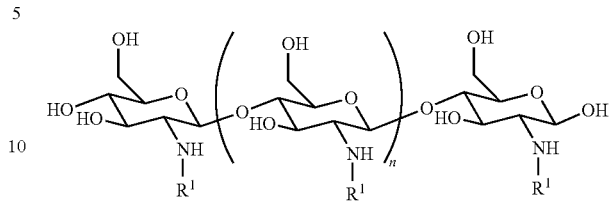

wherein each R is independently selected from hydrogen, acetyl, and a group in which $R^1$, together with the nitrogen to which it is attached, forms a guanidine moiety; wherein at least 25% of $R^1$ substituents are H, at least 1% are acetyl, and at least 2% form a guanidine moiety together with the nitrogen to which it is attached.

(F) Neutral Chitosan Derivative Compounds

In some embodiments, the present invention is directed to neutral chitosan derivative compounds. Exemplary neutral chitosan derivative compounds include those where one or more amine nitrogens of the chitosan has been covalently attached to a neutral moiety such as a sugar:

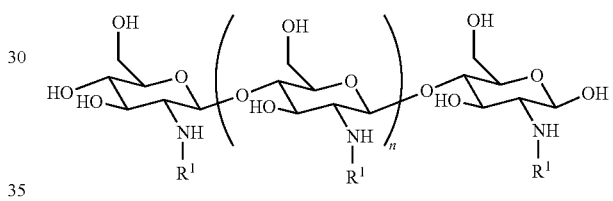

wherein each $R^1$ is independently selected from hydrogen, acetyl, and a sugar (e.g., a naturally occurring or modified sugar) or an α-hydroxy acid. Sugars can be monosaccharides, disaccharides or polysaccharides such as glucose, mannose, lactose, maltose, cellubiose, sucrose, amylose, glycogen, cellulose, gluconate, or pyruvate. Sugars can be covalently attached via a spacer or via the carboxylic acid, ketone or aldehyde group of the terminal sugar. Examples of α-hydroxy acids include glycolic acid, lactic acid, and citric acid. In some preferred embodiments, the neutral chitosan derivative is chitosan-lactobionic acid compound or chitosan-glycolic acid compound. Exemplary salts and coderivatives include those known in the art, for example, those described in US 2007/0281904, the contents of which is incorporated by reference in its entirety.

Formulations and Routes of Administration

The compounds described herein can be formulated in a variety of manners, including for topical or oral delivery. For example, the compounds can be administered, e.g., topically (e.g., by solution (e.g., oral rinse, throat gargle, eye drop), lotion, cream, ointment, gel, foam, transdermal patch, powder, solid, ponge, tape, vapor, inhalation or intranasal spray (e.g., nasal spray, nasal mists, sinus spray, nebulizer), enema, eye drops), or enterally (e.g., orally, gastric feeding tube, duodenal feeding tube, gastrostomy, rectally, buccally). In some embodiments, oral rinse is used for the delivery of a compound described herein to locally treat a wound or condition described herein, e.g., mucositis, e.g., oral mucositis. In some embodiments, inhalation sprays (e.g., nasal spray, nasal mists, or sinus spray), are used for the nasal delivery of a compound descried herein, to locally treat a wound or condition described herein, e.g., mucositis, e.g., in the respiratory or pulmonary tract. Inclusion in feed, water or an inhaled formulation is particularly desirable for use with animals. In some embodiments, a compound is formulated so as to allow the soluble chitosan or soluble chitosan derivative thereof to diffuse into a subject (e.g., into the wound, body cavities, or skin of a subject) upon administration to the subject or to be ingested, inhaled or swabbed while incorporated into a time release formulation.

The compound described herein (e.g., a soluble chitosan or a derivatized chitosan) can be administered before, during or after the onset of the condition or disorder described herein. For example, the compound described herein can be administered in a subject who has been treated or is being treated with one or more cancer therapy, e.g., chemotherapy or radiation therapy, or immunosuppressive therapy, to treat mucositis. The methods herein contemplate administration of an effective amount of compound or compound composition to achieve the desired or stated effect. Typically, the compositions of this invention will be administered from about 1 to about 12 times, about 3 to about 10 times, or about 5 to 8 times per day. Alternatively, the compounds can be administered as a continuous time-release or ad-libitim in water or food. Such administration can be used as a chronic or acute therapy. The amount of active ingredient that may be combined with the carrier materials to produce a single dosage form will vary depending upon the host treated and the particular mode of administration. A typical solution preparation will contain from about 1 µg/mL to about 1000 µg/mL, about 5 µg/mL to about 500 µg/mL, about µg/mL to about 250 µg/mL, about 50 µg/mL to about 200 µg/mL, or about 100 µg/mL to about 200 µg/mL. A typical solid diffusible preparation will contain from about 0.1% to about 10%, about 0.2% to about 10%, or about 0.05% to about 5% by weight. A typical solid dissolvable preparation will contain from about 0.1% to about 95%, about 0.2% to about 70%, about 0.5% to about 40%, about 1% to about 10% by weight.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the type and nature of the bacteria, the patient's disposition to the disease, condition or symptoms, and the judgment of the treating physician.

In an embodiment, the compounds described herein (e.g., a soluble chitosan or a derivatized chitosan) can be formulated, e.g., as a solution, gel, ointment, or dressing, e.g., for treating a wound, e.g., in the absence of wound infection. In an embodiment, the dosage (e.g., solution dosage) is from about 10 µg/mL to about 1000 µg/mL, about 50 µg/mL to about 500 µg/mL, or about 100 µg/mL to about 300 µg/mL, applied e.g., sufficiently to rinse a wound area. In an embodiment, the dosage (e.g., solution dosage) is from about 10 to about 1000 µg/mL, about 500 µg/mL to about 500 µg/mL, or about 100 g/mL to about 300 µg/mL, applied to coat the wound at least 1, 2, 3, 4, 5 or 6 times daily. In an embodiment, the dosage (e.g., solution dosage) is from about 10 to about 500 µg/mL, about 50 µg/mL to about 400 µg/mL, about 60 to about 350 µg/mL, about 75 to about 300 µg/mL, (typically about 200 g/mL), about 30 to about 50 µg/mL, about 50 to about 70 µg/mL, about 70 to about 100 µg/mL, or about 100 to about 200 µg/mL, applied to a wound or ulcer in the eye, at least 1, 2, 3, 4, 5, or 6 times daily. In an embodiment, the solid diffusible composition (dressing) is from about 0.1% to about 10%, about 0.2% to about 8%, or about 0.5% to about 5%, by weight applied to cover the wound at least 1, 2, 3, 4, 5 or 6 times daily. In an embodiment, the composition is applied to a thickness of at least about 1/128, 1/64, 1/32, or 1/16 inch.

In an embodiment, the compounds described herein (e.g., a soluble chitosan or a derivatized chitosan) can be formulated, e.g., as a solution, encapsulated time release, gel, or enema, e.g., for treating a wound or condition in the mucous membrane, e.g., mucositis, e.g., in gastrointestinal tract. In an embodiment, the dosage is from about 10 µg/mL to about 1000 µg/mL, about 20 µg/mL to about 900 g/mL, about 50 µg/mL to about 500 µg/mL, about 60 µg/mL to about 300 µg/mL, or about 50 to about 200 µg/mL in solution, e.g., ad libitum, e.g., in water or fluid. In an embodiment, the composition is administered at least 1, 2, 3, or 4 times daily. In an embodiment, the dosage is from about 1 mg/kg to about 200 mg/kg, about 2 mg/kg to about 100 mg/kg, about 4 mg/kg to about 75 mg/kg, or about 5 mg/kg to about 40 mg/kg body weight in an encapsulated time release, gel, capsule or enema. In an embodiment, the composition is administered at least 1, 2, 3, 4, 5 or 6 times daily.

In an embodiment, the compounds described herein (e.g., a soluble chitosan or a derivatized chitosan) can be formulated as a nebulized solution or powder, or lavage, e.g., for treating a wound or condition in respiratory tract. In a preferred embodiment, the dosage is from about 500 µg to about 50000 j g, about 1000 µg to about 25000 µg, about 2000 µg to about 10000 µg, or about 4000 µg to about 6000 µg, per kg body weight, every 2, 4, 6, 8, 10, 12, or 24 hours. In an embodiment, the composition is administered at least 1, 2, 3, 4, 5 or 6 times daily.

In an embodiment, the compounds described herein (e.g., a soluble chitosan or a derivatized chitosan) can be formulated, e.g., as a spray, ointment, gel or inhalant, e.g., for treating a disorder or condition in throat, ear, or nose. In a preferred embodiment, the dosage is from about 10 µg/mL to about 1000 µg/mL, about 20 µg/mL to about 500 µg/mL, about 50 µg/mL to about 300 µg/mL in solution, about 0.1% to about 10%, about 0.5% to about 5%, or about 1% to about 2%, by weight in an ointment or gel. In an embodiment, the composition is administered at least 1, 2, 3, 4, 5 or 6 times daily.

In an embodiment, the compounds described herein (e.g., a soluble chitosan or a derivatized chitosan) can be formulated, e.g., as a solution, or encapsulated time release (e.g., enteric coating), e.g., for treating an inflammatory gastrointestinal disorder. In a preferred embodiment, the dosage is from about 0.1 to about 100 mg/kg body weight, about 1 to about 90 mg/kg body weight, about 10 to about 80 mg/kg body weight, about 20 to about 70 mg/kg body weight, about 30 to about 60 mg/kg body weight, about 0.1 to about 1 mg/kg body weight, about 1 to about 10 mg/kg body weight, about 10 to about 20 mg/kg body weight, about 20 to about 40 mg/kg body weight, about 40 to about 60 mg/kg body weight, about 30 to about 50 mg/kg body weight (typically 40 mg/kg body weight), about 60 to about 80 mg/kg body weight, or about 80 to about 100 mg/kg body weight. In an embodiment, the composition is administered at least 1, 2, 3, 4, 5 or 6 times daily.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained. Patients may, however, require intermittent treatment on a long-term basis upon any recurrence of disease symptoms.

Pharmaceutical compositions of this invention comprise a compound of the formulae described herein or a pharmaceutically acceptable salt thereof; an additional compound including for example, a steroid or an analgesic; and any pharmaceutically acceptable carrier, adjuvant or vehicle. Alternate compositions of this invention comprise a compound described herein or a pharmaceutically acceptable salt thereof; and a pharmaceutically acceptable carrier, adjuvant or vehicle. The compositions delineated herein include the compounds described herein, as well as additional therapeutic compounds if present, in amounts effective for achieving a modulation of disease or disease symptoms.

The compositions are generally made by methods including the steps of combining a compound described herein with one or more carriers and, optionally, one or more additional therapeutic compounds delineated herein.

The term "pharmaceutically acceptable carrier or adjuvant" refers to a carrier or adjuvant that may be administered to a patient, together with a compound of this invention, and which does not destroy the pharmacological activity thereof and is nontoxic when administered in doses sufficient to deliver a therapeutic amount of the compound.

The pharmaceutical compositions of this invention may be orally administered in any orally acceptable dosage form including, but not limited to, capsules, tablets, chewing gum, dissolving gel, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase which can be combined with emulsifying and/or suspending agents. If desired, certain sweetening and/or flavoring and/or coloring agents may be added.

The compounds of this invention may be administered by aerosol, nebulizer, or inhalation. In some embodiments, the composition is in the form of a dry powder, a suspension, or a solution. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. Exemplary methods and devices for aerosol or inhalation include those described in U.S. Pat. No. 6,962,151, which is incorporated herein by reference in its entirety.

Compositions formulated for inhaled delivery generally include particles having a mean diameter of from about 0.01 µm to about 50 µm (e.g., from about 0.01 µm to about 10 µm, or from about 0.2 µm to about 5 µm). In some embodiments, the composition includes a dispersion of suitably-sized dry particles, for example, precipitants or crystals) or a dispersion of a solution (e.g., droplets) of a suitable size.

The pharmaceutical compositions of this invention may also be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

Pharmaceutically acceptable carriers, adjuvants and vehicles that may be used in the pharmaceutical compositions of this invention include, but are not limited to, ion exchangers, alumina, aluminum stearate, lecithin, self-emulsifying drug delivery systems (SEDDS) such as d-α-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, may also be advantageously used to enhance delivery of compounds of the formulae described herein.

In some cases, the pH of the formulation may be adjusted with pharmaceutically acceptable acids, bases or buffers to enhance the stability of the formulated compound or its delivery form for delivery in particular regions of the body, such as the colon.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

When the compositions of this invention comprise a combination of compounds described herein, both the compounds are generally present at dosage levels of between about 0.01 to 100%, and more preferably between about 1 to 95% of the dosage normally administered in a monotherapy regimen. Additionally, combinations of a plurality of compounds described herein are also envisioned. The compounds may be administered separately, as part of a multiple dose regimen, from the compounds of this invention. The compounds may be administered in a manner and dose where they act synergistically as describe e.g., in U.S. Patent Application No. 61/113,904, which is incorporated herein by reference in its entirety. Alternatively, those compounds may be part of a single dosage form, mixed together with the compounds of this invention in a single composition.

Kits and Medical Devices

A compound described herein (e.g., a soluble chitosan or a derivatized chitosan) can be provided in a kit. The kit includes (a) a composition that includes a compound described herein, and, optionally (b) informational material. The informational material can be descriptive, instructional, marketing or other material that relates to the methods described herein and/or the use of the compound described herein for the methods described herein.

The informational material of the kits is not limited in its form. In one embodiment, the informational material can include information about production of the compound, molecular weight of the compound, concentration, date of expiration, batch or production site information, and so forth. In one embodiment, the informational material relates to use of the compound described herein to treat a disorder described herein.

In one embodiment, the informational material can include instructions to administer the compound described herein in a suitable manner to perform the methods described herein, e.g., in a suitable dose, dosage form, or mode of administration (e.g., a dose, dosage form, or mode of administration described herein). In another embodiment, the informational material can include instructions to administer the compound described herein to a suitable subject, e.g., a human, e.g., a human having or at risk for a disorder or condition described herein. For example, the material can include instructions to administer the compound described herein to such a subject.

The informational material of the kits is not limited in its form. In many cases, the informational material, e.g., instructions, is provided in printed matter, e.g., a printed text, drawing, and/or photograph, e.g., a label or printed sheet. However, the informational material can also be provided in other formats, such as computer readable material, video recording, or audio recording. In another embodiment, the informational material of the kit is contact information, e.g., a physical address, email address, website, or telephone number, where a user of the kit can obtain substantive information about a compound described herein and/or its use in the methods described herein. Of course, the informational material can also be provided in any combination of formats.

In addition to a compound described herein, the composition of the kit can include other ingredients, such as a solvent or buffer, a stabilizer, a preservative, and/or a second compound for treating a condition or disorder described herein. Alternatively, the other ingredients can be included in the kit, but in different compositions or containers than the compound described herein. In such embodiments, the kit can include instructions for admixing the compound described herein and the other ingredients, or for using a compound described herein together with the other ingredients.

The compound described herein can be provided in any form, e.g., liquid, dried or lyophilized form. It is preferred that the compound described herein be substantially pure and/or sterile. When the compound described herein is provided in a liquid solution, the liquid solution preferably is an aqueous solution, with a sterile aqueous solution being preferred. When the compound described herein is provided as a dried form, reconstitution generally is by the addition of a suitable solvent. The solvent, e.g., sterile water or buffer, can optionally be provided in the kit.

The kit can include one or more containers for the composition containing the compound described herein. In some embodiments, the kit contains separate containers, dividers or compartments for the composition and informational material. For example, the composition can be contained in a bottle, vial, or syringe, and the informational material can be contained in a plastic sleeve or packet. In other embodiments, the separate elements of the kit are contained within a single, undivided container. For example, the composition is contained in a bottle, vial or syringe that has attached thereto the informational material in the form of a label. In some embodiments, the kit includes a plurality (e.g., a pack) of individual containers, each containing one or more unit dosage forms (e.g., a dosage form described herein) of a compound described herein. For example, the kit includes a plurality of syringes, ampules, foil packets, or blister packs, each containing a single unit dose of a compound described herein. The containers of the kits can be air tight, waterproof (e.g., impermeable to changes in moisture or evaporation), and/or light-tight.

The kit optionally includes a device suitable for administration of the composition, e.g., a syringe, inhalant, pipette, forceps, measured spoon, dropper (e.g., eye dropper), swab (e.g., a cotton swab or wooden swab), or any such delivery device. The composition described herein can be used in a medical device for wound treatment, e.g., a device used in negative pressure wound therapy or a vacuum assisted closure unit, e.g., as described in U.S. Pat. No. 7,618,382, the content of which is incorported herein by reference.

Negavie Pressure Wound Therapy

Negative pressure wound therapy (NPWT), also known as topical negative pressure, sub-atmospheric pressure dressings or vacuum sealing technique, is a therapeutic technique used to promote healing in acute or chronic wounds, fight infection and enhance healing of burns. A vacuum source is used to create sub-atmospheric pressure in the local wound environment.

NPWT seals the wound to prevent dehiscence with a gauze or foam filler dressing, a drape and a vacuum source that and applies negative pressure to the wound bed with a tube threaded through the dressing. The vacuum may be applied continuously or intermittently, depending on the type of wound being treated and the clinical objectives. Intermittent removal of used instillation fluid supports the cleaning and drainage of the wound bed and the removal of infectious material.

NPWT has two forms which mainly differ in the type of dressing used to transfer NPWT to the wound surface: gauze or foam. For pain sensitive patients with shallow or irregular wounds, wounds with undermining or explored tracts or tunnels, and for facilitating wound healing, gauze may be a better choice for the wound bed, while foam may be cut easily to fit a patient's wound that has a regular contour and perform better when aggressive granulation formation and wound contraction is the desired goal.

A dressing, containing a drainage tube, is fitted to the contours of a deep or irregularly-shaped wound and sealed with a transparent film. The tube is connected to a vacuum source, turning an open wound into a controlled, closed wound while removing excess fluid from the wound bed to enhance circulation and remove waste from the lymphatic system. Fluid or treatments may be circulated to the wound through the foam or dissociated from the foam. The technique can be used with chronic wounds or wounds that are expected to present difficulties while healing (such as those associated with a chronic disease, e.g., diabetes or when the veins and arteries are unable to provide or remove blood adequately).

EXAMPLES

As provided in the Examples below, CA and C/A refer to chitosan-arginine. A fraction of the amines of the glucosamine on chitosan are reacted with a single arginine, as apposed to a dimer, trimer or larger polyarginine. This monoargylation of each reacted amine is accomplished by using a protecting group on the primary amine of the arginine upon coupling as described in U.S. patent application Ser. No. 11/657,382, the contents of which are incorporated herein by reference.

As shown in the Examples below, in vitro data (e.g., up-regulated IL-10 and down-regulated TNF-α or IL-8) suggest the generation of a less pro-inflammatory environment. Epithelial cells in a scratch assay filled in the scratch more quickly indicating enhancement of healing. The in vivo data show an immediate reduction in inflammation associated with an increased epithelialization and healing rate, both when given prophylactically and as a post damage treatment.

These results demonstrate that chitosan-arginine has the ability to reduce initial and downstream inflammation, e.g., by topical application. Further, it enhances the healing rate of topical damage. It is suggested that there is an early inhibition of various pathways that lead to NF-κB activation as the nexus of control, both in regulating inflammation and the onset of an environment conducive to healing in radiation induced lesions, where there is damage and inflammation followed by a healing period.

Example 1: Scratch Assay

Method

A431 epidermal cells were seeded into 4-well chamber slides in DMEM plus 10% FBS at $5 \times 10^5$ cells/well to be confluent the next day. The following day two scratches were made across the confluent monolayer using a sterile 10 μl tip, to form a cross in the middle of the well, and the wells were rinsed with DMEM to remove floating debris. Serum free DMEM was added to all wells and additives were added to the indicated final concentrations. Cells were incubated for 24 or 48 hours before being fixed with 3% paraformaldehyde in PBS for 10 minutes at room temperature. After rinsing with water, cells were stained with hematoxylin solution for 1 minute, rinsed with water, incubated with PBS for 1 minute, air dried and mounted. Pictures were taken at 4× magnification.

In Vitro Scratch Wound Healing is Accelerated by Chitosan-Arginine (CA)

A431 cells were cultured on glass chamber slides until confluent then scratched with a sterile pipet tip. A representative time 0 scratch is shown at the top of each treatment column for reference. CA (18 kD, 25% functionalization) was added to a final concentration of 100 ug/ml (0.01%) and 200 ug/ml (0.02%). EGF (epidermal growth factor) was used as a positive control, added to a final concentration of 10 ng/ml. Cells were incubated with the indicated treatment for 24 and 48 hours before being fixed. FIG. 1 shows the time dependence of treatment of scratches with medium (with serum) as the negative control and with EGF as the positive control. As shown in FIG. 1, addition of CA causes the scratch to be filled in more rapidly at both 24 and 48 hours than the no addition controls, and appears to be as effective as EGF, known to be effective in promoting reepitheliazation. Scratch tests on A431 epithelial cells demonstrate more rapid closure of a scratch in a monolayer in the presence of chitosan-arginine.

Figure 2:
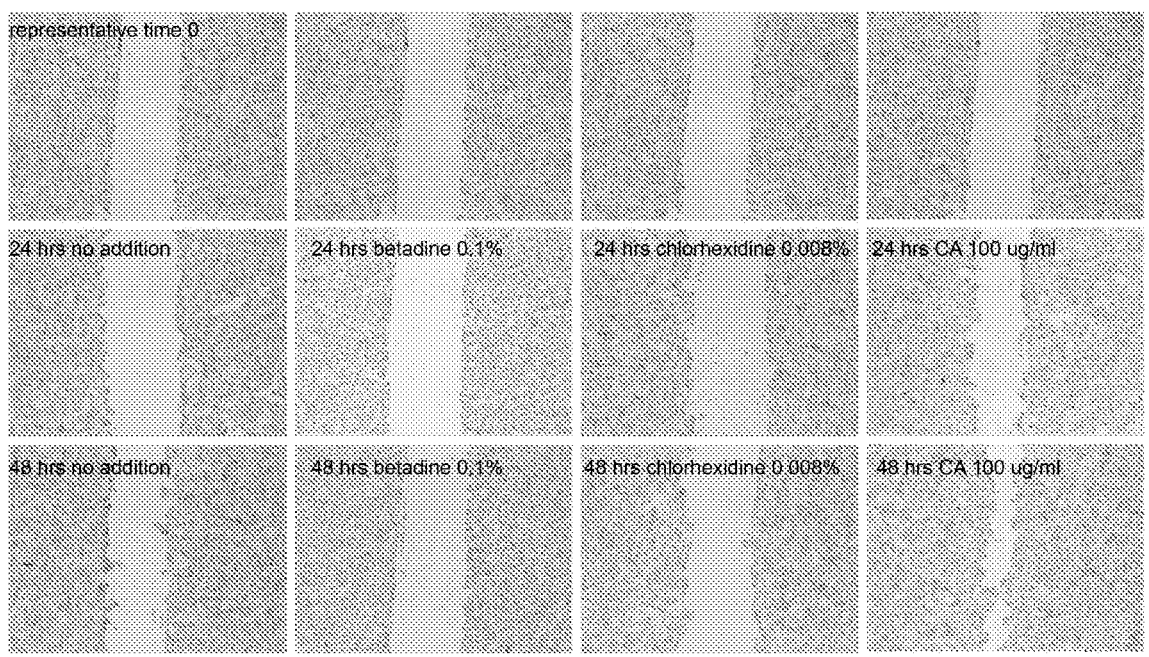
FIG. 2 depicts the comparison of the effects of chitosan-arginine with betadine and chlorhexidine.

Comparison of the Effects of Chitosan-Arginine (CA) with Betadine and Chlorhexidine Scratches were performed as described, with the betadine, chlorhexidine and CA (18 kD, 35% functionalization) added to the indicated final concentrations. Cells were incubated for 24 or 48 hrs, fixed, stained and photographed. As shown in FIG. 2, addition of CA causes the scratch to be filled in more rapidly than the addition of betadine or chlorhexidine.

Figure 3:
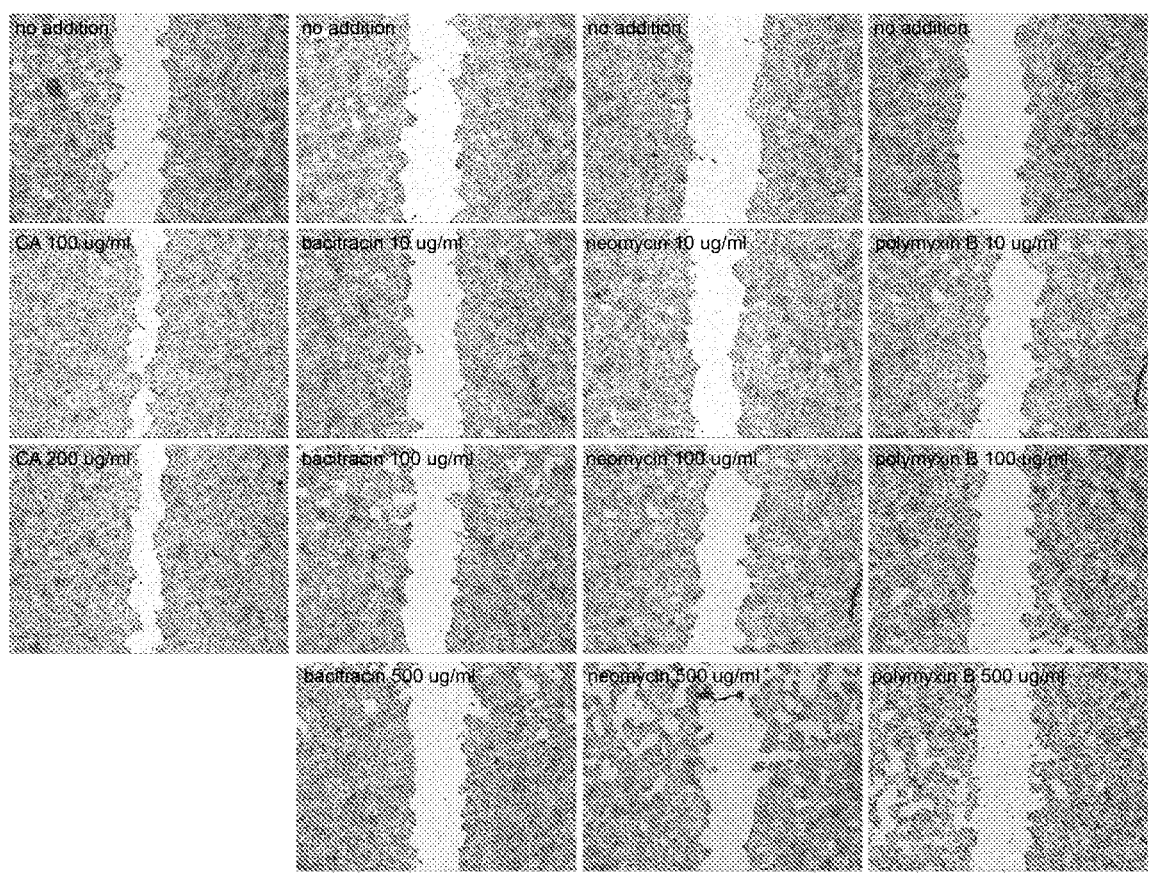
FIG. 3 depicts the comparison of the effects of chitosan-arginine with bacitracin, neomycin, polymyxin B.

Comparison of the Effects of Chitosan-Arginine (CA) with Bacitracin, Neomycin, Polymyxin B Scratches were performed as described, with bacitracin, neomycin, polymyxin B and CA (18 kD, 35% functionalization) added to the indicated final concentrations. Cells were incubated for 24 or 48 hrs, fixed, stained and photographed. As shown in FIG. 3, addition of CA causes the scratch to be filled in more rapidly than the addition of bacitracin, neomycin or polymyxin B.

Figure 4:
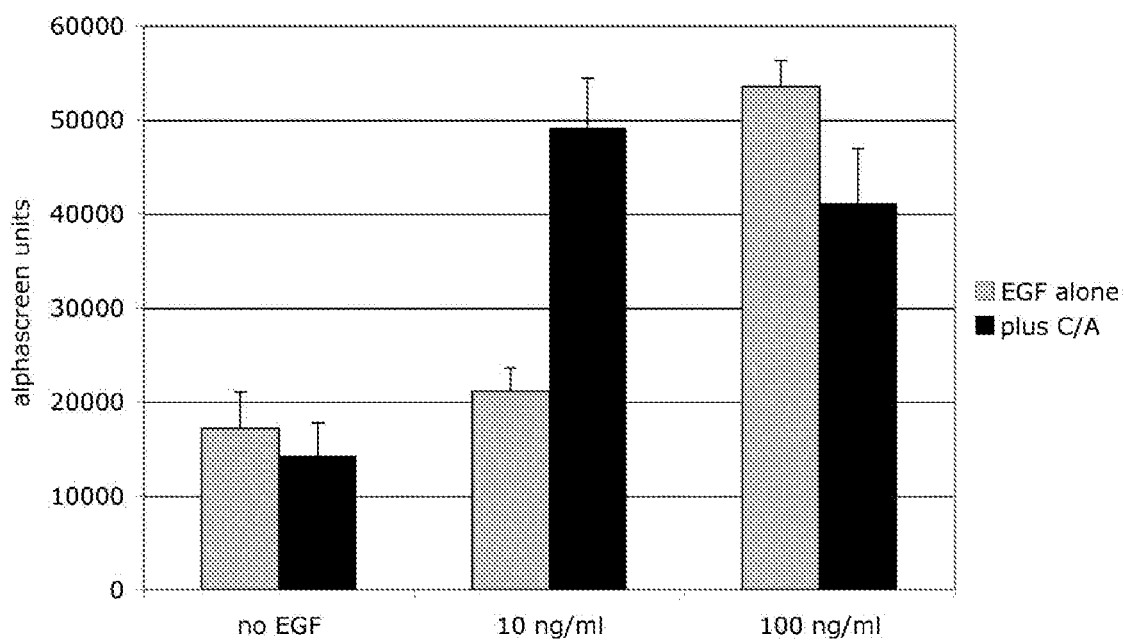
FIG. 4 depicts the effect of chitosan-arginine on enhancing ERK phophorylation in response to submaximal EGF concentration in Caco2 cells.

Example 2: Chitosan-Arginine Enhances the Ability of Submaximal EGF Concentration to Induce Activation of ERK in Caco2 Cells Caco2 intestinal epithelial cells were cultured in 96-well tissue culture plates for 5 days in serum containing medium until cells were confluent. Medium was replaced with serum free medium for one hour before cells were stimulated. Cells were treated by adding CA alone to a final concentration of 100 μg/ml, EGF alone at a final concentration of 10 or 100 ng/ml or the combination of EGF and C/A at the same final concentrations but incubated together for one hour before adding to the cells. After 10 minutes the medium was aspirated and the cells lysed in 50 μl lysis buffer. The plate was gently agitated for 10 minutes before 4 μl aliquots of each sample were added to duplicate wells on a 384 well white proxiplate. The level of ERK phosphorylation was assayed using the SureFire® Phospho-ERK 1/2 assay kit. AlphaScreen™ SureFire™ (PerkinElmer) is an immunosandwich based assay that provides a quantitiative method to measure activation of cellular proteins. Briefly, an antibody that recogizes non-activated epitope of the target protein is coupled with a donor bead, and a second antibody that specifically recognizes the active form of the target protein is coupled to an acceptor bead. A signal is emitted when the donor and acceptor are brought into close proximity by binding the same protein. Signals are measured using the Envision plate reader (excitation at 680 nm, emission at 520-620 nm)(PerkinElmer), and the magnitude of the signal is directly proportional to the amount of activated protein present in the sample. Data shown are from one experiment in which each condition was carried out in triplicate wells of the 96 well tissue culture plate and each well was assayed in duplicate. As shown in FIG. 4, chitosan arginine enhances ERK phosphorylation in response to submaximal EGF concentration in Caco2 cells.

Figure 5:
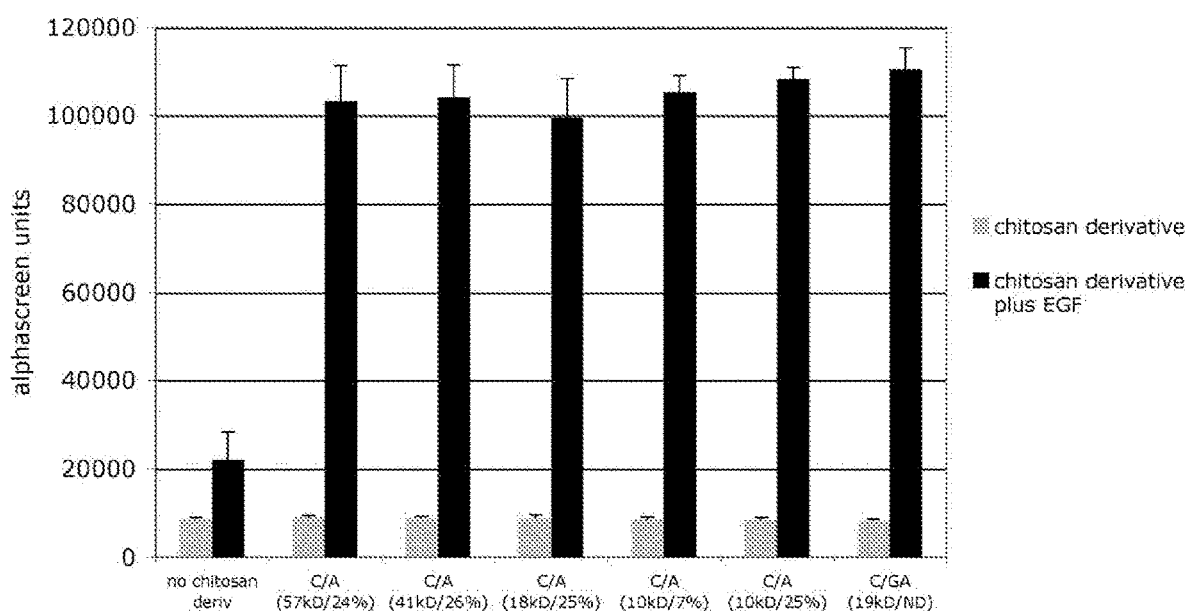
FIG. 5 depicts the effect of chitosan-arginine of different molecular weights and degree of functionalization, and chitosan glycolic acid on enhancing EGF induced ERK phosphorylation.

Example 3: The Molecular Weight, Degree of Functionalization and Type of Modification of Chitosan Derivatives do not Affect the Enhancement of EGF Induced Signaling Events by Chitosan Derivatives A431 epidermal cells were cultured for one day in 96 well tissue culture plates to achieve confluent monolayers. Serum containing medium was replaced with serum free medium approximately 12 hours before stimulations. Cells were treated with 100 g/ml of each chitosan derivative for one hour before addition of 10 ng/ml EGF (submaximal concentration) for 10 minutes. Level of ERK phosphorylation was measured using the AlphaScreen® SureFire® Phospho-ERK assay as described previously. Data shown are from one experiment in which each condition was carried out in triplicate wells of the 96 well tissue culture plate and each well was assayed in duplicate. As shown in FIG. 5, chitosan-arginine of different molecular weights and degree of functionalization, and chitosan glycolic all enhance EGF induced ERK phosphorylation.

Figure 6:
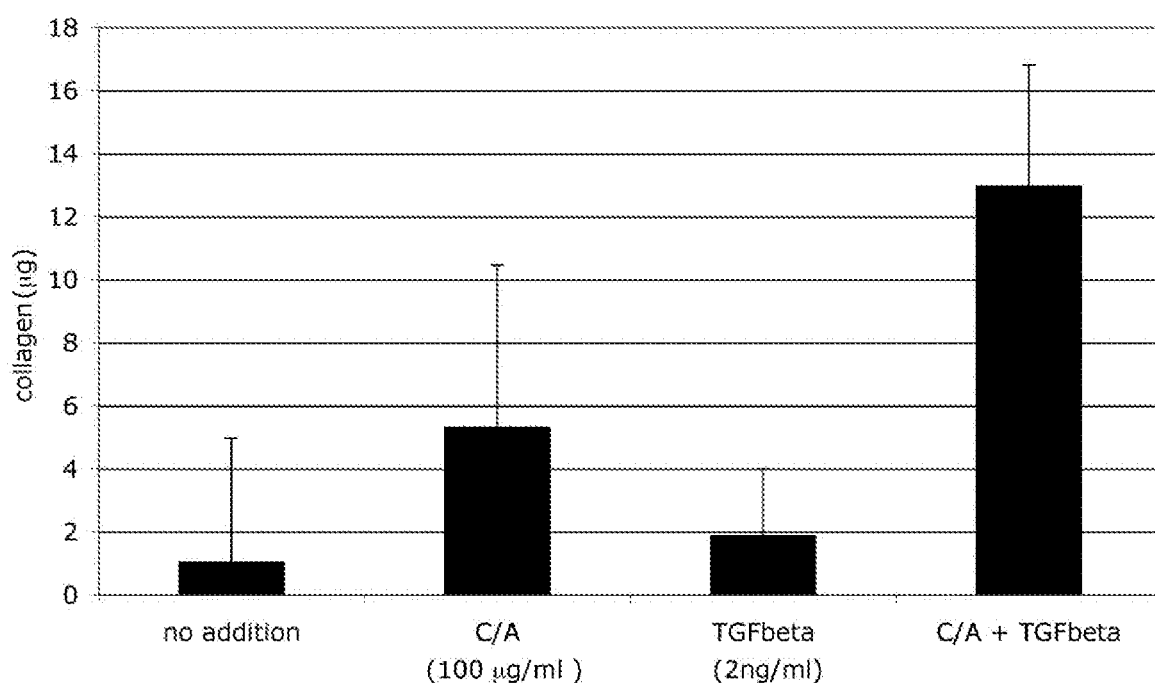
FIG. 6 depicts the effect of chitosan-arginine on enhancing collagen production by TGFβ.

Example 4: Addition of Chitosan-Arginine (CA) Enhances Responses to Submaximal TGF-β Concentration Hs68 human foreskin fibroblasts were seeded into 96 well plates at a density of 4000 cells per well and cultured in DMEM containing 10% FBS for 24 hours to form confluent monolayers of cells. Medium was replaced with serum free DMEM and cells allowed to equilibrate for 2 hours. Cells were treated by addition of 100 g/ml CA (18 kD, 25% functionalization) alone, 2 ng/ml TGF-β alone or a combination of both with the CA being added to the cells immediately prior to the addition of the TGF-β. Cells were incubated with the different treatment for 24 hours before the medium was removed and assayed for the amount of soluble collagen present using the Sircol™ colorimetric assay. A standard curve was performed using collagen type I. As shown in FIG. 6, chitosan arginine enhances collagen production by TGF-β.

Example 5: Elephant Wound Testing

Two elephants with chronic wounds, "Shine" 7,000 lb female with deep, chronic, inflamed infected wound beneath toenail and "Tusko" 13,000 lb male, with wide, moderately deep, chronic, inflamed infected wound on footbed, were tested under veterinary guidance. Wounds were cleaned and debrided weekly, and rinsed daily with water and then 200 ppm chitosan-arginine.

"Shine"

On day 0, necrotic tissue was cut away from the wound and the wound was rinsed. First treatment was about 50 mL chitosan-arginine rinsed into the wound. In week 1, the proliferative polypoid mass of loose tissue coming off the granulation bed, which usually needed to be trimmed back, was not present in the central part of the lesion. The lesion was consisted of a cavitary lesion lined with granulation tissue with epithelium encroaching from all sides. The encroaching epithelium appeared bright white and healthy. The epithelium was debrided back slightly to provide better drainage of the wound, and the granulation bed was expected to catch up with the epithelium. In week 2, the foot lesion looked to be progressing well and appeared to be essentially covered with epithelium internally, though some of it remained very thin. In week 3, the white-colored epithelium, surrounded by darker epithelium that had been walked on and stained, was almost fully closed but there was a vertical defect about ¾" deep that was trimmed to open for irrigation. The inflammation and healing progressed, despite the ability of the wound to close completely due to the consequences of the mass of the elephant on the open lesion.

"Tusko"

In week 1, lesion on the left pad was overgrown with epithelium which was not attached in the central part of the wound. This is a common occurrence in healing wounds on elephants and wounds' epithelial margins must be kept trimming back to avoid trapping debris in the lesion. Small Rongeurs were used to remove some of the overgrown epithelium to re-expose the granulation bed. In week 2, the lesion was nearly unapparent. The wound was opened up with some small Rongeurs and it bled almost immediately indicating it was close to being fully healed. In week 3, no trimming was required with the lesion as it was shallower. Irrigation was performed using bulb tip and irrigation needle only. The lesion was healed in three weeks.

Figure 7:
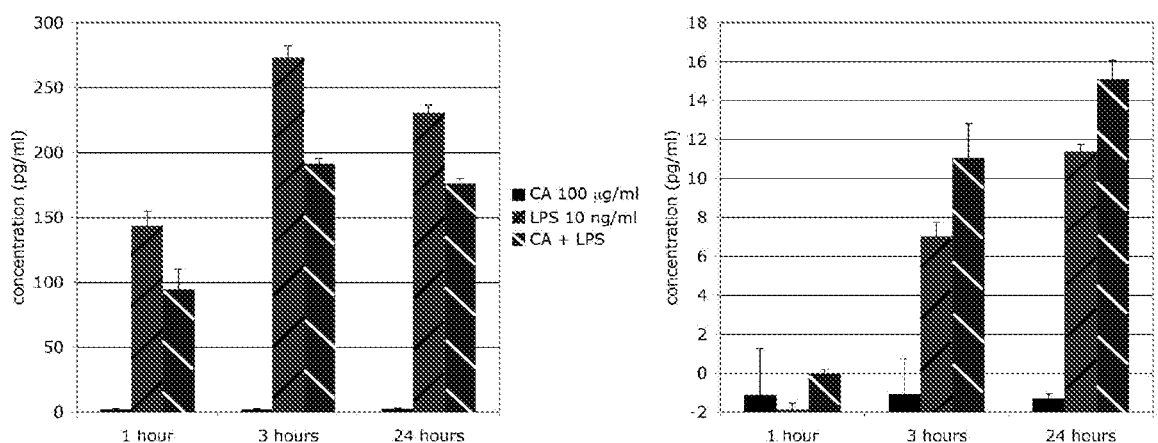
FIG. 7 depicts the TNF-α concentration (left panel) and IL-10 concentration (right panel) in THP-1 human monocytes treated with chitosan arginine alone, liposaccharide (LPS) alone, or chitosan arginine after LPS stimulation.

Example 6: In Vitro Study of the Anti-Inflammatory Activity of Chitosan-Arginine in Immune Cells THP-1 human monocyte cells were treated with 100 μg/ml chitosan-arginine alone, 10 ng/ml liposaccharide (LPS) alone, or 100 μg/ml chitosan-arginine after stimulation with 10 ng/ml LPS. The concentrations of TNF-α and IL-10 were determined at 1, 3, and 24 hours after treatment. As shown in FIG. 7, chitosan-arginine added after LPS stimulation reduced the inflammatory TNF-α response relative to the response initiated by LPS alone without chitosan-arginine treatment. FIG. 7 also shows that chitosan-arginine increased the relative response of an anti-inflammatory cytokine, IL-10. In data not shown, epidermal growth factor signaling was increased in the presence of chitosan-arginine in EGF-rich cells, suggesting that endogenous EGF is either carried more effectively to the receptors on the cells or that the polysaccharide chitosan-arginine increases access to EGF receptors. This signaling was blocked by the addition of EGFR inhibitors, further suggesting that chitosan-arginine enhances the normal endogenous activity of EGF.

Example 7: Chemical Induced Inflammatory Bowel Model

Two pre-clinical studies were conducted to examine the effect of chitosan-arginine as a treatment for gastrointestinal (GI) mucosal inflammation, ulceration and damage in mice. In these studies, the damage was chemically induced at the mucosal surface. These studies represent standard models for inflammatory bowel disease (IBD) (SGN-01) and for Crohn's disease (SGN-02). The results of the studies suggest that chitosan-arginine has a role in healing and reduction of inflammation at the mucosal interface.

Two studies were performed on male C57Bl/6 mice (Biomodels, Inc.; Watertown, Mass.) to examine the effect of treatment of chitosan-arginine on damaged mucosa. In the dextran sodium sulfate (DSS) model (SGN-01), 10 mice each arm were dosed DSS in their drinking water for 5 days, then DSS was discontinued and treatment of control vehicle (water), 1 mg/kg prednisolone, 4 mg/kg chitosan-arginine or 40 mg/kg chitosan-arginine was given via oral gavage 3× daily for 12 days. For the second study (SGN-02), trinitrobenzene sulfonic acid (TNBS) in ethanol was used to directly damage the colon. The same four treatments in 10 mice each arm were started 1 day before TNBS challenge, and continued for 5 days. In each case, the colon was examined by endoscopy at two points in the study. Histological examination of the colon can be performed at the termination of the study.

Figure 8:
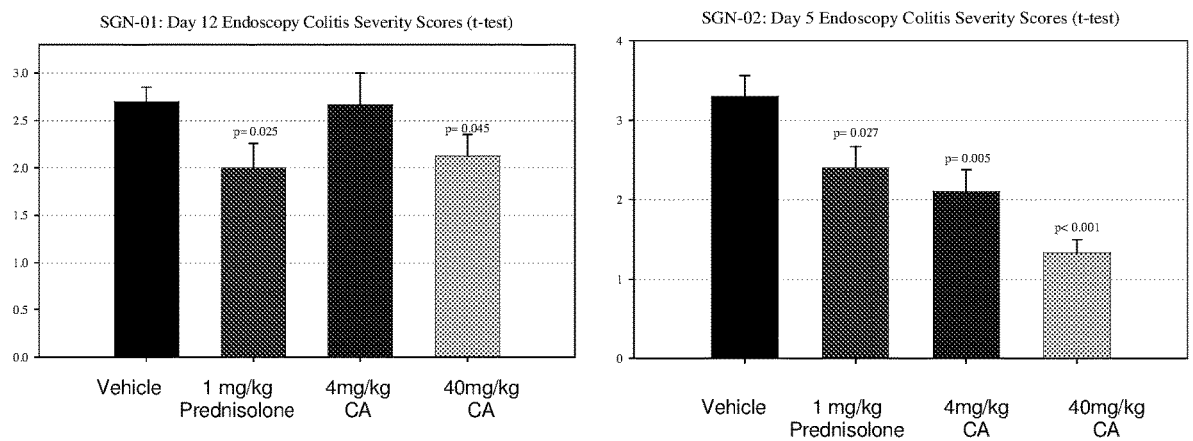
FIG. 8 depicts the endoscopy colitis severity scores for the DSS model (SGN-01, left) and the TNBS model (SGN-02, right) for a vehicle control, the standard of care prednisolone, and two doses of chitosan-arginine, given t.i.d via oral gavage in mice. P scores are calculated relative to the vehicle control.

The results of the study, endoscopy scores are shown in FIG. 8. Note that the endoscopy scores range from 1-4, with 1 being minimal damage. In the TNBS model, a clear dose response was observed, with both doses of chitosan-arginine being as least as good as prednisolone, and the highest dose having a P value of <0.001.

Figure 9:
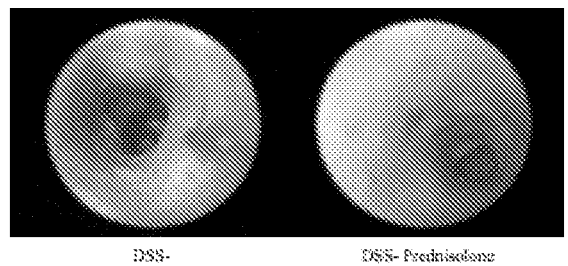
FIG. 9 depicts the representative endoscopy images for the DSS model (SGN-01, left) and the TNBS model (SGN-02, right) for a vehicle control, the standard of care prednisolone, and two doses of chitosan-arginine, given t.i.d via oral gavage in mice.
Figure 9:
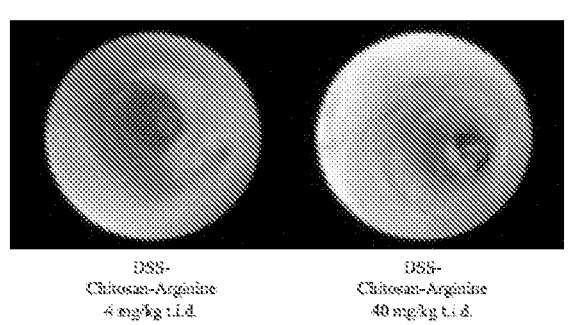
Figure 9:
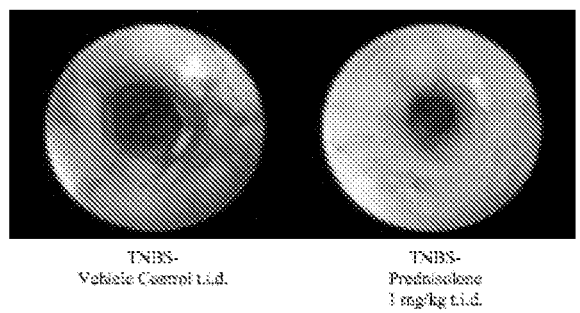
Figure 9:
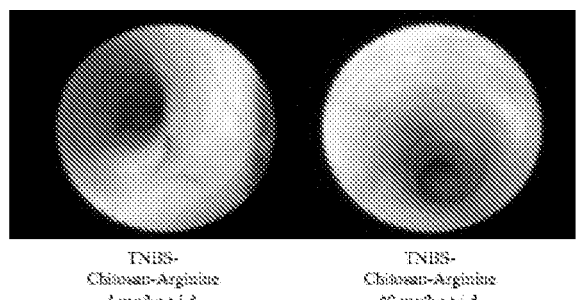

Chitosan-arginine at the highest dose was similar to the standard of care in the DSS model; however, due to the severity of the insult, almost half the mice were lost, resulting in decreased statistics. However, the higher dose of chitosan-arginine was statistically better than controls, and similar to the standard of care, prednisolone. The endoscopy images are shown in FIG. 9.

The study results reflect the ability of the oral chitosan-arginine treatment to reduce the inflammation and enhance the healing relative to control, and in the latter model, significantly better than the standard of care. In the DSS model, the damages were more severe, and additional data on the recovery phase of the treatment as well as larger numbers of animals will be necessary to determine the actual efficacy of chitosan-arginine. In the TNBS model, both doses had significant effects relative to control that are easy to discern visually.

This study demonstrates the topical efficacy of chitosan-arginine on the treatment of local inflammation caused by local damage and mucosal trauma resulting in reduction of ulceration.

Example 8: Alkali Burn in the Eye

This study was designed to evaluate the ocular biocompatibility and effect on healing of alkali corneal wounds of chitosan-arginine formulations and their vehicle in rabbits. Specifically, the onset of inflammation and occurrence of healing rates in rabbits treated with chitosan-arginine were examined.

Experimental Design

In this study, 5 female New Zealand White (NZW) rabbits/arm were given an 8 mm alkali burn to the eye and treated 4× daily for 216 hours after wound creation with two test formulations of chitosan-arginine (Formulation 1 or Formulation 2) and control (vehicle). Detailed ocular examinations were performed every 12 hours and inflammation was scored using a microscopic ocular grading system (modified Hackett-McDonald). Corneal fluorescein staining was photographed using a Digital Photo Slit Lamp every 12 hours and ulceration area (corneal ulcer size (OS—left eye)) was quantitated using image analysis software. Other parameters that were evaluated include: physical examination (acclimation study release); viability (daily); and clinical observations (daily).

Materials and Methods

Test Article.

Two separate chitosan formulations (#1-200 μg/ml chitosan-arginine Lot HI07 in 5% dextrose, sterile filtered; #2-1000 μg/ml chitosan-arginine Lot HI07 in 5% dextrose, sterile filtered) and a vehicle control (5% dextrose, sterile filtered) were evaluated in this animal model. Each treatment consisted of 35 μL of test article applied via a micropipette to the ocular surface of each eye. Application of the test article occurred at least 5 minutes after fluorescein dye application.

Surgical Procedure.

After induction of anesthesia with subcutaneous ketamine (Ketaset, Fort Dodge Animal Health, Fort Dodge, Iowa) and dexmedetomidine (Dexdomitor, Orion Corporation, Espoo, Finland) the left eye of the rabbits were surgically prepped. After application of 1 drop of 0.5% proparacaine HCL, a lid speculum was inserted, and a round piece of filter paper, 8 mm in diameter, containing 2 mL of 1 N NaOH was centered over the pupil and applied to the left cornea for 30 seconds to produce a corneal burn. The anterior surface and inner aspect of the eyelids were gently irrigated with 20 mL of sterile balanced salt solution for 1 minute and loose epithelium was gently removed with Weck-Cel cellulose spears. Eye drops were applied (35 uL drop, 4 times a day) beginning immediately after the completion of the procedure.

Microscopic Ocular Examination.

The anterior segment of each eye, including conjunctiva, flare, iris, cornea, lens, and anterior vitreous, was examined using a Kowa portable slit lamp (model SL-15, Japan). The slit lamp examination included, but was not limited to, pupillary evaluation and examination of the conjunctiva, cornea (including fluorescein staining), anterior chamber, iris and lens. A board-certified veterinary ophthalmologist performed the examinations. Ocular findings were recorded using a microscopic ocular grading system (modified Hackett and McDonald scoring method).

Ocular Surface Staining with Fluorescein.

Five minutes following a 5 μL instillation of 1% sodium fluorescein, corneal staining was photographed under cobalt blue light using a Topcon Digital Photo Slit Lamp (Topcon SL-D7 Digital Slit Lamp with a Nikon D200 Digital SLR Camera). Area (in pixels) of fluorescein staining for each eye at each time point was determined using ImageJ Software (NIH).

Ocular Histopathology.

Rabbits were euthanized after the examination at 216 hours by an overdose of a barbiturate euthanasia solution. The eyes were immediately removed and fixed in 10% neutral buffered formalin. The eyes were dehydrated in alcohol, sectioned, and stained with hematoxylin and eosin. The slides were examined using light microscroscopy and results reported subjectively.

Statistical Analysis.

An ANOVA with Tukey's HSD test was used to compare area pixel counts in corneal ulceration. Non-parametric data (microscopic scoring) was compared using a Kruskal-Wallis test. A univariate survival analysis was done to compare healing (survival) curves per day per group. A Wilcoxin test provided statistical analysis for homogeneity among the groups for the healing curves. Differences were considered significant at P<0.05. All means, probabilities, and powers were calculated using computerized statistical software (JMP version 8.0, SAS Institute, Cary, N.C.).

Results

Figure 10:
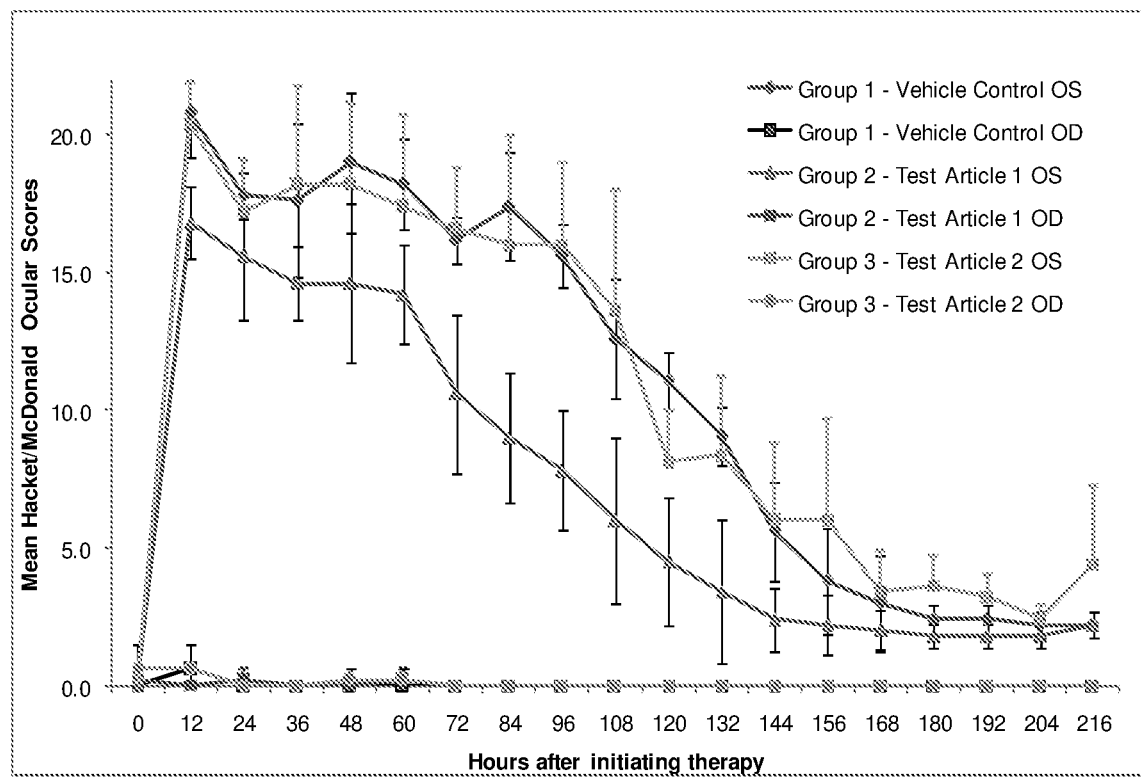
FIG. 10 depicts the mean (±SD) cumulative microscopic ocular scores in eyes after creating an 8 mm central alkali corneal wound ulcer (OS) and treatment with vehicle (Group 1); Formulation 1 (Group 2); or Formulation 2 (Group 3) in both eyes. Group 2 is significantly less than groups 1 and 3 (P<0.0085) at 12, 60-144 except 120 hours. Groups 1, 2, and 3 significantly differ from each other (P<0.0055) at 120 hours. OS: left eye; OD: right eye.

All formulations were well tolerated as demonstrated by the unwounded eye. There were no abnormal clinical or ocular observations noted prior to creation of the corneal wound. All animals had moderate to severe ocular hyperemia and chemosis in the left eye and moderate blepharospasm for ~24 to 72 hours after creation of the corneal wound. There was only occasional mild ocular hyperemia in the right eye at all time points. Results were recorded using individual animal microscopic ocular scoring (Modified Hackett-MacDonald). There were no significant differences in cumulative scores in the unwounded right eyes. This suggests that formulations were as well tolerated as the vehicle in the right eye and thus were well tolerated in general. Group 2 animals (treated with Formulation 1) had significantly lower cumulative microscopic ocular scores in the left eye compared to vehicle (Group 1) and Formulation 2 (Group 3) animals at 12 and 60 to 144 hours after creating of the wound (P<0.0085). Group 3 animals had significantly lower cumulative ocular scores in the left eye compared to the left eyes of Group 1 at 120 hours after creating the wound (P<0.0055). In FIG. 10, the mean Hacket/McDonald ocular scores, which reflect local and overall inflammation, are shown as a function of time for the 3 treatments, Group 1 (control), Group 2 (low dose chitosan-arginine), and Group 3 (high dose chitosan-arginine). Importantly, the initial inflammation at 12 hours was reduced and the subsequent cumulative inflammation resulting from continued inflammatory cytokines and subsequent neutrophil invasion and reactive oxygen species remained low.

Figure 11:
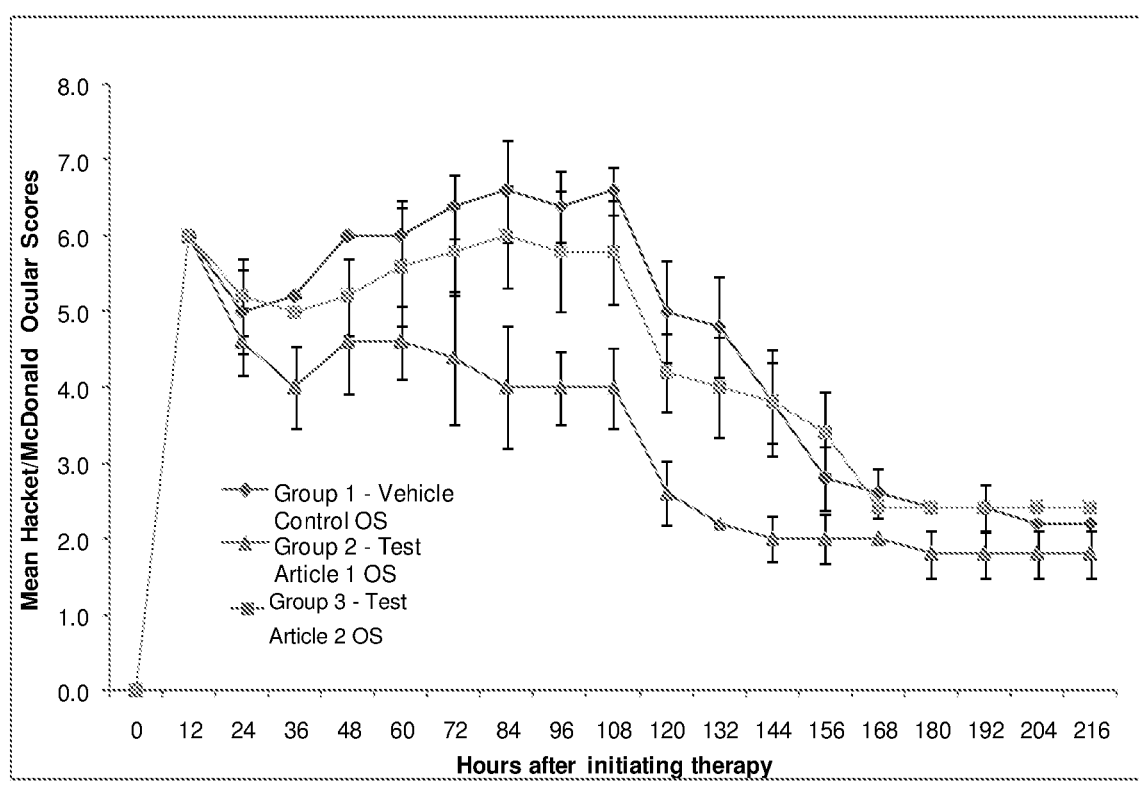
FIG. 11 depicts the mean (±SD) cumulative microscopic cornea scores (i.e., keratitis scores) in eyes after creating an 8 mm central alkali corneal wound ulcer (OS) and treatment with vehicle (Group 1); Formulation 1 (Group 2); or Formulation 2 (Group 3) in both eyes. Group 2 is significantly less than Groups 1 and 3 (P<0.0005). OS: left eye.

When evaluating just the corneal scores, which would indicate the level of corneal inflammation or keratitis, Group 2 animals had significantly lower cumulative corneal scores OS (left eye) compared to vehicle (Group 1) and Formulation 2 (Group 3) animals at 36 and 72 to 144 hours after creation of the wound (P<0.0005) (FIG. 11). These results suggest that treatment with Formulation 1 was associated with reduced overall signs of ocular inflammation and keratitis for much of the post-injury time period.

Figure 12:
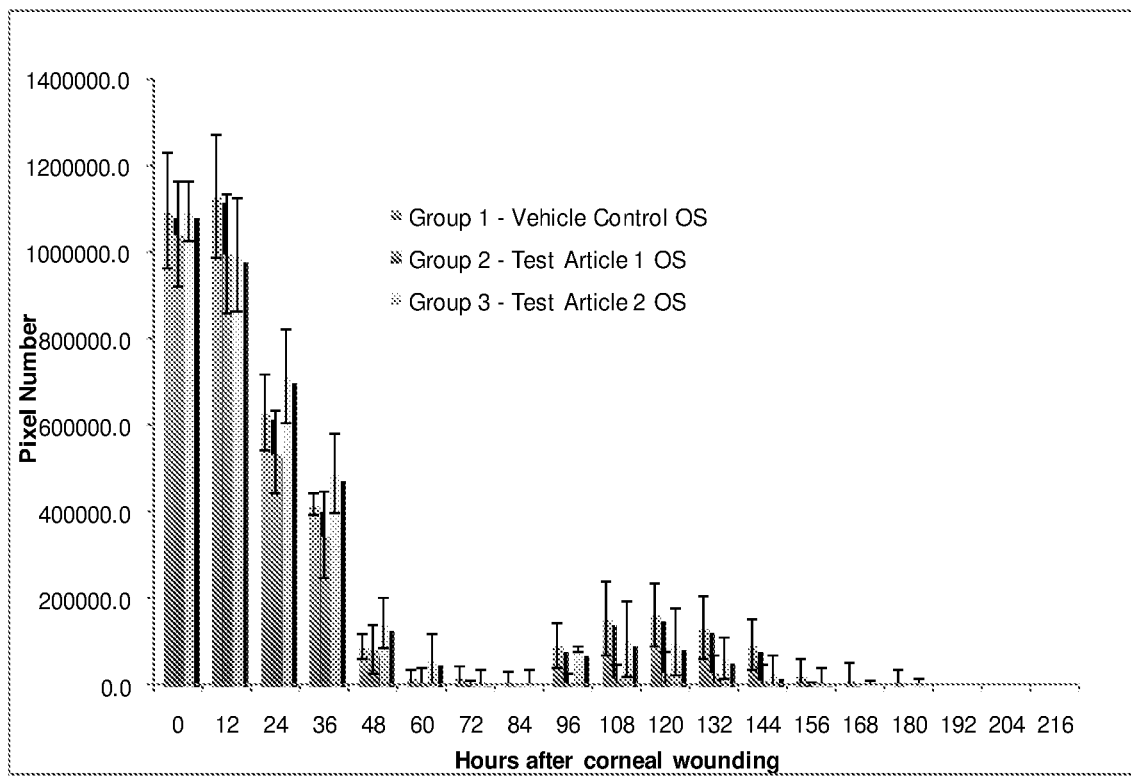
FIG. 12 depicts the mean±SD area of corneal ulceration (fluorescein positive areas) in pixels. Groups 1, 2, and 3 are represented in order from left to right at each time-point as indicated in the figure. Group 2 is significantly less than group 3 (P=0.0148) at 24, 36 hours. Group 2 is significantly less than group 1 (P<0.0128) at 108 and 120 hours. Groups 2 and 3 are significantly less than group 1 (P=0.0472) at 144 hours.

Following creation of an 8 mm diameter central corneal alkali wound, each eye was stained with topically applied fluorescein and photographed in a standardized method using a digital slit lamp every 12 hours. Images were analyzed using ImageJ software (NIH) to determine the area (in number of pixels) of corneal ulceration (fluorescein positive areas) of each wounded eye at each time point. FIG. 12 shows the total number of pixels in the eye associated with ulceration and damage for each of the test conditions. The area of ulceration rapidly decreased in size over 72 hours. Then as the keratitis increased, the corneas re-ulcerated from approximately 96 to 156 hours after initiation of the corneal wound (FIG. 12). There was little difference between the groups in size of corneal ulcers during the first 72 hours, although Group 2 eyes had significantly smaller areas of ulceration than Group 3 eyes at 24 and 36 hours after corneal wounding (P=0.0148). However, Group 2 eyes appeared to be less likely to re-ulcerate in the second phase of inflammation and had a significantly smaller mean area of ulceration compared to Groups 1 and 3 from 108 to 144 hours after wounding (FIG. 12). Group 3 had significantly less mean area of ulceration than Group 1 at 144 hours after wounding.

Figure 13:
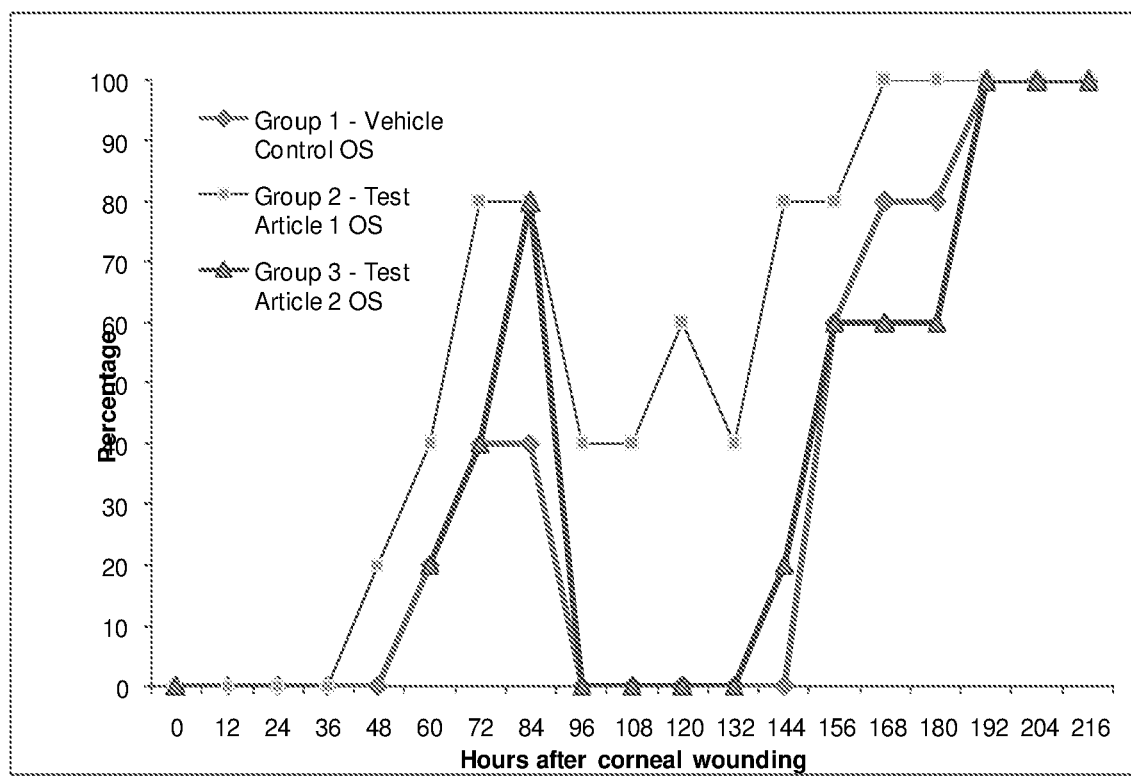
FIG. 13 depicts the percentage of eyes per group that were fluorescein negative (no ulceration)
Figure 14:
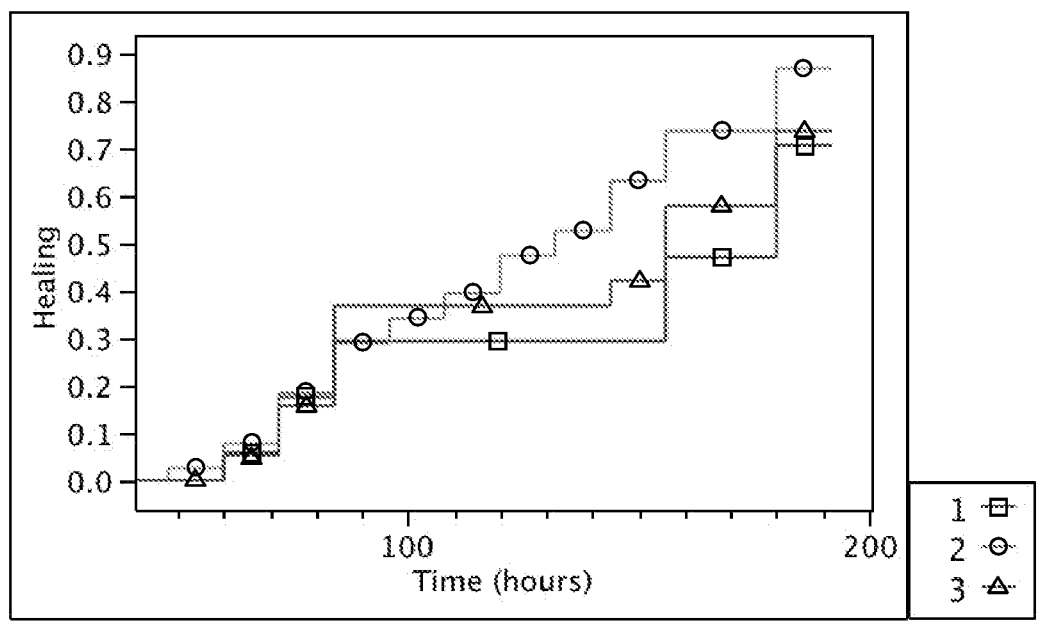
FIG. 14 depicts a healing plot—univariate survival analysis of the number of ulcers that have healed per time. Group 2 had significantly higher healing (survival) than Groups 1 or 3 (P<0.0001).

Rate of healing of the corneal wounds of the left eye appeared faster in Group 2 compared to Groups 1 and 3. By 60 hours, 80% of eyes were fluorescein negative (healed corneal epithelium) in Group 2 compared to 40% in Groups 1 and 3. All left eyes of Groups 1 and 3 were ulcerated from time 96 to 132 hours, while during this same time period 40 to 60% of Group 2 eyes were fluorescein negative. Finally, all Group 2 eyes became fluorescein negative by 144 hours, but it took 180 hours for all eyes to be negative in Groups 1 and 3 (FIG. 13). A univariate survival analysis of the number of ulcers that have healed per time determined that the three groups were not homogenous, indicating that Group 2 had significantly higher healing (survival) than Groups 1 or 3 (P<0.0001) (FIG. 14).

Thus, healing with the low dose was significant relative to control and the higher dose. Furthermore, the treatment prevented the secondary ulceration that results from continued inflammation, edema and neutrophil invasion. The eye healed faster using a survivability type analysis (statistical significance P<0.0001 relative to control) with the low dose formulation. The fact that high dose of the chitosan-arginine was not significantly better than control suggests that there is an optimal dose to maintain the balance between reduction of inflammation and healing, as shown for EGF based healing in Mathers et al., *Invest Ophthalmol Vis Sci.* 1989; 30(11):2403-6.

Figure 15A:
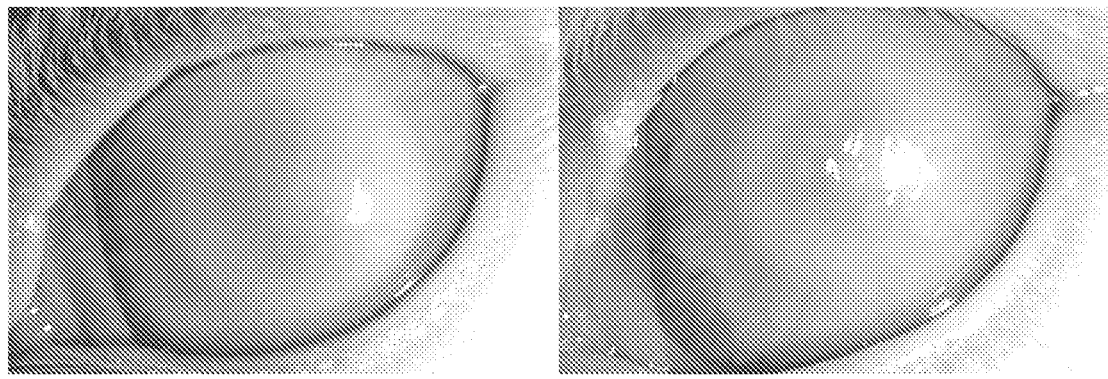
FIG. 15A depicts the representative images of eyes given an alkali burn and treated with control, shown at 192 hours.
Figure 15B:
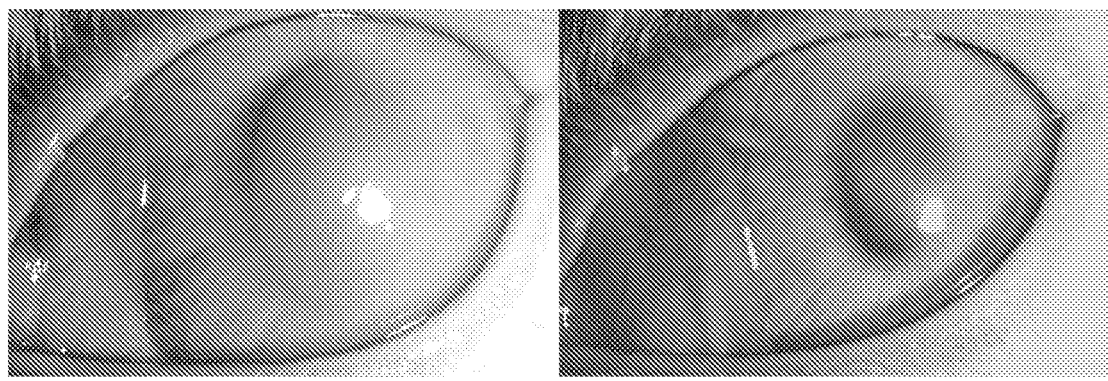
FIG. 15B depicts the representative images of eyes given an alkali burn and treated with chitosan-arginine formulation 1 (Group 2), shown at 192 hours.

Scarring is an undesirable process that results from inflammation, tissue damage and reactive oxygen species. An important result of decreased inflammation is typically reduction in the reactive oxygen species, faster healing and less scarring. The amount of scarring is qualitatively determined by the opacity and "cloudiness" of the cornea. Corneal opacity is shown in FIG. 15A for control eyes, and chitosan-arginine formulation 1 (Group 2) treated eyes (low dose) in FIG. 15B. The best and worst eyes of each group visually, are presented in each figure for comparison. Note that variability between eyes is observed, but the treatment produced less scarring than the control in all cases (visual comparison).

SUMMARY

In this study, a central 8 mm corneal alkali wound was created in the left eye of New Zealand White rabbits and both eyes were treated with Formulation 1, Formulation 2, or vehicle. Based on the study results:

1) All topical medications (Formulation 1, Formulation 2, and vehicle) were very well tolerated with only background clinical ocular irritation scores in the OD (right eye) throughout the 216 hours of 4 times a day topical administration.

2) Rapid moderate to severe ocular hyperemia and chemosis OS (left eye) and moderate blepharospasm for ~24 to 72 hours developed after creation of the corneal wound. Inflammation persisted in most eyes for 168 to 180 hours after wounding. However, eyes treated with Formulation 1 (Group 2) had significantly less inflammation (lower cumulative microscopic ocular scores) compared to both vehicle (Group 1) and Formulation 2 (Group 3) treated eyes for most of the post-injury study period.

3) Eyes treated with Formulation 1 also had significantly lower corneal inflammation (cumulative microscopic scores of the cornea) compared to vehicle and Formulation 2 treated animals for most of the post-injury study period.

4) Together, these results suggest that treatment with Formulation 1 was associated with reduced overall signs of ocular inflammation and keratitis for much of the post-injury time period.

5) Although there was little difference between the groups in size of corneal ulcers during the first 72 hours after corneal injury, eyes treated with Formulation 1 appeared to be less likely to re-ulcerate during the second phase of keratitis and had significantly smaller mean area of ulceration compared to Groups 1 and 3 from 108 to 144 hours after wounding.

6) Eyes treated with Formulation 1 became fluorescein negative (healed epithelium) quicker than in eyes treated with vehicle or Formulation 2. By 60 hours after injury, 80% of eyes treated with Formulation 1 were fluorescein negative compared to 40% in Groups 1 and 3. All eyes treated with Formulation 1 became fluorescein negative by 144 hours, but it took 180 hours for all eyes to be negative in Groups 1 and 3. A univariate survival analysis of the number of ulcers that have healed per time determined that the three groups were not homogenous, indicating that Group 2 had significantly higher healing (survival) than Groups 1 or 3 (P<0.0001).

Thus, topical treatments 4× daily reduced inflammation, increased the healing, and reduced scarring in eyes subjected to a chemical burn. The higher dose of chitosan-arginine was similar to control, suggesting that an optimal dosing in required in the case of inflammation and healing in order to balance the environment to encourage re-epithelialization while suppressing inflammation.

Example 9: IL-8 Production in Macrophages Exposed to Bacteria

Figure 16:
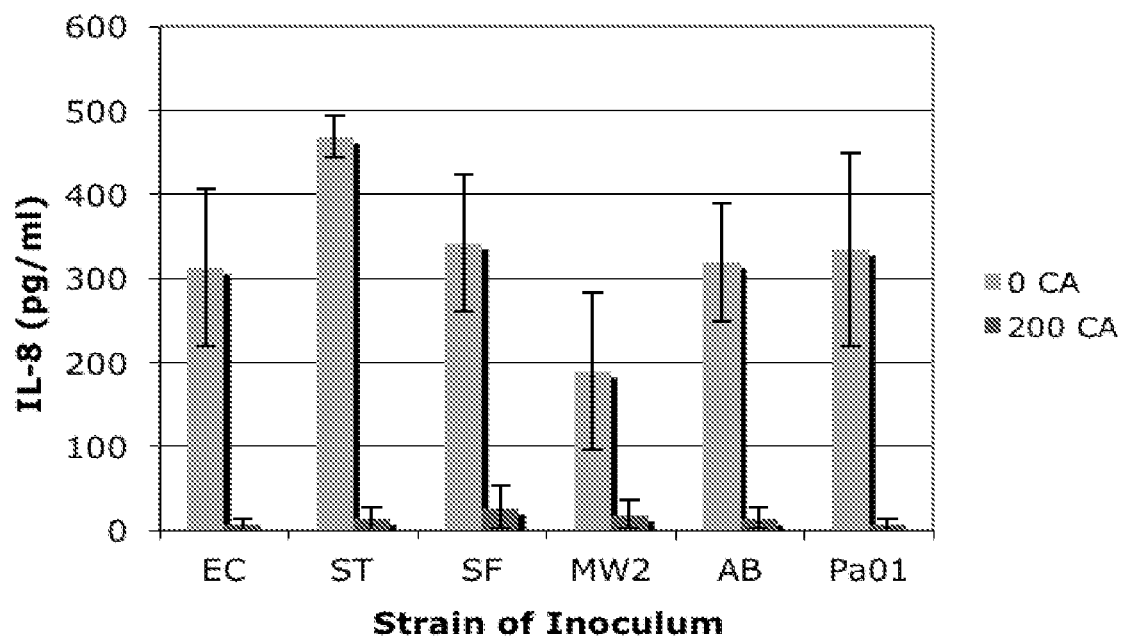
FIG. 16 depicts the average concentration of IL-8 secreted in 24 hours from human U937 macrophages after a series of treatments with or without 200 ppm chitosan-arginine. EC=*E. Coli*; ST=*Salmonella enterica* serovar *Typhi*; SF=*Shigella flexneri*; MW2=methicillin resistant *Staphylococcus aureus* (wound isolate); AB=*Acinetobacter baumannii*; PA01=*Pseudomonas aeruginosa*.

U937 cells (human macrophage cell line) were grown to confluence in 96-well plates. Cells were treated with 0 or 200 ppm of chitosan-arginine for 1 hour. Then the cells were rinsed twice with media to remove chitosan-arginine that was not associated with the cell surface. Next, cells were exposed to various bacteria strains as indicated in FIG. 16 for three hours. Supernatant was measured 24 hours after exposure for IL-8. As shown in FIG. 16, the chitosan-arginine pretreatment dramatically reduced the IL-8 secretion by macrophages stimulated by bacterial exposure.

What is claimed is:

1. A method of treating a wound in the eye of a subject, the method comprising topically administering to the eye of the subject an effective amount of an aqueous pharmaceutical composition comprising:
dextrose;
sterile water; and
a soluble derivatized chitosan, wherein the derivatized chitosan is of the following formula (I):

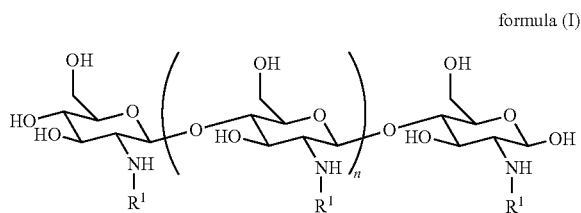

formula (I)

wherein:
n is an integer between 20 and 6000; and
each R¹ is independently selected for each occurrence from hydrogen, acetyl,

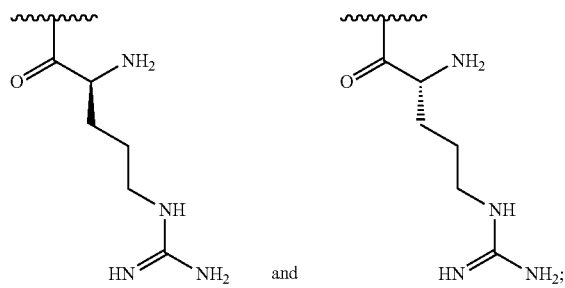 [SMILES: *C(=O)[C@@H](N)CCCNC(=N)N ; *C(=O)[C@H](N)CCCNC(=N)N]

wherein at least 25% of R¹ substituents are H, at least 1% of R¹ substituents are acetyl, and at least 2% of R¹ substituents are

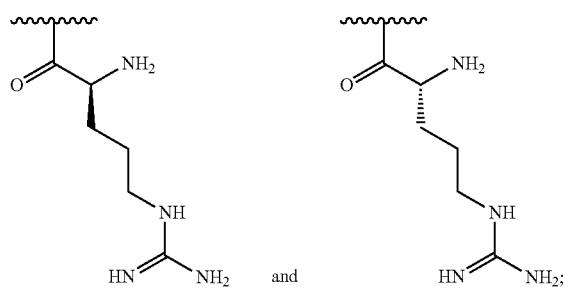

wherein the molecular weight of the derivatized chitosan is between about 10,000 and 350,000 Da,
wherein 36 hours after administration of the aqueous pharmaceutical composition, the eye wound has lower cumulative corneal scores compared to an eye wound treated with a composition consisting essentially of dextrose and sterile water,
thereby treating the wound in the eye of the subject.

2. The method of claim 1, wherein the composition decreases the inflammation associated with the wound or healing of the wound.

3. The method of claim 1, wherein the composition reduces the healing time or increases the healing rate of the wound.

4. The method of claim 1, wherein the composition is administered at least 1, 2, 3, 4, 5, or 6 times daily.

5. The method of claim 1, wherein the composition comprises from about 50 μg/mL to about 500 μg/mL of the compound of Formula (I).

6. The method of claim 1, wherein the derivatized chitosan is functionalized at between 5% and 50%.

7. The method of claim 1, wherein the derivatized chitosan has a polydispersity index of from 1.0 to 2.5.

8. The method of claim 1, wherein the derivatized chitosan is soluble in the composition from about pH 6 to about pH 8.

9. The method of claim 1, wherein the derivatized chitosan is soluble in the composition from about pH 6.8 to about pH 7.4.

10. The method of claim 1, wherein the subject has undergone a surgical procedure, wherein the surgical procedure is laser eye surgery, refractive surgery, cataract surgery, glaucoma surgery, canaloplasty, corneal surgery, vitreo-retinal surgery, eye muscle surgery, or oculoplastic surgery.

11. The method of claim 1, wherein the wound is from a surgical procedure.

12. The method of claim 1, wherein the method reduces scarring in the eye.

13. The method of claim 1, wherein the method reduces loss of vision due to scarring in the eye.

14. The method of claim 1, wherein the wound is not a result of an infection.

15. The method of claim 1, wherein the wound is from exposure to a chemical warfare agent selected from the group consisting of lachrymatory agents, vomiting agents, psychological agents, blister agents, arsenicals, urticants, blood agents, choking agents or pulmonary agent, and nerve agents.

16. The method of claim 1, wherein the method further comprises administering to the subject an analgesic.

17. The method of claim 1, wherein the method further comprises administering to the subject an antibiotic.

18. The method of claim 1, wherein the wound is from exposure to a chemical warfare agent, wherein the chemical warfare agent is nitrogen mustards or sulfur mustards.

19. The method of claim 1, wherein the wound is from exposure to a chemical warfare agent selected from the group consisting of chlorotoluene, benzyl bromide, bromoacetone, bromobenzylcyanide, bromomethyl ethyl ketone, capsaicin, chloracetophenone, chloromethyl chloroformate, dibenzoxazepine, ethyl iodoacetate, ortho-chlorobenzylidene malononitrile, trichloromethyl chloroformate, and xylyl bromide, adamsite, diphenylchloroarsine, diphenylcyanoarsine, 3-quinuclidinyl benzilate, phencyclidine, lysergic acid diethylamide, bis(2-chloroethyl)ethylamine, bis(2-chloroethyl)methylamine, tris(2-chloroethyl)amine, 1,2-bis(2-chloroethylthio)ethane, 1,3-bis(2-chloroethylthio)-n-propane, 1,4-bis(2-chloroethylthio)-n-butane, 1,5-bis(2-chloroethylthio)-n-pentane, 2-chloroethylchloromethylsulfide, bis(2-chloroethyl)sulfide, bis(2-chloroethylthio)methane, bis(2-chloroethylthiomethyl)ether, bis(2-chloroethylthioethyl) ether, ethyldichloroarsine, methyldichloroarsine, phenyldichloroarsine, 2-chlorovinyldichloroarsine, phosgene oxime, cyanogen chloride, hydrogen cyanide, arsine, chlorine, chloropicrin, diphosgene, phosgene, G series, GV series, and V series.

* * * * *